US011768203B2

(12) United States Patent
Chaudhary

(10) Patent No.: US 11,768,203 B2
(45) Date of Patent: Sep. 26, 2023

(54) HIGHLY SENSITIVE AND SPECIFIC LUCIFERASE BASED REPORTER ASSAY FOR ANTIGEN DETECTION

(71) Applicant: University of Southern California, Los Angeles, CA (US)

(72) Inventor: Preet M. Chaudhary, Toluca Lake, CA (US)

(73) Assignee: University of Southern California, Los Angeles, CA (US)

( * ) Notice: Subject to any disclaimer, the term of this patent is extended or adjusted under 35 U.S.C. 154(b) by 209 days.

(21) Appl. No.: 16/089,278

(22) PCT Filed: Mar. 31, 2017

(86) PCT No.: PCT/US2017/025602
§ 371 (c)(1),
(2) Date: Sep. 27, 2018

(87) PCT Pub. No.: WO2017/173403
PCT Pub. Date: Oct. 5, 2017

(65) Prior Publication Data
US 2019/0107537 A1    Apr. 11, 2019

Related U.S. Application Data

(60) Provisional application No. 62/316,489, filed on Mar. 31, 2016.

(51) Int. Cl.
*G01N 33/58* (2006.01)
*G01N 33/535* (2006.01)
*G01N 33/569* (2006.01)
*G01N 33/50* (2006.01)
*C07K 16/28* (2006.01)

(52) U.S. Cl.
CPC ... *G01N 33/56972* (2013.01); *C07K 16/2803* (2013.01); *C07K 16/2827* (2013.01); *C07K 16/2866* (2013.01); *C07K 16/2878* (2013.01); *C07K 16/2887* (2013.01); *C07K 16/2896* (2013.01); *G01N 33/5023* (2013.01); *G01N 33/5044* (2013.01); *G01N 33/56966* (2013.01); *G01N 33/581* (2013.01); *C07K 2317/622* (2013.01); *C07K 2319/02* (2013.01); *C07K 2319/43* (2013.01); *C07K 2319/60* (2013.01); *G01N 2333/70503* (2013.01); *G01N 2333/72* (2013.01); *G01N 2800/52* (2013.01)

(58) Field of Classification Search
CPC ............ C07K 16/2887; C07K 16/2827; C07K 16/2866; C07K 16/2803; C07K 16/2878; C07K 16/2896; C07K 2319/43; C07K 2317/622; C07K 2319/60; C07K 2319/02; G01N 33/581; G01N 33/5044; G01N 33/5023; G01N 33/56972; G01N 33/56966; G01N 33/536; G01N 33/535; G01N 2333/70503; G01N 2800/52; G01N 2333/72

See application file for complete search history.

(56) References Cited

U.S. PATENT DOCUMENTS

| 4,959,303 A | 9/1990 | Milburn et al. |
| 2013/0273582 A1 | 10/2013 | Daly et al. |
| 2014/0194307 A1* | 7/2014 | Hitko ................... G01N 33/582 506/9 |
| 2015/0219647 A1 | 8/2015 | Burbelo et al. |
| 2015/0376296 A1* | 12/2015 | Fedorov ......... A61K 39/001188 424/93.71 |

FOREIGN PATENT DOCUMENTS

| WO | 2012050374 A2 | 4/2012 |
| WO | 2012/135854 A2 | 10/2012 |
| WO | 2014/127261 A1 | 8/2014 |

OTHER PUBLICATIONS

Venisnik et al. Fusion of Gaussia Luciferase to an engineered anti-carcinoembryonic antigen (CEA) antibody for in vivo optical imaging. Mol. Imaging Biol. 2007, vol. 9. pp. 267-277. (Year: 2007).*
Oliveira et al. A CD19/Fc fusion protein for detection of anti-CD19 chimeric antigen receptors. J. of Translational Medicine 2013, vol. 11, pp. 1-9 (Year: 2013).*
Luker et al. Bioluminescent CXCL12 fusion protein for cellular studies of CXCR4 and CXCR7. Biotechniques 2009, vol. 47, No. 1, pp. 625-632. (Year: 2009).*
Boute et al., "NanoLuc Luciferase—A Multifunctional Tool for High Throughput Antibody Screening", Frontiers in Pharmacology, Feb. 18, 2016, pp. 1-11.
Burbelo P.D. et al., "A simplified immunoprecipitation method for quantitatively measuring antibody responses in clinical sera samples by using mammalian-produced Renilla luciferase-antigen fusion proteins", BMC Biotechnology, vol. 5:22, Aug. 18, 2005, pp. 1-10.
De Oliveira et al., "A CD19/Fc fusion protein for detection of anti-CD19 chimeric antigen receptors", Journal of Translational Medicine, vol. 11, No. 1, Dec. 1, 2013, pp. 1-9.
Krenciute et al., "Characterization and Functional Analysis of scFv-based Chimeric Antigen Receptors to Redirect T Cells to IL13R[alpha]2-positive Glioma", Molecular Therapy, vol. 24, No. 2, Feb. 1, 2016, pp. 354-363.

(Continued)

*Primary Examiner* — Shafiqul Haq
(74) *Attorney, Agent, or Firm* — Gavrilovich, Dodd & Lindsey LLP

(57) ABSTRACT

Provided herein are methods for detecting an antigen or for detecting expression of a chimeric antigen receptor (CAR). The methods include obtaining a sample from a subject, contacting the sample with a fusion protein comprising a reporter fused to a single chain antibody specific to the antigen or fused to an extracellular domain of an antigen targeted by the CAR or fused to Protein L and assaying the activity of the reporter, wherein presence of reporter activity or increase in reporter activity relative to a reference value is indicative of presence of the antigen or presence of the expression of the chimeric antigen receptor in the sample.

20 Claims, 9 Drawing Sheets

Specification includes a Sequence Listing.

(56) References Cited

OTHER PUBLICATIONS

Medina-Kauwe et al., "Assessing the Binding and Endocytosis Activity of Cellular Receptors Using GFP-Ligand Fusions", Bio Techniques, vol. 29, Sep. 1, 2000, pp. 602-609.
Ren et al., "Modification of cytokine-induced killer cells with chimeric antigen receptors (CARs) enhances antitumor immunity to epidermal growth factor receptor (EGFR)-positive malignancies", Cancer Immunology, Immunotherapy, vol. 64, No. 12, Sep. 19, 2015, pp. 1517-1529.
Song et al., "Quick preparation of nanoluciferase-based tracers for novel bioluminescent receptor-binding assays of protein hormones: Using erythropoietin as a model", Journal of Photochemistry and Photobiology, B. Biology, vol. 153, Oct. 19, 2015, pp. 311-316.
Wiesner, Martina, Extended European Search Report, European Patent Office, Application No. 17776873.6, dated Nov. 6, 2019.
Burbelo et al., "Luciferase Immunoprecipitation Systems for Measuring Antibodies in Autoimmune and Infectious Disease," Translational Research, 165(2):325-335, Sep. 1, 2014.
Zubair et al., "Microfluidic LIPS for serum antibody detection: Demonstration of a rapid test for HSV-2 Infection," Biomed. Microdevices, 13(6):1053-1062, Dec. 31, 2011.
Meng, He et al., "Biochemical Characterization and Cellular Effects of CADASIL Mutants of NOTCH3", PLOS One, Sep. 2012, vol. 7, Issue 9, e44964.
Wiesner, Martina, Communication Pursuant to Article 94(3) EPC, European Patent Application No. 17776873.6, European Patent Office, dated Feb. 17, 2021.
Bagashev et al., "CD19 Alternations Emerging after CD19-Directed Immunotherapy Cause Retention of the Misfolded Protein in the Endoplasmic Reticulum," Mol. & Cellular Biol., 38(21):1-17, 2018.
Hu et al., "The Chimeric Antigen Receptor Detection Toolkit," Front. Immunol. 11:1770, 2020.
Patel et al., "Cell-free production of Gaussia princeps luciferase—antibody fragment bioconjugates for ex vivo detection of tumor cells," Biochem. Biophys. Res. Commun., 390:971-976, 2009.
Wozniak-Knopp et al., "Stabilisation of the Fc Fragment of Human IgG1 by Engineered Intradomain Disulfide Bonds," PLoS One, 7(1):e30083, 2012.
Yu et al., "Gaussia princepts luciferase: A bioluminescent substrate for oxidative protein folding," Protein Sci., 27:1509-1517, 2018.

\* cited by examiner

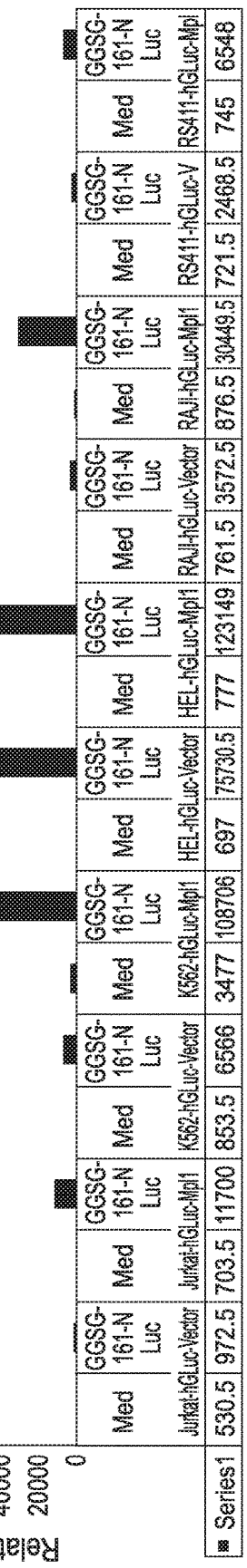
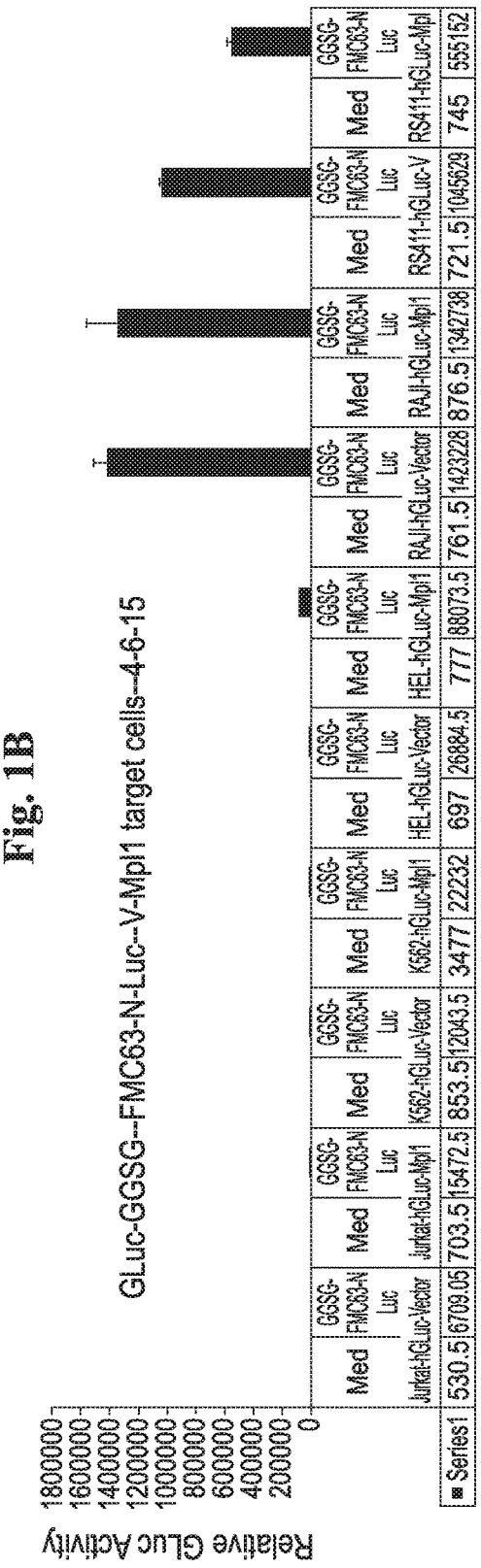

Fig. 7A
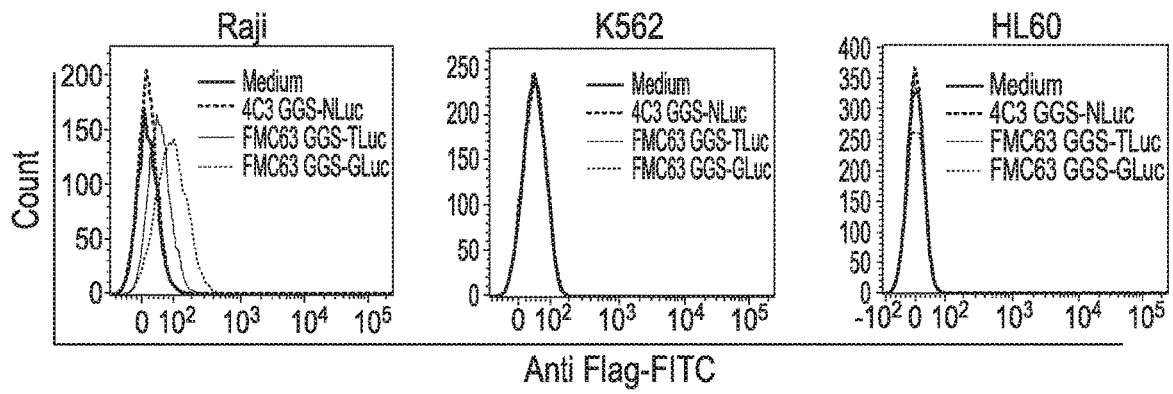
Fig. 7B
| Mean Fluorescence Intensity | | | |
|---|---|---|---|
|  | Raji | K562 | HL60 |
| Medium alone | 22 | 66 | 8 |
| 4C3 GGS NLuc AcV5 H04 | 22 | 47 | 8 |
| FMC63 GGS TurboLuc16 x 3 flag A04 | 59 | 49 | 8 |
| FMC63 GGS GLuc x 3 flag B02 | 111 | 49 | 8 |
Fig. 8A
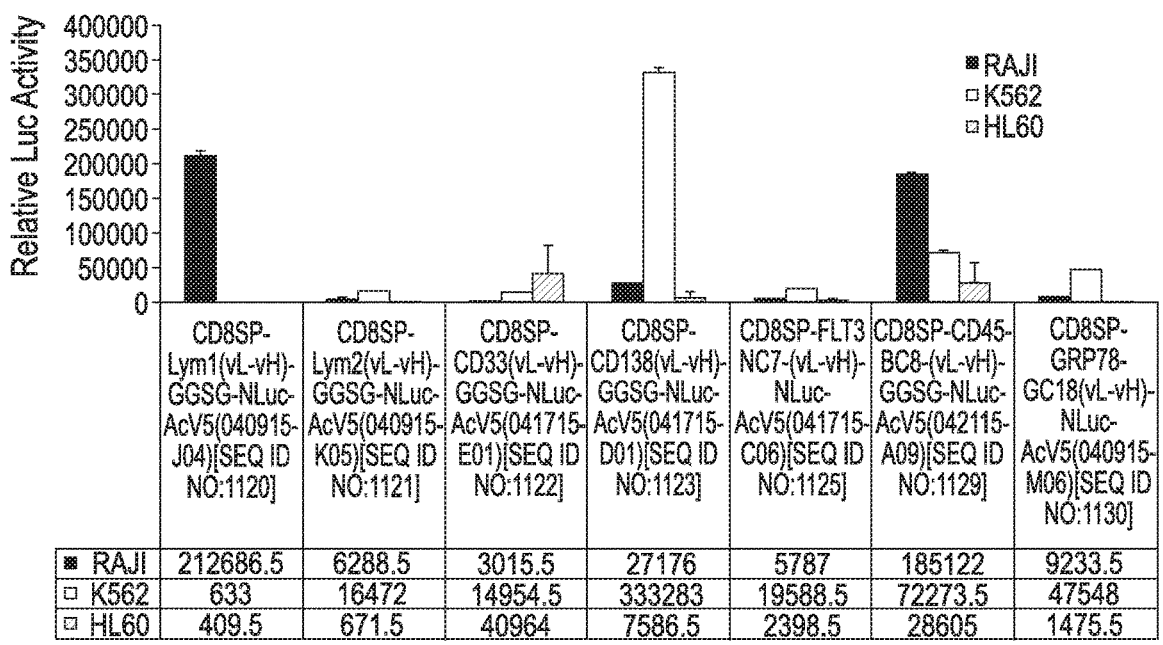

HIGHLY SENSITIVE AND SPECIFIC LUCIFERASE BASED REPORTER ASSAY FOR ANTIGEN DETECTION

CROSS-REFERENCE TO RELATED APPLICATIONS

This application is a U.S. National Stage Application filed under 35 U.S.C. § 371 and claims priority to International Application No. PCT/US2017/025602, filed Mar. 31, 2017, which application claims benefit of priority under 35 U.S.C. § 119(e) of U.S. Provisional Patent Application No. 62/316, 489, filed Mar. 31, 2016, the contents of which are incorporated by reference in their entirety.

STATEMENT REGARDING FEDERALLY SPONSORED RESEARCH OR DEVELOPMENT

This invention was made with government support under Grant No. DE019811 awarded by National Institutes of Health. The government has certain rights in the invention.

TECHNICAL FIELD

Provided herein are assays to detect expression of antigens and cells expressing chimeric antigen receptors.

INCORPORATION BY REFERENCE OF SEQUENCE LISTING

Accompanying this filing is a Sequence Listing entitled "Sequence_ST25.txt", with a date of Sep. 27, 2018 and having 5,318,395 bytes of data, machine formatted on IBM-PC, MS-Windows operating system. The accompanying sequence listing is identical to the sequence listing filed in PCT/US2017/025602 on Mar. 31, 2017. The sequence listing is hereby incorporated herein by reference in its entirety for all purposes.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

There are several methods currently in use for detection of a particular antigen, including flow cytometry, ELISA and western blotting. However, these methods require expensive equipment (such as flow cytometry), suffer from poor sensitivity and specificity (e.g., ELISA and Western blotting) or are time consuming. The poor sensitivity of the current methods of antigen detection is particularly significant in light of development of new targeted therapies using antibody drug conjugates and chimeric antigen receptors. These new therapies are extremely potent at killing cells expressing their target antigen even at very low levels, which are below the detection limits of current methods. For example, Brentuximab vedotin (Adcetris), an antibody drug conjugate, that targets CD30 antigen has shown impressive clinical activity in diffuse large cell lymphoma in several clinical trials. However, the response to Brentuximab vedotin does not always correlate with CD30 positivity, as determined by conventional immunohistochemistry, and patients with diffuse large cell lymphomas that are CD30-ve frequently respond to this agent. This has led to the hypothesis that Brentuximab vedotin requires very low level expression of CD30 for its activity and its efficacy in CD30-ve diffuse large cell lymphoma is, in part, due to low level expression of CD30 in these samples, which is below the detection of conventional methods.

Chimeric antigen receptor based T cell therapy represents another example where detection of low level expression of an antigen in a patient sample is critically important to predict response to therapy. It is believed that CAR-T cells can kill a target cell expressing as few as 100 molecules of their target antigen. Consistent with this, CAR-T cells targeting CD19 antigen have shown impressive clinical activity in multiple myeloma, a disease which is believed to be CD19-ve based on conventional detection methods (Hajek, R et al., Br J Haematol 163:551-564, 2013). Thus, availability of highly sensitive and specific method for detection of CD30, CD19 and other antigens would be of great benefit in determining the patients who are likely to respond to targeted therapies as well as to predict toxicity to normal tissues. In addition to clinical use, a highly sensitive and specific method for antigen detection, which is inexpensive, quick and does not require special equipment, would also have utility for research applications.

Another challenge in the field of CAR-T cell therapy is the lack of a fast, economical, sensitive and robust assay for detection of chimeric antigen receptors on the surface of T cells. Current methods for detection of CAR on cell surface have several limitations. For example, CD19-specific CARs have been detected following staining with an Alexa Flour 488-conjugated CD19-Fc fusion protein consisting of human CD19 extracellular domain and Fc region of human IgG1 (De Oliveira, S N et al., Journal of translational medicine 11:23, 2013). However, this protocol required the extra steps and cost of purification of the fusion protein followed by its conjugation with Alexa Flour 488. CAR-expressing T cells have been also detected using anti-human IgG1 Fc or biotinylated Protein L. However, these approaches suffer from significant background and limited discrimination (De Oliveira, S N et al., Journal of translational medicine 11:23, 2013). Staining using biotinylated Protein L necessitates secondary staining with labeled streptavidin, with additional protocol steps and potential loss of cells (De Oliveira, S N et al., Journal of translational medicine 11:23, 2013).

In various embodiments, the instant invention provides a fast, economical, sensitive and specific assay for detection of chimeric antigen receptors on the surface of T cells that does not require any expensive equipment. Due to its extreme sensitivity and broad dynamic range, this assay can be used as a quality-control tool during the manufacturing of CAR-T cells and to monitor the persistence of CAR-T cells in the body after infusion.

There is a need in the art for sensitive methods for detecting antigens that are expressed at low levels and selecting patients for therapy based on detection of antigens of interest. There is also need in the art for sensitive, specific, fast and economical method for detecting chimeric antigen receptor-modified immune cells.

SUMMARY

The following embodiments and aspects thereof are described and illustrated in conjunction with systems, compositions and methods which are meant to be exemplary and illustrative, not limiting in scope.

Provided herein is a method for detecting expression of a chimeric antigen receptor (CAR), comprising: obtaining a sample from a subject in need determination of expression of the CAR; contacting the sample with a fusion protein comprising a reporter fused to an extracellular domain of an antigen targeted by the CAR; and assaying the activity of the reporter; wherein presence of reporter activity or increase in reporter activity relative to a reference value is indicative of the expression of the CAR in the sample.

In one embodiment, the reporter is a non-secretory form of a luciferase. In exemplary embodiments, the non-secretory form of luciferase is obtained from copepods, deep sea shrimp or homologs or orthologs thereof or mutants or derivatives thereof.

In some embodiments, the copepods are selected from the group consisting of any one or more of *Gaussia princeps*, *Pleuromamma abdominalis*, *Metridia pacifica*, *Metridia curticauda*, *Metridia asymmetrica*, *Metridia okhotensis*, *Metridia longa*, *Lucicutia ovaliformis*, *Heterorhabdus tanneri*, and *Pleuromamma scutullata*.

In some embodiments, the luciferase is any one or more of GLuc, NanoLuc (NLuc), MLuc7, HtLuc, LoLuc, PaLuc1, PaLuc2, MpLuc1, McLuc1, MaLuc1, MoLuc1, MoLuc2, MLuc39, PsLuc1, LocLuc1-3, HtLuc2 *Renilla*, TurboLuc16 (TLuc) or homologs or orthologs thereof or mutants or functional derivatives thereof.

In some embodiments, the reporter activity is assayed by exposing the target cells to a luciferase specific substrate. In one embodiment, the luciferase-specific substrate is coelentrazine or a derivative thereof. In another embodiment, the luciferase-specific substrate is imidazopyrazinone substrate (furimazine) or a derivative thereof.

In some embodiments, the CAR is expressed on an immune cell. In one embodiment, the immune cell is a T cell. In another embodiment, the immune cell is a CD4 T cell. In a further embodiment, the immune cell is a CD8 T cell. In an embodiment, the immune cell is a Treg cell. In some embodiments, the immune cell is a naive T cell. In some embodiments, the immune cell is a memory T cell. In some embodiments, the immune cell is central memory T cell. In an embodiment, the immune cell is an effector memory T cell. In an embodiment, immune cell is an NK cell.

In some embodiments, the CAR is expressed on a stem cell. In an embodiment, the CAR is expressed on a hematopoietic stem cell. In an embodiment, the CAR is expressed on an induced pluripotent stem cell.

In some embodiments, the target antigen of the CAR is any one or more of but are not limited to CD19, CD20, CS1/SLAMF7, BCMA, CD123, CD33, MPLLym1, Lym2, CD200R, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD200, CD22, CD221, CD23 (IgE receptor), CD28, CD30 (TNFRSF8), CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, integrin α5β1, integrin αvβ3FLT3, MORAb-009, MS4A1, MUC1, mucin CanAg, N-glycolylneuraminic acid, NPC-1C, PDGF-R α, PDL192, phosphatidylserine, prostatic carcinoma cells, RANKL, RON, ROR1, SCH 900105, SDC1, SLAMF7, (MPL), TAG-72, tenascin C, TGF beta 2, TGF-β, TRAIL-R1, TRAIL-R2, tumor antigen CTAA16.88, VEGF-A, VEGFR-1, VEGFR2, or vimentin.

In an embodiment, the target antigen of CAR is a complex of a HLA molecule with a peptide antigen. In an embodiment, the HLA molecule is HLA-A2.

In an embodiment, the subject has cancer or an immune disorder. In an embodiment, the subject is being assessed for immune therapy. In an embodiment, the immune therapy comprises CAR T cells In some embodiments, the fusion protein further comprises a tag. In exemplary embodiments, the tag is any one or more of chitin binding protein (CBP), glutathione-S-transferase (GST), polyhistidine (His) tag, FLAG tag, HA tag, Myc tag, V5 tag, AcV5 tag, Streptag or a combination thereof.

In some embodiments, the reference value is the reporter activity in any one or more of (i) cells that do not express the CAR; (ii) cells that express the CAR but are treated with fusion protein which is not targeted by the CAR; (iii) cells that are not treated with the substrate for the reporter; or (iv) combinations thereof.

In some embodiments, the reporter is fused to the extracellular domain of an antigen targeted by the chimeric antigen receptor through a covalent bond.

In some embodiments, the reporter is fused to the extracellular domain of an antigen targeted by the chimeric antigen receptor through a non-covalent bond.

In some embodiments, the reporter is fused to the extracellular domain of an antigen targeted by the chimeric antigen receptor through an intermediate molecule.

In some embodiments, a single molecule of the reporter is fused to the extracellular domain of an antigen targeted by the chimeric antigen receptor.

In some embodiments, more than one molecules of the reporter are fused to the extracellular domain of an antigen targeted by the chimeric antigen receptor.

In one embodiment, the assay is performed in vitro. In another embodiment, the assay is performed in vivo.

Also provided herein are kits for practicing the invention.

BRIEF DESCRIPTION OF FIGURES

Exemplary embodiments are illustrated in referenced figures. It is intended that the embodiments and figures disclosed herein are to be considered illustrative rather than restrictive.

FIG. 1A-FIG. 1B depict, in accordance with various embodiments of the invention, that strong binding with 161-GGSG-NLuc-AcV5 was observed on HEL.92.1.7-Gluc-vector cells.

FIG. 7A-FIG. 7B depicts, in accordance with various embodiments of the invention, fluorescence activity of RAJI cells stained with FMC63-GGS-GLuc-×3FLAG and FMC63-GGS-TurboLuc16-×3Flag.

FIG. 8A-FIG. 8B depicts, in accordance with various embodiments of the invention, relative LUC activity of different fusion proteins on the 3 cell lines.

DETAILED DESCRIPTION

Figure 2:
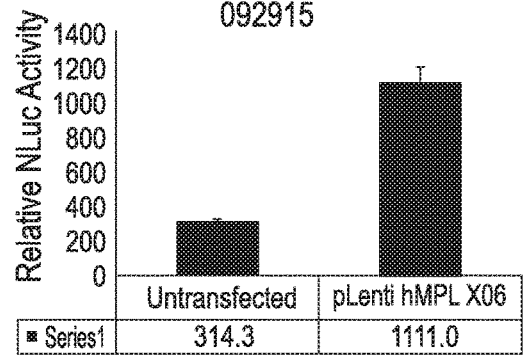
FIG. 2 depicts, in accordance with various embodiments of the invention, increased binding of 161-GGSG-NLuc-AcV5 supernatant to cells that had been transfected with MPL as compared to the untransfected cells.

All references cited herein are incorporated by reference in their entirety as though fully set forth. Unless defined otherwise, technical and scientific terms used herein have the same meaning as commonly understood by one of ordinary skill in the art to which this invention belongs. Allen et al., Remington: The Science and Practice of Pharmacy 22nd ed., Pharmaceutical Press (Sep. 15, 2012); Hornyak et al., Introduction to Nanoscience and Nanotechnology, CRC Press (2008); Singleton and Sainsbury, Dictionary of Microbiology and Molecular Biology 3rd ed., revised ed., J. Wiley & Sons (New York, N.Y. 2006); Smith, March's Advanced Organic Chemistry Reactions, Mechanisms and Structure 7th ed., J. Wiley & Sons (New York, N.Y. 2013); Singleton, Dictionary of DNA and Genome Technology 3rd ed., Wiley-Blackwell (Nov. 28, 2012); and Green and Sambrook, Molecular Cloning: A Laboratory Manual 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, Antibodies A Laboratory Manual 2nd ed., Cold Spring Harbor Press (Cold Spring Harbor N.Y., 2013); Köhler and Milstein, Derivation of specific antibody-producing tissue culture and tumor lines by cell fusion, Eur. J. Immunol. 1976 Jul. 6(7):511-9; Queen and Selick, Humanized immunoglobulins, U.S. Pat. No. 5,585,089 (1996 December); and Riechmann et al., Reshaping human antibodies for therapy, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the term "about" refers to a measurable value such as an amount, a time duration, and the like, and encompasses variations of ±20%, ±10%, ±5%, ±1%, ±0.5% or ±0.1% from the specified value.

As used herein, "amino acid" is meant to include both natural and synthetic amino acids, and both D and L amino acids. "Standard amino acid" means any of the twenty L-amino acids commonly found in naturally occurring peptides. "Nonstandard amino acid" means any amino acid, other than the standard amino acids, regardless of whether it is prepared synthetically or derived from a natural source.

As used herein, "synthetic amino acid" also encompasses chemically modified amino acids, including but not limited to salts, amino acid derivatives (such as amides), and substitutions. Amino acids contained within the peptides disclosed herein, and particularly at the carboxy- or amino-terminus, can be modified by methylation, amidation, acetylation or substitution with other chemical groups which can change the peptide's circulating half-life without adversely affecting their biological activity. Additionally, a disulfide linkage may be present or absent in the peptides disclosed herein.

Herein, "peptide" and "protein" are used interchangeably, and refer to a compound comprised of at least two amino acid residues covalently linked by peptide bonds or modified peptide bonds (e.g., peptide isosteres). No limitation is placed on the maximum number of amino acids which may comprise a protein or peptide. The amino acids comprising the peptides or proteins described herein and in the appended claims are understood to be either D or L amino acids with L amino acids being preferred. The amino acid comprising the peptides or proteins described herein may also be modified either by natural processes, such as post-translational processing, or by chemical modification techniques which are well known in the art. Modifications can occur anywhere in a peptide, including the peptide backbone, the amino acid side-chains and the amino or carboxyl termini. It is understood that the same type of modification may be present in the same or varying degrees at several sites in a given peptide. Also, a given peptide may contain many types of modifications. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure and Molecular Properties, 2nd Ed., T. E. Creighton, W.H. Freeman and Company, New York, 1993 and Wold F, Posttranslational Protein Modifications: Perspectives and Prospects, pgs. 1-12 in Posttranslational Covalent Modification of Proteins, B. C. Johnson, Ed., Academic Press, New York, 1983; Seifter et al., "Analysis for protein modifications and nonprotein cofactors," Meth. Enzymol. (1990) 182: 626-646 and Rattan et al. (1992), "Protein Synthesis: Posttranslational Modifications and Aging," Ann NY Acad Sci 663: 48-62.

"Polynucleotide" as used herein includes but is not limited to DNA, RNA, cDNA (complementary DNA), mRNA (messenger RNA), rRNA (ribosomal RNA), shRNA (small hairpin RNA), snRNA (small nuclear RNA), snoRNA (short nucleolar RNA), miRNA (microRNA), genomic DNA, synthetic DNA, synthetic RNA, and/or tRNA.

As used herein, the term "polypeptide" encompasses amino acid chains of any length, including full length proteins (i.e., antigens), wherein the amino acid residues are linked by covalent peptide bonds.

It is to be inferred without explicit recitation and unless otherwise intended, that when the present disclosure relates to a polypeptide, protein, polynucleotide, antibody or fragment thereof, an equivalent or a biologically equivalent of such is intended within the scope of this disclosure. As used herein, the term "biological equivalent thereof" is intended to be synonymous with "equivalent thereof" when referring to a reference protein, antibody or fragment thereof, polypeptide or nucleic acid, intends those having minimal homology while still maintaining desired structure or functionality. Unless specifically recited herein, it is contemplated that any of the above also includes equivalents thereof. For example, an equivalent intends at least about 70% homology or identity, or at least 80% homology or identity and alternatively, or at least about 85%, or alternatively at least about 90%, or alternatively at least about 95%, or alternatively at least 98% percent homology or identity and exhibits substantially equivalent biological activity to the reference protein, polypeptide, antibody or fragment thereof or nucleic acid. Alternatively, when referring to polynucleotides, an equivalent thereof is a polynucleotide that hybridizes under stringent conditions to the reference polynucleotide or its complement. Alternatively, when referring to polypeptides or proteins, an equivalent thereof is a expressed polypeptide or protein from a polynucleotide that hybridizes under stringent conditions to the polynucleotide or its complement that encodes the reference polypeptide or protein.

A polypeptide "variant," as used herein, is a polypeptide that differs from the recited polypeptide only in conservative substitutions and/or modifications, such that the therapeutic, antigenic and/or immunogenic properties of the polypeptide are retained. Polypeptide variants preferably exhibit at least about 70%, more preferably at least about 90% and most preferably at least about 95% homology to the identified polypeptides. For polypeptides with immunoreactive properties, variants can, alternatively, be identified by modifying the amino acid sequence of one of the above polypeptides, and evaluating the immunoreactivity of the modified polypeptide. Such modified sequences can be prepared and tested using, for example, the representative procedures described herein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, fly asp, gln, asn, set, thr; (2) cys, ser, fyr, thr; (3) val, ile, leu, met, ala, phe; (4) lys, arg, his; and (5) phe, tyr, trp, his.

Variants can also, or alternatively, contain other modifications, including the deletion or addition of amino acids that have minimal influence on the antigenic properties, secondary structure and hydropathic nature of the polypeptide. For example, a polypeptide can be conjugated to a signal (or leader) sequence at the N-terminal end of the protein which co-translationally or post-translationally directs transfer of the protein. The polypeptide can also be conjugated to a linker or other sequence for ease of synthesis, purification or identification of the polypeptide (e.g., poly-His), or to enhance binding of the polypeptide to a solid support. For example, a polypeptide can be conjugated to an immunoglobulin Fc region.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

The term "isolated" as used herein refers to molecules or biologicals or cellular materials being substantially free from other materials. In one aspect, the term "isolated" refers to nucleic acid, such as DNA or RNA, or protein or polypeptide (e.g., an antibody or derivative thereof), or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. The term "isolated" is also used herein to refer to cells or tissues that are isolated from other cells or tissues and is meant to encompass both, cultured and engineered cells or tissues.

"Sample" or "biological sample" as used herein refers to tissues or body fluids removed from a mammal, preferably human, and which contain $CD8^+$ T cells. Samples can be blood and/or blood fractions, including peripheral blood sample like peripheral blood mononuclear cell (PBMC) sample or blood, bone marrow cell sample. A sample can also include any specific tissues/organ sample of interest, including, without limitation, lymphoid, thymus, pancreas, eye, heart, liver, nerves, intestine, skin, muscle, cartilage, ligament, synovial fluid, and/or joints. The samples can be taken from any individual including a healthy individual or an individual having cells, tissues, and/or an organ afflicted with the unwanted immune response. For example, a sample can be taken from an individual having an allergy, a graft vs. host disease, a cell or organ transplant, or an autoimmune disease or disorder. Methods for obtaining such samples are well known to a person of ordinary skill in the art of immunology and medicine. They include drawing and processing blood and blood components using routine procedures, or obtaining biopsies from the bone marrow or other tissue or organ using standard medical techniques.

"Chimeric antigen receptor" or "CAR" or "CARs" as used herein refers to engineered receptors, which graft an antigen specificity onto cells (for example T cells such as naïve T cells, central memory T cells, effector memory T cells or combination thereof). CARs are also known as artificial T-cell receptors, chimeric T-cell receptors or chimeric immunoreceptors. In various embodiments, CARs are recombinant polypeptides comprising an antigen-specific domain (ASD), a hinge region (HR), a transmembrane domain (TMD), co-stimulatory domain (CSD) and an intracellular signaling domain (ISD).

"Endogenous T cell receptor" or "TCR" as used herein refers to a T cell receptors that is expressed in T cells endogenously.

"Exogenous T cell receptor" or "transgenic T cell receptor" or "transgenic TCR" as used herein refers to T cell receptors that are expressed in T cells from outside.

As used herein, the term "antibody" refers to an intact immunoglobulin or to a monoclonal or polyclonal antigen-binding fragment with the Fc (crystallizable fragment) region or FcRn binding fragment of the Fc region, referred to herein as the "Fc fragment" or "Fc domain". Antigen-binding fragments may be produced by recombinant DNA techniques or by enzymatic or chemical cleavage of intact antibodies. Antigen-binding fragments include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The Fc domain includes portions of two heavy chains contributing to two or three classes of the antibody. The Fc domain may be produced by recombinant DNA techniques or by enzymatic (e.g. papain cleavage) or via chemical cleavage of intact antibodies.

The term "antibody fragment," as used herein, refer to a protein fragment that comprises only a portion of an intact antibody, generally including an antigen binding site of the intact antibody and thus retaining the ability to bind antigen. Examples of antibody fragments encompassed by the present definition include: (i) the Fab fragment, having VL (or vL), CL, VH (or vH) and CH1 domains; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment (Ward et al., Nature 341, 544-546 (1989)) which consists of a VH domain; (vii) isolated CDR regions; (viii) F(ab')2 fragments, a bivalent fragment including two Fab' fragments linked by a disulphide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain (VH) connected to a light chain variable domain (VL) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments (VH-CH1-VH-CH1) which, together with complementary light chain polypeptides, form a pair of antigen binding regions (Zapata et al. Protein Eng. 8(10):1057-1062 (1995); and U.S. Pat. No. 5,641,870).

"Single chain variable fragment", "single-chain antibody variable fragments" or "scFv" antibodies as used herein refer to forms of antibodies comprising the variable regions of only the heavy ($V_H$) and light ($V_L$) chains, connected by a linker peptide. The scFvs are capable of being expressed as a single chain polypeptide. The scFvs retain the specificity of the intact antibody from which it is derived. The light and heavy chains may be in any order, for example, $V_H$-linker-$V_L$ or $V_L$-linker-$V_H$, so long as the specificity of the scFv to the target antigen is retained.

"Complementarity determining region" (CDR) as used herein refers to the amino acid sequences within the variable regions of antibodies which regions confer specificity and binding affinity. In general, there are three CDRs in each of the light chain variable regions (LCDR1, LCDR2 and LCDR3) and three CDRs in each of the heavy chain variable regions (HCD1, HCDr2 and HCDR3). The boundaries of the CDRs may be determined using methods well known in the art including the "Kabat" numbering scheme and/or "Chothia" number scheme (Kabat et al. Sequences of Proteins of Immunological Interest, $5^{th}$ Ed. Public Health Services, National Institutes of Health, Bethesda, Md.; Al-Lazikani et al., (1997) JMB 273,927-948).

As used herein, the term "specific binding" means the contact between an antibody and an antigen with a binding affinity of at least $10^{-6}$M. In certain aspects, antibodies bind with affinities of at least about $10^{-7}$M, and preferably $10^{-8}$M, $10^{-9}$M, $10^{-10}$ M, $10^{-11}$ M, or $10^{-12}$ M.

"Cancer" and "cancerous" refer to or describe the physiological condition in mammals that is typically characterized by unregulated cell growth. The term "cancer" is meant to include all types of cancerous growths or oncogenic processes, metastatic tissues or malignantly transformed cells, tissues, or organs, irrespective of histopathologic type or stage of invasiveness. Examples of solid tumors include malignancies, e.g., sarcomas, adenocarcinomas, and carcinomas, of the various organ systems, such as those affecting liver, lung, breast, lymphoid, gastrointestinal (e.g., colon), genitourinary tract (e.g., renal, urothelial cells), prostate and pharynx. Adenocarcinomas include malignancies such as most colon cancers, rectal cancer, renal-cell carcinoma, liver cancer, non-small cell carcinoma of the lung, cancer of the small intestine and cancer of the esophagus. In one embodiment, the cancer is a melanoma, e.g., an advanced stage melanoma. Metastatic lesions of the aforementioned cancers can also be treated or prevented using the methods and compositions of the invention. Examples of other cancers that can be treated include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin Disease, non-Hodgkin lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. Treatment of metastatic cancers, e.g., metastatic cancers that express PD-L1 (Iwai et al. (2005) Int. Immunol. 17:133-144) can be effected using the antibody molecules described herein.

"Immunogenic," as used herein, refers to the ability to elicit an immune response (e.g., cellular) in a patient, such as a human, and/or in a biological sample.

"Luciferase" or "Luciferases" as used herein refer class of oxidative enzymes that produce bioluminescence. The non-secretory form of luciferases for use in the compositions and methods described herein lack the N-terminal secretory sequence but produce bioluminescence. In exemplary embodiments, the luciferase is obtained from copepods, deep sea shrimp or homologs or orthologs thereof or mutants or derivatives thereof. In some embodiments, the copepods are any one or more of *Gaussia princeps, Pleuromamma abdominalis, Metridia pacifica, Metridia curticauda, Metridia asymmetrica, Metridia okhotensis, Metridia longa, Lucicutia ovaliformis, Heterorhabdus tanneri,* and *Pleuromamma scutullata.* In exemplary embodiments, the luciferases are any one or more of GLuc, NanoLuc (NLuc), MLuc7, HtLuc, LoLuc, PaLuc1, PaLuc2, MpLuc1, McLuc1, MaLuc1, MoLuc1, MoLuc2, MLuc39, PsLuc1, LocLuc1-3, HtLuc2 *Renilla,* TurboLuc16 (TLuc) or homologs or orthologs thereof or mutants or functional derivatives thereof. In various embodiments, mutants or functional derivatives of the luciferases retain at least 100%, 90%, 80%, 70%, 60% or 50% of the bioluminescence activity from which the mutant or function derivative is derived. As described in Takenaka et al (Evolution of bioluminescence in marine planktonic copepods. 2012 *Mol Biol Evol* 29(6): 1669-1681), the copepod luciferases comprise two domains and each domain includes conserved sequences across the various luciferases. In some embodiments, any luciferase comprising the consensus sequence C-x(3)-C-L-x(2)-L-x(4)-C-x(8)-P-x-R-C(SEQ ID NO: 2437) in each of domains 1 and 2 as described by Takenaka et al., may be used in the compositions and methods described herein. In some embodiments, any luciferase comprising the consensus sequence K-x(7)-E-M-E-A-N-A-x(3)-G-C-x-R-x-C-L-I-x-L-S-x-I—K-C-T-x-K-M-x(4)-P-G-R—C-H-X-Y-x(8)-G (SEQ ID NO: 2438) in domain 1 as described by Takenaka et al. and consensus sequences I-x-G-x(6)-M-x-Q-F-x(2)-Q-V-x(2)-C-x(2)-C-x(3)-C-L-K-G-L-A-N-x(2)-C-S-x(2)-L-x(3)-L-P-x-R-C-x(2)-F-x(3)-I-x (8)-G (SEQ ID NO: 2439) in domain 2 as described by Takenaka et al., may be used in the compositions and methods described herein. In various embodiments, the functional fragments or mutants of luciferases for use with the compositions or methods described herein comprise the consensus sequence C-x(3)-C-L-x(2)-L-x(4)-C-x(8)-P-x-R-C (SEQ ID NO: 2437) in domain 1 as described by Takenaka et al. In various embodiments, the functional fragments or mutants of luciferases for use with the compositions or methods described herein comprise the consensus sequence C-x(3)-C-L-x(2)-L-x(4)-C-x(8)-P-x-R-C (SEQ ID NO: 2437) in domain 2 as described by Takenaka et al. In various embodiments, the functional fragments or mutants of luciferases for use with the compositions or methods described herein comprise the consensus sequence C-x(3)-C-L-x(2)-L-x(4)-C-x(8)-P-x-R-C (SEQ ID NO: 2437) in domain 1 and in domain 2, as described by Takenaka et al.

"Label" as used herein refers to as used herein refers to any atom or molecule that can be used to provide a detectable (preferably quantifiable) signal, and that can be attached to a nucleic acid or protein. Labels may provide signals detectable by fluorescence, radioactivity, colorimetry, gravimetry, X-ray diffraction or absorption, magnetism, enzymatic activity, and the like. A label may be a charged moiety (positive or negative charge) or alternatively, may be charge neutral. Labels can include or consist of nucleic acid or protein sequence, so long as the sequence comprising the label is detectable.

There are several methods currently in use for detection of a particular antigen, including flow cytometry, ELISA and Western blotting. However, these methods require expensive equipment (such as flow cytometry), suffer from poor sensitivity and specificity (e.g. ELISA and Western blotting) or are time consuming. The poor sensitivity of the current methods of antigen detection is particularly significant in light of development of new targeted therapies using antibody drug conjugates and chimeric antigen receptors. These new therapies are extremely potent at killing cells expressing their target antigen even at very low levels, which are below the detection limits of current methods. For example, Brentuximab vedotin (Adcetris), an antibody drug conjugate, that targets CD30 antigen, has shown impressive clinical activity in diffuse large cell lymphoma in several clinical trials. However, the response to Brentuximab vedotin (Adcetris) does not correlate with CD30 positivity, as determined by conventional immunohistochemistry, and patients with lymphomas that are CD30-ve frequently respond to this agent. This has led to the hypothesis that Brentuximab vedotin (Adcetris) requires very low level expression of CD30 for its activity and its efficacy in CD30-ve diffuse large cell lymphoma is, in part, due to low level expression of CD30 in these samples, which is below the detection of conventional methods.

Chimeric antigen receptor based T cell therapy represents another example where detection of low level expression of an antigen in a patient sample is critically important to predict response to therapy. It is believed that CAR-T cells can kill a target cell expressing as few as 100 molecules of their target antigen. Consistent with this, CAR-T cells targeting CD19 antigen have shown impressive clinical activity in multiple myeloma (Hajek, R et al., Br J Haematol 163:551-564, 2013), a disease which is believed to be CD19-ve based on conventional detection methods. Thus, availability of highly sensitive and specific method for detection of CD30, CD19 and other antigens would be of great benefit in determining the patients who are likely to respond to targeted therapies as well as to predict toxicity to normal tissues.

A frequent challenge in the field of CAR-T cell therapy is the lack of a fast, economical, sensitive and robust assay for detection of chimeric antigen receptors on the surface of T cells. A sensitive, specific, economical assay for the detection of CAR would be of great benefit as a quality-control tool during the manufacturing of CAR-T cells and to monitor the persistence of CAR-T cells in the body after infusion.

The current method also has advantage over molecular assay, such as PCR, that rely on mRNA measurement for detection of low level antigens. These molecular tests, although quite sensitive, measure mRNA levels, which may or may not correlate with the level of expression of the protein due to alternative splicing of mRNA or protein degradation. In contrast, the present invention relates to the measurement of low levels of protein antigens, which are the real target of CAR-T cells and therapeutic antibodies. Additionally, the antigen binding fragment (e.g. scFv or the CDRs contained therein) used for the detection of the target antigen in the current invention could be derived from or identical to the antigen binding fragment of a therapeutic antibody or CAR-T cells and therefore is likely to have similar or identical non-specific binding profile. This has obvious advantage in predicting the off-target side-effects of CAR-T cells and therapeutic antibodies due to their even low-level non-specific binding and cross-reactivity with other protein antigens. In addition to clinical use, a highly sensitive and specific method for antigen detection, which is inexpensive, quick and does not require special equipment, would also have utility for research applications.

The inventor has taken advantage of the extremely high brightness, sensitivity, specificity, stability and small size of luciferases from the copepods (e.g. GLuc, MLuc7, Turbo-Luc16 etc.) and deep sea shrimp (e.g. NLuc) to develop a sensitive, specific, cost-effective and rapid assay for detection of an antigen. The assay is extremely useful for detection of CAR and for detection of low level antigens on the surface of cells.

Compositions

Provided herein are compositions comprising fusion proteins for detecting antigens in a sample obtained from a subject. In various embodiments, the fusion protein comprises a first polypeptide chain comprising an antigen recognition domain joined to a second polypeptide chain comprising a reporter protein. In some embodiments, the first and second polypeptide chains are linked via a linker (Table 5).

In one embodiment, the antigen recognition domain comprises a single chain antibody fragments (scFv) or the CDRs contained therein. In some embodiments, the antigen recognition domain comprises more than one single chain antibody, wherein each copy of the single chain antibody recognizes the same epitope on the target antigen. In another embodiment, the antigen recognition domain comprises more than one single chain antibody, wherein each single chain antibody recognizes a different epitope on the same target antigen. Examples of single chain antibodies are described in Table 14. Provided herein are compositions comprising polynucleotides encoding, polypeptides encoded by and vectors encoding, single chain antibodies as described in Table 14.

In one embodiment, the antigen recognition domain comprises a VL fragment (Table 4). In some embodiments, the antigen recognition domain comprises more than one VL fragment, wherein each copy of the VL fragment recognizes the same epitope on the target antigen. In another embodiment, the antigen recognition domain comprises more than one VL fragment, wherein each VL fragment recognizes a different epitope on the same target antigen. Examples of VL fragments are described in Table 4. Provided herein are compositions comprising polynucleotides encoding, polypeptides encoded by and vectors encoding, VL fragments as described in Table 4.

In one embodiment, the antigen recognition domain comprises a VH fragment (Table 6). In some embodiments, the antigen recognition domain comprises more than one VH fragment, wherein each copy of the VH fragment recognizes the same epitope on the target antigen. In another embodiment, the antigen recognition domain comprises more than one VH fragment, wherein each VH fragment recognizes a different epitope on the same target antigen. Examples of VH fragments are described in Table 6. Provided herein are compositions comprising polynucleotides encoding, polypeptides encoded by and vectors encoding, VH fragments as described in Table 6.

In one embodiment, the antigen recognition domain comprises a VHH domain (nanobodies) (Table 7). In some embodiments, the antigen recognition domain comprises more than one VHH domain, wherein each copy of the VHH domain recognizes the same epitope on the target antigen. In another embodiment, the antigen recognition domain comprises more than one VHH domain, wherein each VHH domain recognizes a different epitope on the same target antigen. Examples of VHH domains are described in Table 7. Provided herein are compositions comprising polynucleotides encoding, polypeptides encoded by and vectors encoding, VHH domains as described in Table 7.

In one embodiment, the antigen recognition domain comprises a non-immunoglobulin antigen binding domain (affibody) (Table 8). In some embodiments, the antigen recognition domain comprises more than one affibody, wherein each copy of the affibody recognizes the same epitope on the target antigen. In another embodiment, the antigen recognition domain comprises more than one affibody, wherein each affibody recognizes a different epitope on the same target antigen. Examples of affibodies are described in Table 8. Provided herein are compositions comprising polynucleotides encoding, polypeptides encoded by and vectors encoding, affibodies as described in Table 8.

In one embodiment, the antigen recognition domain comprises a darpin (Table 8). In some embodiments, the antigen recognition domain comprises more than one darpin, wherein each copy of the darpin recognizes the same epitope on the target antigen. In another embodiment, the antigen recognition domain comprises more than one darpin, wherein each darpin recognizes a different epitope on the same target antigen. Examples of darpins are described in Table 8. Provided herein are compositions comprising polynucleotides encoding, polypeptides encoded by and vectors encoding, darpins as described in Table 8.

In one embodiment, the antigen recognition domain comprises an extracellular domain of a receptor (Table 9). In some embodiments, the antigen recognition domain comprises more than one extracellular domain of a receptor, wherein each extracellular domain of a receptor recognizes the same epitope on the target antigen. In another embodiment, the antigen recognition domain comprises more than one extracellular domain of a receptor, wherein each extracellular domain of a receptor recognizes a different epitope on the same target antigen. Examples of an extracellular domain of a receptor are described in Table 9. Provided herein are compositions comprising polynucleotides encoding, polypeptides encoded by and vectors encoding, extracellular domains of a receptor as described in Table 9.

In one embodiment, the antigen recognition domain comprises a ligand (Table 10). In some embodiments, the antigen recognition domain comprises more than ligand, wherein the ligand recognizes the same epitope on the target antigen. In another embodiment, the antigen recognition domain comprises more than one ligand, wherein each ligand recognizes a different epitope on the same target antigen. Examples of ligands are described in Table 10. Provided herein are compositions comprising polynucleotides encoding, polypeptides encoded by and vectors encoding, ligands as described in Table 10.

In various embodiments, the reporter protein component of the composition comprising a fusion protein is a non-secretory form of a luciferase. In various embodiments, the non-secretory form of luciferase is obtained from copepods, deep sea shrimp or homologs or orthologs thereof or mutants or derivatives thereof.

In exemplary embodiments, the copepods are selected from the group consisting of any one or more of *Gaussia princeps, Pleuromamma abdominalis, Metridia pacifica, Metridia curticauda, Metridia asymmetrica, Metridia okhotensis, Metridia longa, Lucicutia ovaliformis, Heterorhabdus tanneri*, and *Pleuromamma scutullata*.

In exemplary embodiments, the reporter luciferase is any one or more of GLuc, NanoLuc (NLuc), MLuc7, HtLuc, LoLuc, PaLuc1, PaLuc2, MpLuc1, McLuc1, MaLuc1, MoLuc1, MoLuc2, MLuc39, PsLuc1, LocLuc1-3, HtLuc2 *Renilla*, TurboLuc16 (TLuc) or homologs or orthologs thereof or mutants or derivatives thereof.

In one embodiment, the reporter luciferase is GLuc (*Gaussia princeps* Luc) and comprises, consists of or consists essentially of the sequence set forth in SEQ ID NO: 813 or SEQ ID NO: 2029 (Table 11) or a sequence with 70-99% homology to sequence set forth in SEQ ID NO: 813 or SEQ ID NO: 2029 (Table 11).

In another embodiment, the reporter luciferase is NLuc (NanoLuc) and comprises, consists of or consists essentially of the sequence set forth in SEQ ID NO: 814 or SEQ ID NO: 2030 (Table 11) or a sequence with 70-99% homology to sequence set forth in SEQ ID NO: 814 or SEQ ID NO: 2030 (Table 11).

In a further embodiment, the reporter luciferase is TLuc (TurboLuc16) and comprises, consists of or consists essentially of the sequence set forth in SEQ ID NO: 815 or SEQ ID NO: 2031 (Table 11) or a sequence with 70-99% homology to sequence set forth in SEQ ID NO: 815 or SEQ ID NO: 2031 (Table 11).

In a further embodiment, the reporter luciferase is MLuc7-(*Metrida longa*) Luc M43L/M110L variant and comprises, consists of or consists essentially of the sequence set forth in SEQ ID NO: 816 or SEQ ID NO: 2032 (Table 11) or a sequence with 70-99% homology to sequence set forth in SEQ ID NO: 816 or SEQ ID NO: 2032 (Table 11).

In another embodiment, the reporter luciferase is LoLuc (*Lucicutia ovaliformis* Luc) and comprises, consists of or consists essentially of the sequence set forth in SEQ ID NO: 817 or SEQ ID NO: 2033 (Table 11) or a sequence with 70-99% homology to sequence set forth in SEQ ID NO: 817 or SEQ ID NO: 2033 (Table 11).

In another embodiment, the reporter luciferase is HtLuc (*Heterorhabdus. tanneri* Luc) and comprises, consists of or consists essentially of the sequence set forth in SEQ ID NO: 818 or SEQ ID NO: 2034 (Table 11 or a sequence with 70-99% homology to sequence set forth in SEQ ID NO: 818 or SEQ ID NO: 2034 (Table 11)).

In another embodiment, the reporter luciferase is PaLuc1 (*Pleuromamma abdominalis* Luc) and comprises, consists of or consists essentially of the sequence set forth in SEQ ID NO: 819, or SEQ ID NO: 2035 (Table 11) or a sequence with 70-99% homology to sequence set forth in SEQ ID NO: 819 or SEQ ID NO: 2035 (Table 11).

In another embodiment, the reporter luciferase is PaLuc2 (*Pleuromamma abdominalis* Luc2) and comprises, consists of or consists essentially of the sequence set forth in SEQ ID NO: 820, or SEQ ID NO: 2036 (Table 11) or a sequence with 70-99% homology to sequence set forth in SEQ ID NO: 820 or SEQ ID NO: 2036 (Table 11).

In another embodiment, the reporter luciferase is MpLuc1 (*Metridia pacifica* Luc1) and comprises, consists of or consists essentially of the sequence set forth in SEQ ID NO: 821, or SEQ ID NO: 2037 (Table 11) or a sequence with 70-99% homology to sequence set forth in SEQ ID NO: 821 or SEQ ID NO: 2037 (Table 11).

In another embodiment, the reporter luciferase is McLuc1 (*Metridia curticauda* Luc1) and comprises, consists of or consists essentially of the sequence set forth in SEQ ID NO: 822, or SEQ ID NO: 2038 (Table 11) or a sequence with 70-99% homology to sequence set forth in SEQ ID NO: 822 or SEQ ID NO: 2038 (Table 11).

In another embodiment, the reporter luciferase is MaLuc1 (*Metridia asymmetrica* Luc1) and comprises, consists of or consists essentially of the sequence set forth in SEQ ID NO: 823 or SEQ ID NO: 2039 (Table 11) or a sequence with 70-99% homology to sequence set forth in SEQ ID NO: 823 or SEQ ID NO: 2039 (Table 11).

In another embodiment, the reporter luciferase is MoLuc1 (*Metridia okhotensis* Luc1) and comprises, consists of or consists essentially of the sequence set forth in SEQ ID NO: 824 or SEQ ID NO: 2040 (Table 11) or a sequence with 70-99% homology to sequence set forth in SEQ ID NO: 824 or SEQ ID NO: 2040 (Table 11).

In another embodiment, the reporter luciferase is MoLuc2 (*Metridia okhotensis* Luc2) and comprises, consists of or consists essentially of the sequence set forth in SEQ ID NO: 825, or 2041 (Table 11) or a sequence with 70-99% homology to sequence set forth in SEQ ID NO: 825 or 2041 (Table 11).

In another embodiment, the reporter luciferase is MLuc39 (*Metridia longa* Luc39) and comprises, consists of or consists essentially of the sequence set forth in SEQ ID NO: 826 or 2042 (Table 11).

In another embodiment, the reporter luciferase is PsLuc1 (*Pleuromamma scutullata* Luc1) and comprises, consists of or consists essentially of the sequence set forth in SEQ ID NO: 827 or 2043 (Table 11).

In another embodiment, the reporter luciferase is LoLuc1-3 (*Lucicutia ovaliformis* Luc1-3) and comprises, consists of or consists essentially of the sequence set forth in SEQ ID NO: 828 or 2044 (Table 11).

In another embodiment, the reporter luciferase is HtLuc2 (*Heterorhabdus tanneri* Luc2) and comprises, consists of or consists essentially of the sequence set forth in SEQ ID NO: 829 or 2045 (Table 11).

In another embodiment, the reporter luciferase is *Renilla* Luc and comprises, consists of or consists essentially of the sequence set forth in SEQ ID NO: 830 or 2046 (Table 11).

In some embodiments, the luciferases are fused to antigen recognition domains that bind to a target antigen. In one embodiment, the luciferases are fused to antigen recognition domains that bind to extracellular antigens. In one embodiment, the luciferases are fused to antigen recognition domains that bind to intracellular antigens. In one embodiment, the luciferases are fused to antigen recognition domains that bind to antigens that are expressed on the surface of cells. In some embodiments, the luciferases are fused to antigen recognition domains that bind to antigens that are naturally expressed on the surface of cells. Exemplary antigens that are naturally expressed on the surface of cells include CD19, CD20, CD33 and an endogenous TCR. In some embodiments, the luciferases are fused to antigen recognition domains that bind to antigens that are expressed on the surface of cells in association with MEW complex. In some embodiments, the luciferases are fused to antigen recognition domains that bind to antigens that are expressed on the surface of cells in association with MEW class I complex. In some embodiments, the luciferases are fused to antigen recognition domains that bind to antigens that are expressed on the surface of cells in association with MHC class II complex. In some embodiments, the luciferases are fused to antigen recognition domains that bind to antigens that are not naturally expressed on the surface of cells. In some embodiments, the luciferases are fused to antigen recognition domains that bind to antigens that are expressed on the surface of cells as a result of an intervention, such as genetic modification. Exemplary antigens that are expressed on the surface of cells as a result of an intervention include artificial or synthetic receptors, such as a chimeric antigen receptor, a transgenic T cell receptor, a synthetic immune receptor or a T-body.

In some embodiments, the luciferases are fused to antigen recognition domains that bind to any one or more of CD19, CD22, CD23, MPL, CD123, CD32, CD138, CD200R, CD276, CD324, CD30, CD171, CS-1, CLL-1 (CLECL1), CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, IL11Ra, Mesothelin, PSCA, VEGFR2, Lewis Y, CD24, PDGFR-beta, PRSS21, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, TSHR, TCR-beta1 constant chain, TCR beta2 constant chain, TCR gamma-delta, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, legumain, HPV E6, E7, HTLV1-Tax, KSHV K8.1 protein, EBV gp350, HIV1-envelop glycoprotein gp120, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, DLL3, TROP2, PTK7, GCC, AFP, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, FITC, Leutenizing hormone receptor (LHR), Follicle stimulating hormone receptor (FSHR), Chorionic Gonadotropin Hormone receptor (CGHR), CCR4, GD3, SLAMF6, SLAMF4, FITC, Leutenizing hormone receptor (LHR), Follicle stimulating hormone receptor (FSHR), Chorionic Gonadotropin Hormone receptor (CGHR), CCR4, GD3, SLAMF6, SLAMF4, or combinations thereof.

In some embodiments, the luciferases are fused to antigen recognition domains that bind to an endogenous T cell receptor (TCR), an exogenous (or transgenic) TCR, or a synthetic (or chimeric) T cell receptors (cTCR) targeting any antigen including but not limited to one or more of CD19, CD22, CD23, MPL, CD99, CD123, CD32, CD138, CD200R, CD276, CD324, CD30, CD70, CD179b CD171, CS-1, CLL-1 (CLECL1), CD33, EGFRvIII, GD2, GD3, BCMA, Tn Ag, FcRH5, PSMA, ROR1, FLT3, FAP, TAG72, CD38, CD44v6, CEA, EPCAM, B7H3, KIT, IL-13Ra2, IL11Ra, Mesothelin, PSCA, VEGFR2, Lewis Y, CD24, PDGFR-beta, PRSS21, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLea, GM3, TGS5, HMWMAA, o-acetyl-GD2, Folate receptor beta, TEM1/CD248, TEM7R, CLDN6, TSHR, TCR-beta1 cosntant chain, TCR beta2 constant chain, TCR gamma-delta, GPRC5D, CXORF61, CD97, CD179a, ALK, Polysialic acid, PLAC1, GloboH, NY-BR-1, UPK2, HAVCR1, ADRB3, PANX3, GPR20, LY6K, 0101E2, TARP, WT1, NY-ESO-1, LAGE-1a, legumain, HPV E6, E7, HTLV1-Tax, KSHV K8.1 protein, EBV gp350, HIV1-envelop glycoprotein gp120, MAGE-A1, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, DLL3, TROP2, PTK7, GCC, AFP, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, FITC, Leutenizing hormone receptor (LHR), Follicle stimulating hormone receptor (FSHR), Chorionic Gonadotropin Hormone receptor (CGHR), CCR4, GD3, SLAMF6, SLAMF4, FITC, Leutenizing hormone receptor (LHR), Follicle stimulating hormone receptor (FSHR), Chorionic Gonadotropin Hormone receptor (CGHR), CCR4, GD3, SLAMF6, SLAMF4, or combinations thereof.

In some embodiments, the luciferases are fused to antigen recognition domains that are scFv fragments (or the CDRs contained therein) specific to the antigen. In some embodiments, the luciferases are fused to antigen recognition domains that are VL fragments (or the CDRs contained therein) specific to the antigen. In some embodiments, the luciferases are fused to antigen recognition domains that are VH fragments (or the CDRs contained therein) specific to the antigen. In some embodiments, the luciferases are fused to antigen recognition domains that are camelid VHH fragments (or the CDRs contained therein) specific to the antigen. In some embodiments, the antigen recognition domains are non-immunoglobulin binding scaffolds specific to the antigen. In some embodiments, the antigen recognition domains are receptor extracellular domains (ECD) that bind to different ligands or are recognized by the antigen specific domains of various natural or synthetic receptors, such as CARs or T cell receptors (TCRs) or artificial TCRs or synthetic TCRs. In some embodiments, the antigen recognition domains are ligands that bind to different receptor or are recognized by the antigen specific domains of various natural or synthetic receptors, such as CARs or T cell receptors (TCRs) or artificial TCRs or synthetic TCRs.

In an embodiment, the luciferase is fused to an antigen recognition domain comprised by a protein that binds to an artificial receptor such as a CAR, a TCR or a chimeric TCR. In some embodiments, the luciferase is fused to an antigen recognition domain comprised by a protein that binds to the antigen recognition domain of a CAR. In some embodiments, the protein that binds to a CAR is a scFv fragment. An exemplary protein containing an antigen recognition domain derived from an scFv fragment that binds to a CAR FMC63-(vL-vH)-Myc-BBz-T2A-Pac(SEQ ID NO: 1208) is CD8SP-FMC136-20-(vL-vH)-GGSG-Turboluc16-4×FLAG-×2STREP-8×His-T2A-PAC. The nucleic acid and protein sequences of this protein are represented by SEQ ID NOs: 1167 and 2367. This protein contains a scFv derived from an anti-idiotype antibody FMC136-20 that recognizes the FMC63 scFv fragment that constitutes the antigen recognition domain of the corresponding CAR FMC63-(vL-vH)-Myc-BBz-T2A-Pac(SEQ ID NO: 1208). In an alternate embodiment, the luciferase is fused to an antigen recognition domain comprised by an antibody or an antibody fragment directed against the variable region of an antibody or an antibody fragment of another species. Such a luciferase fusion protein can be used to detect a CAR containing an antigen recognition domain comprised by the variable region of the said antibody. In an exemplary embodiment, a scFv fragment derived from a mouse antibody directed against the variable region of human IgG can be fused to NLuc and the resulting fusion protein can be used to detect a CAR whose antigen recognition domain is comprised of a scFv fragment derived from a human or a humanized antibody. In an alternate embodiment, the luciferase is fused to an antigen recognition domain comprised by an antibody or an antibody fragment (e.g., scFv) directed against an epitope tag, such as a Myc Tag, that is present on a CAR. In an alternate embodiment, the luciferase is fused to an antigen recognition domain comprised by an antibody or an antibody fragment (e.g., scFv) directed against a label, such as FITC. In some embodiments, the luciferase is fused to an antigen recognition domain comprised by Protein L (SEQ ID NOS. 2431-2434) that is known to bind to the kappa light chain of a CAR. Exemplary nucleotide sequences encoding luciferase and Protein L fusion proteins are CD8SP-Protein-L-GGSG-NLuc-4×FLAG-×2STREP-8×His-T2A-PAC (112316-Q02)[ SEQ ID NO:1206] and CD8SP-Protein-L-2-GGSG-NLuc-4×FLAG-×2STREP-8×His-T2A-PAC (101916-P03)[ SEQ ID NO:1207]. The corresponding protein sequences are represented by SEQ ID NO: 2406 and 2407, respectively. In some embodiments, the luciferase is fused to an antigen recognition domain comprised by the extracellular domain of a protein which is the target of a CAR. In an exemplary embodiment, the luciferase NLuc is fused to the extracellular domain of MPL (SEQ ID NO: 1749) and the resulting MPL-ECD-GGSG-Nluc-AcV5 (082214-Z01)[ SEQ ID NO:1169] fusion protein is used to detect a CAR 161-(vL-vH)-Myc-BBz-T2A-Pac (SEQ ID NO: 1209) that targets MPL. In one embodiment, one or more luciferases are fused to antigen recognition domains that target specific antigens.

In exemplary embodiments, the antigen recognition domains that target specific antigens are scFv fragments (or the CDRs contained within) and comprise any one or more of the antigen specific scFv sequences described in Table 14 or sequences with 70-99% identity to antigen specific scFv sequences in Table 14 or sequences with 70-99% identity in the six complementarity determining regions (CDRs) to the antigen specific scFv sequences in Table 14 or sequences that bind to the same epitopes on the target antigens as the antigen specific scFv sequences in Table 14. In some embodiments, provided herein are compositions comprising polynucleotides encoding, polypeptides encoded by and vectors encoding, scFv-GGS-Luc constructs that target specific antigens and comprise the sequences described in Table 15.

In exemplary embodiments, one or more luciferases are fused to antigen recognition domains that are receptor extracellular domains (ECD) and comprise any one or more of the antigen-specific ECD sequences described in Table 9 or sequences with 70-99% identity to antigen-specific ECDs sequences described in Table 9 or deletion mutants and point mutants of the antigen-specific ECD sequences described in Table 9 as long as they retain the ability to bind to the target antigen. In some embodiments, provided herein are compositions comprising polynucleotides encoding, polypeptides encoded by and vectors encoding, ECD-GGS-Luc constructs that target an antigen and comprise the antigen-specific sequences described in Table 16.

CD19

In one embodiment, the one or more luciferases are fused to antigen recognition domains that target CD19. In exemplary embodiments, the antigen recognition domains that targets CD19 are scFv fragments and comprise any one or more of the CD19 scFv sequences described in Table 14 or sequences with 70-99% identity to CD19 scFv sequences in Table 14 or sequences with 70-99% identity in the six complementarity determining regions (CDRs) to the CD19 scFv sequences in Table 14 or sequences that bind to the same epitopes on the target antigen as the CD19 scFv sequences in Table 14. The nucleotide and proteins sequences of exemplary scFv sequences targeting CD19 are provided in SEQ ID NOs: 564-577 and 1783-1796, respectively. In some embodiments, provided herein are compositions comprising polynucleotides encoding, polypeptides encoded by and vectors encoding, scFv-GGS-Luc constructs that target CD19 and comprise the sequences described in Table 15.

MPL

In one embodiment, the one or more luciferases are fused to antigen recognition domains that target MPL. In exemplary embodiments, the antigen recognition domains that targets MPL are scFv fragments and comprise any one or more of the MPL scFv sequences described in Table 14 or sequences with 70-99% identity to MPL scFv sequences in Table 14 or sequences with 70-99% identity in the six complementarity determining regions (CDRs) to the MPL scFv sequences in Table 14 or sequences that bind to the same epitopes on the target antigen as the MPL scFv sequences in Table 14. The nucleotide and proteins sequences of exemplary scFv sequences targeting MPL are provided in SEQ ID NOs: 729-736 and 1948-1955, respectively. In some embodiments, provided herein are compositions comprising polynucleotides encoding, polypeptides encoded by and vectors encoding, scFv-GGS-Luc constructs that target MPL and comprise the sequences described in Table 15.

CD20

In one embodiment, the one or more luciferases are fused to antigen recognition domains that target CD20. In exemplary embodiments, the antigen recognition domains that targets CD20 are scFv fragments and comprise any one or more of the CD20 scFv sequences described in Table 14 or sequences with 70-99% identity to CD20 scFv sequences in Table 14 or sequences with 70-99% identity in the six complementarity determining regions (CDRs) to the CD20 scFv sequences in Table 14 or sequences that bind to the same epitopes on the target antigen as the CD20 scFv sequences in Table 14. In some embodiments, provided herein are compositions comprising polynucleotides encoding, polypeptides encoded by and vectors encoding, scFv-GGS-Luc constructs that target CD20 and comprise the sequences described in Table 15.

PDL1

In one embodiment, the one or more luciferases are fused to antigen recognition domains that target PDL1. In exemplary embodiments, the antigen recognition domains that targets PDL1 are scFv fragments and comprise any one or more of the PDL1 scFv sequences described in Table 14 or sequences with 70-99% identity to PDL1 scFv sequences in Table 14 or sequences with 70-99% identity in the six complementarity determining regions (CDRs) to the PDL1 scFv sequences in Table 14 or sequences that bind to the same epitopes on the target antigen as the PDL1 scFv sequences in Table 14. The nucleotide and proteins sequences of exemplary scFv sequences targeting PDL1 are provided in SEQ ID NOs: 745-747 and 1964-1966, respectively. In some embodiments, provided herein are compositions comprising polynucleotides encoding, polypeptides encoded by and vectors encoding, scFv-GGS-Luc constructs that target PDL1 and comprise the sequences (SEQ ID NO: 1062-1064 and 2062-2064) described in Table 15.

BCMA

In one embodiment, the one or more luciferases are fused to antigen recognition domains that target BCMA. In exemplary embodiments, the antigen recognition domains that targets BCMA are scFv fragments and comprise any one or more of the BCMA scFv sequences described in Table 14 or sequences with 70-99% identity to BCMA scFv sequences in Table 14 or sequences with 70-99% identity in the six complementarity determining regions (CDRs) to the BCMA scFv sequences in Table 14 or sequences that bind to the same epitopes on the target antigen as the BCMA scFv sequences in Table 14. The nucleotide and proteins sequences of exemplary scFv sequences targeting BCMA are provided in SEQ ID NOs: 586-592 and 1805-1811, respectively. In some embodiments, provided herein are compositions comprising polynucleotides encoding, polypeptides encoded by and vectors encoding, scFv-GGS-Luc constructs that target BCMA and comprise the sequences (SEQ ID NO: 878-884 and 2078-2084) described in Table 15.

CD30

In one embodiment, the one or more luciferases are fused to antigen recognition domains that target CD30. In exemplary embodiments, the antigen recognition domains that targets CD30 are scFv fragments and comprise any one or more of the CD30 scFv sequences described in Table 14 or sequences with 70-99% identity to CD30 scFv sequences in Table 14 or sequences with 70-99% identity in the six complementarity determining regions (CDRs) to the CD30 scFv sequences in Table 14 or sequences that bind to the same epitopes on the target antigen as the CD30 scFv sequences in Table 14. In some embodiments, provided herein are compositions comprising polynucleotides encoding, polypeptides encoded by and vectors encoding, scFv-GGS-Luc constructs that target CD30 and comprise the sequences described in Table 15.

CD33

In one embodiment, the one or more luciferases are fused to antigen recognition domains that target CD33. In exemplary embodiments, the antigen recognition domains that targets CD33 are scFv fragments and comprise any one or more of the CD33 scFv sequences described in Table 14 or sequences with 70-99% identity to CD33 scFv sequences in Table 14 or sequences with 70-99% identity in the six complementarity determining regions (CDRs) to the CD33 scFv sequences in Table 14 or sequences that bind to the same epitopes on the target antigen as the CD33 scFv sequences in Table 14. In some embodiments, provided herein are compositions comprising polynucleotides encoding, polypeptides encoded by and vectors encoding, scFv-GGS-Luc constructs that target CD33 and comprise the sequences described in Table 15.

CD123

In one embodiment, the one or more luciferases are fused to antigen recognition domains that target CD123. In exemplary embodiments, the antigen recognition domains that targets CD123 are scFv fragments and comprise any one or more of the CD123 scFv sequences described in Table 14 or sequences with 70-99% identity to CD123 scFv sequences in Table 14 or sequences with 70-99% identity in the six complementarity determining regions (CDRs) to the CD123 scFv sequences in Table 14 or sequences that bind to the same epitopes on the target antigen as the CD123 scFv sequences in Table 14. In some embodiments, provided herein are compositions comprising polynucleotides encoding, polypeptides encoded by and vectors encoding, scFv-GGS-Luc constructs that target CD123 and comprise the sequences described in Table 15.

CD138

In one embodiment, the one or more luciferases are fused to antigen recognition domains that target CD138. In exemplary embodiments, the antigen recognition domains that targets CD138 are scFv fragments and comprise any one or more of the CD138 scFv sequences described in Table 14 or sequences with 70-99% identity to CD138 scFv sequences in Table 14 or sequences with 70-99% identity in the six complementarity determining regions (CDRs) to the CD138 scFv sequences in Table 14 or sequences that bind to the same epitopes on the target antigen as the CD138 scFv sequences in Table 14. In some embodiments, provided herein are compositions comprising polynucleotides encoding, polypeptides encoded by and vectors encoding, scFv-GGS-Luc constructs that target CD138 and comprise the sequences described in Table 15.

Her2

In one embodiment, the one or more luciferases are fused to antigen recognition domains that target Her2. In exemplary embodiments, the antigen recognition domains that targets Her2 are scFv fragments and comprise any one or more of the Her2 scFv sequences described in Table 14 or sequences with 70-99% identity to Her2 scFv sequences in Table 14 or sequences with 70-99% identity in the six complementarity determining regions (CDRs) to the Her2 scFv sequences in Table 14 or sequences that bind to the same epitopes on the target antigen as the Her2 scFv sequences in Table 14. In some embodiments, provided herein are compositions comprising polynucleotides encoding, polypeptides encoded by and vectors encoding, scFv-GGS-Luc constructs that target Her2 and comprise the sequences described in Table 15.

HIV1 Envelop Glycoprotein gp120

In one embodiment, the one or more luciferases are fused to antigen recognition domains that target HIV1 envelop glycoprotein gp120. In exemplary embodiments, the antigen recognition domains that targets HIV1 envelop glycoprotein gp120 are scFv fragments and comprise any one or more of the HIV1 envelop glycoprotein gp120 scFv sequences described in Table 14 or sequences with 70-99% identity to HIV1 envelop glycoprotein gp120 scFv sequence in Table 14 or sequences with 70-99% identity in the six complementarity determining regions (CDRs) to the HIV1 envelop glycoprotein gp120 scFv sequences in Table 14 or sequences that bind to the same epitopes on the target antigens as the HIV1 envelop glycoprotein gp120 scFv sequences in Table 14. In some embodiments, provided herein are compositions comprising polynucleotides encoding, polypeptides encoded by and vectors encoding, scFv-GGS-Luc constructs that target HIV1 envelop glycoprotein gp120 and comprise the sequences described in Table 15.

Amyloid

In one embodiment, the one or more luciferases are fused to antigen recognition domains that target Amyloid. In exemplary embodiments, the antigen recognition domains that targets Amyloid are scFv fragments and comprise any one or more of the Amyloid scFv sequences described in Table 14 or sequences with 70-99% identity to Amyloid scFv sequences in Table 14 or sequences with 70-99% identity in the six complementarity determining regions (CDRs) to the Amyloid scFv sequences in Table 14 or sequences that bind to the same epitopes on the target antigen as the Amyloid scFv sequences in Table 14. In some embodiments, provided herein are compositions comprising polynucleotides encoding, polypeptides encoded by and vectors encoding, scFv-GGS-Luc constructs that target Amyloid and comprise the sequences described in Table 15.

AFP/MHC Class I Complex

In one embodiment, the one or more luciferases are fused to antigen recognition domains that target AFP/MHC class I complex. In exemplary embodiments, the antigen recognition domains that targets AFP/MHC class I complex are scFv fragments and comprise any one or more of the AFP/MHC class I complex scFv sequences described in Table 14 or sequences with 70-99% identity to AFP/MHC class I complex scFv sequences in Table 14 or sequences with 70-99% identity in the six complementarity determining regions (CDRs) to the AFP/MHC class I complex scFv sequences in Table 14 or sequences that bind to the same epitopes on the target antigen as the AFP/MHC class I complex scFv sequences in Table 14. In some embodiments, provided herein are compositions comprising polynucleotides encoding, polypeptides encoded by and vectors encoding, scFv-GGS-Luc constructs that target AFP/MHC class I complex and comprise the sequences described in Table 15.

CD22

In one embodiment, the one or more luciferases are fused to antigen recognition domains that target CD22. In exemplary embodiments, the antigen recognition domains that targets CD22 are scFv fragments and comprise any one or more of the CD22 scFv sequences described in Table 14 or sequences with 70-99% identity to CD22 scFv sequences in Table 14 or sequences with 70-99% identity in the six complementarity determining regions (CDRs) to the CD22 scFv sequences in Table 14 or sequences that bind to the same epitopes on the target antigen as the CD22 scFv sequences in Table 14. In some embodiments, provided herein are compositions comprising polynucleotides encoding, polypeptides encoded by and vectors encoding, scFv-GGS-Luc constructs that target CD22 and comprise the sequences described in Table 15.

CD19-Specific CAR

In exemplary embodiments, the antigen recognition domain that targets a CD19-specific CARs is a receptor extracellular domains (ECD) and comprises the CD19 ECD sequences as described in Table 9 or sequences with 70-99% identity to CD19 ECD sequences described in Table 9 or deletion mutants and point mutants of the CD19 ECD sequences described in Table 9 as long as they retain the ability to bind to CD19-specific CARs. The nucleic acid and protein sequences of exemplary receptor ECD sequences targeting CD19-specific CARs are provided in SEQ ID NOs: 529 and 1748, respectively. In some embodiments, provided herein are compositions comprising polynucleotides encoding, polypeptides encoded by and vectors encoding, ECD-GGS-Luc constructs that target CD19 and comprise the sequences described in Table 16. The nucleotide and proteins sequences of exemplary ECD-GGS-Luc constructs targeting CD19-CARs are provided in SEQ ID NOs: 1170-1176 and 2370-2376, respectively.

In exemplary embodiments, the antigen recognition domain that targets a CD19-specific FMC63-scFv based CAR is comprised of the scFV fragment of an anti-idiotype antibody FMC136-20 directed against the CD19-specific antibody FMC63. The nucleotide and proteins sequences of exemplary FMC136-20-GGS-Luc constructs targeting CD19-specific FMC63-scFv based CAR are provided in SEQ ID NOs: 1167 and 2367, respectively.

MPL-CAR

In exemplary embodiments, the antigen recognition domain that targets an MPL-specific CAR is a receptor extracellular domains (ECD) and comprise the MPL ECD sequence described in Table 9 or sequences with 70-99% identity to MPL ECDs sequences described in Table 9 or deletion mutants and point mutants of the MPL ECD sequences described in Table 9 as long as they retain the ability to bind to MPL-specific CARs. The nucleotide and protein sequences of exemplary receptor ECD sequences targeting MPL-CARs are provided in SEQ ID NOs: 530 and 1749, respectively. In some embodiments, provided herein are compositions comprising polynucleotides encoding, polypeptides encoded by and vectors encoding, ECD-GGS-Luc constructs that target MPL and comprise the sequences described in Table 16. The nucleotide and proteins sequences of exemplary ECD-GGS-Luc constructs targeting MPL-CAR are provided in SEQ ID NOs: 1169 and 2369, respectively.

CD20-Specific CAR

In exemplary embodiments, the antigen recognition domain that targets a CD20-specific CAR is a receptor extracellular domain (ECD) and comprises the CD20 ECD sequences described in Table 9 or sequences with 70-99% identity to CD20 ECDs sequences described in Table 9 or deletion mutants and point mutants of the CD20 ECD sequences described in Table 9 as long as they retain the ability to bind to CD20-specific CARs. The nucleotide and protein sequences of exemplary receptor ECD sequences targeting CD20-specific CARs are provided in SEQ ID NOs: 545-546 and 1764-1765, respectively. In some embodiments, provided herein are compositions comprising polynucleotides encoding, polypeptides encoded by and vectors encoding, ECD-GGS-Luc constructs that target CD20 and comprise the sequences described in Table 16. The nucleotide and proteins sequences of exemplary ECD-GGS-Luc constructs targeting CD20-specific CARs are provided in SEQ ID NOs: 1197-1198 and 2397-2398, respectively.

CD33-Specific CAR

In exemplary embodiments, the antigen recognition domain that targets a CD33-specific CAR is a receptor extracellular domain (ECD) and comprises the CD33 ECD sequence described in Table 9 or sequences with 70-99% identity to CD33 ECDs sequences described in Table 9 or deletion mutants and point mutants of the CD33 ECD sequences described in Table 9 as long as they retain the ability to bind to CD33-specific CARs. The nucleotide and protein sequences of exemplary receptor ECD sequences targeting CD33-specific CARs are provided in SEQ ID NOs: 541 and 1761, respectively. In some embodiments, provided herein are compositions comprising polynucleotides encoding, polypeptides encoded by and vectors encoding, ECD-GGS-Luc constructs that target CD33 and comprise the sequences described in Table 16. The nucleotide and proteins sequences of exemplary ECD-GGS-Luc constructs targeting CD33-specific CARs are provided in SEQ ID NOs: 1177-1182 and 2377-2382, respectively.

CD123-Specific CAR

In exemplary embodiments, the antigen recognition domain that targets a CD123-specific CAR is a receptor extracellular domain (ECD) and comprises the CD123 ECD sequence described in Table 9 or sequences with 70-99% identity to CD123 ECDs sequences described in Table 9 or deletion mutants and point mutants of the CD123 ECD sequences described in Table 9 as long as they retain the ability to bind to CD123-specific CARs. The nucleotide and protein sequences of exemplary receptor ECD sequences targeting CD123-specific CARs are provided in SEQ ID NOs: 536 and 1755, respectively. In some embodiments, provided herein are compositions comprising polynucleotides encoding, polypeptides encoded by and vectors encoding, ECD-GGS-Luc constructs that target CD123 and comprise the sequences described in Table 16. The nucleotide and proteins sequences of exemplary ECD-GGS-Luc constructs targeting CD123-specific CARs are provided in SEQ ID NOs: 1188 and 2388, respectively.

CD138-Specific CAR

In exemplary embodiments, the antigen recognition domain that targets a CD138-specific CAR is a receptor extracellular domains (ECD) and comprise the CD138 ECD sequence described in Table 9 or sequences with 70-99% identity to CD138 ECDs sequences described in Table 9 or deletion mutants and point mutants of the CD138 ECD sequences described in Table 9 as long as they retain the ability to bind to CD138-specific CARs. The nucleotide and protein sequences of exemplary receptor ECD sequences targeting CD138-specific CARs are provided in SEQ ID NOs: 535 and 1754, respectively. In some embodiments, provided herein are compositions comprising polynucleotides encoding, polypeptides encoded by and vectors encoding, ECD-GGS-Luc constructs that target CD138 and comprise the sequences described in Table 16. The nucleotide and proteins sequences of exemplary ECD-GGS-Luc constructs targeting CD138-specific CARs are provided in SEQ ID NOs: 1183-1187 and 2383-2387, respectively.

CD200R-Specific CAR

In exemplary embodiments, the antigen recognition domain that targets a CD200R-specific CAR is a receptor extracellular domain (ECD) and comprises the CD200R ECD sequence described in Table 9 or sequences with 70-99% identity to CD200R ECDs sequences described in Table 9 or deletion mutants and point mutants of the CD200R ECD sequences described in Table 9 as long as they retain the ability to bind to CD200R-specific CARs. The nucleotide and protein sequences of exemplary receptor ECD sequences targeting CD200R-specific CARs are provided in SEQ ID NOs: 538 and 1757, respectively. In some embodiments, provided herein are compositions comprising polynucleotides encoding, polypeptides encoded by and vectors encoding, ECD-GGS-Luc constructs that target CD200R and comprise the sequences described in Table 16. The nucleotide and proteins sequences of exemplary ECD-GGS-Luc constructs targeting CD200R-specific CARs are provided in SEQ ID NOs: 1190 and 2390, respectively.

CD22-Specific CAR

In exemplary embodiments, the antigen recognition domain that targets a CD22-specific CAR is a receptor extracellular domain (ECD) and comprises the CD22 ECD sequence described in Table 9 or sequences with 70-99% identity to CD22 ECDs sequences described in Table 9 or deletion mutants and point mutants of the CD22 ECD sequences described in Table 9 as long as they retain the ability to bind to CD22-specific CARs. The nucleotide and protein sequences of exemplary receptor ECD sequences targeting CD22-specific CARs are provided in SEQ ID NOs: 547 and 1766, respectively. In some embodiments, provided herein are compositions comprising polynucleotides encoding, polypeptides encoded by and vectors encoding, ECD-GGS-Luc constructs that target CD22 and comprise the sequences described in Table 16. The nucleotide and proteins sequences of exemplary ECD-GGS-Luc constructs targeting CD22-specific CARs are provided in SEQ ID NOs: 1198 and 2398, respectively.

BCMA-Specific CAR

In exemplary embodiments, the antigen recognition domain that targets a BCMA-specific CAR is a receptor extracellular domain (ECD) and comprises the BCMA ECD sequence described in Table 9 or sequences with 70-99% identity to BCMA ECDs sequences described in Table 9 or deletion mutants and point mutants of the BCMA ECD sequences described in Table 9 as long as they retain the ability to bind to BCMA-specific CARs. The nucleotide and protein sequences of exemplary receptor ECD sequences targeting BCMA-specific CARs are provided in SEQ ID NOs: 550 and 1769, respectively. In some embodiments, provided herein are compositions comprising polynucleotides encoding, polypeptides encoded by and vectors encoding, ECD-GGS-Luc constructs that target BCMA and comprise the sequences described in Table 16. The nucleotide and proteins sequences of exemplary ECD-GGS-Luc constructs targeting BCMA-specific CARs are provided in SEQ ID NOs: 1201 and 2401, respectively.

SLAMF7/CS1-Specific CAR

In exemplary embodiments, the antigen recognition domain that targets a SLAMF7/CS1-specific CAR is a receptor extracellular domain (ECD) and comprises the SLAMF7/CS1 ECD sequence described in Table 9 or sequences with 70-99% identity to SLAMF7/CS1 ECDs sequences described in Table 9 or deletion mutants and point mutants of the SLAMF7/CS1 ECD sequences described in Table 9 as long as they retain the ability to bind to SLAMF7/CS1-specific CARs. The nucleotide and protein sequences of exemplary receptor ECD sequences targeting SLAMF7/CS1-specific CARs are provided in SEQ ID NOs: 551 and 1770, respectively. In some embodiments, provided herein are compositions comprising polynucleotides encoding, polypeptides encoded by and vectors encoding, ECD-GGS-Luc constructs that target SLAMF7/CS1 and comprise the sequences described in Table 16. The nucleotide and proteins sequences of exemplary ECD-GGS-Luc constructs targeting SLAMF7/CS1-specific CARs are provided in SEQ ID NOs: 1202 and 2402, respectively.

PTK7-Specific CAR

In exemplary embodiments, the antigen recognition domain that targets a PTK7-specific CAR is a receptor extracellular domain (ECD) and comprises the PTK7 ECD sequence described in Table 9 or sequences with 70-99% identity to PTK7 ECDs sequences described in Table 9 or deletion mutants and point mutants of the PTK7 ECD sequences described in Table 9 as long as they retain the ability to bind to PTK7-specific CARs. The nucleotide and protein sequences of exemplary receptor ECD sequences targeting PTK7-specific CARs are provided in SEQ ID NOs: 540 and 1759, respectively. In some embodiments, provided herein are compositions comprising polynucleotides encoding, polypeptides encoded by and vectors encoding, ECD-GGS-Luc constructs that target PTK7 and comprise the sequences described in Table 16. The nucleotide and proteins sequences of exemplary ECD-GGS-Luc constructs targeting PTK7-specific CARs are provided in SEQ ID NOs: 1192 and 2392, respectively.

EGFRviii-Specific CAR

In exemplary embodiments, the antigen recognition domain that targets a EGFRviii-specific CAR is a receptor extracellular domain (ECD) and comprises the EGFRviii ECD sequence described in Table 9 or sequences with 70-99% identity to EGFRviii ECDs sequences described in Table 9 or deletion mutants and point mutants of the EGFRviii ECD sequences described in Table 9 as long as they retain the ability to bind to EGFRviii-specific CARs. The nucleotide and protein sequences of exemplary receptor ECD sequences targeting EGFRviii-specific CARs are provided in SEQ ID NOs: 549 and 1768, respectively. In some embodiments, provided herein are compositions comprising polynucleotides encoding, polypeptides encoded by and vectors encoding, ECD-GGS-Luc constructs that target EGFRviii and comprise the sequences described in Table 16. The nucleotide and proteins sequences of exemplary ECD-GGS-Luc constructs targeting EGFRviii-specific CARs are provided in SEQ ID NOs: 1200 and 2400, respectively.

TSHR-Specific CAR

In exemplary embodiments, the antigen recognition domain that targets a TSHR-specific CAR is a receptor extracellular domain (ECD) and comprises the TSHR ECD sequence described in Table 9 or sequences with 70-99% identity to TSHR ECDs sequences described in Table 9 or deletion mutants and point mutants of the TSHR ECD sequences described in Table 9 as long as they retain the ability to bind to TSHR-specific CARs. The nucleotide and protein sequences of exemplary receptor ECD sequences targeting TSHR-specific CARs are provided in SEQ ID NOs: 548 and 1767, respectively. In some embodiments, provided herein are compositions comprising polynucleotides encoding, polypeptides encoded by and vectors encoding, ECD-GGS-Luc constructs that target TSHR and comprise the sequences described in Table 16. The nucleotide and proteins sequences of exemplary ECD-GGS-Luc constructs targeting TSHR-specific CARs are provided in SEQ ID NOs: 1191 and 2391, respectively.

gpNMB-specific CAR

In exemplary embodiments, the antigen recognition domain that targets a gpNMB-specific CAR is a receptor extracellular domain (ECD) and comprises the gpNMB ECD sequence described in Table 9 or sequences with 70-99% identity to gpNMB ECDs sequences described in Table 9 or deletion mutants and point mutants of the gpNMB ECD sequences described in Table 9 as long as they retain the ability to bind to gpNMB-specific CARs. The nucleotide and protein sequences of exemplary receptor ECD sequences targeting gpNMB-specific CARs are provided in SEQ ID NOs: 539 and 1758, respectively. In some embodiments, provided herein are compositions comprising polynucleotides encoding, polypeptides encoded by and vectors encoding, ECD-GGS-Luc constructs that target gpNMB and comprise the sequences described in Table 16. The nucleotide and proteins sequences of exemplary ECD-GGS-Luc constructs targeting gpNMB-specific CARs are provided in SEQ ID NOs: 1169 and 2369, respectively.

EpCam-Specific CAR

In exemplary embodiments, the antigen recognition domain that targets an EpCam-specific CAR is a receptor extracellular domain (ECD) and comprises the EpCam ECD sequence described in Table 9. The nucleotide and protein sequences of exemplary receptor ECD sequences targeting EpCam-specific CARs are provided in SEQ ID NOs: 543 and 1762, respectively. In some embodiments, provided herein are compositions comprising polynucleotides encoding, polypeptides encoded by and vectors encoding, ECD-GGS-Luc constructs that target Epcam and comprise the sequences described in Table 16. The nucleotide and proteins sequences of exemplary ECD-GGS-Luc constructs targeting EpCam-specific CARs are provided in SEQ ID NOs: 1194 and 2394, respectively.

CD34-Specific CARS

In exemplary embodiments, the antigen recognition domain that targets a CD34-specific CAR is a receptor extracellular domain (ECD) and comprises the CD34 ECD sequence described in Table 9. The nucleotide and protein sequences of exemplary receptor ECD sequences targeting CD34-specific CARs are provided in SEQ ID NOs: 542 and 1761, respectively. In some embodiments, provided herein are compositions comprising polynucleotides encoding, polypeptides encoded by and vectors encoding, ECD-GGS-Luc constructs that target CD34 and comprise the sequences described in Table 16. The nucleotide and proteins sequences of exemplary ECD-GGS-Luc constructs targeting CD34-specific CARs are provided in SEQ ID NOs: 1193 and 2393, respectively.

CDH1-Specific CAR

In exemplary embodiments, the antigen recognition domain that targets a CDH1-specific CAR is a receptor extracellular domain (ECD) and comprises the CDH1 (CD324) ECD sequence described in Table 9. The nucleotide and protein sequences of exemplary receptor ECD sequences targeting CDH1-specific CARs are provided in SEQ ID NOs: 537 and 1756, respectively. In some embodiments, provided herein are compositions comprising polynucleotides encoding, polypeptides encoded by and vectors encoding, ECD-GGS-Luc constructs that target CDH1 and comprise the sequences described in Table 16. The nucleotide and proteins sequences of exemplary ECD-GGS-Luc constructs targeting CDH1-specific CARs are provided in SEQ ID NOs: 1189 and 2389, respectively.

PD1-Specific CAR

In exemplary embodiments, the antigen recognition domain that targets a PD1-specific CAR is a receptor extracellular domain (ECD) and comprises the PD1 ECD sequence described in Table 9. The nucleotide and protein sequences of exemplary receptor ECD sequences targeting PD1-specific CARs are provided in SEQ ID NOs: 531-534 and 1750-1752, respectively. In some embodiments, provided herein are compositions comprising polynucleotides encoding, polypeptides encoded by and vectors encoding, ECD-GGS-Luc constructs that target PD1 and comprise the sequences described in Table 16. The nucleotide and proteins sequences of exemplary ECD-GGS-Luc constructs targeting PD1-specific CARs are provided in SEQ ID NOs: 1203 and 2403, respectively.

CTLA4-Specific CAR

In exemplary embodiments, the antigen recognition domain that targets a CTLA4-specific CAR is a receptor extracellular domain (ECD) and comprises the CTLA4 ECD sequence described in Table 9. The nucleotide and protein sequences of exemplary receptor ECD sequences targeting CTLA4-specific CARs are provided in SEQ ID NOs: 534 and 1753, respectively. In some embodiments, provided herein are compositions comprising polynucleotides encoding, polypeptides encoded by and vectors encoding, ECD-GGS-Luc constructs that target CTLA4 and comprise the sequences described in Table 16. The nucleotide and proteins sequences of exemplary ECD-GGS-Luc constructs targeting CTLA4-specific CARs are provided in SEQ ID NOs: 1204 and 2404, respectively.

NKG2D-Specific CAR

In exemplary embodiments, the antigen recognition domain that targets a NKG2D-specific CAR is a receptor extracellular domain (ECD) and comprises the NKG2D ECD sequence described in Table 9. The nucleotide and protein sequences of an exemplary receptor ECD sequence (lacking the signal peptide) targeting NKG2D-specific CARs is provided in SEQ ID NOs: 552 and 1771, respectively. In some embodiments, provided herein are compositions comprising polynucleotides encoding, polypeptides encoded by and vectors encoding, ECD-GGS-Luc constructs that target NKG2D and comprise the sequences described in Table 16. The nucleotide and proteins sequences of exemplary ECD-GGS-Luc constructs targeting NKG2D-specific CARs are provided in SEQ ID NOs: 1205 and 2405, respectively.

Kappa Light Chain Containing CAR

In exemplary embodiments, the antigen recognition domain that targets any kappa light chain containing CAR comprises, consists or essentially consists of Protein L. The nucleotide and protein sequences of exemplary Protein L sequences targeting any kappa light chain containing CAR are provided in SEQ ID NOs: 2431-2432 and 2433-2434, respectively or sequences with 70-99% identity to Protein L sequences provided in SEQ ID NOs: 2431-2432 and 2433-2434, respectively, or deletion mutants and point mutants of the Protein L sequences provided in SEQ ID NOs: 2431-2432 and 2433-2434, respectively, as long as they retain the ability to bind to Kappa light chains. In some embodiments, provided herein are compositions comprising polynucleotides encoding, polypeptides encoded by and vectors encoding, ECD-GGS-Luc constructs that target NKG2D and comprise the sequences described in Table 16. The nucleotide and proteins sequences of exemplary ECD-GGS-Luc constructs targeting NKG2D-specific CARs are provided in SEQ ID NOs: 1206-1207 and 2406-2407, respectively.

Detection Methods

Broadly, the detection methods include linking an antigen binding domain to a luciferase and using the fusion protein to detect the antigen.

In the preferred embodiment, the detection methods include fusing the nucleotide sequence encoding a scFV fragment or, another antigen binding fragment (such as nanobodies, affibodies, Darpins etc.), in frame to the nucleotide sequences encoding the luciferases. The expression cassette may also carry nucleotide sequences encoding single or multiple copies of additional epitope tags, such as FLAG, HA and MYC tags, as well tags for purification, such as Streptag and polyhistidine tag. They could also carry nucleotide sequences encoding fluorescent proteins (e.g. EGFP, mcherry) or other reporters (e.g. Horse reddish peroxidase or alkaline phosphatase). The above fusion protein is expressed in appropriate host and then used to detect the expression of the antigen targeted by the scFV (or other antigen binding fragment) by incubation with the target cell (or tissue or biological specimen) followed by extensive washes and then measurement of the bound fusion protein by luciferase reporter assay. In an alternate embodiment, the fusion protein is used to detect an antigen by indirect labeling. In some embodiments, a luciferase fusion protein with an antigen recognition domain directed against another antibody, an epitope tag or a label (e.g., FITC) can be used to identify a target antigen in an indirect labeling protocol. In an exemplary embodiment, a cell expressing a CAR containing a humanized scFv fragment can be first labeled with a FITC-conjugated antibody against human IgG variable region (e.g., a Goat anti-Human IgG F(ab')2 fragment specific; Jackson Immuno Research Laboratory; Cat No: 109-096-006) and then labeled with a luciferase fusion protein containing an antigen recognition domain comprised by a scFv directed against FITC (e.g., SEQ ID NO: 2184 or 2185). Such an indirect labeling approach is expected to improve the sensitivity of the assay by amplifying the signal as each molecule of CAR is expected to be bound by many molecules of the FITC-conjugated goat anti-human antibody, which in turn would be bound by many molecules of the anti-FITC-luciferase fusion protein (e.g., SEQ ID NO: 2184 or 2185). In another exemplary embodiment, a CAR containing a humanized scFv fragment is first labeled with an antibody against human IgG variable region (e.g., a Goat anti-Human IgG F(ab')2 fragment specific; Jackson Immuno Research Laboratory; Cat No: 109-006-006) and then labeled with a luciferase fusion protein containing an antigen recognition domain comprised by a scFv directed against Goat IgG Fc region. The fusion proteins can be also used to detect the presence of very low level target antigens by other methods, including western blotting and microscopy. Finally, the fusion proteins described in this invention can be used to detect the presence of low level antigens in in vivo by bioluminescence imaging for research as well as clinical applications. A potential limitation of the current invention for in vivo application is the immunogenicity of the Luc moiety, which could limit the use to a single or a few applications. However, since the current invention is not limited to a single Luc moiety, it is possible to develop a panel of fusion proteins containing the same antigen binding fragment but different Luc fragments. Thus, a subject who has received FMC63-NLuc fusion protein and has become immunized to it, might receive FMC63-GLuc fusion protein in the future, thereby overcoming the immune response to the NLuc moiety.

The CAR-T cells are living drugs as the cells once infused can multiply in the patient. They can also kill a target cell that expresses as few as 100 molecules of their target antigen. In addition, CAR cells can kill healthy cells that do not express their target via a bystander effect through production of cytokines. Therefore, toxicity of the CAR and other immunotherapy products (including antibody drug conjugates, and Bispecific T cell engagers or BiTE, and DARTs) on normal tissues is a major concern as even low level expression of the target antigen on a vital organ can be lethal. The assay described herein is sensitive provides a useful platform to monitor low level target antigen expression on normal tissues.

Antigen Detection Methods

Provided herein are methods for detecting the presence or absence of an antigen. The methods include contacting a fusion protein comprising an antigen recognition domain fused to a reporter and assaying the activity of the reporter in the presence of a reporter-specific substrate. In one embodiment, the presence of reporter activity is indicative of presence of antigen. In another embodiment, an increase in reporter activity relative to a reference value is indicative of presence of antigen. In one embodiment, the antigen recognition domain of the fusion protein is directed against the antigen to be detected. In another embodiment, the antigen recognition domain of the fusion protein is directed against an antigen (i.e., a protein) that is directed against the antigen to be detected. In some embodiments, the fusion protein comprising an antigen recognition domain fused to a reporter binds directly to the antigen to be detected (i.e., direct labeling). In some embodiments, the fusion protein comprising an antigen recognition domain fused to a reporter binds to the antigen to be detected through one or more intermediates (i.e., indirect labeling). In some embodiments, the reporter is a luciferase as described herein. In one embodiment, the antigen is detected in a subject (i.e., in vivo). In another embodiment, the antigen is detected outside a subject. In one embodiment, the antigen is detected in a sample obtained from a subject. In some embodiments, the antigens are expressed on cancer cells. In one embodiment, the subject is diagnosed with cancer. In another embodiment, the subject is suspected of having cancer. The methods further comprise removing the unbound fusion protein prior to assaying using the reporter-specific substrates. In some embodiments, the reporter is a non-secretory form of a luciferase. In some embodiments, the non-secretory form of luciferase is obtained from copepods, deep sea shrimp or homologs or orthologs thereof or mutants or derivatives thereof. In exemplary embodiments, the copepods are selected from the group consisting of any one or more of *Gaussia princeps, Pleuromamma abdominalis, Metridia pacifica, Metridia curticauda, Metridia asymmetrica, Metridia okhotensis, Metridia longa, Lucicutia ovaliformis, Heterorhabdus tanneri*, and *Pleuromamma scutullata*. In further exemplary embodiments, the luciferase is any one or more of GLuc, NLuc, MLuc7, PaLuc1, PaLuc2, MpLuc1, MoLuc1, MoLuc2, MLuc39, HtLuc, HtLuc2, PsLuc1, H-tanneri, *Lucicutia ovaliformis* (LoLuc), LoLuc1-3, *Renilla* or TLuc (TurboLuc16) or derivatives thereof. In some embodiments, the reporter activity is assayed by exposing the target cells to a luciferase-specific substrate. In one embodiment, the luciferase-specific substrate is coelentrazine or a derivative thereof. In another embodiment, the luciferase-specific substrate is imidazopyrazinone substrate (furimazine) or a derivative thereof.

Provided herein are methods for detecting the presence or absence of an antigen in a subject in need thereof. The methods include providing a fusion protein comprising an antigen recognition domain fused to a reporter; providing a sample from the subject; exposing the sample to the fusion protein; and assaying the activity of the reporter in the presence of a reporter-specific substrate. In one embodiment, the presence of reporter activity is indicative of presence of antigen. In another embodiment, an increase in reporter activity relative to a reference value is indicative of presence of antigen. In some embodiments, the antigens are expressed on cancer cells. In one embodiment, the subject has cancer. The methods further comprise removing the unbound fusion protein prior to assaying using reporter-specific substrates. In some embodiments, the reporter is a non-secretory form of a luciferase. In some embodiments, the non-secretory form of luciferase is obtained from copepods, deep sea shrimp or homologs or orthologs thereof or mutants or derivatives thereof. In exemplary embodiments, the copepods are selected from the group consisting of any one or more of *Gaussia princeps, Pleuromamma abdominalis, Metridia pacifica, Metridia curticauda, Metridia asymmetrica, Metridia okhotensis, Metridia longa, Lucicutia ovaliformis, Heterorhabdus tanneri*, and *Pleuromamma scutullata*. In further exemplary embodiments, the luciferase is any one or more of GLuc, NLuc, MLuc7, PaLuc1, PaLuc2, MpLuc1, MoLuc1, MoLuc2, MLuc39, HtLuc, HtLuc2, PsLuc, LoLuc, LoLuc1-3, *Renilla* or TLuc or derivative thereof. In some embodiments, the reporter activity is assayed by exposing the target cells to a luciferase-specific substrate. In one embodiment, the luciferase-specific substrate is coelentrazine or a derivative thereof. In another embodiment, the luciferase-specific substrate is imidazopyrazinone substrate (furimazine) or a derivative thereof.

In some embodiments of the methods described herein, the antigen targeting domains comprise an antibody or a functional equivalent thereof or a fragment thereof or a derivative thereof specific to the antigen of interest. The targeting regions may comprise full length heavy chain, Fab fragments, single chain Fv (scFv) fragments (or the CDRs contained therein), divalent single chain antibodies or diabodies, each of which are specific to the target antigen. In some embodiments, the antigen specific targeting region is linked cytokines (which leads to recognition of cells bearing the cytokine receptor), affibodies, ligand binding domains from naturally occurring receptors, soluble protein/peptide ligand for a receptor (for example on a tumor cell), peptides, and vaccines to prompt an immune response, which may each be used in various embodiments of the invention. In some embodiments, almost any molecule that binds a given antigen with high affinity can be used as an antigen specific targeting region, as will be appreciated by those of skill in the art.

In some embodiments of the methods described herein, the fusion proteins may be tagged with different tags (e.g. FLAG, HA, MYC, T7, AcV5, V5, StrepTagII, poly His, etc.), either singly or in combination. The fusion proteins comprising the tags may then be detected with flourochrome labeled antibodies against the epitope tags. Alternatively, the fusion proteins may be fused to fluorescent proteins, such as EGFP, RFP and mcherry, for detection directly. Finally, the epitope tags, such as StrepTagII and polyHis tags, can be also used for the purification of the scFV fusion proteins. The tags may be also used to join the antigen specific domain to the luciferase. In an exemplary embodiment, both the antigen specific domain (e.g., a scFv) and the luciferase (e.g., NLuc) carry a StrepTagII. Both the StreptagII fusion proteins are expressed separately and purified. Subsequently, the scFv-Streptag fusion protein is incubated with Streptavidin at a molar ratio of 1:1 or 1:2 or 1:5 so that not all StreptagII binding sites on streptavidin are occupied by the scFv-StreptagII fusion protein. Next, the Streptavidin-scFv-StreptagII complex is incubated with NLuc-StreptagII fusion protein so that the free sites on streptavidin are occupied by the StreptagII present on the Nluc fusion protein. Thus, in alternate embodiments of the invention, it is possible to link an antigen specific domain to a luciferase by methods other than expressing them as a single polypeptide.

In various embodiments, examples of disease specific antigens that may be detected by the methods described herein include but are not limited to PDL1, Her2, PD1, 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R α, PDL192, phosphatidylserine, prostatic carcinoma cells, RANKL, RON, ROR1, SCH 900105, SDC1, SLAMF7, thrombopoietin receptor, TAG-72, tenascin C, TGF beta 2, TGF-β, TRAIL-R1, TRAIL-R2, tumor antigen CTAA16.88, VEGF-A, VEGFR-1, VEGFR2 or vimentin. Other antigens specific for disease, including cancer, infectious diseases, allergic diseases and autoimmune diseases, will be apparent to those of skill in the art and may be used in connection with alternate embodiments of the invention.

In one embodiment of the antigen detection methods described herein, the antigen recognition domain comprises VL fragments of antibodies that recognize and bind specific antigens. In exemplary embodiments, the VL fragments for use with the antigen detection methods are described in Table 4 and are fused with any luciferase reporters described in Table 11. In some embodiments, the VL fragments are linked to the luciferase reporter via the linkers described in Table 5. In some embodiments, the fusion protein comprising VL fragments and luciferase reporter further comprise one or more epitope tags described in Table 13.

In one embodiment of the antigen detection methods described herein, the antigen recognition domain comprises VH fragments of antibodies that recognize and bind specific antigens. In exemplary embodiments, the VH fragments for use with the antigen detection methods are described in Table 6 and are fused with any luciferase reporter described in Table 11. In some embodiments, the VH fragments are linked to the luciferase reporter via the linkers described in Table 5. In some embodiments the fusion protein comprising VH fragments and luciferase reporter further comprise one or more epitope tags described in Table 13.

In one embodiment of the antigen detection methods described herein, the antigen recognition domain comprises VHH fragments of antibodies that recognize and bind specific antigens. In exemplary embodiments, the VHH fragments for use with the antigen detection methods are described in Table 7 and are fused with any luciferase described in Table 11. In some embodiments, the VHH fragments are linked to the luciferase reporter via the linkers described in Table 5. In some embodiments the fusion protein comprising VHH fragments and luciferase reporter further comprise one or more epitope tags described in Table 13.

In one embodiment of the antigen detection methods described herein, the antigen recognition domain comprises non-immunoglobulin antigen binding scaffolds, such as affibodies, that recognize and bind specific antigens. In exemplary embodiments, the affibodies for use with the antigen detection methods are described in Table 8 and are fused with any luciferase described in Table 11. In some embodiments, the affibodies are linked to the luciferase reporter via the linkers described in Table 5. In some embodiments the fusion protein comprising affibodies and luciferase reporter further comprise one or more epitope tags described in Table 13.

In one embodiment of the antigen detection methods described herein, the antigen recognition domain comprises darpins that recognize and bind specific antigens. In exemplary embodiments, the darpins for use with the antigen detection methods are described in Table 8 and are fused with any luciferase described in Table 11. In some embodiments, the darpins are linked to the luciferase reporter via the linkers described in Table 5. In some embodiments the fusion protein comprising darpins and luciferase reporter further comprise one or more epitope tags described in Table 13.

In one embodiment of the antigen detection methods described herein, the antigen recognition domain comprises receptor extracellular domains that recognize and bind specific antigens. In exemplary embodiments, the extracellular domains for use with the antigen detection methods are described in Table 9 and are fused with any luciferase described in Table 11. In some embodiments, the extracellular domains are linked to the luciferase reporter via the linkers described in Table 5. In some embodiments the fusion protein comprising receptor extracellular domains and luciferase reporter further comprise one or more epitope tags described in Table 13.

In one embodiment of the antigen detection methods described herein, the antigen recognition domain comprises ligands that recognize and bind specific antigens. In exemplary embodiments, the ligands for use with the antigen detection methods are described in Table 10 and are fused with any luciferase described in Table 11. In some embodiments, the ligands are linked to the luciferase reporter via the linkers described in Table 5. In some embodiments the fusion protein comprising ligands and luciferase reporter further comprise one or more epitope tags described in Table 13.

In one embodiment of the antigen detection methods described herein, the antigen recognition domain comprises scFv fragments (or the CDRs contained therein) of antibodies that recognize and bind specific antigens. In exemplary embodiments, the scFv fragments for use with the antigen detection methods are described in Table 14 and are fused with any luciferase described in Table 11. In some embodiments, the VL fragments are linked to the luciferase reporter via the linkers described in Table 5. In some embodiments the fusion protein comprising scFv fragments (or the CDRs contained therein) and luciferase reporter further comprise one or more epitope tags described in Table 13.

In some embodiments, provided herein are methods for detecting presence or absence of CD19 expressing cells comprising contacting a sample from a subject with a fusion protein comprising scFv specific to CD19 for a sufficient amount of time to allow the CD19-specific fusion protein to bind CD19 expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of presence of CD19 expressing cells. In another embodiment, an increase in luciferase activity relative to a reference value is indicative of presence of CD19 expressing cells. In one embodiment, the method further comprises selecting a therapy if presence of CD19 expressing cells in the sample is determined. In exemplary embodiments, the CD19 specific fusion protein comprises GGS linker and NLuc reporter as described in any one or more of SEQ ID Nos: 854-868 or 2054-2068 (Table 15).

In some embodiments, provided herein are methods for detecting presence or absence of CD20 expressing cells comprising contacting a sample from a subject with a fusion protein comprising scFv specific to CD20 for a sufficient amount of time to allow the CD20-specific fusion protein to bind CD20 expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of presence of CD20 expressing cells. In another embodiment, an increase in luciferase activity relative to a reference value is indicative of presence of CD20 expressing cells. In one embodiment, the method further comprises selecting a therapy if presence of CD20 expressing cells in the sample is determined. In exemplary embodiments, the CD20 specific fusion protein comprises GGS linker and NLuc reporter as described in any one or more of SEQ ID Nos 891-903 or 2091-2103 (Table 15).

In some embodiments, provided herein are methods for detecting presence or absence of CD30 expressing cells comprising contacting a sample from a subject with a fusion protein comprising scFv specific to CD30 for a sufficient amount of time to allow the CD30-specific fusion protein to bind CD30 expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of presence of CD30 expressing cells. In another embodiment, an increase in luciferase activity relative to a reference value is indicative of presence of CD30 expressing cells. In one embodiment, the method further comprises selecting a therapy if presence of CD30 expressing cells in the sample is determined. In exemplary embodiments, the CD30 specific fusion protein comprises GGS linker and NLuc reporter as described in any one or more of SEQ ID Nos: 908-909 or 2108-2109 (Table 15).

In some embodiments, provided herein are methods for detecting presence or absence of Lym1 expressing cells comprising contacting a sample from a subject with a fusion protein comprising scFv specific to Lym1 for a sufficient amount of time to allow the Lym1-specific fusion protein to bind Lym1 expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of presence of Lym1 expressing cells. In another embodiment, an increase in luciferase activity relative to a reference value is indicative of presence of Lym1 expressing cells. In one embodiment, the method further comprises selecting a therapy if presence of Lym1 expressing cells in the sample is determined. In exemplary embodiments, the Lym1 specific fusion protein comprises GGS linker and NLuc reporter as described in any one or more of SEQ ID NO: 1036 or 2236 (Table 15).

In some embodiments, provided herein are methods for detecting presence or absence of Lym2 expressing cells comprising contacting a sample from a subject with a fusion protein comprising scFv specific to Lym2 for a sufficient amount of time to allow the Lym2-specific fusion protein to bind Lym2 expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of presence of Lym2 expressing cells. In another embodiment, an increase in luciferase activity relative to a reference value is indicative of presence of Lym2 expressing cells. In one embodiment, the method further comprises selecting a therapy if presence of Lym2 expressing cells in the sample is determined. In exemplary embodiments, the Lym2 specific fusion protein comprises GGS linker and NLuc reporter as described in any one or more of SEQ ID NO: 1037 or 2237 (Table 15).

In some embodiments, provided herein are methods for detecting presence or absence of MPL expressing cells comprising contacting a sample from a subject with a fusion protein comprising scFv specific to MPL for a sufficient amount of time to allow the MPL-specific fusion protein to bind MPL expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of presence of MPL expressing cells. In another embodiment, an increase in luciferase activity relative to reference value is indicative of presence of MPL expressing cells. In one embodiment, the method further comprises selecting a therapy if presence of MPL expressing cells in the sample is determined. In exemplary embodiments, the MPL specific fusion protein comprises GGS linker and NLuc reporter as described in any one or more of SEQ ID NOs: 1044-1051 or 2244-2251 (Table 15).

In some embodiments, provided herein are methods for detecting presence or absence of PDL1 expressing cells comprising contacting a sample from a subject with a fusion protein comprising scFv specific to PDL1 for a sufficient amount of time to allow the PDL1-specific fusion protein to bind PDL1 expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of presence of PDL1 expressing cells. In another embodiment, an increase in luciferase activity relative to reference value is indicative of presence of PDL1 expressing cells. In one embodiment, the method further comprises selecting a therapy if presence of PDL1 expressing cells in the sample is determined. In exemplary embodiments, the PDL1 specific fusion protein comprises GGS linker and NLuc reporter as described in any one or more of SEQ ID NOs: 1062-1064 or 2262-2264 (Table 15).

In some embodiments, provided herein are methods for detecting presence or absence of cells expressing targeting antigens described in Table 15. The methods comprise contacting a sample from a subject with a fusion protein comprising a scFv, a camelid VHH, a non-immunoglobulin antigen binding scaffold, a cytokine or a receptor specific to the target antigens, for a sufficient amount of time to allow the fusion protein to bind the target antigen expressed on the cells in the sample wherein the fusions proteins are any one or more of the fusion proteins described in Table 15. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of presence of targeting antigen expressing cells. In another embodiment, an increase in luciferase activity relative to a reference value is indicative of presence of target antigen expressing cells. In one embodiment, the method further comprises selecting a therapy if presence of the target antigen expressing cells in the sample is determined. In exemplary embodiments, the antigen specific fusion protein comprises GGS linker and Luc reporter as described in Table 15.

In exemplary embodiments, the sample and the fusion protein are incubated for any of 1 min, 5 mins, 10 mins, 20 mins, 30 mins, 1 hour, 3 hours, 5 hours, 10 hours, 15 hours, 20 hours, 24 hour or combinations thereof. An appropriate length of time will be apparent to a person of skill in the art.

In exemplary embodiments, repeated washing comprises washing the sample-fusion protein mixture 1, 2, 3, 4, 5, 6, 7, 8, 9, 10 times or more with an appropriate buffer. Appropriate number of washings of the mixture will be apparent to a person of skill in the art.

In exemplary embodiments, buffers include but are not limited to PBS, PBS with 2% BSA, PBS with 10% BSA, normal saline and RPMI media with 10% FCS. Appropriate buffers for use with the instant invention will be apparent to a person of skill in the art.

Detection of Cells Expressing Chimeric Antigen Receptors

Provided herein are methods for detecting the presence or absence of expression of an artificial receptor or synthetic receptor in a sample obtained from a subject. Non-limiting exemplary embodiments of artificial or synthetic receptors include a chimeric antigen receptor, a chimeric T cell receptor, a transgenic (exogenous) TCR, and a synthetic notch receptor. The methods include contacting a fusion protein comprising an antigen recognition domain fused to a reporter and assaying the activity of the reporter in the presence of a reporter-specific substrate. In one embodiment, the presence of reporter activity is indicative of presence of CAR expressing cells. In another embodiment, an increase in reporter activity relative to a reference value is indicative of presence of CAR expressing cells in the sample. In some embodiments, the antigen recognition domain comprises of, consists of, or consists essentially of the antigen that is targeted by the CAR. In some embodiment, the antigen recognition domain comprises of, consists of, or consists essentially of a protein that binds to the antigen specific domain of CAR. In an exemplary embodiment, the antigen recognition domain comprises of, consists of, or consists essentially of the antigen that is targeted by the CAR. In an exemplary embodiment, the antigen recognition domain comprises of, consists of, or consists essentially of Protein L. In an exemplary embodiment, the antigen recognition domain comprises of, consists of, or consists essentially of an antibody or an antibody fragment (e.g., a scFv) that binds to any one or more of the components of the CAR. In some embodiments, the reporter is a luciferase as described herein. In some embodiments, the CARs are expressed by the immune effector cells (T cells, NK cells) in the sample. The methods further comprise removing the unbound fusion protein prior to assaying for reporter activity using reporter-specific substrates. In some embodiments, the reporter is a non-secretory form of a luciferase. In some embodiments, the non-secretory form of luciferase is obtained from copepods, deep sea shrimp or homologs or orthologs thereof or mutants or derivatives thereof. In exemplary embodiments, the copepods are selected from the group consisting of any one or more of *Gaussia princeps, Pleuromamma abdominalis, Metridia pacifica, Metridia curticauda, Metridia asymmetrica, Metridia okhotensis, Metridia longa, Lucicutia ovaliformis, Heterorhabdus tanneri,* and *Pleuromamma scutullata*. In further exemplary embodiments, the luciferase is any one or more of GLuc, NLuc, MLuc7, PaLuc1, PaLuc2, MpLuc1, MoLuc1, MoLuc2, MLuc39, HtLuc, HtLuc2, PsLuc1, H-tanneri, *Lucicutia ovaliformis* LoLuc, LoLuc1-3, *Renilla* or TLuc (TurboLuc16) or derivatives thereof. In some embodiments, the reporter activity is assayed by exposing the target cells to a luciferase-specific substrate. In one embodiment, the luciferase-specific substrate is coelentrazine or a derivative thereof. In another embodiment, the luciferase-specific substrate is imidazopyrazinone substrate (furimazine) or a derivative thereof.

Provided herein are methods for detecting the presence or absence of expression of chimeric antigen receptors in a sample obtained from a subject. The methods include providing a fusion protein comprising an antigen recognition domain fused to a reporter; providing a sample from the subject; exposing the sample to the fusion protein; and assaying the activity of the reporter in the presence of a reporter-specific substrate. In one embodiment, the presence of reporter activity is indicative of presence of CAR expressing cells. In another embodiment, an increase in reporter activity relative to a reference value is indicative of presence of CAR expressing cells in the sample. In some embodiments, the reporter is a luciferase as described herein. In some embodiments, the CARs are expressed by the immune effector cells (T cells, NK cells) in the sample. The methods further comprise removing the unbound fusion protein prior to assaying for reporter activity using reporter-specific substrates. In some embodiments, the reporter is a non-secretory form of a luciferase. In some embodiments, the non-secretory form of luciferase is obtained from copepods, deep sea shrimp or homologs or orthologs thereof or mutants or derivatives thereof. In exemplary embodiments, the copepods are selected from the group consisting of any one or more of *Gaussia princeps, Pleuromamma abdominalis, Metridia pacifica, Metridia curticauda, Metridia asymmetrica, Metridia okhotensis, Metridia longa, Lucicutia ovaliformis, Heterorhabdus tanneri,* and *Pleuromamma scutullata*. In further exemplary embodiments, the luciferase is any one or more of GLuc, NLuc, MLuc7, PaLuc1, PaLuc2, MpLuc1, MoLuc1, MoLuc2, MLuc39, HtLuc, HtLuc2, PsLuc1, H-tanneri, *Lucicutia ovaliformis* LoLuc, LoLuc1-3, *Renilla* or TLuc (TurboLuc16) or derivatives thereof. In some embodiments, the reporter activity is assayed by exposing the target cells to a luciferase-specific substrate. In one embodiment, the luciferase-specific substrate is coelentrazine or a derivative thereof. In another embodiment, the luciferase-specific substrate is imidazopyrazinone substrate (furimazine) or a derivative thereof.

In various embodiments of the methods for detecting expression of chimeric antigen receptors, the antigen recognition domain comprises the extracellular domain (ECD) of the antigen of interest. For example, a fusion protein comprising an ECD of an antigen binds the scFv of a CAR that is specific to the ECD. In an exemplary embodiment, the fusion protein comprises an ECD of CD19 and the fusion protein binds to a CD19 specific CAR.

In various embodiments, the extracellular domains in the fusion protein for detection of CAR expressing cells may be the extracellular domains of disease specific antigens including but are not limited to 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R α, PDL192, phosphatidylserine, prostatic carcinoma cells, RANKL, RON, ROR1, SCH 900105, SDC1, SLAMF7, thrombopoietin receptor, TAG-72, tenascin C, TGF beta 2, TGF-β, TRAIL-R1, TRAIL-R2, tumor antigen CTAA16.88, VEGF-A, VEGFR-1, VEGFR2 or vimentin. Other antigens specific for cancer will be apparent to those of skill in the art and may be used in connection with alternate embodiments of the invention.

In some embodiments, the fusion proteins further comprise a tag. In exemplary embodiments, that tag is tag is any one or more of chitin binding protein (CBP), glutathione-S-transferase (GST), polyhistidine (His) tag, FLAG tag, HA tag, Myc tag, V5 tag, AcV5 tag, Myristoylation (Myr) tag or a combination thereof.

In some embodiments, the luciferase activity is measured by any one or more of methods for measuring light production such as a luminometer, x-ray films, microscopy, or combinations thereof.

In exemplary embodiments of the methods for detecting expression of chimeric antigen receptors, extracellular domains of antigens for use in detecting CARs are described in Table 9.

In some embodiments, provided herein are methods for detecting presence or absence of expression of a CD19 CAR in a sample obtained from a subject. The method includes contacting a sample from a subject with a fusion protein comprising ECD of CD19 fused to luciferase, for a sufficient amount of time to allow the CD19 ECD fusion protein to bind to CD19 CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of CD19 CAR in the sample. In another embodiment, an increase in luciferase activity relative to a reference value is indicative of expression of CD19 CAR in the sample. In exemplary embodiments, the CD19 ECD fusion protein comprises GGS linker and Luc reporter as described in any one or more of SEQ ID Nos 1170-1176 or 2370-2376 (Table 16).

In some embodiments, provided herein are methods for detecting presence or absence of expression of a MPL CAR in a sample obtained from a subject. The method includes contacting a sample from a subject with a fusion protein comprising ECD of MPL fused to luciferase, for a sufficient amount of time to allow the MPL ECD fusion protein to bind to MPL CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of MPL CAR sample. In another embodiment, an increase in luciferase activity relative to a reference value is indicative of expression of MPL CAR in the sample. In exemplary embodiments, the MPL ECD fusion protein comprises GGS linker and Luc reporter as described in any one or more of SEQ ID NO: 1169 or 2369 (Table 16).

In some embodiments, provided herein are methods for detecting presence or absence of expression of a CD33 CAR in a sample obtained from a subject. The method includes contacting a sample from a subject with a fusion protein comprising ECD of CD33 fused to luciferase, for a sufficient amount of time to allow the CD33 ECD fusion protein to bind to CD33 CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of CD33 CAR in the sample. In another embodiment, an increase in luciferase activity relative to a reference value is indicative of expression of CD33 CAR in the sample. In exemplary embodiments, the CD33 ECD fusion protein comprises GGS linker and Luc reporter as described in any one or more of SEQ ID NO: 1177-1182 or 2377-2382 (Table 16).

In some embodiments, provided herein are methods for detecting presence or absence of expression of a CD138 CAR in a sample obtained from a subject. The method includes contacting a sample from a subject with a fusion protein comprising ECD of CD138 fused to luciferase, for a sufficient amount of time to allow the CD138 ECD fusion protein to bind to CD138 CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of CD138 CAR in the sample. In another embodiment, an increase in luciferase activity relative to a reference value is indicative of expression of CD138 CAR in the sample. In exemplary embodiments, the CD138 ECD fusion protein comprises GGS linker and Luc reporter as described in any one or more of SEQ ID NO: 1183-1187 or 2383-2387 (Table 16).

In some embodiments, provided herein are methods for detecting presence or absence of expression of a CD123 CAR in a sample obtained from a subject. The method includes contacting a sample from a subject with a fusion protein comprising ECD of CD123 fused to luciferase, for a sufficient amount of time to allow the CD123 ECD fusion protein to bind to CD123 CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of CD123 CAR in the sample. In another embodiment, an increase in luciferase activity relative to a reference value is indicative of expression of CD123 CAR in the sample. In exemplary embodiments, the CD123 ECD fusion protein comprises GGS linker and Luc reporter as described in any one or more of SEQ ID NO: 1188 or 2388 (Table 16).

In some embodiments, provided herein are methods for detecting presence or absence of expression of a CDH1 CAR in a sample obtained from a subject. The method includes contacting a sample from a subject with a fusion protein comprising ECD of CDH1 fused to luciferase, for a sufficient amount of time to allow the CDH1 ECD fusion protein to bind to CDH1 CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of CDH1 CAR in the sample. In another embodiment, an increase in luciferase activity relative to a reference value is indicative of expression of CDH1 CAR in the sample. In exemplary embodiments, the CDH1 ECD fusion protein comprises GGS linker and Luc reporter as described in any one or more of SEQ ID NO: 1189 or 2389 (Table 16).

In some embodiments, provided herein are methods for detecting presence or absence of expression of a CD200R CAR in a sample obtained from a subject. The method includes contacting a sample from a subject with a fusion protein comprising ECD of CD200R fused to luciferase, for a sufficient amount of time to allow the CD200R ECD fusion protein to bind to CD200R CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of CD200R in the CAR sample. In another embodiment, an increase in luciferase activity relative to a reference value is indicative of expression of CD200R CAR in the sample. In exemplary embodiments, the CD200R ECD fusion protein comprises GGS linker and Luc reporter as described in any one or more of SEQ ID NO: 1190 or 2390 (Table 16).

In some embodiments, provided herein are methods for detecting presence or absence of expression of a GPNMB CAR in a sample obtained from a subject. The method includes contacting a sample from a subject with a fusion protein comprising ECD of GPNMB fused to luciferase, for a sufficient amount of time to allow the GPNMB ECD fusion protein to bind to GPNMB CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of GPNMB in the CAR sample. In another embodiment, an increase in luciferase activity relative to a reference value is indicative of expression of GPNMB CAR in the sample. In exemplary embodiments, the GPNMB ECD fusion protein comprises GGS linker and Luc reporter as described in any one or more of SEQ ID NO: 1191 or 2391 (Table 16).

In some embodiments, provided herein are methods for detecting presence or absence of expression of a PTK7 CAR in a sample obtained from a subject. The method includes contacting a sample from a subject with a fusion protein comprising ECD of PTK7 fused to luciferase, for a sufficient amount of time to allow the PTK7 ECD fusion protein to bind to PTK7 CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of PTK7 CAR in the sample. In another embodiment, an increase in luciferase activity relative to a reference value is indicative of expression of PTK7 CAR in the sample. In exemplary embodiments, the PTK7 ECD fusion protein comprises GGS linker and Luc reporter as described in any one or more of SEQ ID NO: 1192 or 2392 (Table 16).

In some embodiments, provided herein are methods for detecting presence or absence of expression of a CD34 CAR in a sample obtained from a subject. The method includes contacting a sample from a subject with a fusion protein comprising ECD of CD34 fused to luciferase, for a sufficient amount of time to allow the CD34 ECD fusion protein to bind to CD34 CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of CD34 CAR in the sample. In another embodiment, an increase in luciferase activity relative to a reference value is indicative of expression of CD34 CAR in the sample. In exemplary embodiments, the CD34 ECD fusion protein comprises GGS linker and Luc reporter as described in any one or more of SEQ ID NO: 1193 or 2393 (Table 16).

In some embodiments, provided herein are methods for detecting presence or absence of expression of a EpCAM CAR in a sample obtained from a subject. The method includes contacting a sample from a subject with a fusion protein comprising ECD of EpCAM fused to luciferase, for a sufficient amount of time to allow the EpCAM ECD fusion protein to bind to EpCAM CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of EpCAM in the CAR sample. In another embodiment, an increase in luciferase activity relative to a reference value is indicative of expression of EpCAM CAR in the sample. In exemplary embodiments, the EpCAM ECD fusion protein comprises GGS linker and Luc reporter as described in any one or more of SEQ ID NO: 1194 or 2394 (Table 16).

In some embodiments, provided herein are methods for detecting presence or absence of expression of a CLEC12A CAR in a sample obtained from a subject. The method includes contacting a sample from a subject with a fusion protein comprising ECD of CLEC12A fused to luciferase, for a sufficient amount of time to allow the CLEC12A ECD fusion protein to bind to CLEC12A CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of CLEC12A in the CAR sample. In another embodiment, an increase in luciferase activity relative to a reference value is indicative of expression of CLEC12A CAR in the sample. In exemplary embodiments, the CLEC12A ECD fusion protein comprises GGS linker and Luc reporter as described in any one or more of SEQ ID NO: 1195 or 2395 (Table 16).

In some embodiments, provided herein are methods for detecting presence or absence of expression of a CD20 CAR in a sample obtained from a subject. The method includes contacting a sample from a subject with a fusion protein comprising ECD of CD20 fused to luciferase, for a sufficient amount of time to allow the CD20 ECD fusion protein to bind to CD20 CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of CD20 CAR in the sample. In another embodiment, an increase in luciferase activity relative to a reference value is indicative of expression of CD20 CAR in the sample. In exemplary embodiments, the CD20 ECD fusion protein comprises GGS linker and Luc reporter as described in any one or more of SEQ ID NO: 1196-1197 or 2396-2397 (Table 16).

In some embodiments, provided herein are methods for detecting presence or absence of expression of a CD22 CAR in a sample obtained from a subject. The method includes contacting a sample from a subject with a fusion protein comprising ECD of CD22 fused to luciferase, for a sufficient amount of time to allow the CD22 ECD fusion protein to bind to CD22 CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of CD22 CAR in the sample. In another embodiment, an increase in luciferase activity relative to a reference value is indicative of expression of CD22 CAR in the sample. In exemplary embodiments, the CD22 ECD fusion protein comprises GGS linker and Luc reporter as described in any one or more of SEQ ID NO: 1198 or 2398 (Table 16).

In some embodiments, provided herein are methods for detecting presence or absence of expression of a TSHR CAR in a sample obtained from a subject. The method includes contacting a sample from a subject with a fusion protein comprising ECD of TSHR fused to luciferase, for a sufficient amount of time to allow the TSHR ECD fusion protein to bind to TSHR CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of TSHR CAR in the sample. In another embodiment, an increase in luciferase activity relative to a reference value is indicative of expression of TSHR CAR in the sample. In exemplary embodiments, the TSHR ECD fusion protein comprises GGS linker and Luc reporter as described in any one or more of SEQ ID NO: 1199 or 2399 (Table 16).

In some embodiments, provided herein are methods for detecting presence or absence of expression of a EGFRviii CAR in a sample obtained from a subject. The method includes contacting a sample from a subject with a fusion protein comprising ECD of EGFRviii fused to luciferase, for a sufficient amount of time to allow the EGFRviii ECD fusion protein to bind to EGFRviii CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of EGFRviii CAR in the sample. In another embodiment, an increase in luciferase activity relative to a reference value is indicative of expression of EGFRviii CAR in the sample. In exemplary embodiments, the EGFRviii ECD fusion protein comprises GGS linker and Luc reporter as described in any one or more of SEQ ID NO: 1200 or 2400 (Table 16).

In some embodiments, provided herein are methods for detecting presence or absence of expression of a BCMA CAR in a sample obtained from a subject. The method includes contacting a sample from a subject with a fusion protein comprising ECD of BCMA fused to luciferase, for a sufficient amount of time to allow the BCMA ECD fusion protein to bind to BCMA CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of BCMA CAR in the sample. In another embodiment, an increase in luciferase activity relative to a reference value is indicative of expression of BCMA CAR in the sample. In exemplary embodiments, the BCMA ECD fusion protein comprises GGS linker and Luc reporter as described in any one or more of SEQ ID NO: 1201 or 2401 (Table 16).

In some embodiments, provided herein are methods for detecting presence or absence of expression of a SLAMF7 CAR in a sample obtained from a subject. The method includes contacting a sample from a subject with a fusion protein comprising ECD of SLAMF7 fused to luciferase, for a sufficient amount of time to allow the EGFRviii ECD fusion protein to bind to SLAMF7 CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of SLAMF7 CAR in the sample. In another embodiment, an increase in luciferase activity relative to a reference value is indicative of expression of SLAMF7 CAR in the sample. In exemplary embodiments, the SLAMF7 ECD fusion protein comprises GGS linker and Luc reporter as described in any one or more of SEQ ID NO: 1202 or 2402 (Table 16).

In some embodiments, provided herein are methods for detecting presence or absence of expression of a PD1 CAR in a sample obtained from a subject. The method includes contacting a sample from a subject with a fusion protein comprising ECD of PD1 fused to luciferase, for a sufficient amount of time to allow the PD1 ECD fusion protein to bind to PD1 CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of PD1 CAR in the sample. In another embodiment, an increase in luciferase activity relative to a reference value is indicative of expression of PD1 CAR in the sample. In exemplary embodiments, the PD1 ECD fusion protein comprises GGS linker and Luc reporter as described in any one or more of SEQ ID NO: 1203 or 2403 (Table 16).

In some embodiments, provided herein are methods for detecting presence or absence of expression of a CTLA4 CAR in a sample obtained from a subject. The method includes contacting a sample from a subject with a fusion protein comprising ECD of CTLA4 fused to luciferase, for a sufficient amount of time to allow the CTLA4 ECD fusion protein to bind to CTLA4 CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity relative to a reference value is indicative of expression of CTLA4 CAR in the sample. In another embodiment, an increase in luciferase activity is indicative of expression of CTLA4 CAR in the sample. In exemplary embodiments, the CTLA4 ECD fusion protein comprises GGS linker and Luc reporter as described in any one or more of SEQ ID NO: 1204 or 2404 (Table 16).

In some embodiments, provided herein are methods for detecting presence or absence of expression of a NKG2D CAR in a sample obtained from a subject. The method includes contacting a sample from a subject with a fusion protein comprising ECD of NKG2D fused to luciferase, for a sufficient amount of time to allow the NKG2D ECD fusion protein to bind to NKG2D CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of NKG2D CAR in the sample. In another embodiment, an increase in luciferase activity relative to a reference value is indicative of expression of NKG2D CAR in the sample. In exemplary embodiments, the NKG2D ECD fusion protein comprises GGS linker and Luc reporter as described in any one or more of SEQ ID NO: 1205 or 2405 (Table 16).

In some embodiments, provided herein are methods for detecting presence or absence of expression of a kappa light chain of a CAR in a sample obtained from a subject. The method includes contacting a sample from a subject with a fusion protein comprising Protein L fused to luciferase, for a sufficient amount of time to allow the Protein L fusion protein to bind to the kappa light chain of CAR expressing cells in the sample. In some embodiments, the method further comprises removing unbound fusion protein, for example by repeatedly washing the sample/fusion protein mixture with a buffer. The method further comprises contacting the sample/fusion protein mixture with a luciferase specific substrate and detecting the luciferase activity. In one embodiment, presence of luciferase activity is indicative of expression of a CAR in the sample. In another embodiment, an increase in luciferase activity relative to a reference value is indicative of expression of a CAR in the sample. In exemplary embodiments, the Protein L fusion protein comprises GGS linker and NLuc reporter as described in any one or more of SEQ ID NO: 1206-1207 or 2406-2407 (Table 16).

In exemplary embodiments, repeated washing comprises washing the sample-fusion protein mixture 1, 2, 3, 4, 5, 6, 7, 8, 9, 10 times or more with an appropriate buffer. Appropriate number of washings of the mixture will be apparent to a person of skill in the art.

In exemplary embodiments, buffers include but are not limited to PBS, normal saline, RPMI, PBS with 5% BSA, PBS with 10% BSA. Appropriate buffers for use with the instant invention will be apparent to a person of skill in the art.

Reference Value

In some embodiments, the reference value is the reporter activity (for example, luciferase activity as described herein) in any one or more of (i) control cells or samples that do not express the target antigen; (ii) control cells or samples that express reporter but are not treated with the test agent(s); (iii) controls cells or samples that are not treated with the substrate for the reporter; (iv) control cells or samples that do express the target antigen but are treated with a fusion protein directed against an antigen that is not expressed on the target cells; (v) a combination thereof.

In some embodiments, the reference value is the reporter activity (for example, luciferase activity as described herein) in any one or more of (i) cells that do not express the CAR, or an exogenous T cell receptor or a synthetic T cell receptor or a chimeric T cell receptor or a hybrid T cell receptor; (ii) cells that express the CAR, or an exogenous T cell receptor or a synthetic T cell receptor or a chimeric T cell receptor or a hybrid T cell receptor but are treated with fusion protein which is not targeted by the CAR, or an exogenous T cell receptor or a synthetic T cell receptor or a chimeric T cell receptor or a hybrid T cell receptor; (iii) cells that are not treated with the substrate for the reporter.

In some embodiments, the reporter activity (for example, luciferase activity as described herein) is increased relative to the reference value by at least or about 5%, 10%, 15%, 20%, 25%, 30%, 35%, 40%, 45%, 50%, 55%, 60%, 65%, 70%, 75%, 80%, 85%, 90%, 95% or 100%.

In some embodiments, the reporter activity (for example, luciferase activity as described herein) is increased relative to the reference value by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold, 1000-fold, 10,000-fold or a combination thereof.

In some embodiments, the detection methods described herein may be used to screen patients for CAR therapies. For example, in patients who have been diagnosed with cancer and are candidates for CAR therapies, the methods described herein may be used to determine the presence or absence and/or the amount of antigen expressed in a sample from the patient, wherein the antigen is targeted by the CAR. If the antigen is detected in the patient, the patient may be a candidate for CAR therapy.

In some embodiments, the detection methods described herein may be used to monitor the persistence of CARs in patients who have received CAR therapies. For example, in patients who have received CAR therapies, the methods described herein may be used to determine the presence or absence of CAR T cells in a sample from the patient at different time intervals following the administration of CAR-T cells. If the CAR-T cells are not detected in the patient, the patient may be at higher risk of relapse.

In some embodiments, the detection methods described herein may be used as a quality control tool to monitor the quality of different lots of CAR-T cells during the manufacturing of CAR-T cells. For example, different lots of CD19-directed CAR-T cells can be compared for their relative binding to CD19-ECD-NLuc fusion protein (SEQ ID NO: 1170) as compared to a reference lot. A key advantage of the detection method of the instant invention is that it not only measures the expression of the CAR protein on the surface of immune cells, but it also measures the ability of the CAR protein to bind to the target antigen.

There are many variables in the design and manufacturing of CARs. Many different CAR constructs can be generated against a particular antigen. These constructs differ in their antigen specific domains, which are generally derived from different antibodies. There exists a need for a fast, economical, sensitive and specific assay to select the scFv fragments for incorporation into a CAR construct. In some embodiments, the detection methods described herein may be used to select the best candidate scFv for incorporation into a CAR construct. For example, different scFv fusion proteins targeting a candidate CAR antigen (e.g., CD19) can be generated and tested rapidly for their relative expression and ability to bind to a panel of CD19+ve and CD19−ve cell lines. The scFv fragment(s) showing the highest expression, binding affinity and specificity would be candidate for incorporation into a CAR. In some embodiments, the detection methods described herein may be used to select the best candidate CAR construct for further development. For example, a number of candidate CD19-specific CAR constructs, which differ base on their antigen specific domain, hinge domain, transmembrane domain, costimulatory domain, activation domain etc., can be rapidly compared using the current method for their ability to bind to FLAG-CD19-ECD-GGSG-NLuc-AcV5(062615-004) [SEQ ID NO:1170] fusion protein, which would provide a relative measure of the ability of the CAR to bind to CD19 on the target cells.

In some embodiments, the detection methods described herein may be used in antibody engineering. For example, antibody engineering, such as affinity maturation and humanization, rely on expression and testing of several different scFv candidate constructs. These constructs can be constructed as luciferase-fusion proteins, which will allow rapid screening of the different constructs for relative expression and binding affinity to their target antigens, including binding affinity in cell-based assays.

Methods for Detecting Luciferase Activity

In various embodiments, luciferase activity described herein is measured by any one or more of methods for measuring light production such as a luminometer, X-ray films, microscopy, or combinations thereof. The nucleic acid and amino acid sequences of the fusion proteins described in the above section are presented in the corresponding sequence sections.

Methods for Expression of Luc Fusion Proteins

The host cell line utilized for expression of the Luc fusion proteins of the present invention can be of mammalian or non-mammalian origin. Those skilled in the art are credited with ability to preferentially determine particular host cell lines which are best suited for the desired gene product to be expressed therein. In one embodiment, the host cell line utilized for generation of the Luc fusion proteins of the invention is mammalian in origin. Exemplary host cell lines include, but are not limited to, DG44 and DUXB11 (Chinese Hamster Ovary lines, DHFR minus), HELA (human cervical carcinoma), CVI (monkey kidney line), COS (a derivative of CVI with SV40 T antigen), R1610 (Chinese hamster fibroblast) BALBC/3T3 (mouse fibroblast), HAK (hamster kidney line), SP2/0 (mouse myeloma), P3×63-Ag3.653 (mouse myeloma), BFA-1c1BPT (bovine endothelial cells), RAJI (human lymphocyte), 293FT and 293 (human kidney). Host cell lines are typically available from commercial services, the American Tissue Culture Collection or from published literature. In another embodiment, the host cell line utilized for generation of the Luc fusion proteins of the invention is of insect origin. In another embodiment, the host cells utilized for generation of the Luc fusion proteins of the invention are bacterial in origin. In another embodiment, the host cells utilized for generation of the Luc fusion proteins of the invention are of yeast origin. Those skilled in the art are credited with ability to preferentially determine particular promoters and vectors which are best suited for the expression of a desired gene product in a particular host cell line. Exemplary vector for expression of the Luc fusion protein of the invention is pLenti-EF1a (SEQ ID NO: 842). Vectors for expression of proteins in other host cell lines are are typically available from commercial sources, such as Thermofisher, Novagen and Sigma. In various embodiments, the fusion proteins described herein may be expressed in bacterial cells, yeasts or insects. The optimum vectors and promoters to be used for expression of the fusions proteins described herein and for the methods described herein will be apparent to a person of skill in the art.

Therapies

As described herein, in various embodiments, if an antigen of interest or a CAR of interest is detected, the methods further comprise selecting a therapy. Examples of therapy include, but are not limited to, active surveillance, observation, surgical intervention, chemotherapy, immunotherapy, radiation therapy (such as external beam radiation, stereotactic radiosurgery (gamma knife), and fractionated stereotactic radiotherapy (FSR)), focal therapy, systemic therapy, vaccine therapies, viral therapies, molecular targeted therapies, or combinations thereof.

In some embodiments, therapies include surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation, peptide vaccine, such as that described in Izumoto et al. 2008 J Neurosurg 108:963-971. Exemplary chemotherapeutic agents include an anthracycline (e.g., doxorubicin (e.g., liposomal doxorubicin)), a *vinca* alkaloid (e.g., vinblastine, vincristine, vindesine, vinorelbine), an alkylating agent (e.g., cyclophosphamide, decarbazine, melphalan, ifosfamide, temozolomide), an immune cell antibody (e.g., alemtuzamab, gemtuzumab, rituximab, ofatumumab, tositumomab, brentuximab), an antimetabolite (including, e.g., folic acid antagonists, pyrimidine analogs, purine analogs and adenosine deaminase inhibitors (e.g., fludarabine)), an mTOR inhibitor, a TNFR glucocorticoid induced TNFR related protein (GITR) agonist, a proteasome inhibitor (e.g., aclacinomycin A, gliotoxin or bortezomib), an immunomodulator such as thalidomide or a thalidomide derivative (e.g., lenalidomide).

In some embodiments, therapies include bone marrow transplantation, T cell ablative therapy using chemotherapy agents such as, fludarabine, external-beam radiation therapy (XRT), cyclophosphamide, and/or antibodies such as OKT3 or CAMP ATH.

Optimum dosages, frequencies of administration and modes of administration will be apparent to a person of skill in the art.

Kits

Kits to practice the invention are also provided. For example, kits for expressing one or more luciferase proteins of the invention. The kits may include a nucleic acid molecule or a polypeptide molecule encoding the luciferase fusion constructs along with a method to introduce the nucleic acid into an appropriate host cell to produce the protein. The kit may include a vector comprising a nucleic acid encoding the fusion protein of the invention and chemicals, such as lipofectamine, to introduce the vector into appropriate host cells. The kit may contain components for the expression, purification and detection of the luciferase fusion protein. For example, the kit may contain buffer and reagents for measuring the activity luciferases. More than one of the disclosed vector can be included in the kit. The kit can include a container and a label or package insert on or associated with the container. The kit may include instructions for storage and shipment of its contents.

Suitable containers include, for example, bottles, vials, syringes, etc. The containers may be formed from a variety of materials such as glass or plastic. The container typically holds a composition including one or more of the nucleic acid molecules, viruses, vectors and proteins. A label or package insert indicates that the composition is used for diagnosing a particular condition. The label or package insert typically will further include instructions for use of a disclosed nucleic acid molecules, proteins, for example, in a method of detecting the presence of a CAR. The package insert typically includes instructions customarily included in commercial packages of diagnostic products that contain information about the composition and health hazards. The instructional materials may be written, in an electronic form (such as a computer diskette or compact disk) or may be visual (such as video files). The kits may also include additional components to facilitate the particular application for which the kit is designed. Thus, for example, the kit may additionally contain means for measuring the expression of CAR on T cells or of determining the number or percentage of T cells that express the CAR or of determining the functionality of CAR-T cells. The kits may additionally include buffers and other reagents routinely used for the practice of a particular method. Such kits and appropriate contents are well known to those of skill in the art.

TABLE 3

Exemplary signal peptides

| NAME | SEQ ID (DNA) | SEQ ID (PRT) |
| --- | --- | --- |
| CD8_Signal_Peptide | 1 | 1781 |
| CD8_Signal_Peptide | 2 | 1781 |
| CD8_Signal_Peptide | 3 | 1781 |
| CD8-SIGNAL-PEPTIDE | 4 | 1781 |
| IgH_Signal_Peptide | 5 | 1782 |
| IgH_Signal_Peptide | 6 | 1782 |
| IgH_Signal-Peptide | 7 | 1782 |
| IgH_Signal Peptide | 8 | 1782 |
| Amyloid-158-158-Signal-peptide | 9 | 1783 |
| hCD19 Signal Peptide | 10 | 1784 |

TABLE 4

| Target | SEQ ID (DNA) | SEQ ID (PRT) | NAME |
|---|---|---|---|
| Exemplary VL fragments | | | |
| AFP/MHC class I complex | 11 | 1785 | AFP-61-vL |
| AFP/MHC class I complex | 12 | 1786 | AFP-76-vL |
| AFP/MHC class I complex | 13 | 1787 | AFP-79-vL |
| ALK | 14 | 1788 | Alk-48-vL |
| ALK | 15 | 1789 | Alk-58-vL |
| Amyloid | 16 | 1790 | Amyloid-158-vL |
| BCMA | 17 | 1791 | BCMA-ET-40-vL |
| BCMA | 18 | 1792 | BCMA-ET-54-vL |
| BCMA | 19 | 1793 | BCMA-huC12A3-vL |
| BCMA | 20 | 1794 | BCMA-J6M0-vL |
| BCMA | 21 | 1795 | BCMA-ET-03-vL |
| BCMA | 22 | 1796 | BCMA-huC11.D5.3L1H3-VL |
| BCMA | 23 | 1797 | BCMA-huC13-F12-vL |
| CCR4 | 24 | 1798 | CCR4-humAb1567-vL |
| CD123 | 25 | 1799 | CD123-CSL362-vL |
| CD123 | 26 | 1800 | CD123-1172-vL |
| CD123 | 27 | 1801 | CD123-DART-1-vL |
| CD123 | 28 | 1802 | CD123-DART-2-vL |
| CD123 | 29 | 1803 | CD123-I3RB18-vL |
| CD123 | 30 | 1804 | CD123-hu3E3-vL |
| CD123 | 31 | 1805 | CD123-9F6-vL |
| CD123 | 32 | 1806 | CD123-I3RB2-vL |
| CD123 | 33 | 1807 | CD123-1176-vL |
| CD123 | 34 | 1808 | CD123-8B11-vL |
| CD123 | 35 | 1809 | CD123-2B8-vL |
| CD123 | 36 | 1810 | CD123-9D7-vL |
| CD123 | 37 | 1811 | CD123-3B10-vL |
| CD138 | 38 | 1812 | CD138-vL |
| CD179b | 39 | 1813 | CD179b-vL |
| CD19 | 40 | 1814 | CD19-4G7-vL |
| CD19 | 41 | 1815 | CD19Bu12-vL |
| CD19 | 42 | 1816 | CD19MM-vL |
| CD19 | 43 | 1817 | FMC63-vL |
| CD19 | 44 | 1818 | FMC63-[2]-vL |
| CD19 | 45 | 1819 | FMC63-[3]-vL |
| CD19 | 46 | 1820 | huFMC63-11-vL |
| CD19 | 47 | 1821 | CD19-MEDI-3649-vL |
| CD19 | 48 | 1822 | CD19-Medrex-24D1-vL |
| CD19 | 49 | 1823 | CD19-MOR0028-vL |
| CD19 | 50 | 1824 | CD19-HD37-H2L1-vL |
| CD19 | 51 | 1825 | CD19-huBly3-vL |
| CD19 | 52 | 1826 | CD19-huSJ25C1-vL |
| CD19 | 53 | 1827 | CD19-hB4-vL |
| CD19 | 54 | 1828 | CD19-hu-mROO5-1-vL |
| CD19 | 55 | 1829 | CD19-hA19-vL |
| CD20 | 56 | 1830 | CD20-2F2-vL |
| CD20 | 57 | 1831 | CD20-GA101-vL |
| CD20 | 58 | 1832 | CD20-Leu16-vL |
| CD20 | 59 | 1833 | CD20-11B8-vL |
| CD20 | 60 | 1834 | CD20-2C6-vL |
| CD20 | 61 | 1835 | CD20-2H7-vL |
| CD20 | 62 | 1836 | CD20-hA20-vL |
| CD20 | 63 | 1837 | CD20-BM-CA-1925-v4-vL |
| CD20 | 64 | 1838 | CD20-Ubli-v4-vL |
| CD20 | 65 | 1839 | CD20-2H7-vL |
| CD20 | 66 | 1840 | CD20-h1F5-vL |
| CD20 | 67 | 1841 | CD20-7D8-vL |
| CD20 | 68 | 1842 | CD20-AME-33-vL |
| CD22 | 69 | 1843 | CD22-h10F4-vL |
| CD22 | 70 | 1844 | CD22-H22Rhov2ACDRKA-vL |
| CD22 | 71 | 1845 | CD22m971-vL |
| CD276 | 72 | 1846 | CD276-17-vL |
| CD30 | 73 | 1847 | CD30-5F11-vL |
| CD30 | 74 | 1848 | CD30-Ac10-vL |
| CD32 | 75 | 1849 | CD32-Med9-vL |
| CD324 | 76 | 1850 | CD324-hSC10-17-vL |
| CD324 | 77 | 1851 | CD324-SC10-6-vL |
| CD33 | 78 | 1852 | CD33-huMyc9-vL |
| CD33 | 79 | 1853 | CD33-AF5-vL |
| CD33 | 80 | 1854 | CD33-Boehr2800308-vL |
| CD33 | 81 | 1855 | CD33-Him3-4-vL |
| CD33 | 82 | 1856 | CD33-SGNh2H12-vL |
| CD33 | 83 | 1857 | CD33-15G15-33-vL |
| CD33 | 84 | 1858 | CD33-33H4-vL |
| CD33 | 85 | 1859 | CD33-9C3-2-vL |
| CD34 | 86 | 1860 | CD34-hu4C7-[2]-vL |

TABLE 4-continued

Exemplary VL fragments

| Target | SEQ ID (DNA) | SEQ ID (PRT) | NAME |
|---|---|---|---|
| CD34 | 87 | 1861 | CD34-hu4C7-vL |
| CD44v6 | 88 | 1862 | CD44v6-Biwa8-vL |
| CD5 | 89 | 1863 | CD5-18-vL |
| CD5 | 90 | 1864 | CD5-9-vL |
| CD70 | 91 | 1865 | CD70-h1F6-vL |
| CD79b | 92 | 1866 | CD79b-2F2-vL |
| CD79b | 93 | 1867 | huMA79bv28-vL |
| CD99 | 94 | 1868 | CD99-hu12E7-vL |
| CDH17 | 95 | 1869 | CDH17-PTA001A4-vL |
| CDH19 | 96 | 1870 | CDH19-16A4-vL |
| CDH6 | 97 | 1871 | CDH6-NOV710-vL |
| CDH6 | 98 | 1872 | CDH6-NOV712-vL |
| CLEC5A | 99 | 1873 | CLEC5A-3E12A2-vL |
| CLEC5A | 100 | 1874 | CLEC5A-8H8F5-vL |
| CLL1 | 101 | 1875 | CLL1-M26-vL |
| CLL1 | 102 | 1876 | CLL1-M32-vL |
| CD123 | 103 | 1877 | CLL1-21C9-L2H3-vL |
| CLL1 | 104 | 1878 | CLL1-6E7L4H1e-vL |
| CLL1 | 105 | 1879 | CLL1-hu1075-v1-vL |
| CLL1 | 106 | 1880 | CLL1-hu1075-v2-vL |
| CMVpp65/MHC class I complex | 107 | 1881 | CMVpp65-F5-vL |
| CS1 | 108 | 1882 | huLuc63-vL |
| CS1 | 109 | 1883 | HuLuc64-[2]-vL |
| CS1 | 110 | 1884 | HuLuc64-vL |
| CS1 | 111 | 1885 | Luc90-vL |
| CS1 | 112 | 1886 | CS1-PDL241-vL |
| CS1 | 113 | 1887 | CS1-Hu27A-vL |
| CS1 | 114 | 1888 | CS1-ScHu34C3-vL |
| CS1 | 115 | 1889 | CS1-Hu31-D2-vL |
| CS1 | 116 | 1890 | CS1-Luc34-vL |
| CS1 | 117 | 1891 | CS1-LucX2-vL |
| CSF2RA | 118 | 1892 | CSF2RA-Ab1-vL |
| CSF2RA | 119 | 1893 | CSF2RA-Ab6-vL |
| DLL3 | 120 | 1894 | DLL3-hSC16-13-vL |
| DLL3 | 121 | 1895 | DLL3-hSC16-56-vL |
| EBNA3c//MHC class I complex | 122 | 1896 | EBNA3c-315-vL |
| EGFR | 123 | 1897 | Cetuximab-vL |
| EGFR | 124 | 1898 | Nimotuzumab-vL |
| EGFRviii | 125 | 1899 | EGFRviii-139-vL |
| EGFRviii | 126 | 1900 | EGFRviii-2173-vL |
| EpCam1 | 127 | 1901 | EpCam1-D5K5-vL |
| EpCam1 | 128 | 1902 | Epcam1-MM1-vL |
| FITC | 129 | 1903 | FITC-vL |
| FITC | 130 | 1904 | FITC-4M-53-vL |
| FITC | 131 | 1905 | FITC-E2-vL |
| FLT3 | 132 | 1906 | FLT3-NC7-vL |
| HIV1-envelop glycoprotein | 133 | 1907 | HIV1-N6-vL |
| FR1 (Folate Receptor a) | 134 | 1908 | FR1-huMov19-vL |
| GAD | 135 | 1909 | GAD-G3H8-vL |
| GD2 | 136 | 1910 | GD2-hu14-18-vL |
| GD2 | 137 | 1911 | GD2-hu3F8-vL |
| GD3 | 138 | 1912 | GD3-KM-641-vL |
| GFRa4 | 139 | 1913 | GFRa4-P4-10-2-vL |
| GFRa4 | 140 | 1914 | GFRa4-P4-10-vL |
| GFRa4 | 141 | 1915 | GFRAlpha4-P4-6-vL |
| GM1 | 142 | 1916 | GM1-5B2-vL |
| GM1 | 143 | 1917 | GM1-7E5-vL |
| gp100//MHC class I complex | 144 | 1918 | gp100-G2D12-vL |
| gp100//MHC class I complex | 145 | 1919 | gp100-vL |
| GPC3 | 146 | 1920 | GPC3-4E5-vL |
| gpNMB | 147 | 1921 | gpNMB-115-vL |
| GPRC5D | 148 | 1922 | GPRC5D-ET150-18-vL |
| GPRC5D | 149 | 1923 | GPRC5D-ET150-5-vL |
| GPRC5D | 150 | 1924 | GPRC5D-ET150-1-vL |
| GPRC5D | 151 | 1925 | GPRC5D-ET150-2-vL |
| Her2 | 152 | 1926 | Her2-Hu4D5-vL |
| HIV1-gag (77-85)//MHC class I complex | 153 | 1927 | HIV1-3BNC117-vL |
| HIV1-envelop glycoprotein | 154 | 1928 | HIV1-E5-vL |
| HIV1-envelop glycoprotein | 155 | 1929 | HIV1-PGT-128-vL |
| HIV1-envelop glycoprotein | 156 | 1930 | HIV1-VR-C01-vL |
| HIV1-envelop glycoprotein | 157 | 1931 | HIV1-X5-vL |
| HLA-A2 | 158 | 1932 | HLA-A2-3PB2-vL |
| HMW-MAA | 159 | 1933 | HMW-MAA-hIND-vL |
| HPV16-E7/MHC class I complex | 160 | 1934 | HPV16-7-8-vL |
| HPV16-E7/MHC class I complex | 161 | 1935 | HPV16-2-vL |

TABLE 4-continued

Exemplary VL fragments

| Target | SEQ ID (DNA) | SEQ ID (PRT) | NAME |
|---|---|---|---|
| HTLV1-TAX/MHC class I complex | 162 | 1936 | TAX-T3E3-vL |
| HTLV1-TAX/MHC class I complex | 163 | 1937 | TAX-T3F2-vL |
| IL11Ra | 164 | 1938 | IL11Ra-8E2-vL |
| IL13Ra2 | 165 | 1939 | IL13Ra2-hu107-vL |
| IL13Ra2 | 166 | 1940 | IL13Ra2-Hu108-vL |
| IL6R | 167 | 1941 | IL6R-M83-vL |
| Influenza A HA | 168 | 1942 | FLU-MEDI-8852-vL |
| KSHV-gH | 169 | 1943 | YC15-vL |
| KSHV-K8.1 | 170 | 1944 | 4C3-vL |
| L1CAM | 171 | 1945 | L1CAM-9-3-HU3-vL |
| LAMP1 | 172 | 1946 | LAMP1-humab1-2-vL |
| LAMP1 | 173 | 1947 | LAMP1-Mb4-vL |
| LewisY | 174 | 1948 | LewisY-huS193-vL |
| Lym1 | 175 | 1949 | Lym1-vL |
| Lym2 | 176 | 1950 | Lym2-vL |
| MART1/MHC class I complex | 177 | 1951 | MART1-CAG10-vL |
| MART1/MHC class I complex | 178 | 1952 | MART1-CLA12-vL |
| Mesothelin | 179 | 1953 | Mesothelin-m912-vL |
| MPL | 180 | 1954 | MPL-111-vL |
| MPL | 181 | 1955 | MPL-161-HL-vL |
| MPL | 182 | 1956 | MPL-161-vL |
| MPL | 183 | 1957 | MPL-175-vL |
| MPL | 184 | 1958 | MPL-178-vL |
| MPL | 185 | 1959 | MPL-huVB22Bw5-vL |
| MPL | 186 | 1960 | MPL-12E10-vL |
| MPL | 187 | 1961 | MPL-AB317-vL |
| Muc1/MHC class I complex | 188 | 1962 | MUC1-D6-M3A1-vL |
| Muc1/MHC class I complex | 189 | 1963 | Muc1-D6-M3B8-vL |
| Muc16 | 190 | 1964 | Muc16-4H11-vL |
| NKG2D | 191 | 1965 | NKG2D-MS-vL |
| NYBR1 | 192 | 1966 | NYBR1-vL |
| NY-ESO/MHC class I complex | 193 | 1967 | NY-ESO-T1-vL |
| PD1 | 194 | 1968 | PD1-4H1-vL |
| PD1 | 195 | 1969 | PD1-5C4-vL |
| PDL1 | 196 | 1970 | PDL1-10A5-vL |
| PDL1 | 197 | 1971 | PDL1-Atezoli-vL |
| PDL1 | 198 | 1972 | PDL1-SP142-vL |
| PR1/MHC class I complex | 199 | 1973 | PR1-vL |
| PSCA | 200 | 1974 | PSCA-Ha14-117-vL |
| PSCA | 201 | 1975 | PSCA-Ha14-121-vL |
| PSMA | 202 | 1976 | PSMA-006-vL |
| PSMA | 203 | 1977 | PSMA-J591-vL |
| PTK7 | 204 | 1978 | PTK7-hSC6-23-vL |
| PTK7 | 205 | 1979 | PTK7-SC6-10-2-vL |
| ROR1 | 206 | 1980 | ROR1-4A5-vL |
| ROR1 | 207 | 1981 | ROR1-4C10-vL |
| SLea | 208 | 1982 | SLea-5B1-vL |
| SLea | 209 | 1983 | SLea-7E3-vL |
| SSEA4 | 210 | 1984 | SSEA4-vL |
| TCRB1 (TCR b1 constant chain) | 211 | 1985 | TCRB1-E09-vL |
| TCRB1 (TCR b1 constant chain) | 212 | 1986 | TCRB1-Jovi1-vL |
| TCRB2 (TCR b2 constant chain) | 213 | 1987 | TCRB2-CP01-D05-vL |
| TCRB2 (TCR b2 constant chain) | 214 | 1988 | TCRB2-CP01-E05-vL |
| TCRgamma delta (TCRgd) | 215 | 1989 | TCRgd-G5-4-vL |
| TERT/MHC class I complex | 216 | 1990 | TERT-3G3-T865-vL |
| TERT/MHC class I complex | 217 | 1991 | TERT-4A9-T540-vL |
| TF1 (Tissue Factor) | 218 | 1992 | TF1-98-vL |
| TGFBR2 | 219 | 1993 | TGFBR2-Ab1-vL |
| TIM1 | 220 | 1994 | TIM1-HVCR1-270-2-vL |
| TIM1 | 221 | 1995 | Tim1HVCR1-ARD5-vL |
| TnAg | 222 | 1996 | TnAg-vL |
| Tn-Muc1 | 223 | 1997 | Tn-Muc1-hu5E5-vL |
| TROP2 | 224 | 1998 | TROP2-ARA47-HV3KV3-vL |
| TROP2 | 225 | 1999 | TROP2-h7E6-SVG-vL |
| TSHR | 226 | 2000 | TSHR-5C9-vL |
| TSHR | 227 | 2001 | TSHR-K1-70-vL |
| TSHR | 228 | 2002 | TSHR-KB1-vL |
| TSLRP | 229 | 2003 | TSLPR-vL |
| Tyrosinase/MHC class I complex | 230 | 2004 | Tyro-B2-vL |
| Tyrosinase/MHC class I complex | 231 | 2005 | Tyro-Mc1-vL |
| Tyrosinase/MHC class I complex | 232 | 2006 | TA2-vL |
| VEGFR3 | 233 | 2007 | VEGFR3-Ab1-vL |
| WT1/MHC class I complex | 234 | 2008 | WT1-Ab13-vL |
| WT1/MHC class I complex | 235 | 2009 | WT1-Ab15-vL |
| WT1/MHC class I complex | 236 | 2010 | WT1-Ab1-vL |
| WT1/MHC class I complex | 237 | 2011 | WT1-Ab5-vL |

TABLE 4-continued

Exemplary VL fragments

| Target | SEQ ID (DNA) | SEQ ID (PRT) | NAME |
|---|---|---|---|
| EBV-gp350 | 238 | 2012 | EBV-gp350-vL |
| CDH19 | 239 | 2013 | CDH19-4B10-vL |
| Folate Receptor b (FRbeta) | 240 | 2014 | FRbeta-m923-vL |
| LHR | 241 | 2015 | LHR-8B7-vL |
| LHR | 242 | 2016 | LHR-5F4-21-vL |
| B7H4 | 243 | 2017 | B7H4-hu22C10-vL |
| B7H4 | 244 | 2018 | B7H4-hu1D11-vL |
| IgE | 245 | 2019 | IgE-omalizumab-vL |
| CD23 | 246 | 2020 | CD23-p5E8-vL |
| GCC | 247 | 2021 | GCC-5F9-vL |
| GCC | 248 | 2022 | GCC-Ab229-vL |
| CD200R | 249 | 2023 | CD200R-huDx182-vL |

TABLE 5

Exemplary Linkers

| NAME | SEQ ID (DNA) | SEQ ID (PRT) |
|---|---|---|
| (GGGGS)x3_LINKER | 250 | 2024 |
| (GGGGS)x3_Linker | 251 | 2024 |
| (Gly4Ser)x3_Linker | 252 | 2024 |
| (Gly4Ser)x3_Linker | 253 | 2024 |
| (GGGGS)x3_Linker | 254 | 2024 |
| (GGGGS)x3_Linker | 255 | 2024 |
| (GGSG)7_Linker | 256 | 2025 |
| (GGSG)7_Linker_2 | 257 | 2026 |
| DDAKK_linker | 258 | 2027 |

TABLE 6

Exemplary V$_H$ fragments

| Target | SEQ ID (DNA) | SEQ ID (PRT) | CONSTRUCT NAME |
|---|---|---|---|
| AFP/MHC class I complex | 259 | 2028 | AFP-61-vH |
| AFP/MHC class I complex | 260 | 2029 | AFP-76-vH |
| AFP/MHC class I complex | 261 | 2030 | AFP-79-vH |
| ALK | 262 | 2031 | Alk-48-vH |
| ALK | 263 | 2032 | Alk-58-vH |
| Amyloid | 264 | 2033 | Amyloid-158-vH |
| BCMA | 265 | 2034 | BCMA-ET-40-vH |
| BCMA | 266 | 2035 | BCMA-ET-54-vH |
| BCMA | 267 | 2036 | BCMA-huC12A3-vH |
| BCMA | 268 | 2037 | BCMA-J6M0-vH |
| BCMA | 269 | 2038 | BCMA-ET-03-vH |
| BCMA | 270 | 2039 | BCMA-huC11.D5.3L1H3-VH |
| BCMA | 271 | 2040 | BCMA-huC13-F12-vH |
| CCR4 | 272 | 2041 | CCR4-humAb1567-vH |
| CD123 | 273 | 2042 | CD123-CSL362-vH |
| CD123 | 274 | 2043 | CD123-1172-vH |
| CD123 | 275 | 2044 | CD123-DART-1-vH |
| CD123 | 276 | 2045 | CD123-DART-2-vH |
| CD123 | 277 | 2046 | CD123-13RB18-vH |
| CD123 | 278 | 2047 | CD123-hu3E3-vH |
| CD123 | 279 | 2048 | CD123-9F6-vH |
| CD123 | 280 | 2049 | CD123-I3RB2-vH |
| CD123 | 281 | 2050 | CD123-1176-vH |
| CD123 | 282 | 2051 | CD123-8B11-vH |
| CD123 | 283 | 2052 | CD123-2B8-vH |
| CD123 | 284 | 2053 | CD123-9D7-vH |
| CD123 | 285 | 2054 | CD123-3B10-vH |
| CD138 | 286 | 2055 | CD138-vH |
| CD179b | 287 | 2056 | CD179b-vH |
| CD19 | 288 | 2057 | CD19-4G7-vH |
| CD19 | 289 | 2058 | CD19Bu12-vH |
| CD19 | 290 | 2059 | CD19Bu12-[2]-vH |
| CD19 | 291 | 2060 | CD19MM-vH |
| CD19 | 292 | 2061 | FMC63-vH |
| CD19 | 293 | 2062 | FMC-63-vH |
| CD19 | 294 | 2063 | huFMC63-11-vH |
| CD19 | 295 | 2064 | CD19-MEDI-3649-vH |
| CD19 | 296 | 2065 | CD19-Medrex-24D1-vH |
| CD19 | 297 | 2066 | CD19-MOR0028-vH |
| CD19 | 298 | 2067 | CD19-HD37-H2L1-vH |
| CD19 | 299 | 2068 | CD19-huBly3-vH |

TABLE 6-continued

| Exemplary V_H fragments | | | |
|---|---|---|---|
| Target | SEQ ID (DNA) | SEQ ID (PRT) | CONSTRUCT NAME |
| CD19 | 300 | 2069 | CD19-huSJ25C1-vH |
| CD19 | 301 | 2070 | CD19-hB4-vH |
| CD19 | 302 | 2071 | CD19-hu-mROO5-1-vH |
| CD19 | 303 | 2072 | CD19-hA19-vH |
| CD20 | 304 | 2073 | CD20-2F2-vH |
| CD20 | 305 | 2074 | CD20-GA101-vH |
| CD20 | 306 | 2075 | CD20-Leu16-vH |
| CD20 | 307 | 2076 | CD20-11B8-vH |
| CD20 | 308 | 2077 | CD20-2C6-vH |
| CD20 | 309 | 2078 | CD20-2H7-vH |
| CD20 | 310 | 2079 | CD20-hA20-vH |
| CD20 | 311 | 2080 | CD20-BM-CA-1925-v4-vH |
| CD20 | 312 | 2081 | CD20-Ubli-v4-vH |
| CD20 | 313 | 2082 | CD20-2H7-vH |
| CD20 | 314 | 2083 | CD20-h1F5-vH |
| CD20 | 315 | 2084 | CD20-7D8-vH |
| CD20 | 316 | 2085 | CD20-AME-33-vH |
| CD22 | 317 | 2086 | CD22-h10F4-vH |
| CD22 | 318 | 2087 | CD22-H22Rhov2ACDRKA-vH |
| CD22 | 319 | 2088 | CD22m971-vH |
| CD276 | 320 | 2089 | CD276-17-vH |
| CD30 | 321 | 2090 | CD30-5F11-vH |
| CD30 | 322 | 2091 | CD30-Ac10-vH |
| CD32 | 323 | 2092 | CD32-Med9-vH |
| CD324 | 324 | 2093 | CD324-hSC10-17-vH |
| CD324 | 325 | 2094 | CD324-SC10-6-vH |
| CD33 | 326 | 2095 | CD33-huMyc9-vH |
| CD33 | 327 | 2096 | CD33-AF5-vH |
| CD33 | 328 | 2097 | CD33-Boehr2800308-vH |
| CD33 | 329 | 2098 | CD33-Him3-4-vH |
| CD33 | 330 | 2099 | CD33-SGNh2H12-vH |
| CD33 | 331 | 2100 | CD33-15G15-33-vH |
| CD33 | 332 | 2101 | CD33-33H4-vH |
| CD33 | 333 | 2102 | CD33-33H4-vH |
| CD33 | 334 | 2103 | CD33-9C3-2-vH |
| CD34 | 335 | 2104 | CD34-hu4C7-vH |
| CD44v6 | 336 | 2105 | CD44v6-Biwa8-vH |
| CD5 | 337 | 2106 | CD5-18-vH |
| CD5 | 338 | 2107 | CD5-9-vH |
| CD70 | 339 | 2108 | CD70-h1F6-vH |
| CD79b | 340 | 2109 | CD79b-2F2-vH |
| CD79b | 341 | 2110 | huMA79bv28-vH |
| CD99 | 342 | 2111 | CD99-hu12E7-vH |
| CDH17 | 343 | 2112 | CDH17-PTA001A4-vH |
| CDH19 | 344 | 2113 | CDH19-16A4-vH |
| CDH6 | 345 | 2114 | CDH6-NOV710-vH |
| CDH6 | 346 | 2115 | CDH6-NOV712-vH |
| CLEC5A | 347 | 2116 | CLEC5A-3E12A2-vH |
| CLEC5A | 348 | 2117 | CLEC5A-8H8F5-vH |
| CLL1 | 349 | 2118 | CLL1-M26-vH |
| CLL1 | 350 | 2119 | CLL1-M32-vH |
| CD123 | 351 | 2120 | CLL1-21C9-L2H3-vH |
| CLL1 | 352 | 2121 | CLL1-6E7L4H1e-vH |
| CLL1 | 353 | 2122 | CLL1-hu1075-v1-vH |
| CLL1 | 354 | 2123 | CLL1-hu1075-v2-vH |
| CMVpp65/MHC class I complex | 355 | 2124 | CMVpp65-F5-vH |
| CS1 | 356 | 2125 | huLuc63-vH |
| CS1 | 357 | 2126 | HuLuc64-vH |
| CS1 | 358 | 2127 | Luc90-vH |
| CS1 | 359 | 2128 | CS1-PDL241-vH |
| CS1 | 360 | 2129 | CS1-Hu27A-vH |
| CS1 | 361 | 2130 | CS1-ScHu34C3-vH |
| CS1 | 362 | 2131 | CS1-Hu31-D2-vH |
| CS1 | 363 | 2132 | CS1-Luc34-vH |
| CS1 | 364 | 2133 | CS1-LucX2-vH |
| CSF2RA | 365 | 2134 | CSF2RA-Ab1-vH |
| CSF2RA | 366 | 2135 | CSF2RA-Ab6-vH |
| DLL3 | 367 | 2136 | DLL3-hSC16-13-vH |
| DLL3 | 368 | 2137 | DLL3-hSC16-56-vH |
| EBNA3c/MHC class I complex | 369 | 2138 | EBNA3c-315-vH |
| EGFR | 370 | 2139 | Cetuximab-vH |
| EGFR | 371 | 2140 | Nimotuzumab-vH |
| EGFRviii | 372 | 2141 | EGFRviii-139-vH |
| EGFRviii | 373 | 2142 | EGFRviii-2173-vH |
| EpCam1 | 374 | 2143 | EpCam1-D5K5-vH |
| EpCam1 | 375 | 2144 | Epcam1-MM1-vH |

TABLE 6-continued

| | Exemplary V_H fragments | | |
|---|---|---|---|
| Target | SEQ ID (DNA) | SEQ ID (PRT) | CONSTRUCT NAME |
| FITC | 376 | 2145 | FITC-vH |
| FITC | 377 | 2146 | FITC-4M-53-vH |
| FITC | 378 | 2147 | FITC-E2-vH |
| FLT3 | 379 | 2148 | FLT3-NC7-vH |
| HIV1-envelop glycoprotein | 380 | 2149 | HIV1-N6-vH |
| FR1 (Folate Receptor a) | 381 | 2150 | FR1-huMov19-vH |
| GAD | 382 | 2151 | GAD-G3H8-vH |
| GD2 | 383 | 2152 | GD2-hu14-18-vH |
| GD2 | 384 | 2153 | GD2-hu3F8-vH |
| GD3 | 385 | 2154 | GD3-KM-641-vH |
| GFRa4 | 386 | 2155 | GFRa4-P4-10-vH |
| GFRa4 | 387 | 2156 | GFRAlpha4-P4-6-vH |
| GM1 | 388 | 2157 | GM1-5B2-vH |
| GM1 | 389 | 2158 | GM1-7E5-vH |
| gp100/MHC class I complex | 390 | 2159 | gp100-G2D12-vH |
| gp100/MHC class I complex | 391 | 2160 | gp100-vH |
| GPC3 | 392 | 2161 | GPC3-4E5-vH |
| gpNMB | 393 | 2162 | gpNMB-115-vH |
| GPRC5D | 394 | 2163 | GPRC5D-ET150-18-vH |
| GPRC5D | 395 | 2164 | GPRC5D-ET150-5-vH |
| GPRC5D | 396 | 2165 | GPRC5D-ET150-1-vH |
| GPRC5D | 397 | 2166 | GPRC5D-ET150-2-vH |
| Her2 | 398 | 2167 | Her2-Hu4D5-vH |
| HIV1-gag (77-85) MHC class I complex | 399 | 2168 | HIV1-3BNC117-vH |
| HIV1-envelop glycoprotein | 400 | 2169 | HIV1-E5-vH |
| HIV1-envelop glycoprotein | 401 | 2170 | HIV1-PGT-128-vH |
| HIV1-envelop glycoprotein | 402 | 2171 | HIV1-VR-C01-vH |
| HIV1-envelop glycoprotein | 403 | 2172 | HIV1-X5-vH |
| HLA-A2 | 404 | 2173 | HLA-A2-3PB2-vH |
| HMW-MAA | 405 | 2174 | HMW-MAA-hIND-vH |
| HPV16-E7/MHC class I complex | 406 | 2175 | HPV16-7-8-vH |
| HPV16-E7/MHC class I complex | 407 | 2176 | HPV16-2-vH |
| HTLV1-TAX/MHC class I | 408 | 2177 | TAX-T3E3-vH |
| HTLV1-TAX/MHC class I | 409 | 2178 | TAX-T3F2-vH |
| IL11Ra | 410 | 2179 | IL11Ra-8E2-vH |
| IL13Ra2 | 411 | 2180 | IL13Ra2-hu107-vH |
| IL13Ra2 | 412 | 2181 | IL13Ra2-Hu108-vH |
| IL6R | 413 | 2182 | IL6R-M83-vH |
| Influenza A HA | 414 | 2183 | FLU-MEDI-8852-vH |
| KSHV-gH | 415 | 2184 | YC15-vH |
| KSHV-K8.1 | 416 | 2185 | 4C3-vH |
| L1CAM | 417 | 2186 | L1CAM-9-3-HU3-vH |
| LAMP1 | 418 | 2187 | LAMP1-humab1-2-vH |
| LAMP1 | 419 | 2188 | LAMP1-Mb4-vH |
| LewisY | 420 | 2189 | LewisY-huS193-vH |
| Lym1 | 421 | 2190 | Lym1-vH |
| Lym2 | 422 | 2191 | Lym2-vH |
| MART1/MHC class I complex | 423 | 2192 | MART1-CAG10-vH |
| MART1/MHC class I complex | 424 | 2193 | MART1-CLA12-vH |
| Mesothelin | 425 | 2194 | Mesothelin-m912-[2]-vH |
| Mesothelin | 426 | 2195 | Mesothelin-m912-vH |
| MPL | 427 | 2196 | MPL-111-vH |
| MPL | 428 | 2197 | MPL-161-HL-vH |
| MPL | 429 | 2198 | MPL-161-vH |
| MPL | 430 | 2199 | MPL-175-vH |
| MPL | 431 | 2200 | MPL-178-vH |
| MPL | 432 | 2201 | MPL-huVB22Bw5-vH |
| MPL | 433 | 2202 | MPL-12E10-vH |
| MPL | 434 | 2203 | MPL-AB317-vH |
| Muc1/MHC class I complex | 435 | 2204 | MUC1-D6-M3A1-vH |
| Muc1/MHC class I complex | 436 | 2205 | Muc1-D6-M3B8-vH |
| Muc16 | 437 | 2206 | Muc16-4H11-vH |
| NKG2D | 438 | 2207 | NKG2D-MS-vH |
| NYBR1 | 439 | 2208 | NYBR1-vH |
| NY-ESO/MHC class I complex | 440 | 2209 | NY-ESO-T1-vH |
| NY-ESO/MHC class I complex | 441 | 2210 | NY-ESO-T2-vH |
| PD1 | 442 | 2211 | PD1-4H1-vH |
| PD1 | 443 | 2212 | PD1-5C4-vH |
| PDL1 | 444 | 2213 | PDL1-Atezoli-vH |
| PDL1 | 445 | 2214 | PDL1-SP142-vH |
| PDL1 | 446 | 2215 | PR1-vH |
| PR1 | 447 | 2216 | PSCA-Ha14-117-vH |
| PSCA | 448 | 2217 | PSCA-Ha14-121-vH |
| PSCA | 449 | 2218 | PSMA-006-vH |
| PSMA | 450 | 2219 | PSMA-J591-vH |

TABLE 6-continued

Exemplary V_H fragments

| Target | SEQ ID (DNA) | SEQ ID (PRT) | CONSTRUCT NAME |
|---|---|---|---|
| PSMA | 451 | 2220 | PTK7-hSC6-23-vH |
| PTK7 | 452 | 2221 | PTK7-SC6-10-2-vH |
| PTK7 | 453 | 2222 | ROR1-4A5-vH |
| ROR1 | 454 | 2223 | ROR1-4C10-vH |
| ROR1 | 455 | 2224 | SLea-5B1-vH |
| SLea | 456 | 2225 | SLea-7E3-vH |
| SLea | 457 | 2226 | SSEA4-vH |
| SSEA4 | 458 | 2227 | TCRB1-E09-vH |
| TCRB1 | 459 | 2228 | TCRB1-Jovi1-vH |
| TCRB1 | 460 | 2229 | TCRB2-CP01-D05-vH |
| TCRB2 | 461 | 2230 | TCRB2-CP01-E05-vH |
| TCRB2 | 462 | 2231 | TCRgd-G5-4-vH |
| TCRgd | 463 | 2232 | TERT-3G3-T865-vH |
| TERT/MHC class I complex | 464 | 2233 | TERT-4A9-T540-vH |
| TERT/MHC class I complex | 465 | 2234 | TF1-98-vH |
| TF1 | 466 | 2235 | TGFBR2-Ab1-vH |
| TGFBR2 | 467 | 2236 | TIM1-HVCR1-270-2-vH |
| TIM1 | 468 | 2237 | Tim1HVCR1-ARD5-vH |
| TIM1 | 469 | 2238 | TnAg-vH |
| TnAg | 470 | 2239 | Tn-Muc1-hu5E5-vH |
| Tn-Muc1 | 471 | 2240 | TROP2-ARA47-HV3KV3-vH |
| TROP2 | 472 | 2241 | TROP2-h7E6-SVG-vH |
| TROP2 | 473 | 2242 | TSHR-5C9-vH |
| TSHR | 474 | 2243 | TSHR-K1-70-vH |
| TSHR | 475 | 2244 | TSHR-KB1-vH |
| TSHR | 476 | 2245 | TSLPR-vH |
| TSLRP | 477 | 2246 | Tyro-B2-vH |
| Tyrosinase/MHC class I complex | 478 | 2247 | Tyro-Mc1-vH |
| Tyrosinase/MHC class I complex | 479 | 2248 | TA2-vH |
| Tyrosinase/MHC class I complex | 480 | 2249 | VEGFR3-Ab1-vH |
| VEGFR3 | 481 | 2250 | WT1-Ab13-vH |
| WT1/MHC class I complex | 482 | 2251 | WT1-Ab15-vH |
| WT1/MHC class I complex | 483 | 2252 | WT1-Ab1-vH |
| WT1/MHC class I complex | 484 | 2253 | WT1-Ab5-[2]-vH |
| WT1/MHC class I complex | 485 | 2254 | WT1-Ab5-vH |
| EBV-gp350 | 486 | 2255 | EBV-gp350-vH |
| CDH19 | 487 | 2256 | CDH19-4B10-vH |
| FRbeta | 488 | 2257 | FRbeta-m923-vH |
| LHR | 489 | 2258 | LHR-8B7-vH |
| LHR | 490 | 2259 | LHR-5F4-21-vH |
| B7H4 | 491 | 2260 | B7H4-hu22C10-vH |
| B7H4 | 492 | 2261 | B7H4-hu1D11-vH |
| IgE | 493 | 2262 | IgE-omalizumab-vH |
| CD23 | 494 | 2263 | CD23-p5E8-vH |
| GCC | 495 | 2264 | GCC-5F9-vH |
| GCC | 496 | 2265 | GCC-Ab229-vH |
| CD200R | 497 | 2266 | CD200R-huDx182-vH |
| PDL1 | 498 | 2268 | PDL1-10A5-vH |

TABLE 7

Exemplary V_HH fragments (Nanobodies)

| Target | SEQ ID (DNA) | SEQ ID (PRT) | NAME |
|---|---|---|---|
| Her2 | 499 | 2269 | Her2-2D3-vHH |
| Her2 | 500 | 2270 | Her2-5F7-vHH |
| Her2 | 501 | 2271 | Her2-47D5-vHH |
| Her3 | 502 | 2272 | Her3-17B05So-vHH |
| Her3 | 503 | 2273 | Her3-21F06-vHH |
| CEA | 504 | 2274 | CEA1-vHH |
| CEA | 505 | 2275 | CEA5-vHH |
| EGFR | 506 | 2276 | EGFR1-vHH |
| EGFR | 507 | 2277 | EGFR33-vHH |
| cMet | 508 | 2278 | cMET-171-vHH |
| CXCR4 | 509 | 2279 | CXCR4-2-vHH |
| CXCR4 | 510 | 2280 | CXCR4-1-vHH |
| Mesothelin | 511 | 2281 | SD1-vHH |
| Mesothelin | 512 | 2282 | SD2-vHH |
| Albumin | 513 | 2283 | Alb8-vHH |
| CD123 | 514 | 2284 | CD123-1-vHH |
| CD123 | 515 | 2285 | CD123-2-vHH |
| IL6R | 516 | 2286 | IL6R-304-vHH |
| EGFR & CEA | 517 | 2287 | EGFR1-vHH-Gly-Ser-Linker-CEA1-vHH |
| EGFR & CEA | 518 | 2288 | EGFR33-vHH-Gly-Ser-Linker-CEA5-vHH |
| Her2 | 519 | 2289 | Her2-5F7-vHH-Gly-Linker-Her2-47D5-vHH |
| Her2 | 520 | 2290 | Her2-Hu4D5-vL-Gly-Ser-Linker-Her2-Hu4D5-vH |
| Her3 & Her2 | 521 | 2291 | Her3-17B05So-vHH-Gly-Ser-Linker-Her2-2D3-vHH |
| cMet & Her3 | 522 | 2292 | cMET-171-vHH-Gly-Ser-Linker-Her3-21F06-VHH |
| Mesothelin | 523 | 2293 | SD1-vHH-Gly-Ser-Linker-SD2-vHH |

TABLE 8

Exemplary non-immunoglobulin antigen binding scaffolds (affibodies, darpins)
Table 8. Non-Immunoglobulin Antigen Binding Scaffolds

| Target | SEQ ID (DNA) | SEQ ID (PRT) | NAME |
|---|---|---|---|
| Her2 | 524 | 1743 | Her2-DARPIN-1 |
| Her2 | 525 | 1744 | Her2-DARPIN-2 |
| Her3 | 526 | 1745 | Her3-affi |
| Her2 | 527 | 1746 | Her2-affi |
| EGFR | 528 | 1747 | EGFR-affi |

TABLE 9

Exemplary receptor extracellular domain

| SEQ ID (DNA) | SEQ ID (PRT) | NAME |
|---|---|---|
| 529 | 2299 | CD19-Extracellular-Domain-minus-signal-peptide(61-867) |
| 530 | 2300 | MPL-Extracellular-Domain-with-signal-peptide |
| 531 | 2301 | CD8-SP-PD1-opt-ECD |
| 532 | 2302 | PD1-opt-ECD-minus-signal-peptide |
| 533 | 2303 | PD1-ECD-with-native-Signal-Peptide |
| 534 | 2304 | CTLA4-opt-ECD with signal peptide |
| 535 | 2305 | CD138-SDC1-ECD |
| 536 | 2306 | Synth-CD123-ECD |
| 537 | 2307 | CDH1-ECD |
| 538 | 2308 | CD200R1L-ECD |
| 539 | 2309 | GPNMB-ECD |
| 540 | 2310 | PTK7-ECD |
| 541 | 2311 | CD33-ECD |
| 542 | 2312 | CD34-ECD |
| 543 | 2313 | EpCAM-ECD |
| 544 | 2314 | CLEC12A-ECD |
| 545 | 2315 | CD20-ECx2-ECD |
| 546 | 2316 | CD20-ECx1-ECD |
| 547 | 2317 | CD22-v5-ECD |
| 548 | 2318 | Thyroid Stimulating Hormone Receptor (TSHR)-ECD |
| 549 | 2319 | EGFRviii-ECD |
| 550 | 2320 | BCMA-ECD |
| 551 | 2321 | SLAMF7-CS1-ECD |
| 552 | 2322 | NKG2D-ECD-minus-signal-peptide |

TABLE 10

Exemplary ligands

| SEQ ID (DNA) | SEQ ID (PRT) | NAME |
|---|---|---|
| 553 | 2323 | hTPO (1-187) |
| 554 | 2324 | mTPO(l-187) |
| 555 | 2325 | CGH-alpha-minus-Signal-Peptide |
| 556 | 2326 | CGH-beta-with-Signal-Peptide |
| 557 | 2327 | FSH-beta-minus-Signal-Peptide |
| 558 | 2328 | LH-beta-with-Signal-Peptide |
| 559 | 2329 | TSH-beta-with-Signal-Peptide |
| 560 | 2330 | SP-CGHb-Gly-Ser-Linker-CGHa |
| 561 | 2331 | CD8SP-FSHb-Gly-Ser-Linker-CGHa |
| 562 | 2332 | SP-LHb-Gly-Ser-Linker-CGHa |
| 563 | 2333 | SP-TSHb-Gly-Ser-Linker-CGHa |

TABLE 11

Exemplary Reporter Fragments

| SEQ ID (DNA) | SEQ ID (Prt) | NAME |
|---|---|---|
| 813 | 2029 | GLuc (*Gaussia princeps* Luc) Minus Secretory Signal |
| 814 | 2030 | NLuc (NanoLuc) |
| 815 | 2031 | TLuc (TurboLuc16) Minus Secretory Signal |
| 816 | 2032 | MLuc7-(*Metrida longa* Luc7) M43L/M110L Variant Minus Secretory Signal |
| 817 | 2033 | LoLuc (*Lucicutia ovaliformis* Luc) Minus Secretory Signal |
| 818 | 2034 | HtLuc (*H. tanneri* Luc) Minus Secretory Signal |
| 819 | 2035 | PaLuc1 (*Pleuromamma abdominalis* Luc1) minus Secretory Signal |
| 820 | 2036 | PaLuc2 (*Pleuromamma abdominalis* Luc2)-minus Secretory Signal |
| 821 | 2037 | MpLuc1 [*Metridia pacifica* Luc1] minus secretory signal |
| 822 | 2038 | McLuc1 [*Metridia curticauda* Luc1] minus secretory signal |
| 823 | 2039 | MaLuc1 [*Metridia asymmetrica* Luc1] minus secretory signal |
| 824 | 2040 | MoLuc1 [*Metridia okhotensis* Luc1] minus secretory signal |
| 825 | 2041 | MoLuc2 [*Metridia okhotensis* Luc2] minus secretory signal |
| 826 | 2042 | MLuc39 [*Metridia longa* Luc39] minus secretory signal |
| 827 | 2043 | PsLuc1 [*Pleuromamma scutullata* Luc1] minus secretory signal |
| 828 | 2044 | LoLuc1-3 [*Lucicutia ovaliformis* Luc1-3] minus secretory signal |
| 829 | 2045 | HtLuc2 [*Heterorhabdus tanneri* Luc2] minus secretory signal |
| 830 | 2046 | *Renilla* Luc |

TABLE 12

Exemplary cleavable linkers and furine cleavage site

| NAME | SEQ ID (DNA) | SEQ ID (PRT) |
|---|---|---|
| F2A | 831 | 2598 |
| T2A | 832 | 2599 |
| T2A | 833 | 2599 |
| P2A | 834 | 2600 |
| P2a-variant | 835 | 2601 |
| E2A | 836 | 2602 |
| SGSG | 837 | 2603 |
| SGSG | 838 | 2603 |
| FURINE CLEAVAGE SITE | 839 | 2604 |
| FURINE CLEAVAGE SITE | 840 | 2604 |
| FURINE Cleavage Site | 841 | 2604 |

TABLE 13

Epitope Tags

| SEQ ID (DNA) | SEQ ID (PRT) | NAME |
|---|---|---|
| 553 | 2569 | Myc-TAG |
| 554 | 2570 | FLAG-TAG |
| 555 | 2571 | AcV5 |
| 556 | 2572 | V5-TAG |
| 557 | 2573 | HA-TAG |
| 558 | 2574 | HIS-TAG |
| 559 | 2575 | AVI-TAG-delta-GSG |
| 560 | 2576 | StrepTagII |
| 561 | 2577 | 4XFLAG-2xSTREP-8xHIS |
| 562 | 2578 | 3xFLAG |
| 563 | 2579 | 4xHA-Strep-8xHis |
| 3526 | 3530 | RITX-TAG |
| 3527 | 3531 | RITX2-TAG |
| 3528 | 3532 | RITX4-TAG |
| 3529 | 3533 | GA-TAG |

TABLE 14

Exemplary scFv fragments

| Target | SEQ ID (DNA) | SEQ ID (PRT) | CONSTRUCT NAME |
|---|---|---|---|
| CD19 | 564 | 2334 | FMC63-(vL-vH) |
| CD19 | 565 | 2335 | huFMC63-11-(vL-vH) |
| CD19 | 566 | 2336 | CD19Bu12-(vL-vH) |
| CD19 | 567 | 2337 | CD19MM-(vL-vH) |
| CD19 | 568 | 2338 | CD19-4G7-(vL-vH) |
| CD19 | 569 | 2339 | CD19-MEDI-3649-(vL-vH) |
| CD19 | 570 | 2340 | CD19-Medrex-24D1-(vL-vH) |
| CD19 | 571 | 2341 | CD8SP-Ritx-CD19-MOR0028-(vL-vH) |
| CD19 | 572 | 2342 | CD19-HD37-H2L1-(vL-vH) |
| CD19 | 573 | 2343 | CD19-huBly3-(vL-vH) |
| CD19 | 574 | 2344 | CD19-huSJ25C1-(vL-vH) |
| CD19 | 575 | 2345 | CD8SP-Ritx-CD19-hB4-(vL-vH) |
| CD19 | 576 | 2346 | CD19-hu-mROO5-1-(vL-vH) |
| CD19 | 577 | 2347 | CD19-hA19-(vL-vH) |
| AFP/MHC class I complex | 578 | 2348 | AFP-61-(vL-vH) |
| AFP/MHC class I complex | 579 | 2349 | AFP-76-(vL-vH) |
| AFP/MHC class I complex | 580 | 2350 | AFP-79-(vL-vH) |
| HIV1-env | 581 | 2351 | HIV1-N6-(vL-vH) |
| ALK | 582 | 2352 | Alk-48-(vL-vH) |
| ALK | 583 | 2353 | Alk-58-(vL-vH) |
| Amyloid | 584 | 2354 | Amyloid-158-(vL-vH) |
| CD45 | 585 | 2355 | BC8-CD45-(vL-vH) |
| BCMA | 586 | 2356 | BCMA-J6M0-(vL-vH) |
| BCMA | 587 | 2357 | BCMA-huC12A3-L3H3-(vL-vH) |
| BCMA | 588 | 2358 | BCMA-ET-40-(vL-vH) |
| BCMA | 589 | 2359 | BCMA-ET-54-(vL-vH) |
| BCMA | 590 | 2360 | BCMA-ET-03-(vL-vH) |
| BCMA | 591 | 2361 | BCMA-huC11.D5.3L1H3-(vL-vH) |
| BCMA | 592 | 2362 | BCMA-huC13-F12-(vL-vH) |
| CCR4 | 593 | 2363 | CCR4-humAb1567-(vL-vH) |
| CD5 | 594 | 2364 | CD5-9-(vL-vH) |
| CD5 | 595 | 2365 | CD5-18-(vL-vH) |
| CD20 | 596 | 2366 | CD20-2F2-(vL-vH) |
| CD20 | 597 | 2367 | CD20-GA101-(vL-vH) |
| CD22 | 598 | 2368 | CD22-h10F4v2-(vL-vH) |
| CD20 | 599 | 2369 | CD20-Leu16-(vL-vH) |
| CD20 | 600 | 2370 | CD20-11B8-(vL-vH) |
| CD20 | 601 | 2371 | CD20-2C6-(vL-vH) |
| CD20 | 602 | 2372 | CD20-2H7-(vL-vH) |
| CD20 | 603 | 2373 | CD20-hA20-(vL-vH) |
| CD20 | 604 | 2374 | CD20-BM-CA-1925-v4-(vL-vH) |
| CD20 | 605 | 2375 | CD20-Ubli-v4-(vL-vH) |
| CD20 | 606 | 2376 | CD20-2H7-(vL-vH) |
| CD20 | 607 | 2377 | CD20-h1F5-(vL-vH) |
| CD20 | 608 | 2378 | CD20-7D8-(vL-vH) |
| CD20 | 609 | 2379 | CD20-7D8-(vL-GA-tag-vH) |
| CD20 | 610 | 2380 | CD20-AME-33-(vL-vH) |
| CD22 | 611 | 2381 | CD22-H22Rhov2ACDRKA-(vL-vH) |
| CD22 | 612 | 2382 | CD22-m971-(vL-vH) |
| CD22 | 613 | 2383 | CD22-m971-HL-(vL-vH) |
| CD30 | 614 | 2384 | CD30-5F11-(vL-vH) |

TABLE 14-continued

Exemplary scFv fragments

| Target | SEQ ID (DNA) | SEQ ID (PRT) | CONSTRUCT NAME |
|---|---|---|---|
| CD30 | 615 | 2385 | CD30-Ac10-(vL-vH) |
| CD32 | 616 | 2386 | CD32-Med9-(vL-vH) |
| CD33 | 617 | 2387 | CD33-AF5-(vL-vH) |
| CD33 | 618 | 2388 | CD33-huMyc9-(vL-vH) |
| CD33 | 619 | 2389 | CD8SP-Ritx2-BC33-Boehr2800308-(vL-vH) |
| CD33 | 620 | 2390 | CD8SP-Ritx2-CD33-Him3-4-(vL-vH) |
| CD33 | 621 | 2391 | CD33-SGNh2H12-(vL-vH) |
| CD33 | 622 | 2392 | CD33-15G15-33-(vL-vH) |
| CD33 | 623 | 2393 | CD33-33H4-(vL-vH) |
| CD33 | 624 | 2394 | CD33-9C3-2-(vL-vH) |
| CD34 | 625 | 2395 | CD34-hu4C7-(vL-vH) |
| CD44v6 | 626 | 2396 | CD44v6-Biwa8-(vL-vH) |
| CD70 | 627 | 2397 | CD70-h1F6-(vL-vH) |
| CD79b | 628 | 2398 | CD79b-2F2-(vL-vH) |
| CD99 | 629 | 2399 | CD99-hu12E7-(vL-vH) |
| CD123 | 630 | 2400 | CD123-CSL362-(vL-vH) |
| CD123 | 631 | 2401 | CD123-1172-(vL-vH) |
| CD123 | 632 | 2402 | CD123-DART1-1-(vL-vH) |
| CD123 | 633 | 2403 | CD123-DART1-2-(vL-vH) |
| CD123 | 634 | 2404 | CD123-I3RB18-(vL-vH) |
| CD123 | 635 | 2405 | CD123-hu3E3-(vL-vH) |
| CD123 | 636 | 2406 | CD123-9F6-(vL-vH) |
| CD123 | 637 | 2407 | CD123-I3RB2-(vL-vH) |
| CD123 | 638 | 2408 | CD123-1176-(vL-vH) |
| CD123 | 639 | 2409 | CD8SP-Ritx2-CD123-8B11-(vL-vH) |
| CD123 | 640 | 2410 | CD123-2B8-(vL-vH) |
| CD123 | 641 | 2411 | CD123-9D7-(vL-vH) |
| CD123 | 642 | 2412 | CD123-3B10-(vL-vH) |
| CD138 | 643 | 2413 | CD138-(vL-vH) |
| CD179b | 644 | 2414 | CD179b-(vL-vH) |
| CD276 | 645 | 2415 | CD276-17-(vL-vH) |
| CD324 | 646 | 2416 | CD324-SC10-6-(vL-vH) |
| CD324 | 647 | 2417 | CD324-hSC10-17-(vL-vH) |
| CDH6 | 648 | 2418 | CDH6-NOV710-(vL-vH) |
| CDH6 | 649 | 2419 | CDH6-NOV712-(vL-vH) |
| CDH17 | 650 | 2420 | CDH17-PTA001A4-(vL-vH) |
| CDH19 | 651 | 2421 | CDH19-16A4-(vL-vH) |
| EGFR | 652 | 2422 | Cetuximab-(vL-vH) |
| CLEC5A | 653 | 2423 | CLEC5A-8H8F5-(vL-vH) |
| CLEC5A | 654 | 2424 | CLEC5A-3E12A2-(vL-vH) |
| CLL1 | 655 | 2425 | CLL1-M26-(vL-vH) |
| CLL1 | 656 | 2426 | CLL1-M32-(vL-vH) |
| CLL1 | 657 | 2427 | CLL1-21C9-L2H3-(vL-vH) |
| CLL1 | 658 | 2428 | CLL1-6E7L4H1e-(vL-vH) |
| CLL1 | 659 | 2429 | CLL1-hu1075-v1-(vL-vH) |
| CLL1 | 660 | 2430 | CLL1-hu1075-v2-(vL-vH) |
| CMVpp65/MHC class I complex | 661 | 2431 | CMVpp65-F5-(vL-vH) |
| CS1 | 662 | 2432 | CS1-huLuc63-(vL-vH) |
| CS1 | 663 | 2433 | CS1-HuLuc64-(vL-vH) |
| CS1 | 664 | 2434 | CS1-Luc90-(vL-vH) |
| CS1 | 665 | 2435 | CS1-PDL241-(vL-vH) |
| CS1 | 666 | 2436 | CS1-Hu27A-(vL-vH) |
| CS1 | 667 | 2437 | CS1-ScHu34C3-(vL-vH) |
| CS1 | 668 | 2438 | CS1-Hu31-D2-(vL-vH) |
| CS1 | 669 | 2439 | CS1-Luc34-(vL-vH) |
| CS1 | 670 | 2440 | CS1-LucX2-(vL-vH) |
| CSF2RA | 671 | 2441 | CSF2RA-Ab6-(vL-vH) |
| CSF2RA | 672 | 2442 | CSF2RA-Ab1-(vL-vH) |
| DLL3 | 673 | 2443 | DLL3-hSC16-13-(vL-vH) |
| DLL3 | 674 | 2444 | DLL3-hSC16-56-(vL-vH) |
| EBNA3c | 675 | 2445 | EBNA3c-315-(vL-vH) |
| EBV-gp350 | 676 | 2446 | EBV-gp350-(vL-vH) |
| EGFRvIII | 677 | 2447 | EGFRvIII-139-(vL-vH) |
| EGFRvIII | 678 | 2448 | EGFRvIII-2173-(vH-vL) |
| EpCam1 | 679 | 2449 | Epcam1-MM1-(vL-vH) |
| EpCam1 | 680 | 2450 | Epcam1-D5K5-(vL-vH) |
| FLT3 | 681 | 2451 | FLT3-NC7-(vL-vH) |
| FITC | 682 | 2452 | FITC-(vL-vH) |
| FITC | 683 | 2453 | FITC-4M-53-(vL-vH) |
| FITC | 684 | 2454 | FITC-E2-HL-(vH-vL) |
| Influenza A HA | 685 | 2455 | FLU-MEDI-8852-(vL-vH) |
| FR1 (Folate Receptor a) | 686 | 2456 | FR1-huMov19-(vL-vH) |
| GAD | 687 | 2457 | GAD-G3H8-(vL-vH) |
| GD2 | 688 | 2458 | GD2-hu14-18-(vL-vH) |
| GD2 | 689 | 2459 | GD2-hu3F8-(vL-vH) |

TABLE 14-continued

Exemplary scFv fragments

| Target | SEQ ID (DNA) | SEQ ID (PRT) | CONSTRUCT NAME |
|---|---|---|---|
| GD3 | 690 | 2460 | GD3-KM-641-(vL-vH) |
| GFRa4 | 691 | 2461 | GFRAlpha4-P4-6-(vL-vH) |
| GFRa4 | 692 | 2462 | GFRa4-P4-10-(vL-vH) |
| GM1 | 693 | 2463 | GM1-5B2-(vL-vH) |
| GM1 | 694 | 2464 | GM1-7E5-(vL-vH) |
| GPRC5D | 695 | 2465 | GPRC5D-ET150-5-(vL-vH) |
| GPRC5D | 696 | 2466 | GPRC5D-ET150-18-(vL-vH) |
| GPRC5D | 697 | 2467 | GPRC5D-ET150-1-(vL-vH) |
| GPRC5D | 698 | 2468 | GPRC5D-ET150-2-(vL-vH) |
| gp100/MHC class I complex | 699 | 2469 | gp100-(vL-vH) |
| gp100/MHC class I complex | 700 | 2470 | gp100-G2D12-(vL-vH) |
| GPC3 | 701 | 2471 | GPC3-4E5-(vL-vH) |
| gpNMB | 702 | 2472 | gpNMB-115-(vL-vH) |
| GRP78 | 703 | 2473 | GRP78-GC18-(vL-vH) |
| HIV-gag/MHC class I complex | 704 | 2474 | HIV1-E5-(vL-vH) |
| HIV1-env | 705 | 2475 | HIV1-3BNC117-(vL-vH) |
| HIV1-env | 706 | 2476 | HIV1-PGT-128-(vL-vH) |
| HIV1-env | 707 | 2477 | HIV1-VR-C01-(vL-vH) |
| HIV1-env | 708 | 2478 | HIV1-X5-(vL-vH) |
| HLA-A2 | 709 | 2479 | HLA-A2-3PB2-(vL-vH) |
| HMW-MAA | 710 | 2480 | HMW-MAA-hIND-(vL-vH) |
| HPV16 | 711 | 2481 | HPV16-7-8-(vL-vH) |
| HPV16 | 712 | 2482 | HPV16-2-(vL-vH) |
| HTLV1-TAX/MHC class I complex | 713 | 2483 | HTLV-TAX-T3F2-(vL-vH) |
| HTLV1-TAX/MHC class I complex | 714 | 2484 | HTLV-TAX-T3E3-(vL-vH) |
| IL11Ra | 715 | 2485 | IL11Ra-8E2-Ts107-(vL-vH) |
| IL13Ra2 | 716 | 2486 | IL13Ra2-hu107-(vL-vH) |
| IL13Ra2 | 717 | 2487 | IL13Ra2-Hu108-(vL-vH) |
| KSHV-K8.1 | 718 | 2488 | KSHV-4C3-(vL-vH) |
| LAMP1 | 719 | 2489 | LAMP1-humab1-2-(vL-vH) |
| LAMP1 | 720 | 2490 | LAMP1-Mb4-(vL-vH) |
| LewisY | 721 | 2491 | LewisY-huS193-(vL-vH) |
| L1CAM | 722 | 2492 | L1CAM-9-3-HU3-(vL-vH) |
| Lym1 | 723 | 2493 | Lym1-(vL-vH) |
| Lym2 | 724 | 2494 | Lym2-(vL-vH) |
| CD79b | 725 | 2495 | huMA79bv28-(vL-vH) |
| MART/MHC class I complex1 | 726 | 2496 | MART1-CAG10-(vL-vH) |
| MART/MHC class I complex1 | 727 | 2497 | MART1-CLA12-(vL-vH) |
| Mesothelin | 728 | 2498 | Mesothelin-m912-(vL-vH) |
| MPL | 729 | 2499 | MPL-175-(vL-vH) |
| MPL | 730 | 2500 | MPL-161-(vL-vH) |
| MPL | 731 | 2501 | MPL-161-HL-(vH-vL) |
| MPL | 732 | 2502 | MPL-111-(vL-vH) |
| MPL | 733 | 2503 | MPL-178-(vL-vH) |
| MPL | 734 | 2504 | MPL-AB317-(vL-vH) |
| MPL | 735 | 2505 | MPL-12E10-(vL-vH) |
| MPL | 736 | 2506 | MPL-huVB22Bw5-(vL-vH) |
| Muc1/MHC class I complex | 737 | 2507 | Muc1-D6-M3B8-(vL-vH) |
| Muc1/MHC class I complex | 738 | 2508 | MUC1-D6-M3A1-(vL-vH) |
| Muc16 | 739 | 2509 | Muc16-4H11-(vL-vH) |
| EGFR | 740 | 2510 | Nimotuzumab-(vL-vH) |
| NKG2D | 741 | 2511 | NKG2D-MS-(vL-vH) |
| NYBR1 | 742 | 2512 | NYBR1-(vL-vH) |
| NY-ESO/MHC class I complex | 743 | 2513 | NYESO-T1-(vL-vH) |
| NY-ESO/MHC class I complex | 744 | 2514 | NYESO-T2-(vL-vH) |
| PDL1 | 745 | 2515 | PDL1-Atezoli-(vL-vH) |
| PDL1 | 746 | 2516 | PDL1-SP142-(vL-vH) |
| PDL1 | 747 | 2517 | PDL1-10A5-(vL-vH) |
| PSCA | 748 | 2518 | PSCA-Ha14-121-(vL-vH) |
| PSCA | 749 | 2519 | PSCA-Ha14-117-(vL-vH) |
| PR1/MHC class I complex | 750 | 2520 | PR1-(vL-vH) |
| PSMA | 751 | 2521 | PSMA-006-(vL-vH) |
| PSMA | 752 | 2522 | PSMA-J591-(vL-vH) |
| PTK7 | 753 | 2523 | PTK7-hSC6-23-(vL-vH) |
| PTK7 | 754 | 2524 | PTK7-SC6-10-2-(vL-vH) |
| ROR1 | 755 | 2525 | ROR1-4A5-(vL-vH) |
| ROR1 | 756 | 2526 | ROR1-4C10-(vL-vH) |
| Mesothelin | 757 | 2527 | SD1-vHH-Gly-Ser-Linker-SD2-vHH |
| SLea | 758 | 2528 | SLea-7E3-(vL-vH) |
| SLea | 759 | 2529 | SLea-5B1-(vL-vH) |
| SSEA4 | 760 | 2530 | SSEA4-(vL-vH) |
| TCRB1 | 761 | 2531 | TCRB1-CP01-E09-(vL-vH) |
| TCRB1 | 762 | 2532 | TCRB1-Jovi1-(vL-vH) |
| TCRB2 | 763 | 2533 | TCRB2-CP01-D05-(vL-vH) |

TABLE 14-continued

Exemplary scFv fragments

| Target | SEQ ID (DNA) | SEQ ID (PRT) | CONSTRUCT NAME |
|---|---|---|---|
| TCRB2 | 764 | 2534 | TCRB2-CP01-E05-(vL-vH) |
| TCRgd | 765 | 2535 | TCRgd-G5-4-(vL-vH) |
| hTERT | 766 | 2536 | TERT-4A9-T540-(vL-vH) |
| hTERT | 767 | 2537 | TERT-3G3-T865-(vL-vH) |
| Tissue Factor | 768 | 2538 | TF1-98-(vL-vH) |
| TGFBR2 | 769 | 2539 | TGFBR2-Ab1-(vL-vH) |
| TIM1 | 770 | 2540 | TIM1-HVCR1-270-2-(vL-vH) |
| TIM1 | 771 | 2541 | TIM1-HVCR1-ARD5-(vL-vH) |
| TnAg | 772 | 2542 | TnAg-(vL-vH) |
| Tn-Muc1 | 773 | 2543 | TnMuc1-hu5E5-RHA8-RKA-2-(vL-vH) |
| TROP2 | 774 | 2544 | TROP2-ARA47-HV3KV3-(vL-vH) |
| TROP2 | 775 | 2545 | TROP2-h7E6-SVG-(vL-vH) |
| TSHR | 776 | 2546 | TSHR-K1-70-(vL-vH) |
| TSHR | 777 | 2547 | TSHR-KB1-(vL-vH) |
| TSHR | 778 | 2548 | TSHR-5C9-(vL-vH) |
| TSLPR | 779 | 2549 | TSLPR-(vL-vH) |
| Tyrosinase/MHC class I complex | 780 | 2550 | Tyros-B2-(vL-vH) |
| Tyrosinase/MHC class I complex | 781 | 2551 | Tyros-MC1-(vL-vH) |
| Tyrosinase/MHC class I complex | 782 | 2552 | Tyros-TA2-(vL-vH) |
| VEGFR3 | 783 | 2553 | VEGFR3-Ab1-(vL-vH) |
| WT1/MHC class I complex | 784 | 2554 | WT1-Ab1-(vL-vH) |
| WT1/MHC class I complex | 785 | 2555 | WT1-Ab5-(vL-vH) |
| WT1/MHC class I complex | 786 | 2556 | WT1-Ab13-(vL-vH) |
| WT1/MHC class I complex | 787 | 2557 | WT1-Ab15-(vL-vH) |
| CDH19 | 788 | 2558 | CDH19-4B10-(vL-vH) |
| Folate Receptor beta | 789 | 2559 | FRbeta-m923-(vL-vH) |
| LHR | 790 | 2560 | LHR-8B7-(vL-vH) |
| LHR | 791 | 2561 | LHR-5F4-21-(vL-vH) |
| B7H4 | 792 | 2562 | B7H4-hu22C10-(vL-vH) |
| B7H4 | 793 | 2563 | B7H4-hu1D11-(vL-vH) |
| IgE | 794 | 2564 | IgE-omalizumab-(vL-vH) |
| CD23 | 795 | 2565 | CD23-p5E8-(vL-vH) |
| GCC | 796 | 2566 | GCC-5F9-(vL-vH) |
| GCC | 797 | 2567 | GCC-Ab229-(vL-vH) |
| CD200R | 798 | 2568 | CD200R-huDx182-(vL-vH) |

TABLE 15

Exemplary scFv-GGS-Luc Constructs

| Clone ID # | Target | SEQ ID (DNA) | SEQ ID (PRT) | CONSTRUCT NAME |
|---|---|---|---|---|
|  | CD19 | 854 | 2054 | CD8SP-FMC63-(vL-vH)-GGSG-NLuc-4xFLAG-x2STREP-8xHis-T2A-PAC |
| 020317-E05 | CD19 | 855 | 2055 | CD8SP-huFMC63-11-(vL-vH)-GGSG-NLuc-4xFLAG-x2STREP-8xHis-T2A-PAC |
| 121516-F01 | CD19 | 856 | 2056 | CD8SP-huFMC63-11-N203Q-(vL-vH)-GGSG-NLuc-4xFLAG-x2STREP-8xHis-T2A-PAC |
|  | CD19 | 857 | 2057 | CD8SP-CD19Bu12-(vL-vH)-GGSG-NLuc-4xFLAG-x2STREP-8xHis-T2A-PAC |
| 021517-L02 | CD19 | 858 | 2058 | CD8SP-2-CD19MM-(vL-vH)-GGSG-NLuc-4xFLAG-x2STREP-8xHis-T2A-PAC |
| 062916-C08 | CD19 | 859 | 2059 | CD8SP-CD19-4G7-(vL-vH)-GGSG-NLuc-4xFLAG-x2STREP-8xHis-T2A-PAC |
| 011817-A01 | CD19 | 860 | 2060 | CD8SP-CD19-MEDI-3649-(vL-vH)-GGSG-NLuc-4xFLAG-x2STREP-8xHis-T2A-PAC |
|  | CD19 | 861 | 2061 | CD8SP-CD19-Medrex-24D1-(vL-vH)-GGSG-NLuc-4xFLAG-x2STREP-8xHis-T2A-PAC |
|  | CD19 | 862 | 2062 | CD8SP-Ritx-CD19-MOR0028-(vL-vH)-GGSG-NLuc-4xFLAG-x2STREP-8xHis-T2A-PAC |
|  | CD19 | 863 | 2063 | CD8SP-CD19-HD37-H2L1-(vL-vH)-GGSG-NLuc-4xFLAG-x2STREP-8xHis-T2A-PAC |
| 020317-I04 | CD19 | 864 | 2064 | CD8SP-CD19-huBly3-(vL-vH)-GGSG-NLuc-4xFLAG-x2STREP-8xHis-T2A-PAC |
| 022817-C04 | CD19 | 865 | 2065 | CD8SP-CD19-huSJ25C1-(vL-vH)-GGSG-NLuc-4xFLAG-x2STREP-8xHis-T2A-PAC |
| 022817-F06 | CD19 | 866 | 2066 | CD8SP-Ritx-CD19-hB4-(vL-vH)-GGSG-NLuc-4xFLAG-x2STREP-8xHis-T2A-PAC |
|  | CD19 | 867 | 2067 | CD8SP-CD19-hu-mROO5-1-(vL-vH)-GGSG-NLuc-4xFLAG-x2STREP-8xHis-T2A-PAC |

TABLE 15-continued

Exemplary scFv-GGS-Luc Constructs

| Clone ID # | Target | SEQ ID (DNA) | SEQ ID (PRT) | CONSTRUCT NAME |
|---|---|---|---|---|
| 022817-H03 | CD19 | 868 | 2068 | CD8SP-CD19-hA19-(vL-vH)-GGSG-NLuc-4xFLAG-x2STREP-8xHis-T2A-PAC |
| 022217-K04 | AFP/MHC class I complex | 869 | 2069 | CD8SP-AFP-61-(vL-vH)-GGSG-NLuc-4xFLAG-x2STREP-8xHis-T2A-PAC |
| | AFP/MHC class I complex | 870 | 2070 | CD8SP-AFP-76-(vL-vH)-GGSG-NLuc-4xFLAG-x2STREP-8xHis-T2A-PAC |
| | AFP/MHC class I complex | 871 | 2071 | CD8SP-AFP-79-(vL-vH)-GGSG-NLuc-4xFLAG-x2STREP-8xHis-T2A-PAC |
| 121516-D05 | HIV1-envelop glycoprotein | 872 | 2072 | CD8SP-HIV1-N6-(vL-vH)-GGSG-NLuc-4xFLAG-x2STREP-8xHis-T2A-PAC |
| 061316-B05 | ALK (Anaplastic Lymphoma Kinase) | 873 | 2073 | CD8SP-Alk-48-(vL-vH)-GGSG-NLuc-4xFLAG-x2STREP-8xHis-T2A-PAC |
| 061416-C04 | ALK (Anaplastic Lymphoma Kinase) | 874 | 2074 | CD8SP-Alk-58-(vL-vH)-GGSG-NLuc-4xFLAG-x2STREP-8xHis-T2A-PAC |
| | Amyloid | 875 | 2075 | SP-Amyloid-158-(vL-vH)-GGSG-NLuc-4xFLAG-x2STREP-8xHis-T2A-PAC |
| 062116-A05 | Biotin | 876 | 2076 | CD8SP-dc-Avidin-GGSG-NLuc-4xFLAG-x2STREP-8xHis-T2A-PAC |
| | CD45 | 877 | 2077 | CD8SP-BC8-CD45-(vL-vH)-GGSG-NLuc-4xFLAG-x2STREP-8xHis-T2A-PAC |
| | BCMA | 878 | 2078 | CD8SP-BCMA-J6M0-(vL-vH)-GGSG-NLuc-4xFLAG-x2STREP-8xHis-T2A-PAC |
| | BCMA | 879 | 2079 | CD8SP-BCMA-huC12A3-L3H3-(vL-vH)-GGSG-NLuc-4xFLAG-x2STREP-8xHis-T2A-PAC |
| 092016-A02 | BCMA | 880 | 2080 | CD8SP-BCMA-ET-40-(vL-vH)-GGSG-NLuc-4xFLAG-x2STREP-8xHis-T2A-PAC |
| 092016-B04 | BCMA | 881 | 2081 | CD8SP-BCMA-ET-54-(vL-vH)-GGSG-NLuc-4xFLAG-x2STREP-8xHis-T2A-PAC |
| | BCMA | 882 | 2082 | CD8SP-BCMA-ET-03-(vL-vH)-GGSG-NLuc-4xFLAG-x2STREP-8xHis-T2A-PAC |
| | BCMA | 883 | 2083 | CD8SP-BCMA-huC11.D5.3L1H3-(vL-vH)-GGSG-NLuc-4xFLAG-x2STREP-8xHis-T2A-PAC |
| | BCMA | 884 | 2084 | CD8SP-BCMA-huC13-F12-(vL-vH)-GGSG-NLuc-4xFLAG-x2STREP-8xHis-T2A-PAC |
| | CCR4 | 885 | 2085 | CD8SP-CCR4-humAb1567-(vL-vH)-GGSG-NLuc-4xFLAG-x2STREP-8xHis-T2A-PAC |
| | HIV1-envelop glycoprotein | 886 | 2086 | CD8SP-CD4-ECD-Gly-Ser-Linker-DC-SIGN-GGSG-NLuc-4xFLAG-x2STREP-8xHis-T2A-PAC |
| | CD5 | 887 | 2087 | CD8SP-CD5-9-(vL-vH)-GGSG-NLuc-4xFLAG-x2STREP-8xHis-T2A-PAC |
| | CD5 | 888 | 2088 | CD8SP-CD5-18-(vL-vH)-GGSG-NLuc-4xFLAG-x2STREP-8xHis-T2A-PAC |
| | Ig Fc | 889 | 2089 | CD8SP-CD16A-V158-ECD-v2-GGSG-NLuc-4xFLAG-x2STREP-8xHis-T2A-PAC |
| | Ig Fc | 890 | 2090 | CD8SP-CD16A-V158-ECD-v1-GGSG-NLuc-4xFLAG-x2STREP-8xHis-T2A-PAC |
| | CD20 | 891 | 2091 | CD8SP-CD20-2F2-(vL-vH)-GGSG-NLuc-4xFLAG-x2STREP-8xHis-T2A-PAC |
| 121516-G07 | CD20 | 892 | 2092 | CD8SP-CD20-GA101-(vL-vH)-GGSG-NLuc-4xFLAG-x2STREP-8xHis-T2A-PAC |
| | CD20 | 893 | 2093 | CD8SP-CD20-Leu16-(vL-vH)-GGSG-NLuc-4xFLAG-x2STREP-8xHis-T2A-PAC |
| | CD20 | 894 | 2094 | CD8SP-CD20-11B8-(vL-vH)-GGSG-NLuc-4xFLAG-x2STREP-8xHis-T2A-PAC |
| | CD20 | 895 | 2095 | CD8SP-CD20-2C6-(vL-vH)-GGSG-NLuc-4xFLAG-x2STREP-8xHis-T2A-PAC |
| | CD20 | 896 | 2096 | CD8SP-CD20-2H7-(vL-vH)-GGSG-NLuc-4xFLAG-x2STREP-8xHis-T2A-PAC |
| | CD20 | 897 | 2097 | CD8SP-CD20-hA20-(vL-vH)-GGSG-NLuc-4xFLAG-x2STREP-8xHis-T2A-PAC |
| | CD20 | 898 | 2098 | CD8SP-CD20-BM-CA-1925-v4-(vL-vH)-GGSG-NLuc-4xFLAG-x2STREP-8xHis-T2A-PAC |
| | CD20 | 899 | 2099 | CD8SP-CD20-Ubli-v4-(vL-vH)-GGSG-NLuc-4xFLAG-x2STREP-8xHis-T2A-PAC |

TABLE 15-continued

Exemplary scFv-GGS-Luc Constructs

| Clone ID # | Target | SEQ ID (DNA) | SEQ ID (PRT) | CONSTRUCT NAME |
|---|---|---|---|---|
| 022817-E05 | CD20 | 900 | 2100 | CD8SP-CD20-2H7-(vL-vH)-GGSG-NLuc-4xFLAG-x2STREP-8xHis-T2A-PAC |
| | CD20 | 901 | 2101 | CD8SP-CD20-h1F5-(vL-vH)-GGSG-NLuc-4xFLAG-x2STREP-8xHis-T2A-PAC |
| | CD20 | 902 | 2102 | CD8SP-CD20-7D8-(vL-vH)-GGSG-NLuc-4xFLAG-x2STREP-8xHis-T2A-PAC |
| | CD20 | 903 | 2103 | CD8SP-CD20-AME-33-(vL-vH)-GGSG-NLuc-4xFLAG-x2STREP-8xHis-T2A-PAC |
| | CD22 | 904 | 2104 | CD8SP-CD22-h10F4v2-(vL-vH)-GGSG-NLuc-4xFLAG-x2STREP-8xHis-T2A-PAC |
| 060716-H05 | CD22 | 905 | 2105 | CD8SP-CD22-H22Rhov2ACDRKA-(vL-vH)-GGSG-NLuc-4xFLAG-x2STREP-8xHis-T2A-PAC |
| | CD22 | 906 | 2106 | CD8SP-CD22-m971-(vL-vH)-GGSG-NLuc-4xFLAG-x2STREP-8xHis-T2A-PAC |
| | CD22 | 907 | 2107 | CD8SP-CD22-m971-HL-(vH-vL)-GGSG-NLuc-4xFLAG-x2STREP-8xHis-T2A-PAC |
| | CD30 | 908 | 2108 | CD8SP-CD30-5F11-(vL-vH)-GGSG-NLuc-4xFLAG-x2STREP-8xHis-T2A-PAC |
| 031816-D02 | CD30 | 909 | 2109 | CD8SP-CD30-Ac10-(vL-vH)-GGSG-NLuc-4xFLAG-x2STREP-8xHis-T2A-PAC |
| 081516-W03 | CD32 | 910 | 2110 | CD8SP-CD32-Med9-(vL-vH)-GGSG-NLuc-4xFLAG-x2STREP-8xHis-T2A-PAC |
| | CD33 | 911 | 2111 | CD8SP-CD33-AF5-(vL-vH)-GGSG-NLuc-4xFLAG-x2STREP-8xHis-T2A-PAC |
| | CD33 | 912 | 2112 | CD8SP-CD33-huMyc9-(vL-vH)-GGSG-NLuc-4xFLAG-x2STREP-8xHis-T2A-PAC |
| | CD33 | 913 | 2113 | CD8SP-CD33-Boehr2800308-(vL-vH)-GGSG-NLuc-4xFLAG-x2STREP-8xHis-T2A-PAC |
| 022217-A02 | CD33 | 914 | 2114 | CD8SP-CD33-Him3-4-(vL-vH)-GGSG-NLuc-4xFLAG-x2STREP-8xHis-T2A-PAC |
| | CD33 | 915 | 2115 | CD8SP-CD33-SGNh2H12-(vL-vH)-GGSG-NLuc-4xFLAG-x2STREP-8xHis-T2A-PAC |
| | CD33 | 916 | 2116 | CD8SP-CD33-15G15-33-(vL-vH)-GGSG-NLuc-4xFLAG-x2STREP-8xHis-T2A-PAC |
| 022217-D03 | CD33 | 917 | 2117 | CD8SP-CD33-33H4-(vL-vH)-GGSG-NLuc-4xFLAG-x2STREP-8xHis-T2A-PAC |
| 022217-E04 | CD33 | 918 | 2118 | CD8SP-CD33-9C3-2-(vL-vH)-GGSG-NLuc-4xFLAG-x2STREP-8xHis-T2A-PAC |
| 062816-B06 | CD34 | 919 | 2119 | CD8SP-CD34-hu4C7-(vL-vH)-GGSG-NLuc-4xFLAG-x2STREP-8xHis-T2A-PAC |
| 120716-O05 | CD44v6 | 920 | 2120 | CD8SP-CD44v6-Biwa8-(vL-vH)-GGSG-NLuc-4xFLAG-x2STREP-8xHis-T2A-PAC |
| | CD70 | 921 | 2121 | CD8SP-CD70-h1F6-(vL-vH)-GGSG-NLuc-4xFLAG-x2STREP-8xHis-T2A-PAC |
| | CD79b | 922 | 2122 | CD8SP-CD79b-2F2-(vL-vH)-GGSG-NLuc-4xFLAG-x2STREP-8xHis-T2A-PAC |
| | CD79b | 923 | 2123 | CD8SP-huMA79bv28-(vL-vH)-GGSG-NLuc-4xFLAG-x2STREP-8xHis-T2A-PAC |
| | CD99 | 924 | 2124 | CD8SP-CD99-hu12E7-(vL-vH)-GGSG-NLuc-4xFLAG-x2STREP-8xHis-T2A-PAC |
| | CD123 | 925 | 2125 | CD8SP-CD123-CSL362-(vL-vH)-GGSG-NLuc-4xFLAG-x2STREP-8xHis-T2A-PAC |
| 112216-B03 | CD123 | 926 | 2126 | CD8SP-CD123-1172-(vL-vH)-GGSG-NLuc-4xFLAG-x2STREP-8xHis-T2A-PAC |
| | CD123 | 927 | 2127 | CD8SP-CD123-DART-1-(vL-vH)-GGSG-NLuc-4xFLAG-x2STREP-8xHis-T2A-PAC |
| | CD123 | 928 | 2128 | CD8SP-CD123-DART-2-(vL-vH)-GGSG-NLuc-4xFLAG-x2STREP-8xHis-T2A-PAC |
| | CD123 | 929 | 2129 | CD8SP-CD123-I3RB18-(vL-vH)-GGSG-NLuc-4xFLAG-x2STREP-8xHis-T2A-PAC |
| | CD123 | 930 | 2130 | CD8SP-CD123-hu3E3-(vL-vH)-GGSG-NLuc-4xFLAG-x2STREP-8xHis-T2A-PAC |
| | CD123 | 931 | 2131 | CD8SP-CD123-9F6-(vL-vH)-GGSG-NLuc-4xFLAG-x2STREP-8xHis-T2A-PAC |
| | CD123 | 932 | 2132 | CD8SP-CD123-I3RB2-(vL-vH)-GGSG-NLuc-4xFLAG-x2STREP-8xHis-T2A-PAC |
| | CD123 | 933 | 2133 | CD8SP-CD123-1176-(vL-vH)-GGSG-NLuc-4xFLAG-x2STREP-8xHis-T2A-PAC |
| | CD123 | 934 | 2134 | CD8SP-Ritx2-CD123-8B11-(vL-vH)-GGSG-NLuc-4xFLAG-x2STREP-8xHis-T2A-PAC |
| | CD123 | 935 | 2135 | CD8SP-CD123-2B8-(vL-vH)-GGSG-NLuc-4xFLAG-x2STREP-8xHis-T2A-PAC |
| | CD123 | 936 | 2136 | CD8SP-CD123-9D7-(vL-vH)-GGSG-NLuc-4xFLAG-x2STREP-8xHis-T2A-PAC |
| | CD123 | 937 | 2137 | CD8SP-CD123-3B10-(vL-vH)-GGSG-NLuc-4xFLAG-x2STREP-8xHis-T2A-PAC |

TABLE 15-continued

Exemplary scFv-GGS-Luc Constructs

| Clone ID # | Target | SEQ ID (DNA) | SEQ ID (PRT) | CONSTRUCT NAME |
|---|---|---|---|---|
| 041715-D08 | CD138 | 938 | 2138 | CD8SP-CD138-(vL-vH)-GGSG-NLuc-4xFLAG-x2STREP-8xHis-T2A-PAC |
|  | CD179b | 939 | 2139 | CD8SP-CD179b-(vL-vH)-GGSG-NLuc-4xFLAG-x2STREP-8xHis-T2A-PAC |
| 060716-C02 | CD276 | 940 | 2140 | CD8SP-CD276-17-(vL-vH)-GGSG-NLuc-4xFLAG-x2STREP-8xHis-T2A-PAC |
|  | CD324 | 941 | 2141 | CD8SP-CD324-SC10-6-(vL-vH)-GGSG-NLuc-4xFLAG-x2STREP-8xHis-T2A-PAC |
|  | CD324 | 942 | 2142 | CD8SP-CD324-hSC10-17-(vL-vH)-GGSG-NLuc-4xFLAG-x2STREP-8xHis-T2A-PAC |
|  | CDH6 | 943 | 2143 | CD8SP-CDH6-NOV710-(vL-vH)-GGSG-NLuc-4xFLAG-x2STREP-8xHis-T2A-PAC |
|  | CDH6 | 944 | 2144 | CD8SP-CDH6-NOV712-(vL-vH)-GGSG-NLuc-4xFLAG-x2STREP-8xHis-T2A-PAC |
|  | CDH17 | 945 | 2145 | CD8SP-CDH17-PTA001A4-(vL-vH)-GGSG-NLuc-4xFLAG-x2STREP-8xHis-T2A-PAC |
|  | CDH19 | 946 | 2146 | CD8SP-CDH19-16A4-(vL-vH)-GGSG-NLuc-4xFLAG-x2STREP-8xHis-T2A-PAC |
| C03-071916 | EGFR | 947 | 2147 | CD8SP-Cetuximab-(vL-vH)-GGSG-NLuc-4xFLAG-x2STREP-8xHis-T2A-PAC |
| 060716-E05 | CLEC5A | 948 | 2148 | CD8SP-CLEC5A-8H8F5-(vL-vH)-GGSG-NLuc-4xFLAG-x2STREP-8xHis-T2A-PAC |
| 060716-G01 | CLEC5A | 949 | 2149 | CD8SP-CLEC5A-3E12A2-(vL-vH)-GGSG-NLuc-4xFLAG-x2STREP-8xHis-T2A-PAC |
| 082216-X02 | GR/LHR (Gonadotropin Receptor) | 950 | 2150 | SP-CGHb-Gly-Ser-Linker-CGHa-GGSG-NLuc-4xFLAG-x2STREP-8xHis-T2A-PAC |
|  | CLL1 | 951 | 2151 | CD8SP-CLL1-M26-(vL-vH)-GGSG-NLuc-4xFLAG-x2STREP-8xHis-T2A-PAC |
|  | CLL1 | 952 | 2152 | CD8SP-CLL1-M32-(vL-vH)-GGSG-NLuc-4xFLAG-x2STREP-8xHis-T2A-PAC |
| 020117-F06 | CLL1 | 953 | 2153 | CD8SP-CLL1-21C9-L2H3-(vL-vH)-GGSG-NLuc-4xFLAG-x2STREP-8xHis-T2A-PAC |
|  | CLL1 | 954 | 2154 | CD8SP-CLL1-6E7L4H1e-(vL-vH)-GGSG-NLuc-4xFLAG-x2STREP-8xHis-T2A-PAC |
| 022217-G06 | CLL1 | 955 | 2155 | CD8SP-CLL1-hu1075-v1-(vL-vH)-GGSG-NLuc-4xFLAG-x2STREP-8xHis-T2A-PAC |
|  | CLL1 | 956 | 2156 | CD8SP-CLL1-hu1075-v2-(vL-vH)-GGSG-NLuc-4xFLAG-x2STREP-8xHis-T2A-PAC |
|  | CMVpp65/MHC class I complex | 957 | 2157 | CD8SP-CMVpp65-F5-(vL-vH)-GGSG-NLuc-4xFLAG-x2STREP-8xHis-T2A-PAC |
|  | CS1 (SLAMF7) | 958 | 2158 | CD8SP-CS1-huLuc63-(vL-vH)-GGSG-NLuc-4xFLAG-x2STREP-8xHis-T2A-PAC |
| 101216-A04 | CS1 (SLAMF7) | 959 | 2159 | CD8SP-CS1-HuLuc64-(vL-vH)-GGSG-NLuc-4xFLAG-x2STREP-8xHis-T2A-PAC |
|  | CS1 (SLAMF7) | 960 | 2160 | CD8SP-CS1-Luc90-(vL-vH)-GGSG-NLuc-4xFLAG-x2STREP-8xHis-T2A-PAC |
|  | CS1 (SLAMF7) | 961 | 2161 | CD8SP-CS1-PDL241-(vL-vH)-GGSG-NLuc-4xFLAG-x2STREP-8xHis-T2A-PAC |
|  | CS1 (SLAMF7) | 962 | 2162 | CD8SP-CS1-Hu27A-(vL-vH)-GGSG-NLuc-4xFLAG-x2STREP-8xHis-T2A-PAC |
|  | CS1 (SLAMF7) | 963 | 2163 | CD8SP-CS1-ScHu34C3-(vL-vH)-GGSG-NLuc-4xFLAG-x2STREP-8xHis-T2A-PAC |
|  | CS1 (SLAMF7) | 964 | 2164 | CD8SP-CS1-Hu31-D2-(vL-vH)-GGSG-NLuc-4xFLAG-x2STREP-8xHis-T2A-PAC |
|  | CS1 (SLAMF7) | 965 | 2165 | CD8SP-CS1-Luc34-(vL-vH)-GGSG-NLuc-4xFLAG-x2STREP-8xHis-T2A-PAC |
|  | CS1 (SLAMF7) | 966 | 2166 | CD8SP-CS1-LucX2-(vL-vH)-GGSG-NLuc-4xFLAG-x2STREP-8xHis-T2A-PAC |
| 061316-H08 | CSF2RA | 967 | 2167 | CD8SP-CSF2RA-Ab6-(vL-vH)-GGSG-NLuc-4xFLAG-x2STREP-8xHis-T2A-PAC |
| 061316-G03 | CSF2RA | 968 | 2168 | CD8SP-CSF2RA-Ab1-(vL-vH)-GGSG-NLuc-4xFLAG-x2STREP-8xHis-T2A-PAC |
|  | CXCR4 and CD123 | 969 | 2169 | CD8SP-CXCR4-1-vHH-Gly-Ser-Linker-CD123-1-vHH-GGSG-NLuc-4xFLAG-x2STREP-8xHis-T2A-PAC |
|  | CXCR4 and CD123 | 970 | 2170 | CD8SP-CXCR4-2-VHH-Gly-Ser-Linker-CD123-2-VHH-GGSG-NLuc-4xFLAG-x2STREP-8xHis-T2A-PAC |

TABLE 15-continued

Exemplary scFv-GGS-Luc Constructs

| Clone ID # | Target | SEQ ID (DNA) | SEQ ID (PRT) | CONSTRUCT NAME |
|---|---|---|---|---|
| | DLL3 (Delta Like Ligand 3) | 971 | 2171 | CD8SP-DLL3-hSC16-13-(vL-vH)-GGSG-NLuc-4xFLAG-x2STREP-8xHis-T2A-PAC |
| | DLL3 (Delta Like Ligand 3) | 972 | 2172 | CD8SP-DLL3-hSC16-56-(vL-vH)-GGSG-NLuc-4xFLAG-x2STREP-8xHis-T2A-PAC |
| | EBNA3c/MHC class I complex | 973 | 2173 | CD8SP-EBNA3c-315-(vL-vH)-GGSG-NLuc-4xFLAG-x2STREP-8xHis-T2A-PAC |
| | EBV-gp350 | 974 | 2174 | CD8SP-EBV-gp350-(vL-vH)-GGSG-NLuc-4xFLAG-x2STREP-8xHis-T2A-PAC |
| | EGFR | 975 | 2175 | CD8SP-EGFR1-vHH-GGSG-NLuc-4xFLAG-x2STREP-8xHis-T2A-PAC |
| 041116-E06 | EGFR & CEA | 976 | 2176 | CD8SP-EGFR1-vHH-Gly-Ser-Linker-CEA1-vHH-GGSG-NLuc-4xFLAG-x2STREP-8xHis-T2A-PAC |
| 041116-F02 | EGFR & CEA | 977 | 2177 | CD8SP-EGFR33-vHH-Gly-Ser-Linker-CEA5-vHH-GGSG-NLuc-4xFLAG-x2STREP-8xHis-T2A-PAC |
| 112316-O02 | EGFRvIII | 978 | 2178 | CD8SP-EGFRvIII-139-(vL-vH)-GGSG-NLuc-4xFLAG-x2STREP-8xHis-T2A-PAC |
| 112316-P02 | EGFRvIII | 979 | 2179 | CD8SP-EGFRvIII-2173-(vL-vH)-GGSG-NLuc-4xFLAG-x2STREP-8xHis-T2A-PAC |
| | EpCam1 | 980 | 2180 | CD8SP-Epcam1-MM1-(vL-vH)-GGSG-NLuc-4xFLAG-x2STREP-8xHis-T2A-PAC |
| | EpCam1 | 981 | 2181 | CD8SP-Epcam1-D5K5-(vL-vH)-GGSG-NLuc-4xFLAG-x2STREP-8xHis-T2A-PAC |
| | FLT3 | 982 | 2182 | CD8SP-FLT3-NC7-(vL-vH)-GGSG-NLuc-4xFLAG-x2STREP-8xHis-T2A-PAC |
| 060716-B07 | FITC | 983 | 2183 | CD8SP-FITC-(vL-vH)-GGSG-NLuc-4xFLAG-x2STREP-8xHis-T2A-PAC |
| | FITC | 984 | 2184 | CD8SP-FITC-4M-53-(vL-vH)-GGSG-NLuc-4xFLAG-x2STREP-8xHis-T2A-PAC |
| 030617-H05 | FITC | 985 | 2185 | CD8SP-FITC-E2-HL-(vH-vL)-GGSG-NLuc-4xFLAG-x2STREP-8xHis-T2A-PAC |
| 092916-B03 | Influenza A HA | 986 | 2186 | CD8SP-FLU-MEDI-8852-(vL-vH)-GGSG-NLuc-4xFLAG-x2STREP-8xHis-T2A-PAC |
| 111516-K08 | FR1 (Folate Receptor alpha) | 987 | 2187 | CD8SP-FR1-huMov19-(vL-vH)-GGSG-NLuc-4xFLAG-x2STREP-8xHis-T2A-PAC |
| 082216-U02 | FSHR (Follicle Stimulating Hormone Receptor) | 988 | 2188 | CD8SP-FSHb-Gly-Ser-Linker-CGHa-GGSG-NLuc-4xFLAG-x2STREP-8xHis-T2A-PAC |
| | GAD (Glutamic Acid Decarboxylase)/ MHC class I complex | 989 | 2189 | CD8SP-GAD-G3H8-(vL-vH)-GGSG-NLuc-4xFLAG-x2STREP-8xHis-T2A-PAC |
| | GD2 | 990 | 2190 | CD8SP-GD2-hu14-18-(vL-vH)-GGSG-NLuc-4xFLAG-x2STREP-8xHis-T2A-PAC |
| | GD2 | 991 | 2191 | CD8SP-GD2-hu3F8-(vL-vH)-GGSG-NLuc-4xFLAG-x2STREP-8xHis-T2A-PAC |
| 060716-A03 | GD3 | 992 | 2192 | CD8SP-GD3-KM-641-(vL-vH)-GGSG-NLuc-4xFLAG-x2STREP-8xHis-T2A-PAC |
| | GFRa4 (GDNF Family Receptor Alpha 4) | 993 | 2193 | CD8SP-GFRAlpha4-P4-6-(vL-vH)-GGSG-NLuc-4xFLAG-x2STREP-8xHis-T2A-PAC |
| | GFRa4 (GDNF Family Receptor Alpha 4) | 994 | 2194 | CD8SP-GFRa4-P4-10-(vL-vH)-GGSG-NLuc-4xFLAG-x2STREP-8xHis-T2A-PAC |
| | GM1 | 995 | 2195 | CD8SP-GM1-5B2-(vL-vH)-GGSG-NLuc-4xFLAG-x2STREP-8xHis-T2A-PAC |
| | GM1 | 996 | 2196 | CD8SP-GM1-7E5-(vL-vH)-GGSG-NLuc-4xFLAG-x2STREP-8xHis-T2A-PAC |
| 092016-C06 | GPRC5D (G-protein coupled receptor family C group 5 member D) | 997 | 2197 | CD8SP-GPRC5D-ET150-5-(vL-vH)-GGSG-NLuc-4xFLAG-x2STREP-8xHis-T2A-PAC |

TABLE 15-continued

Exemplary scFv-GGS-Luc Constructs

| Clone ID # | Target | SEQ ID (DNA) | SEQ ID (PRT) | CONSTRUCT NAME |
|---|---|---|---|---|
| 100516-A06 | GPRC5D | 998 | 2198 | CD8SP-GPRC5D-ET150-18-(vL-vH)-GGSG-NLuc-4xFLAG-x2STREP-8xHis-T2A-PAC |
| | GPRC5D | 999 | 2199 | CD8SP-GPRC5D-ET150-1-(vL-vH)-GGSG-NLuc-4xFLAG-x2STREP-8xHis-T2A-PAC |
| | GPRC5D | 1000 | 2200 | CD8SP-GPRC5D-ET150-2-(vL-vH)-GGSG-NLuc-4xFLAG-x2STREP-8xHis-T2A-PAC |
| | gp100/MHC class I complex | 1001 | 2201 | CD8SP-gp100-(vL-vH)-GGSG-NLuc-4xFLAG-x2STREP-8xHis-T2A-PAC |
| | gp100/MHC class I complex | 1002 | 2202 | CD8SP-gp100-G2D12-(vL-vH)-GGSG-NLuc-4xFLAG-x2STREP-8xHis-T2A-PAC |
| 092116-C04 | GPC3 (Glypican 3) | 1003 | 2203 | CD8SP-GPC3-4E5-(vL-vH)-GGSG-NLuc-4xFLAG-x2STREP-8xHis-T2A-PAC |
| | gpNMB (Glycoprotein Nmb) | 1004 | 2204 | CD8SP-gpNMB-115-(vL-vH)-GGSG-NLuc-4xFLAG-x2STREP-8xHis-T2A-PAC |
| | GRP78 | 1005 | 2205 | CD8SP-GRP78-GC18-(vL-vH)-GGSG-NLuc-4xFLAG-x2STREP-8xHis-T2A-PAC |
| | Her2 | 1006 | 2206 | CD8SP-Her2-5F7-vHH-GGSG-NLuc-4xFLAG-x2STREP-8xHis-T2A-PAC |
| | Her2 | 1007 | 2207 | IgHSP-Her2-Affi-GGSG-NLuc-4xFLAG-x2STREP-8xHis-T2A-PAC |
| | Her2 | 1008 | 2208 | CD8SP-Her2-1-Darpin-GGSG-NLuc-4xFLAG-x2STREP-8xHis-T2A-PAC |
| | Her2 | 1009 | 2209 | IgHSP-Her2-2-Darpin-GGSG-NLuc-4xFLAG-x2STREP-8xHis-T2A-PAC |
| 041116-G07 | Her2 | 1010 | 2210 | CD8SP-Her2-5F7-vHH-Gly-Ser-Linker-Her2-47D5-vHH-GGSG-NLuc-4xFLAG-x2STREP-8xHis-T2A-PAC |
| 061316-L02 | Her2 | 1011 | 2211 | CD8SP-Her2-Hu4D5-(vL-vH)-GGSG-NLuc-4xFLAG-x2STREP-8xHis-T2A-PAC |
| | Her3 | 1012 | 2212 | CD8SP-Her3-17B05So-vHH-GGSG-NLuc-4xFLAG-x2STREP-8xHis-T2A-PAC |
| | Her3 | 1013 | 2213 | CD8SP-Her3-Affi-GGSG-NLuc-4xFLAG-x2STREP-8xHis-T2A-PAC |
| 041116-D05 | Her2 and Her3 | 1014 | 2214 | CD8SP-Her3-17B05So-vHH-Gly-Ser-Linker-Her2-2D3-vHH-GGSG-NLuc-4xFLAG-x2STREP-8xHis-T2A-PAC |
| 090716-B05 | HIV1-gag/MHC class I complex | 1015 | 2215 | CD8SP-HIV1-E5-(vL-vH)-GGSG-NLuc-4xFLAG-x2STREP-8xHis-T2A-PAC |
| 093016-Z11 | HIV1-envelop glycoprotein | 1016 | 2216 | CD8SP-HIV1-3BNC117-(vL-vH)-GGSG-NLuc-4xFLAG-x2STREP-8xHis-T2A-PAC |
| | HIV1-envelop glycoprotein | 1017 | 2217 | CD8SP-HIV1-PGT-128-(vL-vH)-GGSG-NLuc-4xFLAG-x2STREP-8xHis-T2A-PAC |
| 093016-X10 | HIV1-envelop glycoprotein | 1018 | 2218 | CD8SP-HIV1-VR-C01-(vL-vH)-GGSG-NLuc-4xFLAG-x2STREP-8xHis-T2A-PAC |
| 093016-Y15 | HIV1-envelop glycoprotein | 1019 | 2219 | CD8SP-HIVl-X5-(vL-vH)-GGSG-NLuc-4xFLAG-x2STREP-8xHis-T2A-PAC |
| | HLA-A2 | 1020 | 2220 | CD8SP-HLA-A2-3PB2-(vL-vH)-GGSG-NLuc-4xFLAG-x2STREP-8xHis-T2A-PAC |
| 061316-E01 | HMW-MAA | 1021 | 2221 | CD8SP-HMW-MAA-hIND-(vL-vH)-GGSG-NLuc-4xFLAG-x2STREP-8xHis-T2A-PAC |
| | HPV16-E7/MHC class I complex | 1022 | 2222 | CD8SP-HPV16-7-8-(vL-vH)-GGSG-NLuc-4xFLAG-x2STREP-8xHis-T2A-PAC |
| | HPV16-E7/MHC class I complex | 1023 | 2223 | CD8SP-HPV16-2-(vL-vH)-GGSG-NLuc-4xFLAG-x2STREP-8xHis-T2A-PAC |
| | HTLV1-TAX/MHC class I complex | 1024 | 2224 | CD8SP-HTLV-TAX-T3F2-(vL-vH)-GGSG-NLuc-4xFLAG-x2STREP-8xHis-T2A-PAC |
| 081216-O01 | HTLV1-TAX/MHC class I complex | 1025 | 2225 | CD8SP-HTLV-TAX-T3E3-(vL-vH)-GGSG-NLuc-4xFLAG-x2STREP-8xHis-T2A-PAC |

TABLE 15-continued

Exemplary scFv-GGS-Luc Constructs

| Clone ID # | Target | SEQ ID (DNA) | SEQ ID (PRT) | CONSTRUCT NAME |
|---|---|---|---|---|
| 060716-D06 | IL11Ra | 1026 | 2226 | CD8SP-IL11Ra-8E2-Ts107-(vL-vH)-GGSG-NLuc-4xFLAG-x2STREP-8xHis-T2A-PAC |
| | IL6Ra | 1027 | 2227 | IgHSP-IL6R-304-vHH-GGSG-NLuc-4xFLAG-x2STREP-8xHis-T2A-PAC |
| | IL13Ra2 | 1028 | 2228 | CD8SP-IL13Ra2-hu107-(vL-vH)-GGSG-NLuc-4xFLAG-x2STREP-8xHis-T2A-PAC |
| 060716-F03 | IL13Ra2 | 1029 | 2229 | CD8SP-IL13Ra2-Hu108-(vL-vH)-GGSG-NLuc-4xFLAG-x2STREP-8xHis-T2A-PAC |
| | KSHV-K8.1 | 1030 | 2230 | CD8SP-KSHV-4C3-(vL-vH)-GGSG-NLuc-4xFLAG-x2STREP-8xHis-T2A-PAC |
| | LAMP1 (Lysosomal-associated membrane protein 1) | 1031 | 2231 | CD8SP-LAMP1-humab1-2-(vL-vH)-GGSG-NLuc-4xFLAG-x2STREP-8xHis-T2A-PAC |
| 061416-B04 | LAMP1 (Lysosomal-associated membrane protein 1) | 1032 | 2232 | CD8SP-LAMP1-Mb4-(vL-vH)-GGSG-NLuc-4xFLAG-x2STREP-8xHis-T2A-PAC |
| 081016-F11 | LewisY | 1033 | 2233 | CD8SP-LewisY-huS193-(vL-vH)-GGSG-NLuc-4xFLAG-x2STREP-8xHis-T2A-PAC |
| | L1CAM | 1034 | 2234 | CD8SP-L1CAM-9-3-HU3-(vL-vH)-GGSG-NLuc-4xFLAG-x2STREP-8xHis-T2A-PAC |
| 082216-W02 | LHR | 1035 | 2235 | SP-LHb-Gly-Ser-Linker-CGHa-GGSG-NLuc-4xFLAG-x2STREP-8xHis-T2A-PAC |
| | Lym1 | 1036 | 2236 | CD8SP-Lym1-(vL-vH)-GGSG-NLuc-4xFLAG-x2STREP-8xHis-T2A-PAC |
| | Lym2 | 1037 | 2237 | CD8SP-Lym2-(vL-vH)-GGSG-NLuc-4xFLAG-x2STREP-8xHis-T2A-PAC |
| | CD79b | 1038 | 2238 | CD8SP-huMA79bv28-(vL-vH)-GGSG-NLuc-4xFLAG-x2STREP-8xHis-T2A-PAC |
| | MART1/MHC class I complex | 1039 | 2239 | CD8SP-MART1-CAG10-(vL-vH)-GGSG-NLuc-4xFLAG-x2STREP-8xHis-T2A-PAC |
| | MART1/MHC class I complex | 1040 | 2240 | CD8SP-MART1-CLA12-(vL-vH)-GGSG-NLuc-4xFLAG-x2STREP-8xHis-T2A-PAC |
| | Mesothelin | 1041 | 2241 | CD8SP-Mesothelin-m912-HL-(vL-vH)-GGSG-NLuc-4xFLAG-x2STREP-8xHis-T2A-PAC |
| | cMet | 1042 | 2242 | CD8SP-cMet-171-vHH-GGSG-NLuc-4xFLAG-x2STREP-8xHis-T2A-PAC |
| 041116-H01 | cMet and Her3 | 1043 | 2243 | CD8SP-cMET-171-vHH-Gly-Ser-Linker-Her3-21F06-vHH-GGSG-NLuc-4xFLAG-x2STREP-8xHis-T2A-PAC |
| | MPL (Thrombopoietin receptor) | 1044 | 2244 | CD8SP-MPL-175-(vL-vH)-GGSG-NLuc-4xFLAG-x2STREP-8xHis-T2A-PAC |
| | MPL (Thrombopoietin receptor) | 1045 | 2245 | CD8SP-MPL-161-(vL-vH)-GGSG-NLuc-4xFLAG-x2STREP-8xHis-T2A-PAC |
| | MPL (Thrombopoietin receptor) | 1046 | 2246 | CD8SP-MPL-161-HL-(vH-vL)-GGSG-NLuc-4xFLAG-x2STREP-8xHis-T2A-PAC |
| 041116-C03 | MPL (Thrombopoietin receptor) | 1047 | 2247 | CD8SP-2-MPL-111-(vL-vH)-GGSG-NLuc-4xFLAG-x2STREP-8xHis-T2A-PAC |
| | MPL (Thrombopoietin receptor) | 1048 | 2248 | CD8SP-MPL-178-(vL-vH)-GGSG-NLuc-4xFLAG-x2STREP-8xHis-T2A-PAC |
| | MPL (Thrombopoietin receptor) | 1049 | 2249 | CD8SP-MPL-AB317-(vL-vH)-GGSG-NLuc-4xFLAG-x2STREP-8xHis-T2A-PAC |
| | MPL (Thrombopoietin receptor) | 1050 | 2250 | CD8SP-MPL-12E10-(vL-vH)-GGSG-NLuc-4xFLAG-x2STREP-8xHis-T2A-PAC |
| | MPL (Thrombopoietin receptor) | 1051 | 2251 | CD8SP-MPL-huVB22Bw5-(vL-vH)-GGSG-NLuc-4xFLAG-x2STREP-8xHis-T2A-PAC |
| | Muc1/MHC class I complex | 1052 | 2252 | CD8SP-Muc1-D6-M3B8-(vL-vH)-GGSG-NLuc-4xFLAG-x2STREP-8xHis-T2A-PAC |
| | Muc1/MHC class I complex | 1053 | 2253 | CD8SP-MUC1-D6-M3A1-(vL-vH)-GGSG-NLuc-4xFLAG-x2STREP-8xHis-T2A-PAC |

TABLE 15-continued

Exemplary scFv-GGS-Luc Constructs

| Clone ID # | Target | SEQ ID (DNA) | SEQ ID (PRT) | CONSTRUCT NAME |
|---|---|---|---|---|
| | Muc16 | 1054 | 2254 | CD8SP-Muc16-4H11-(vL-vH)-GGSG-NLuc-4xFLAG-x2STREP-8xHis-T2A-PAC |
| 062916-A02 | EGFR | 1055 | 2255 | CD8SP-Nimotuzumab-(vL-vH)-GGSG-NLuc-4xFLAG-x2STREP-8xHis-T2A-PAC |
| 060716-J06 | NKG2D Ligand | 1056 | 2256 | CD8SP-NKG2D-(GGGGS-GGGGD)-GGSG-NLuc-4xFLAG-x2STREP-8xHis-T2A-PAC |
| 090716-C02 | NKG2D | 1057 | 2257 | CD8SP-NKG2D-MS-(vL-vH)-GGSG-NLuc-4xFLAG-x2STREP-8xHis-T2A-PAC |
| | NY-BR1 | 1058 | 2258 | CD8SP-NYBR1-(vL-vH)-GGSG-NLuc-4xFLAG-x2STREP-8xHis-T2A-PAC |
| 081216-M04 | NY-ESO/MHC class I complex | 1059 | 2259 | CD8SP-NYESO-T1-(vL-vH)-GGSG-NLuc-4xFLAG-x2STREP-8xHis-T2A-PAC |
| | NY-ESO/MHC class I complex | 1060 | 2260 | CD8SP-NYESO-T1-(vL-vH)-GGSG-NLuc-4xFLAG-x2STREP-8xHis-T2A-PAC |
| | PD1 ligand (e.g., PDL1) | 1061 | 2261 | CD8SP-PD1-ECD-GGSG-NLuc-4xFLAG-x2STREP-8xHis-T2A-PAC |
| 100516-G03 | PDL1 | 1062 | 2262 | CD8SP-PDL1-Atezoli-(vL-vH)-GGSG-NLuc-4xFLAG-x2STREP-8xHis-T2A-PAC |
| 100516-H05 | PDL1 | 1063 | 2263 | CD8SP-PDL1-SP142-(vL-vH)-GGSG-NLuc-4xFLAG-x2STREP-8xHis-T2A-PAC |
| 100516-F03 | PDL1 | 1064 | 2264 | CD8SP-PDL1-10A5-(vL-vH)-GGSG-NLuc-4xFLAG-x2STREP-8xHis-T2A-PAC |
| 090716-E02 | PSCA (Prostate stem cell antigen) | 1065 | 2265 | CD8SP-PSCA-Ha14-121-(vL-vH)-GGSG-NLuc-4xFLAG-x2STREP-8xHis-T2A-PAC |
| | PSCA (Prostate stem cell antigen) | 1066 | 2266 | CD8SP-PSCA-Ha14-117-(vL-vH)-GGSG-NLuc-4xFLAG-x2STREP-8xHis-T2A-PAC |
| | PR1/MHC class I complex | 1067 | 2267 | CD8SP-PR1-(vL-vH)-GGSG-NLuc-4xFLAG-x2STREP-8xHis-T2A-PAC |
| | PSMA (Prostate Specific Membrane Antigen) | 1068 | 2268 | CD8SP-PSMA-006-(vL-vH)-GGSG-NLuc-4xFLAG-x2STREP-8xHis-T2A-PAC |
| | PSMA (Prostate Specific Membrane Antigen) | 1069 | 2269 | CD8SP-PSMA-J591-(vL-vH)-GGSG-NLuc-4xFLAG-x2STREP-8xHis-T2A-PAC |
| | PTK7 (Tyrosine-protein kinase-like 7) | 1070 | 2270 | CD8SP-PTK7-hSC6-23-(vL-vH)-GGSG-NLuc-4xFLAG-x2STREP-8xHis-T2A-PAC |
| | PTK7 (Tyrosine-protein kinase-like 7) | 1071 | 2271 | CD8SP-PTK7-SC6-10-2-(vL-vH)-GGSG-NLuc-4xFLAG-x2STREP-8xHis-T2A-PAC |
| | ROR1 | 1072 | 2272 | CD8SP-ROR1-4A5-(vL-vH)-GGSG-NLuc-4xFLAG-x2STREP-8xHis-T2A-PAC |
| | ROR1 | 1073 | 2273 | CD8SP-ROR1-4C10-(vL-vH)-GGSG-NLuc-4xFLAG-x2STREP-8xHis-T2A-PAC |
| | Mesothelin | 1074 | 2274 | CD8SP-SD1-vHH-Gly-Ser-Linker-SD2-vHH-GGSG-NLuc-4xFLAG-x2STREP-8xHis-T2A-PAC |
| 111116-A05 | SLea | 1075 | 2275 | CD8SP-SLea-7E3-(vL-vH)-GGSG-NLuc-4xFLAG-x2STREP-8xHis-T2A-PAC |
| | SLea | 1076 | 2276 | CD8SP-SLea-5B1-(vL-vH)-GGSG-NLuc-4xFLAG-x2STREP-8xHis-T2A-PAC |
| 082216-Y02 | SSEA4 (stage-specific embryonic antigen 4) | 1077 | 2277 | CD8SP-SSEA4-(vL-vH)-GGSG-NLuc-4xFLAG-x2STREP-8xHis-T2A-PAC |
| | TCRB1 (TCR beta 1 constant chain) | 1078 | 2278 | CD8SP-TCRB1-CP01-E09-(vL-vH)-GGSG-NLuc-4xFLAG-x2STREP-8xHis-T2A-PAC |

TABLE 15-continued

Exemplary scFv-GGS-Luc Constructs

| Clone ID # | Target | SEQ ID (DNA) | SEQ ID (PRT) | CONSTRUCT NAME |
|---|---|---|---|---|
| | TCRB1 (TCR beta 1 constant chain) | 1079 | 2279 | CD8SP-TCRB1-Jovi1-(vL-vH)-GGSG-NLuc-4xFLAG-x2STREP-8xHis-T2A-PAC |
| | TCRB2 (TCR beta 2 constant chain) | 1080 | 2280 | CD8SP-TCRB2-CP01-D05-(vL-vH)-GGSG-NLuc-4xFLAG-x2STREP-8xHis-T2A-PAC |
| | TCRB2 (TCR beta 2 constant chain) | 1081 | 2281 | CD8SP-TCRB2-CP01-E05-(vL-vH)-GGSG-NLuc-4xFLAG-x2STREP-8xHis-T2A-PAC |
| 110216-B02-PB | TCRgd (TCR gamma/delta) | 1082 | 2282 | CD8SP-TCRgd-G5-4-(vL-vH)-GGSG-NLuc-4xFLAG-x2STREP-8xHis-T2A-PAC |
| | hTERT/MHC class I complex | 1083 | 2283 | CD8SP-TERT-4A9-T540-(vL-vH)-GGSG-NLuc-4xFLAG-x2STREP-8xHis-T2A-PAC |
| 081516-U07 | hTERT/MHC class I complex | 1084 | 2284 | CD8SP-TERT-3G3-T865-(vL-vH)-GGSG-NLuc-4xFLAG-x2STREP-8xHis-T2A-PAC |
| | Tissue Factor | 1085 | 2285 | CD8SP-TF1-98-(vL-vH)-GGSG-NLuc-4xFLAG-x2STREP-8xHis-T2A-PAC |
| | TGFBR2 | 1086 | 2286 | CD8SP-TGFBR2-Ab1-(vL-vH)-GGSG-NLuc-4xFLAG-x2STREP-8xHis-T2A-PAC |
| | TIM1/HAVCR | 1087 | 2287 | CD8SP-TIM1-HVCR1-270-2-(vL-vH)-GGSG-NLuc-4xFLAG-x2STREP-8xHis-T2A-PAC |
| | TIM1/HAVCR | 1088 | 2288 | CD8SP-TIM1-HVCR1-ARD5-(vL-vH)-GGSG-NLuc-4xFLAG-x2STREP-8xHis-T2A-PAC |
| 061316-F06 | TnAg | 1089 | 2289 | CD8SP-TnAg-(vL-vH)-GGSG-NLuc-4xFLAG-x2STREP-8xHis-T2A-PAC |
| 080916-C02 | Tn-Muc1 | 1090 | 2290 | CD8SP-TnMuc1-hu5E5-RHA8-RKA-2-(vL-vH)-GGSG-NLuc-4xFLAG-x2STREP-8xHis-T2A-PAC |
| | MPL (Thrombopoietin receptor) | 1091 | 2291 | CD8SP-hTPO-GGSG-NLuc-4xFLAG-x2STREP-8xHis-T2A-PAC |
| | TROP2 (Trophoblast cell-surface antigen-2) | 1092 | 2292 | CD8SP-TROP2-ARA47-HV3KV3-(vL-vH)-GGSG-NLuc-4xFLAG-x2STREP-8xHis-T2A-PAC |
| | TROP2 (Trophoblast cell-surface antigen-2) | 1093 | 2293 | CD8SP-TROP2-h7E6-SVG-(vL-vH)-GGSG-NLuc-4xFLAG-x2STREP-8xHis-T2A-PAC |
| 082216-V02 | TSHR (Thyrotropin receptor) | 1094 | 2294 | SP-TSHb-Gly-Ser-Linker-CGHa-GGSG-NLuc-4xFLAG-x2STREP-8xHis-T2A-PAC |
| | TSHR (Thyrotropin receptor) | 1095 | 2295 | CD8SP-TSHR-K1-70-(vL-vH)-GGSG-NLuc-4xFLAG-x2STREP-8xHis-T2A-PAC |
| 061316-D01 | TSHR (Thyrotropin receptor) | 1096 | 2296 | CD8SP-TSHR-KB1-(vL-vH)-GGSG-NLuc-4xFLAG-x2STREP-8xHis-T2A-PAC |
| 062916-B07 | TSHR (Thyrotropin receptor) | 1097 | 2297 | CD8SP-TSHR-5C9-(vL-vH)-GGSG-NLuc-4xFLAG-x2STREP-8xHis-T2A-PAC |
| | TSLPR (thymic stromal lymphopoietin receptor) | 1098 | 2298 | CD8SP-TSLPR-(vL-vH)-GGSG-NLuc-4xFLAG-x2STREP-8xHis-T2A-PAC |
| | Tyrosinase/MHC class I complex | 1099 | 2299 | CD8SP-Tyros-B2-(vL-vH)-GGSG-NLuc-4xFLAG-x2STREP-8xHis-T2A-PAC |
| | Tyrosinase/MHC class I complex | 1100 | 2300 | CD8SP-Tyros-MC1-(vL-vH)-GGSG-NLuc-4xFLAG-x2STREP-8xHis-T2A-PAC |
| | Tyrosinase/MHC class I complex | 1101 | 2301 | CD8SP-Tyros-TA2-(vL-vH)-GGSG-NLuc-4xFLAG-x2STREP-8xHis-T2A-PAC |
| | VEGFR3 | 1102 | 2302 | CD8SP-VEGFR3-Ab1-(vL-vH)-GGSG-NLuc-4xFLAG-x2STREP-8xHis-T2A-PAC |
| | WT1/MHC class I complex | 1103 | 2303 | CD8SP-WT1-Ab1-(vL-vH)-GGSG-NLuc-4xFLAG-x2STREP-8xHis-T2A-PAC |

TABLE 15-continued

Exemplary scFv-GGS-Luc Constructs

| Clone ID # | Target | SEQ ID (DNA) | SEQ ID (PRT) | CONSTRUCT NAME |
|---|---|---|---|---|
| | WT1/MHC class I complex | 1104 | 2304 | CD8SP-WT1-Ab5-(vL-vH)-GGSG-NLuc-4xFLAG-x2STREP-8xHis-T2A-PAC |
| | WT1/MHC class I complex | 1105 | 2305 | CD8SP-MYC3-WT1-Ab13-(vL-vH)-GGSG-NLuc-4xFLAG-x2STREP-8xHis-T2A-PAC |
| | WT1/MHC class I complex | 1106 | 2306 | CD8SP-MYC3-WT1-Ab15-(vL-vH)-GGSG-NLuc-4xFLAG-x2STREP-8xHis-T2A-PAC |
| | CDH19 | 1107 | 2307 | CD8SP-CDH19-4B10-(vL-vH)-GGSG-NLuc-4xFLAG-x2STREP-8xHis-T2A-PAC |
| 112216-A02 | Folate Receptor beta | 1108 | 2308 | CD8SP-FRbeta-m923-(vL-vH)-GGSG-NLuc-4xFLAG-x2STREP-8xHis-T2A-PAC |
| | LHR (Luteinizing hormone Receptor) | 1109 | 2309 | CD8SP-LHR-8B7-(vL-vH)-GGSG-NLuc-4xFLAG-x2STREP-8xHis-T2A-PAC |
| | LHR (Luteinizing hormone Receptor) | 1110 | 2310 | CD8SP-LHR-5F4-21-(vL-vH)-GGSG-NLuc-4xFLAG-x2STREP-8xHis-T2A-PAC |
| | B7H4 | 1111 | 2311 | CD8SP-B7H4-hu22Cl0-(vL-vH)-GGSG-NLuc-4xFLAG-x2STREP-8xHis-T2A-PAC |
| | B7H4 | 1112 | 2312 | CD8SP-B7H4-hu1D11-(vL-vH)-GGSG-NLuc-4xFLAG-x2STREP-8xHis-T2A-PAC |
| | IgE | 1113 | 2313 | CD8SP-IgE-omalizumab-(vL-vH)-GGSG-NLuc-4xFLAG-x2STREP-8xHis-T2A-PAC |
| 121516-A08 | CD23 | 1114 | 2314 | CD8SP-CD23-p5E8-(vL-vH)-GGSG-NLuc-4xFLAG-x2STREP-8xHis-T2A-PAC |
| 121516-C03 | GCC (Guanylyl cyclase C) | 1115 | 2315 | CD8SP-GCC-5F9-(vL-vH)-GGSG-NLuc-4xFLAG-x2STREP-8xHis-T2A-PAC |
| 121516-B06 | GCC (Guanylyl cyclase C) | 1116 | 2316 | CD8SP-GCC-Ab229-(vL-vH)-GGSG-NLuc-4xFLAG-x2STREP-8xHis-T2A-PAC |
| | CD200R | 1117 | 2317 | CD8SP-CD200R-huDx182-(vL-vH)-GGSG-NLuc-4xFLAG-x2STREP-8xHis-T2A-PAC |
| 021015-T07 | MPL | 1118 | 2318 | CD8SP-161-(vL-vH)-GGSG-NLuc-AcV5 |
| 021015-U09 | CD19 | 1119 | 2319 | CD8SP-FMC63(vL-vH)-GGSG-NLuc-AcV5 |
| 040915-J04 | Lym1 | 1120 | 2320 | CD8SP-Lym1(vL-vH)-GGSG-NLuc-AcV5 |
| 040915-K05 | Lym2 | 1121 | 2321 | CD8SP-Lym2(vL-vH)-GGSG-NLuc-AcV5 |
| 041715-E01 | CD33 | 1122 | 2322 | CD8SP-CD33(vL-vH)-GGSG-NLuc-AcV5 |
| 041715-D01 | CD138 | 1123 | 2323 | CD8SP-CD138(vL-vH)-GGSG-NLuc-AcV5 |
| 041615-X08 | BCMA | 1124 | 2324 | CD8SP-BCMA-J6MO-(vL-vH)-NLuc-AcV5 |
| 041715-C06 | FLT3 | 1125 | 2325 | CD8SP-FLT3-NC7-(vL-vH)-NLuc-AcV5 |
| 041415-V08 | CS1 | 1126 | 2326 | CD8SP-Luc63-(vL-vH)-GGGS-NLuc-AcV5 |
| 041515-W03 | CS1 | 1127 | 2327 | CD8SP-Luc90-(vL-vH)-NLuc-AcV5 |
| 041515-U04 | CD79b | 1128 | 2328 | CD8SP-huMA79bv28-(vL-vH)-GGGS-Nluc-AcV5 |
| 042115-A09 | CD45 | 1129 | 2329 | CD8SP-CD45-BC8-(vL-vH)-GGSG-NLuc-AcV5 |
| 040915-M06 | GRP78 | 1130 | 2330 | CD8SP-GRP78-GC18(vL-vH)-NLuc-AcV5 |
| 041715-B03 | CD3 | 1131 | 2331 | CD8SP-CD3-Hum291-(vL-vH)-GGS-NLuc-AcV5 |
| 040915-N01 | MPL | 1132 | 2332 | hTPO(1-187)-GGSG-NLuc-AcV5 |
| 040915-O07 | MPL | 1133 | 2333 | mTPO(1-187)-GGSG-NLuc-AcV5 |
| 021216-A06 | CD19 | 1134 | 2334 | CD8SP-FMC63(vL-vH)-GGS-NLuc-x3-FLAG |
| 113015-A04 | CD19 | 1135 | 2335 | CD8SP-FMC63(vL-vH)-GGS-TurboLuc16-x3-FLAG |
| 113015-B02 | CD19 | 1136 | 2336 | CD8SP-FMC63(vL-vH)-GGS-GLuc-x3-FLAG |
| 111815-K07 | CD19 | 1137 | 2337 | CD8SP-FMC63(vL-vH)-GGS-MLuc-MM-LL-HA |
| 111815-G04 | CD19 | 1138 | 2338 | CD8SP-FMC63(vL-vH)-GGS-L-ovaliformis-Luc-AcV5 |
| 111815-L05 | CD19 | 1139 | 2339 | CD8SP-FMC63(vL-vH)-GGS-Htanneri-Luc-x3-FLAG |
| 071416-M08 | FMC63 | 1140 | 2340 | CD8SP-FMC136-20-L-ovalformi-luc-AcV5 |
| 030916-B02 | CD30 | 1141 | 2341 | CD8SP-CD30-5F11(vL-vH)-GGSG-NLuc-x3-Flag |
| | CD30 | 1142 | 2342 | CD8SP-CD30-Ac10(vL-vH)-NLuc-x3-Flag |
| 030816-E04 | TCRB1 (TCR beta 1 constant chain) | 1143 | 2343 | CD8SP-TCRB1-Jovi1(vL-vH)-GGSG-NLuc-x3-FLAG |
| 030816-G01 | TCRB1 (TCR beta 1 constant chain) | 1144 | 2344 | CD8SP-TCRB1-E09(vL-vH)-GGSG-NLuc-x3-Flag |
| 021417-T05 | CD19 | 1145 | 2345 | CD8SP-hCD19-Bu12-(vL-vH)-GGSG-NLuc-AcV5 |
| 021417-U01 | CD19 | 1146 | 2346 | CD8SP-hCD19MM-(vL-vH)-GGSG-NLuc-AcV5 |

TABLE 15-continued

Exemplary scFv-GGS-Luc Constructs

| Clone ID # | Target | SEQ ID (DNA) | SEQ ID (PRT) | CONSTRUCT NAME |
|---|---|---|---|---|
| 021417-V05 | CD19 | 1147 | 2347 | CD8SP-huFMC63-11-(vL-vH)-GGSG-NLuc-AcV5 |
| 021417-W05 | CD19 | 1148 | 2348 | CD8SP-huFMC63-11-N203Q-(vL-vH)-GGSG-NLuc-AcV5 |
| 021417-X05 | CD19 | 1149 | 2349 | CD8SP-huFMC63-11-N203S-(vL-VH)-GGSG-NLuc-AcV5 |
| 021417-Y05 | CD19 | 1150 | 2350 | CD8SP-CD19-Medi-3649-(vL-vH)-GGSG-NLuc-AcV5 |
| 021417-Z04 | CD19 | 1151 | 2351 | CD8SP-CD19-4G7-Mlu-GSG-NLuc-AcV5 |
| 021417-A05 | CD19 | 1152 | 2352 | CD8SP-RTX-CD19-MOR0028-(vL-vH)-GGSG-NLuc-AcV5 |
| 031816-B04 | CD19 | 1153 | 2353 | CD8SP-FMC63-(vL-vH)-GGSG-Turboluc16-4xFLAG-x2STREP-8xHis-T2A-PAC |
| 071416-F03 | CD22 | 1154 | 2354 | CD8SP-CD22-h10F4v2-(vL-vH)-GGSG-Turboluc16-4xFLAG-x2STREP-8xHis-T2A-PAC |
| 071416-C03 | CD276 | 1155 | 2355 | CD8SP-CD276-17-(vL-vH)-GGSG-Turboluc16-4xFLAG-x2STREP-8xHis-T2A-PAC |
| 071416-E03 | CLEC5A | 1156 | 2356 | CD8SP-CLEC5A-3E12A2-(vL-vH)-GGSG-Turboluc16-4xFLAG-x2STREP-8xHis-T2A-PAC |
| 072616-M04 | CSF2RA | 1157 | 2357 | CD8SP-CSF2RA-Ab6-(vL-vH)-GGSG-Turboluc16-4xFLAG-x2STREP-8xHis-T2A-PAC |
| 071416-G03 | Her2 | 1158 | 2358 | CD8SP-Her2-Hu4D5-(vL-vH)-GGSG-Turboluc16-4xFLAG-x2STREP-8xHis-T2A-PAC |
| 072616-E04 | IL13Ra2 | 1159 | 2359 | CD8SP-IL13Ra2-hu107-(vL-vH)-GGSG-Turboluc16-4xFLAG-x2STREP-8xHis-T2A-PAC |
| 072616-G04 | L1CAM | 1160 | 2360 | CD8SP-L1CAM-9-3-HU3-(vL-vH)-GGSG-Turboluc16-4xFLAG-x2STREP-8xHis-T2A-PAC |
| 072616-F02 | Mesothelin | 1161 | 2361 | CD8SP-Mesothelin-m912-(vL-vH)-GGSG-Turboluc16-4xFLAG-x2STREP-8xHis-T2A-PAC |
| 072616-D04 | PSMA | 1162 | 2362 | CD8SP-PSMA-006-(vL-vH)-GGSG-Turboluc16-4xFLAG-x2STREP-8xHis-T2A-PAC |
| 071416-I03 | PTK7 | 1163 | 2363 | CD8SP-PTK7-hSC6-23-(vL-vH)-GGSG-Turboluc16-4xFLAG-x2STREP-8xHis-T2A-PAC |
| 072616-L02 | TnAg | 1164 | 2364 | CD8SP-TnAg-(vL-vH)-GGSG-Turboluc16-4xFLAG-x2STREP-8xHis-T2A-PAC |
| 072616-C03 | WT1 | 1165 | 2365 | CD8SP-WT1-Ab5-(vL-vH)-GGSG-Turboluc16-4xFLAG-x2STREP-8xHis-T2A-PAC |
| 072616-P01 | WT1 | 1166 | 2366 | CD8SP-MYC3-WT1-Ab15-(vL-vH)-GGSG-Turboluc16-4xFLAG-x2STREP-8xHis-T2A-PAC |
| 071416-L06 | FMC63 | 1167 | 2367 | CD8SP-FMC136-20-(vL-vH)-GGSG-Turboluc16-4xFLAG-x2STREP-8xHis-T2A-PAC |
| 022217-I05 | NY-ESO | 1168 | 2368 | CD8SP-NY-ESO-IG4-HA-scTCR-Nluc-GGSG-4xFLAG-x2STREP-8xHis-T2A-PAC |

TABLE 16

Exemplary ECD-GGS-Luc Constructs

| Clone ID # | Target | SEQ ID (DNA) | SEQ ID (Prt) | CONSTRUCT NAME |
|---|---|---|---|---|
| 082214-Z01 | MPL-CAR | 1169 | 2369 | MPL-ECD-GGSG-Nluc-AcV5 |
| 062615-C04 | CD19-CAR | 1170 | 2370 | FLAG-CD19-ECD-GGSG-NLuc-AcV5 |
|  | CD19-CAR | 1171 | 2371 | CD19-ECD-GGSG-NLuc-4xFlag-2xStreptag-8xHis-T2A-Pac |
| 111616-J04 | CD19-CAR | 1172 | 2372 | FLAG-CD19-ECD-GGS-Turboluc16-4xFlag-2xStreptag-8xHis-T2A-Pac |
| 111616-K07 | CD19-CAR | 1173 | 2373 | FLAG-CD19-ECD-GGS-PaLuc1-HA-Streptag-3xHA-8xHis-T2A-pac |
| 111616-L02 | CD19-CAR | 1174 | 2374 | FLAG-CD19-ECD-GGS-LoLuc-Luc-AcV5 |
| 111616-M07 | CD19-CAR | 1175 | 2375 | FLAG-CD19-ECD-GGS-MLuc7-MM-LL-HA |
| 111616-N05 | CD19-CAR | 1176 | 2376 | CD19-ECD-GGS-HtLuc-x3Flag |
| 060816-A02 | CD33-CAR | 1177 | 2377 | CD33-ECD-GGSG-NLuc-4xFlag-2xStreptag-8xHis-T2A-Pac |
| 100616-J04 | CD33-CAR | 1178 | 2378 | CD33-ECD-GGSG-Turboluc16-4xFlag-2xStreptag-8xHis-T2A-Pac |
| 100616-K07 | CD33-CAR | 1179 | 2379 | CD33-ECD-PaLuc1-HA-Streptag-3xHA-8xHis-T2A-pac |
| 100616-L07 | CD33-CAR | 1180 | 2380 | CD33-ECD-LoLuc-AcV5 |
| 100616-M02 | CD33-CAR | 1181 | 2381 | CD33-ECD-MLuc7-MM-LL-HA |
| 100616-N05 | CD33-CAR | 1182 | 2382 | CD33-ECD-HtLuc-x3Flag |
| 060816-C02 | CD138-CAR | 1183 | 2383 | CD138-SDC1-ECD-GGSG-NLuc-4xFlag-2xStreptag-8xHis-T2A-Pac |
| 101216-E04 | CD138-CAR | 1184 | 2384 | CD138-SDC1-ECD-GGS-Turboluc16-4xFlag-2xStreptag-8xHis-T2A-Pac |

TABLE 16-continued

Exemplary ECD-GGS-Luc Constructs

| Clone ID # | Target | SEQ ID (DNA) | SEQ ID (Prt) | CONSTRUCT NAME |
|---|---|---|---|---|
| 101216-F04 | CD138-CAR | 1185 | 2385 | CD138-SDC1-ECD-GGS-PaLuc1-HA-Streptag-3xHA-8xHis-T2A-pac |
| 101216-G04 | CD138-CAR | 1186 | 2386 | CD138-SDC1-ECD-GGS-LoLuc-Luc-AcV5 |
| 111616-H04 | CD138-CAR | 1187 | 2387 | CD138-SDC1-ECD-GGS-MLuc7-MM-LL-HA |
| 060816-D02 | CD123-CAR | 1188 | 2388 | Synth-CD123-ECD-GGSG-NLuc-4xFlag-2xStreptag-8xHis-T2A-Pac |
| 062816-G02 | CDH1 (CD324) CAR | 1189 | 2389 | CDH1-ECD-GGSG-NLuc-4xFlag-2xStreptag-8xHis-T2A-Pac |
| 082616-C07 | CD200R-CAR | 1190 | 2390 | CD200R-ECD-GGSG-NLuc-4xFlag-2xStreptag-8xHis-T2A-Pac |
| 081716-R07 | GPNMB-CAR | 1191 | 2391 | GPNMB-ECD-GGSG-NLuc-4xFlag-2xStreptag-8xHis-T2A-Pac |
| 082216-S02-F | PTK7-CAR | 1192 | 2392 | PTK7-ECD-GGSG-NLuc-4xFlag-2xStreptag-8xHis-T2A-Pac |
| 062816-B06 | CD34-CAR | 1193 | 2393 | CD34-ECD-GGSG-NLuc-4xFlag-2xStreptag-8xHis-T2A-Pac |
| 060816-F08 | EpCAM-CAR | 1194 | 2394 | EpCAM-ECD-GGSG-NLuc-4xFlag-2xStreptag-8xHis-T2A-Pac |
| 061716-B07 | CLEC12A-CAR | 1195 | 2395 | CLEC12A-ECD-GGSG-NLuc-4xFlag-2xStreptag-8xHis-T2A-Pac |
| 060816-I04 | CD20-CAR | 1196 | 2396 | CD20-ECx2-ECD-GGSG-TurboLuc16-4xFlag-2xStreptag-8xHis-T2A-Pac |
| 060816-J14 | CD20-CAR | 1197 | 2397 | CD20-ECx1-ECD-GGSG-TurboLuc16-4xFlag-2xStreptag-8xHis-T2A-Pac |
| 082616-B03 | CD22-CAR | 1198 | 2398 | CD22v5-ECD-GGSG-NLuc-4xFlag-2xStreptag-8xHis-T2A-Pac |
| 062816-C06 | TSHR-CAR | 1199 | 2399 | TSHR-ECD-GGSG-NLuc-4xFlag-2xStreptag-8xHis-T2A-Pac |
| 060816-E01 | EGFRviii-CAR | 1200 | 2400 | EGFRviii-ECD-GGSG-NLuc-4xFlag-2xStreptag-8xHis-T2A-Pac |
| 103116-Q07 | BCMA-CAR | 1201 | 2401 | BCMA-ECD-GGSG-NLuc-4xFlag-2xStreptag-8xHis-T2A-Pac |
| 062816-A01 | SLAMF7-CS1-CAR | 1202 | 2402 | SLAMF7-CS1-ECD-GGSG-NLuc-4xFlag-2xStreptag-8xHis-T2A-Pac |
| | PD1-CAR or PDL1 | 1203 | 2403 | PD1-ECD-GGSG-NLuc-4xFlag-2xStreptag-8xHis-T2A-Pac |
| | CTLA4-CAR | 1204 | 2404 | CTLA4-opt-ECD-NLuc-4xFLAG-x2STREP-8xHis-T2A-PAC |
| | NKG2D-CAR | 1205 | 2405 | CD8SP-NKG2D-ECD-4xFLAG-x2STREP-8xHis-T2A-PAC |
| 112316-Q02 | Kappa Light chain CAR | 1206 | 2406 | CD8SP-Protein-L-GGSG-NLuc-4xFLAG-x2STREP-8xHis-T2A-PAC |
| 101916-P03 | Kappa Light chain CAR | 1207 | 2407 | CD8SP-Protein-L-2-GGSG-NLuc-4xFLAG-x2STREP-8xHis-T2A-PAC |

TABLE 17

Exemplary CAR Constructs

| Clone ID # | Target | SEQ ID (DNA) | SEQ ID (Prt) | CONSTRUCT NAME |
|---|---|---|---|---|
| 112014-A13 | CD19 | 1208 | 2408 | FMC63-(vL-vH)-Myc-BBz-T2A-Pac |
| 021015-R07 | MPL | 1209 | 2409 | 161-(vL-vH)-Myc-BBz-T2A-Pac |
| 032415-N06 | CD138 | 1210 | 2410 | CD138-(vL-vH)-Myc-28z-T2A-Pac |
| 032415-O01 | CD33 | 1211 | 2411 | CD33-(vL-vH)-Myc-28z-T2A-Pac |
| 052115-A02 | CD138 | 1212 | 2412 | CD138-(vL-vH)-MYC-BBz-T2A-Pac |
| 031915-G02 | BCMA | 1213 | 2413 | J6MO-(vL-vH)-MYC-28z-T2A-Pac |
| 052516-I07 | CD22 | 1214 | 2414 | CD22-h10F4v2-(vL-vH)-MYC-BBz-T2A-Pac |
| 081115-X01 | CD123 | 1215 | 2415 | CD123-CSL362-(vL-vH)-MYC-BBz-T2A-Pac |
| 081115-A02 | EGFRviii | 1216 | 2416 | EGFRvIII-139-(vL-vH)-Myc-BBz-T2A-PAC |
| 081115-E01 | EGFRviii | 1217 | 2417 | EGFRvIII-2173-(vH-vL)-Myc-BBz-T2A-PAC |
| | CD200R | 1218 | 2418 | CD200R-huDx182-(vL-vH)-Myc-BBz-T2A-PAC |
| 111915-E05 | Epcam | 1219 | 2419 | Epcam1-D5K5-(vL-vH)-MYC-BBz-T2A-PAC |
| 111815-A03 | CD20 | 1220 | 2420 | CD20-GA10-(vL-vH)-MYC-BBz-T2A-PAC |
| 052516-B07 | CD324 | 1221 | 2421 | CD324-SC10-6-(vL-vH)-MYC-BBz-T2A-PAC |
| 052516-A07 | CD324 | 1222 | 2422 | CD324-hSC10-17-(vL-vH)-MYC-BBz-T2A-PAC |
| 052516-F07 | PTK7 | 1223 | 2423 | PTK7-hSC6-23-(vL-vH)-MYC-BBz-T2A-PAC |
| 052516-E07 | PTK7 | 1224 | 2424 | PTK7-SC6-10-2-(vL-vH)-MYC-BBz-T2A-PAC |
| 052516-G07 | gpNMB | 1225 | 2425 | gpNMB-115-(vL-vH)-MYC-BBz-T2A-PAC |

TABLE 17-continued

Exemplary CAR Constructs

| Clone ID # | Target | SEQ ID (DNA) | SEQ ID (Prt) | CONSTRUCT NAME |
|---|---|---|---|---|
| 052616-H06 | CD34 | 1226 | 2426 | CD34-hu4C7-(vL-vH)-MYC-BBz-T2A-PAC |
| 052616-E05 | TSHR | 1227 | 2427 | TSHR-KB1-(vL-vH)-MYC-BBz-T2A-PAC |
| 052616-U05 | CS1 | 1228 | 2428 | HuLuc64-(vL-vH)-Myc-BBz-T2A-Pac |
| 031915-F03 | CS1 | 1229 | 2429 | Luc90-(vL-vH)-MYC-CD28z-T2A-Pac |
| 042315-N01 | KSHV-K8.1 | 1230 | 2430 | KSHV-4C3(vL-vH)-Myc-BBz-T2A-Pac |

TABLE 18

Protein L

| SEQ ID (DNA) | SEQ ID (PRT) | |
|---|---|---|
| 2431 | 2433 | Protein-L |
| 2432 | 2434 | Protein-L-2 |

EXAMPLES

The following examples are not intended to limit the scope of the claims to the invention, but are rather intended to be exemplary of certain embodiments. Any variations in the exemplified methods which occur to the skilled artisan are intended to fall within the scope of the present invention The cell lines used in this invention and their growth media are shown in the Table 19. Cells were cultured at 37° C., in a 5% CO2 humidified incubator. The cell lines were obtained from ATCC, NIH AIDS reagent program or were available in our laboratory or obtained from other laboratories.

TABLE 19

Cell lines and growth media

| Cell lines | Media | Cell lines | Media |
|---|---|---|---|
| BC-1 | RPMI, 20% FCS | THP-1 | RPMI, 10% FCS |
| BC-3 | RPMI, 20% FCS | U87MG | DMEM, 10% FCS |
| BCBL-1 | RPMI, 20% FCS | NCI-H540 | DMEM, 10% FCS |
| JSC-1 | RPMI, 20% FCS | LoVo | DMEM, 10% FCS |
| UMPEL-1 | RPMI, 20% FCS | SKOV-3 | DMEM, 10% FCS |
| MM1S | RPMI, 10% FCS | NCI-H1993 | DMEM, 10% FCS |
| U266 | RPMI, 10% FCS | Kasumi-1 | RPMI, 20% FCS |
| L363 | RPMI, 10% FCS | Jeko-1 | RPMI, 20% FCS |
| K562 | RPMI, 10% FCS | PC-3 | DMEM, 10% FCS |
| BV173 | RPMI, 10% FCS | HeLa | DMEM, 10% FCS |
| Nalm6 | RPMI, 10% FCS | NCI-H2452 | DMEM, 10% FCS |
| HL60 | RPMI, 10% FCS | LnCap | DMEM, 10% FCS |
| U937 | RPMI, 10% FCS | SNU-5 | RPMI, 20% FCS |
| RS: 411 | RPMI, 20% FCS | OVCAR-3 | DMEM, 10% FCS |
| MV: 411 | RPMI, 10% FCS | MEL-624 | DMEM, 10% FCS |
| Raji | RPMI, 10% FCS | LS174-T | DMEM, 10% FCS |
| HEL-92.1.7 | RPMI, 10% FCS | MEL-526 | DMEM, 10% FCS |
| Meg-01 | RPMI, 10% FCS | MDA-MB231 | DMEM, 10% FCS |
| Jurkat | RPMI, 10% FCS | L1236 | RPMI, 20% FCS |
| MM1 | DMEM, 10% FCS | L428 | RPMI, 20% FCS |
| Daudi | RPMI, 10% FCS | Molt-16 | RPMI, 20% FCS |
| REC-1 | RPMI, 10% FCS | RPMI8402 | RPMI, 20% FCS |
| U2932 | RPMI, 10% FCS | KN5-5F2 | RPMI, 20% FCS |
| H929 | RPMI, 10% FCS beta Mercapto-ethanol (BME) | CCRF-CEM (ATCC) | RPMI, 10% FCS |
| KMS28 | RPMI, 10% FCS | MG-63 | DMEM, 10% FCS |
| EJM | RPMI, 10% FCS | Karpass-299 | RPMI, 20% FCS |
| MRC-5 | DMEM, 10% FCS | MCF7 | DMEM, 10% FCS |
| CMK | RPMI, 20% FCS | SUDHL-1 | RPMI, 10% FCS |
| TF-1 | RPMI, 10% FCS + GMCSF | AA-2 | RPMI, 10% FCS |
| ML-2 | RPMI, 20% FCS | HL2/3 | DMEM, 10% FCS |
| A20 | RPMI, 10% FCS + BME | TF228.1.16 | DMEM, 10% FCS |
| KMS28BM | RPMI, 10% FCS | MT-4 | RPMI, 10% FCS |
| KG-1 | RPMI, 20% FCS | Sup-T1 | RPMI, 10% FCS |
| CEM | RPMI, 10% FCS | HuT-78 | RPMI, 10% FCS |
| U937 | RPMI, 10% FCS | TT | DMEM, 10% FCS |
| LAMA5 | RPMI, 10% FCS | DMS79 | RPMI, 10% FCS |
| A549 | DMEM, 10% FCS | LAN-5 | DMEM, 10% FCS |
| HT29 | DMEM, 10% FCS | PEER1 | RPMI, 10% FCS |
| Molm-13 | RPMI, 20% FCS | SK-MEL-37 | DMEM, 10% FCS |
| A431 | DMEM, 10% FCS | Jurkat-NFAT-GFP | RPMI, 10% FCS |
| P19 | DMEM, 10% FCS | F9 | DMEM, 10% FCS |

Jurkat cell line (clone E6-1) engineered with a NFAT-dependent EGFP (or GFP) reporter gene was a gift from Dr. Arthur Weiss at University of California San Francisco and have been described to study CAR-signaling ((Wu, C Y et al., Science 350:293-302, 2015). Jurkat cells were maintained in RPMI-1640 medium supplemented with 10% FBS, penicillin and streptomycin. 293FT cells were obtained from Thermofisher and maintained in DMEM medium supplemented with 10% FBS, penicillin and streptomycin.

Generation of Lentiviral Vectors Encoding Chimeric Antigen Receptors Against MPL The pLENTI-Blast vector was derived from pLenti6v5gw_lacz vector (Invitrogen; ThermoFisher Scientific) by removal of the LacZ gene. pLenti-MP2 was a gift from Pantelis Tsoulfas (Addgene plasmid #36097) and was used to generate pLenti-EF1a or pLenti-EF1α lentiviral vector by replacement of the CMV promoter with human EF1α promoter using standard molecular biology techniques. pLenti-EF1a-DWPRE was derived from the pLENTI-EF1α vector by deletion of WPRE sequence. The psPAX2 vector was a gift from Didier Trono (Addgene plasmid #12260). The pLP/VSVG envelope plasmid and 293FT cells were obtained from Invitrogen (ThermoFisher Scientific). The retroviral transfer vector MSCVneo, MSCVhygro, and MSCVpac and the packaging vector pKAT were obtained from Dr. Robert Illaria's laboratory. phRGTK *Renilla* Luciferase plasmid was from Promega.

Example 1. Assay to Detect the Expression of CD19 and MPL (Thrombopoietin Receptor) Antigens Both CD19 and MPL (also known as Thrombopoietin receptor or TPO-R) are expressed on hematopoietic cells but show differential expression in cells of different lineages. FMC63 is a well characterized mouse monoclonal antibody that specifically recognizes human CD19. Similarly, 161 (also designated as 1.6.1) is a monoclonal antibody that recognizes human MPL and is described in U.S. patent application US 2012/0269814 A1. We generated a FMC63 single chain Fv (scFv) fragment based on the known sequence of FMC63 vL and vH fragments. The cDNA encoding FMC63 scFv fragment consisted from 5' to 3' ends a nucleotide sequences encoding a signal peptide derived from human CD8 molecule, FMC63 vL fragment, a (Gly$_4$Ser)×3 linker and FMC63-vH fragment. The cDNA encoding the FMC63 scFv fragment was then fused in-frame at its 3' end to cDNA encoding AcV5-tagged NLuc through a Gly-Gly-Ser-Gly (GGSG) linker to generate FMC63-GGSG-NLuc-AcV5, which was then cloned downstream of the human EF1α promoter into the lentiviral vector pLenti-EF1 (SEQ ID NO: 842). The DNA and PRT sequences of the insert fragment are provided in SEQ ID NO: 1119 and SEQ ID NO: 2319, respectively. A construct encoding 161-GGSG-NLuc was similarly generated using the vL and vH fragment of 161 (1.6.1) monoclonal antibody against MPL. The DNA and PRT sequences of the insert fragment are provided in SEQ ID NO: 1118 and SEQ ID NO: 2318, respectively.

The pLenti-EF1-FMC63-GGSG-NLuc-AcV5 and pLenti-EF1-161-GGSG-NLuc-AcV5 plasmids were transfected into 293FT cells by calcium phosphate co-precipitation method. Approximately 20 h post-transfection, the cell culture media was replaced with XVIVO medium. The conditioned media containing the secreted FMC63-GGSG-NLuc-AcV5 and 161-GGSG-NLuc-AcV5 proteins was collected 48-72 h later.

The supernatant containing FMC63-GGSG-NLuc-AcV5 and 161-GGSG-NLuc-AcV5 proteins were used to detect the expression of CD19 and MPL on the surface of Jurkat, K562, RAJI, RS-4-11 (RS411) and HEL 92.1.7 (HEL) cells that had been engineered to express a c-MPL cDNA by transducing these cells with a lentiviral vector expressing human c-MPL cDNA or an empty vector. The cells also expressed a humanized Gluc cDNA lacking its signal peptide.

The vector- and MPL-expressing Jurkat-Gluc, K562-Gluc, HEL 92.1.7-Gluc, RAJI-Gluc and RS411-Gluc cells were incubated with the FMC63-GGSG-NLuc-AcV5 and 161-GGSG-NLuc-AcV5 supernatants at 4° C. for 1 h followed by extensive washings with cold PBS supplemented with 0.1% BSA. The cells were re-suspended in cold PBS and 30 μl of cell suspension was plated per well in a flat-bottom 384 well plate (Greiner, 384 well white plate cat. #781075) in triplicate. NLuc assay buffer containing native coelenterazine (CTZ) as NLuc substrate (30 μl/well of native coelenterazine diluted in PBS) was added to each well by an automatic dispenser in a well mode using a BioTek synergy H4 plate reader and light emission as a measure of NLuc activity was measured.

FIG. 1A-FIG. 1B show that strong binding with 161-GGSG-NLuc-AcV5 was observed on HEL.92.1.7-Gluc-vector cells suggesting significant expression of MPL endogenously. Ectopic expression of MPL in HEL.92.1.7-Gluc-MPL cells led to a modest increase in 161-GGSG-NLuc-AcV5 binding. In contrast, very weak binding with 161-GGSG-NLuc-AcV5 was observed on vector-expressing Jurkat, RAJI and RS411 cells and was only modestly increased upon ectopic expression of MPL. Finally, weak but stronger binding of 161-GGSG-NLuc-AcV5 was observed on K562-vector cells, and was significantly increased on K562-MPL cells. In contrast to 161-GGSG-NLuc-AcV5, the FMC63-GGSG-NLuc-AcV5 supernatant showed strongest binding on vector- and MPL-expressing RAJI cells, modestly strong binding on RS411 cells and very weak to negligible binding on the other cells.

Example 2. Assay to Detect the Expression of MPL (Thrombopoietin Receptor) Using 161-GGSG-NLuc-AcV5 Supernatant 293FT cells were transiently transfected with a construct encoding human MPL (pLenti-MPL) or left untransfected. Next day morning, approximately 18 hours post-transfection, cells were collected by pipetting up and down in 1.5 ml tubes. The tubes were spun down at 1500 RPM for 5 minutes. Then the cells were washed once with wash buffer (1% FBS in PBS), followed by incubation with 100 μl of 161-GGSG-NLuc-AcV5 supernatant. The cells were incubated at 4° C. for 1 hour. After the incubation, cells were washed 5 times with wash buffer (1 ml each wash). Finally the pellet was resuspended in 200 μl wash buffer. Resuspended cells were placed in a 384 well plate in triplicate (25 μl each). Luciferase activity was measured using a BioTek synergy H4 plate reader after addition of NLuc assay buffer (Promega) containing native coelenterazine (25 μl each well) directly to each well (one at a time). FIG. 2 shows significant increased binding of 161-GGSG-NLuc-AcV5 supernatant to cells that had been transfected with MPL as compared to the untransfected cells.

Example 3. Assay to Detect the Expression of Chimeric Antigen Receptors Targeting CD19 and MPL (Thrombopoietin Receptor)

A frequent problem in the field of chimeric antigen receptors is lack of a sensitive and specific assay that can detect cells that express chimeric antigen receptors. To detect the expression of CAR targeting CD19 and MPL, we fused the extracellular domains (ECD) of human CD19 and human MPL, including their signal peptides, in frame with nucleotide sequence encoding a Gly-Gly-Ser-Gly linker, NLuc (without a secretory signal) and an AcV5 epitope tag. In the case of CD19 construct, a FLAG tag was inserted between the signal peptide and the beginning of the extracellular domain. The whole cassette was cloned downstream of the human EF1α promoter into the lentiviral vector pLenti-EF1 (SEQ ID NO: 842) to make constructs pLenti-EF1-FLAG-CD19-ECD-GGSG-NLuc-AcV5 (SEQ ID NO: 845) and pLenti-EF1-MPL-ECD-GGSG-NLuc-AcV5, respectively. The nucleic acid sequences of the insert fragments are provided in SEQ ID NO: 1170 and SEQ ID NO: 1169, respectively. The protein sequences of the insert fragments are provided in SEQ ID NO: 2370 and SEQ ID NO: 2369, respectively. The constructs were transfected into 293FT cells by calcium phosphate co-precipitation method. Approximately 20 h post-transfection, the cell culture media was replaced with fresh medium. The conditioned media containing the secreted FLAG-CD19-ECD-GGSG-NLuc-AcV5 (also referred to as CD19-GGSG-NLuc-AcV5) and MPL-ECD-GGSG-NLuc-AcV5 (also referred to as MPL-GGSG-NLuc-AcV5) proteins was collected 48-72 h later.

T-cells engineered to express a chimeric antigen receptor targeting CD19-specific CAR(FMC63-CAR; or FMC63-(vL-vH)-Myc-BBz-T2A-Pac(112014-A13)[ SEQ ID NO:1208]) or a control CAR (4C3-CAR or KSHV-4C3(vL-vH)-Myc-BBz-T2A-Pac(042315-N01)[ SEQ ID NO:1230]) targeting a protein encoded by Kaposi's sarcoma associated herpesvirus were incubated with CD19-GGSG-NLuc-AcV5 supernatant at 4° C. for 1 h followed by extensive washing with cold PBS supplemented with 0.1% Bovine Serum Albumin (BSA). The cells were re-suspended in cold PBS and 30 µl of cell suspension was plated per well in a flat-bottom 384 well plate (Greiner, 384 well white plate cat. #781075) in triplicate. NLuc assay buffer (Promega) containing native coelenterazine (CTZ) (30 µl/well of native coelenterazine diluted in PBS) was added to each well by an automatic dispenser in a well mode using a BioTek synergy H4 plate reader and light emission as a measure of NLuc activity was measured.

Figure 3:
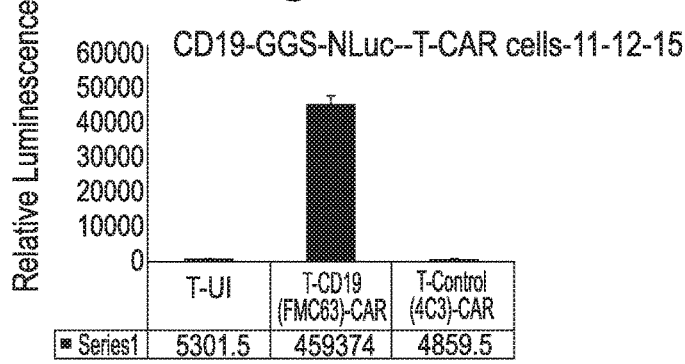
FIG. 3 depicts, in accordance with various embodiments of the invention, NLuc assay to measure expression of CAR in T cells. The uninfected T cells (UI) and T cells expressing CD19 (FMC63) and control (4C3) CAR were incubated with CD19-GGSG-NLuc-AcV5 supernatants as described in material and methods section followed by washing with PBS and measurement of NLuc activity by Coeleoentrazine (CTZ; Nanolight) diluted in PBS. Luminescence was quantified using a BioTek plate reader. Data represents mean values of triplicate wells +/− standard deviation (SD).

As shown in FIG. 3, T cells expressing CD19 (FMC63)-CAR demonstrated strong binding to CD19-GGSG-NLuc-AcV5 as measured by NLuc assay while very little binding was seen on uninfected T cells (UI) or those expressing control (4C3) CAR. The NLuc value on CD19 (FMC63)-CAR cells was more than 85 fold more than on the uninfected or control CAR expressing cells, thereby demonstrating the extreme sensitivity of the assay.

Example 4. Assay to Detect the Expression of Chimeric Antigen Receptors Targeting CD19 and MPL (Thrombopoietin Receptor) on 293FT Cells that had been Transfected with the Corresponding Constructs 293FT-cells were transiently transfected (in a 24-well plate, 500 ul volume) with lentiviral constructs expressing chimeric antigen receptors targeting CD19 (FMC63-BBZ-PAC-A13; also referred to as FMC63-(vL-vH)-Myc-BBz-T2A-Pac(112014-A13)[ SEQ ID NO:1208]) and MPL (161-BBZ-PAC-R07; also referred to as 161-(vL-vH)-Myc-BBz-T2A-Pac(021015-R07)[ SEQ ID NO:1209]) using calcium phosphate cotransfection method or left untransfected. Next day morning, approximately 18 hours post-transfection, cells were collected by pipetting up and down in 1.5 ml tubes. The tubes were spun down at 1500 RPM for 5 minutes. Then the cells were washed once with wash buffer (1% FBS in PBS), followed by incubation with 100 µl of indicated secretory forms of GGS NLuc supernatant. The cells were incubated at 4° C. for 1 hour. After the incubation, cells were washed 5 times with wash buffer (1 ml each wash). Finally the pellet was resuspended in 200 µl wash buffer. Resuspended cells were placed in a 384 well plate in triplicate (25 µl each). Luciferase activity was measured using a BioTek synergy H4 plate reader after addition of NLuc assay buffer (Promega) containing native coelenterazine (25 µl each well) directly to each well (one at a time).

Figure 4A:
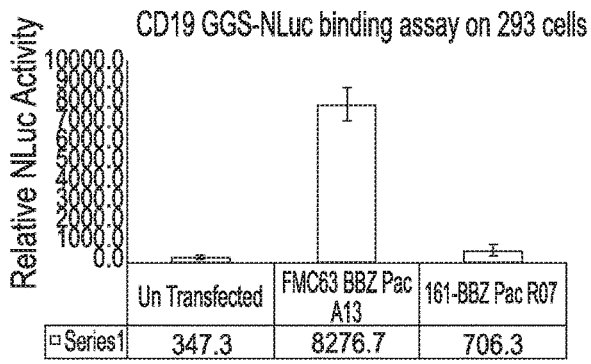
FIG. 4A-FIG. 4B depict, in accordance with various embodiments of the invention, NLuc assay to measure expression of CAR in 293FT cells. The untransfected 293FT cells, and those transfected with CD19 (FMC63-BBZ-PAC) and 161-BBZ-PAC CAR were incubated with CD19-GGSG-NLuc-AcV5 and MPL-GGSG-NLuc-AcV5 supernatants as described in material and methods section followed by washing with PBS and measurement of NLuc activity by Coeleoentrazine (CTZ; Nanolight) diluted in PBS. Luminescence was quantified using a BioTek plate reader. Data represents mean values of triplicate wells +/− standard deviation (SD).
Figure 4B:
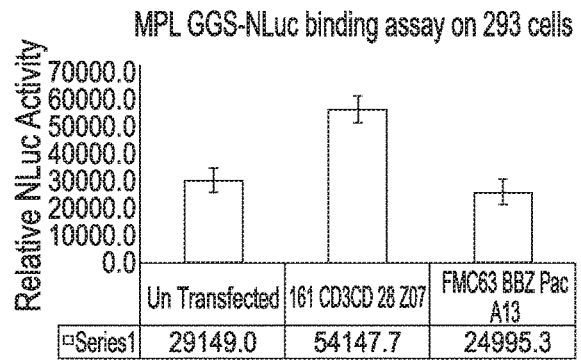

As shown in FIG. 4A-FIG. 4B, 293FT cells expressing CD19 (FMC63-BBZ-PAC)-CAR demonstrated strong binding to CD19-GGSG-NLuc-AcV5 as measured by NLuc assay while very little binding was seen on uninfected T cells (UI) or those expressing control 161-BBZ-PAC CAR. Similarly, 293FT cells expressing 161-BBZ-PAC CAR showed strong binding with MPL-GGSG-NLuc-AcV5 supernatant as compared to untransfected 293FT cells or those transfected with FMC63-BBZ-PAC CAR.

Example 5. Assay to Detect the Expression of Chimeric Antigen Receptors Targeting MPL (Thrombopoietin Receptor) on 293FT Cells that had been Transfected with the Different CAR Constructs Three different chimeric antigen receptor constructs were made. The construct hTPO-CD28z-Pac consisted of the extracellular receptor binding domains of human thrombopoietin (TPO; SEQ ID NO: 553) fused to the CD28 hinge, transmembrane and cytosolic domains and CD3z cytosolic domains. The construct mTPO-CD28z-Pac was similar in design except that it consisted of the extracellular receptor binding domains of mouse thrombopoietin (TPO; SEQ ID NO: 554) in place of human TPO. Finally, the construct 161-BBz-Pac (161-(vL-vH)-Myc-BBz-T2A-Pac(021015-R07)[ SEQ ID NO:1209]) consisted of a scFv fragment (SEQ ID NO: 730) derived from a monoclonal antibody against human MPL fused to a cassette containing the hinge and transmembrane domain of human CD8, the cytosolic domain of human 41BB (CD137) receptor and the cytosolic domain of human CD3z. A control CAR containing a scFv (SEQ ID NO: 718) derived from an irrelevant antibody against a viral protein was constructed as well. All the constructs were transiently transfected into 293FT cells and incubated with MPL-GGSG-NLuc-AcV5 supernatant essentially as described in the preceding example.

Figure 5:
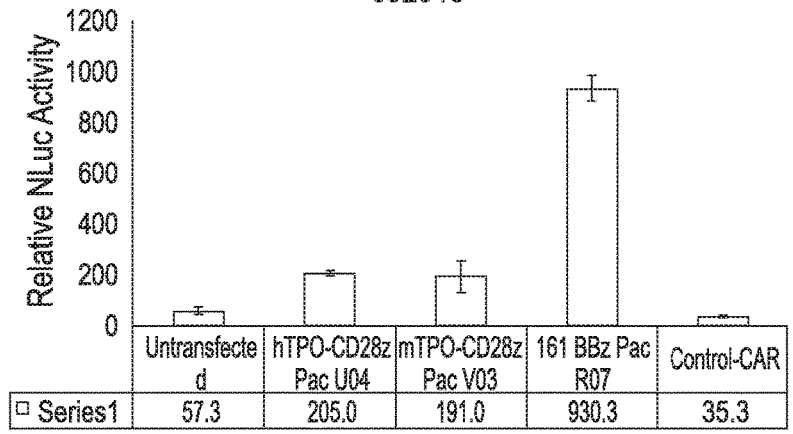
FIG. 5 depicts, in accordance with various embodiments of the invention, modest binding of MPL-GGSG-NLuc-AcV5 to 293FT cells transfected with hTPO-CD28z-Pac and mTPO-CD28z-Pac constructs and strong binding to 293FT cells transfected with 161-BBz-Pac construct as compared to untransfected cells or cells that had been transfected with control CAR construct.

FIG. 5 shows modest binding of MPL-GGSG-NLuc-AcV5 to 293FT cells transfected with hTPO-CD28z-Pac and mTPO-CD28z-Pac constructs and strong binding to 293FT cells transfected with 161-BBz-Pac construct as compared to untransfected cells or cells that had been transfected with control CAR construct.

Example 6. Assay to Detect the Expression of CD19 Using FMC63 scFV Fused to GLuc, MLuc7, TurboLuc16, *L. Ovaliformi*-Luc and Htanneri-Luc In Example 1, we demonstrated the ability of FMC63-GGSG-NLuc-AcV5 fusion protein to detect the expression of CD19 antigen. To demonstrate that this ability is not limited to NLuc fusion proteins, we generated lentiviral expression vectors encoding EF1α promoter driven fusion constructs containing FMC63 scFv fragment linked via a GGS linker to luciferases from *Gaussia princeps* (GLuc), *Lucicutia ovaliformis* (Lovaliformis-Luc or LoLuc), *Heterorhabdus tanneri* (Htanneri Luc or HtLuc), *Metridia longa* 7 (MLuc7) and TurboLuc16 (or TLuc purchased from Life Technologies). All the luciferases lacked any N-terminal secretory peptide. The GLuc, TurboLuc16 and Htanneri-Luc constructs carried a carboxy terminal x3Flag epitope tag, while the Lovaliformis-Luc carried a carboxy terminal AcV5 tag and the MLuc7 construct carried a carboxy terminal HA epitope tag. The MLuc7 cDNA also carried M43L and M110L substitutions. The corresponding substitutions in GLuc have been previously shown to result in Glow type luminescence. The expression vectors encoding the above fusion proteins were transiently transfected into 293FT cells and supernatant containing the fusion proteins collected essentially as described in Example 1. The FMC63-GGSG-NLuc-AcV5 supernatant was generated as described in Example 1 and stored at −20° C. prior to use.

The supernatant containing the fusion proteins were used to detect the expression of CD19 on the surface of RAJI, K562, and HL60 cells. Approximately, 250,000 cells of each kind were mixed with 100 µl of supernatant (50 µl of supernatant in case of GLuc and MLuc7) on ice for approximately 1 h. Cells were washed 4 times with PBS containing 1% FBS. Finally after the 4th wash, the cells were re-suspended in cold PBS and 25 µl of cell suspension was plated per well in a flat-bottom 384 well plate (Greiner, 384 well white plate cat. #781075) in duplicate. Luc assay buffer containing native coelenterazine (25 µl/well of native coelenterazine diluted in PBS) was added to each well by an automatic dispenser in a well mode using a BioTek synergy H4 plate reader and light emission as a measure of Luc activity was measured.

Figure 6A:
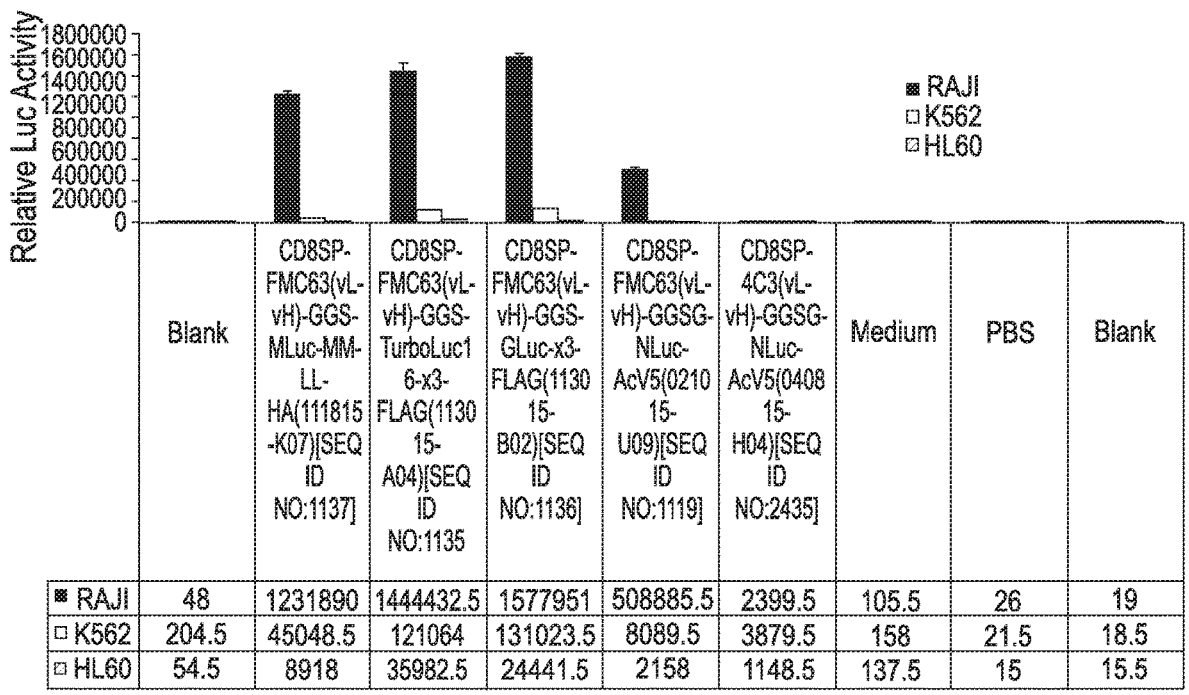
FIG. 6A-FIG. 6C depicts, in accordance with various embodiments of the invention, LUC activity of FMC63-GGSG-MLuc7-MM-LL-HA, FMC63-GGS-TurboLuc16-×3Flag, FMC63-GGS-GLuc-×3FLAG, and FMC63-GGS-NLuc-AcV5 on RAJI cells (known to be CD19 positive cell line) as compared to the Luc activity observed with media control.
Figure 6B:
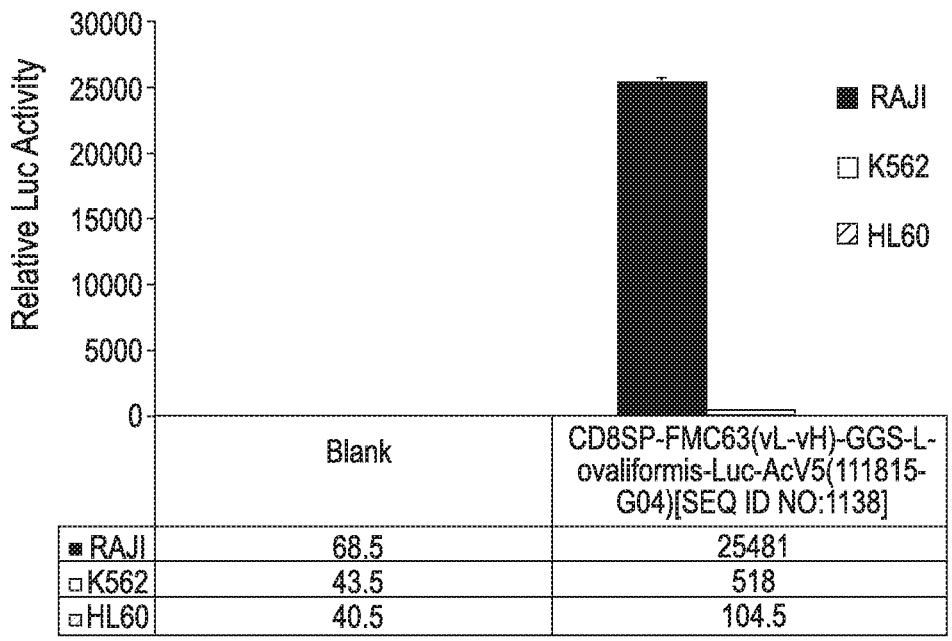
Figure 6C:
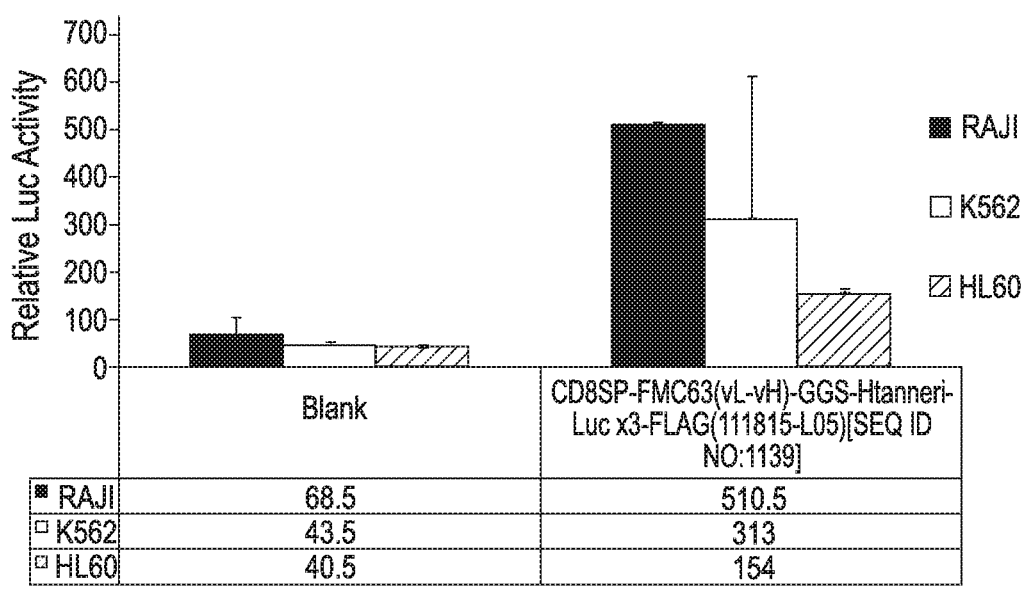

As shown in FIG. 6A, CD8SP-FMC63(vL-vH)-GGS-MLuc-MM-LL-HA(111815-K07)[ SEQ ID NO:1137], CD8SP-FMC63(vL-vH)-GGS-TurboLuc16-x3-FLAG (113015-A04)[ SEQ ID NO:1135], CD8SP-FMC63(vL-vH)-GGS-GLuc-x3-FLAG(113015-B02)[ SEQ ID NO:1136], and CD8SP-FMC63(vL-vH)-GGSG-NLuc-AcV5(021015-U09)[ SEQ ID NO:1119] showed approximately 11676 fold, 13691 fold, 14956 fold and 4823 fold higher Luc activity on RAJI cells (known to be CD19 positive cell line) as compared to the Luc activity observed with media control. Weak binding with all the fusion proteins was also observed on K562 cells, while very weak binding was seen on HL60 cells. Even though K562 cells showed weak binding as compared to RAJI cells, they showed approximately 285 fold, 766 fold, 829 fold and 51 fold increase in Luc activity with CD8SP-FMC63(vL-vH)-GGS-MLuc-MM-LL-HA(111815-K07)[ SEQ ID NO:1137], CD8 SP-FMC63 (vL-vH)-GGS-TurboLuc16-x3-FLAG(113015-A04)[ SEQ ID NO:1135], CD8 SP-FMC63 (vL-vH)-GGS-GLuc-x3-FLAG(113015-B02) [ SEQ ID NO:1136] and CD8 SP-FMC63(vL-vH)-GGSG-NLuc-AcV5(021015-U09)[ SEQ ID NO:1119], respectively, over that observed with media alone control, thereby demonstrating the extreme sensitivity of the assay. Similarly, even the very weak Luc activity observed on HL60 cells with CD8SP-FMC63(vL-vH)-GGS-MLuc-MM-LL-HA(111815-K07)[ SEQ ID NO:1137], CD8 SP-FMC63 (vL-vH)-GGS-TurboLuc16-x3-FLAG(113015-A04)[ SEQ ID NO:1135], CD8 SP-FMC63 (vL-vH)-GGS-GLuc-x3-FLAG(113015-B02) [ SEQ ID NO:1136] and CD8 SP-FMC63(vL-vH)-GGSG-NLuc-AcV5(021015-U09)[ SEQ ID NO:1119]fusion proteins was still approximately 65 fold, 262 fold, 178 fold and 15 fold higher than that observed with the media alone. CD8SP-4C3-(vL-vH)-GGSG-NLuc-AcV5(040815-H04)[ SEQ ID NO:2435], a fusion protein targeting a lytic protein expressed by Kaposi's sarcoma associated was used as a negative control and showed negligible binding, demonstrating the specificity of the assay. Essentially similar results were obtained upon staining with CD8SP-FMC63 (vL-vH)-GGS-L-ovaliformis-Luc-AcV5 (111815-G04) [ SEQ ID NO: 1138] and CD8SP-FMC63(vL-vH)-GGS-Htanneri-Luc-x3-FLAG(111815-L05)[ SEQ ID NO:1139] fusion proteins (FIG. 6B and FIG. 6C), although the light produced by these fusion proteins was of lower intensity.

Example 7. scFV-Luc Fusion Proteins can be Used to Detect the Expression of their Target Antigen by Immunofluorescence Staining and Flow Cytometry We also tested the ability of fusion proteins to detect the expression of CD19 by immunofluorescence staining followed by flow cytometry. For this purpose, RAJI, K562 and HL60 cells (300,000 cells each) were stained with the supernatant (100 µl) containing the CD8 SP-FMC63 (vL-vH)-GGS-GLuc-x3-FLAG(113015-B02)[ SEQ ID NO:1136], CD8 SP-FMC63 (vL-vH)-GGS-TurboLuc16-x3-FLAG(113015-A04)[ SEQ ID NO:1135] and CD8 SP-4C3-(vL-vH)-GGSG-NLuc-AcV5(040815-H04)[ SEQ ID NO:2435] (-ve control) fusion proteins (1 hour at 4° C.). After extensive washes (5 washes, 1 mL each) with PBS containing 1% FBS (Wash buffer), cells were stained (1 hour at 4° C.) with FITC-conjugated antibody against FLAG-epitope tag (1 ug/mL; SIGMA, FITC-M2 FLAG antibody; catalog #F4049). After incubation, cells were further washed 3 times with wash buffer. Finally, the cell pellets were re-suspended with 400 µl wash buffer and were analyzed by flow cytometry on a BD FACS Verse machine.

As shown in FIG. 7A-FIG. 7B, RAJI cells CD8SP-FMC63(vL-vH)-GGS-GLuc-x3-FLAG(113015-B02)[ SEQ ID NO:1136] and CD8SP-FMC63(vL-vH)-GGS-TurboLuc16-x3-FLAG(113015-A04)[ SEQ ID NO:1135] showed clear increase (approximately 3-5 fold) in fluorescence [as seen by a significant shift in the FITC peak and by mean fluorescence intensity (MFI)], when compared with those stained with CD8SP-4C3-(vL-vH)-GGSG-NLuc-AcV5 (040815-H04)[ SEQ ID NO:2435] or medium alone (-ve controls). However, the 3-5 fold increase in mean fluorescence observed over the media alone control using Flow cytometry was still weak as compared to the approximately 13691 fold, 14956 fold increase in Luc activity observed using the Luc assay using the same fusion proteins in Example 6. No significant increase in fluorescence was detected on K562 and HL60 cells when stained with CD8SP-FMC63(vL-vH)-GGS-GLuc-x3-FLAG(113015-B02)[ SEQ ID NO:1136] and CD8SP-FMC63(vL-vH)-GGS-TurboLuc16-x3-FLAG(113015-A04)[ SEQ ID NO:1135] as compared to the CD8SP-4C3-(vL-vH)-GGSG-NLuc-AcV5(040815-H04)[ SEQ ID NO:2435] and media control. In contrast, both K562 and HL60 cells showed easily detectable activity, which was several hundred fold higher over the media control, when measured by Luc assay (see FIG. 6A-FIG. 6C of Example 6).

Taken together, these results demonstrate that the greater sensitivity of the Luc assay as compared to the immunofluorescence/Flow cytometry analysis, which has significance for development of companion diagnostics for cellular therapy products, bispecific antibodies and antibody drug conjugates. These results also demonstrate the versatility of the epitope-tagged scFV-Luc-fusion proteins for detection of their target antigens by immunofluorescence staining. The fusion proteins can be tagged with different tags (e.g. FLAG, HA, MYC, T7, AcV5, V5, StrepTagII, poly His, etc.), either singly or in combination, and can then be detected by flourochrome labeled antibodies against the epitope tags. Alternatively, they can be fused to fluorescent proteins, such as EGFP, RFP and mcherry, for detection directly. Finally, the epitope tags, such as StrepTagII and polyHis tags, can be also used for the purification of the scFV fusion proteins.

Example 8. scFV-NLuc Fusion Proteins Targeting Different Tumor Antigens

To demonstrate that the assay described in Example 1 is not limited to detection of CD19 and MPL, lentiviral expression vectors encoding NLuc fusion proteins containing NH2-terminal scFV fragments derived from antibodies targeting different antigens were generated essentially as described for FMC63-NLuc fusion proteins in Example 1. The names of the different scFVs and their target antigens are shown in Table 1. In addition NLuc fusion proteins containing extracellular ligand binding domains (amino acid residues 1-187) of human and mouse thrombopoietin (TPO) were generated. The expression vectors encoding the NLuc fusion proteins were transfected in 293FT cells and supernatant containing the secreted fusion proteins were collected as described for Example 1. The supernatant containing the secreted NLuc fusion proteins was used to stain RAJI, K562 and HL60 cell lines and bound proteins detected by addition of coelenterazine (25 µl/well of native coelenterazine diluted in PBS), essentially as described for Example 1.

TABLE 1

| scFV/Ligand | Target |
|---|---|
| FMC63 | CD19 |
| 161 | MPL |
| huMA79b-v28 | CD79b |
| Luc90 | CS1 |
| HuLuc63 | CS1 |
| J6M0 | BCMA |
| Hum291 | CD3 |
| Lym1 | Lym1 |
| Lym2 | Lym2 |
| CD33 | CD33 |
| CD138 | CD138 |
| NC7 | FLT3 |
| BC8 | CD45 |
| GRP78-GC18 | GRP78 |
| hTPO (1-187) | MPL |
| mTPO (1-187) | MPL |

Figure 8B:
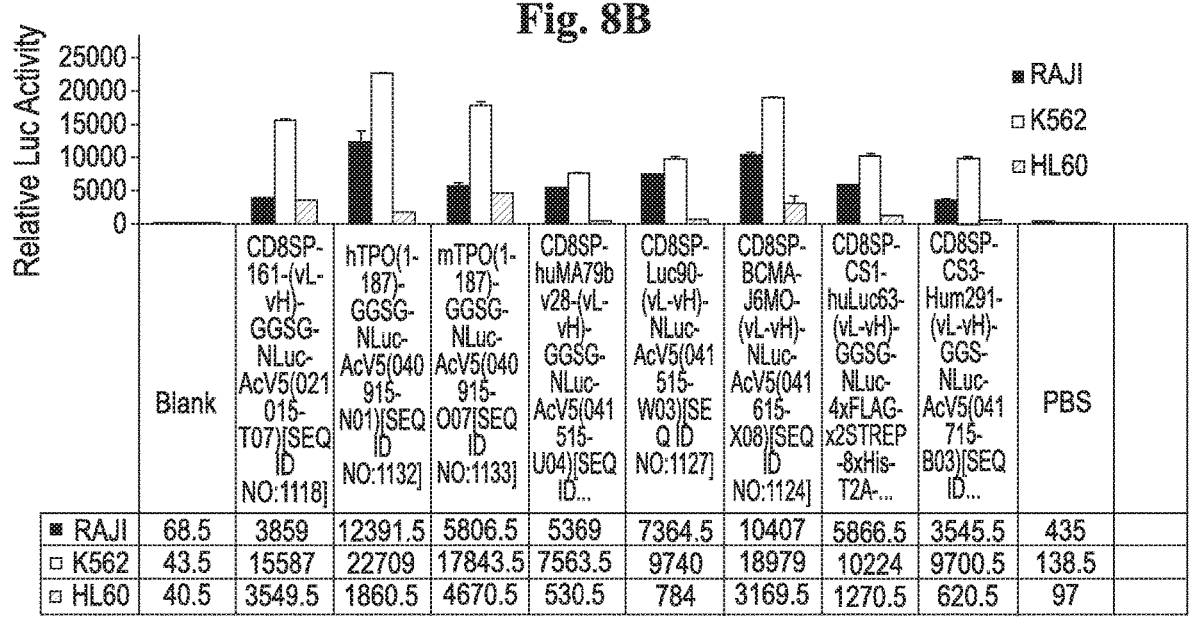

As shown in FIG. 8A-FIG. 8B, the different fusion proteins showed differential staining on the 3 cell lines. Thus, greater binding of NLuc fusion proteins containing 161, hTPO (1-187), mTPO (1-87), huMA79b-v28, Luc90, HuLuc63, J6M0, Hum291, CD138, BC8 and GRP78-GC18 was observed on K562 cells as compared to HL60 cells. RAJI cells showed highest binding of Lym1 and BC8 fusion proteins, while HL60 cells showed highest binding of CD33 fusion protein.

Example 9. scFv-NLuc Fusion Proteins Targeting CD30

Figure 9:
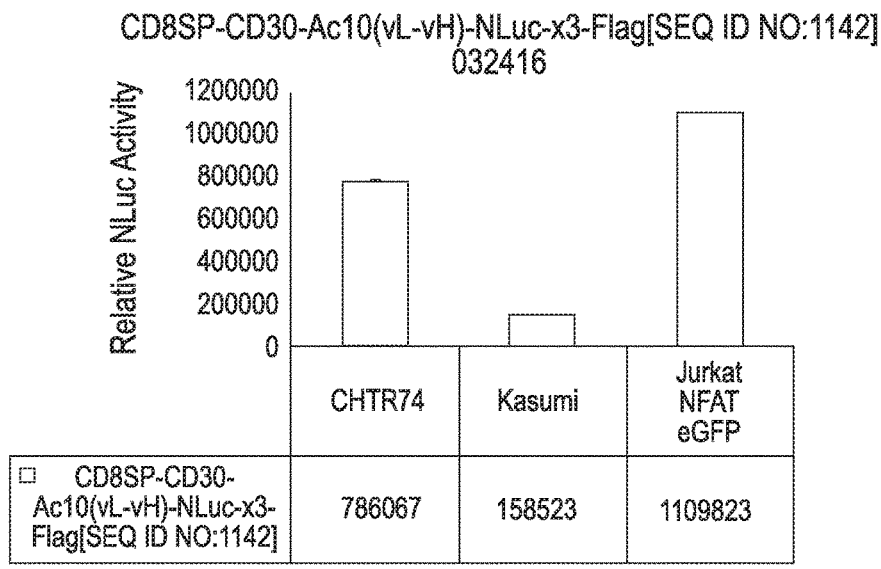
FIG. 9A-FIG. 9B depicts, in accordance with various embodiments of the invention, show binding of CD30-Ac10 (vL-vH)-GGSG-NLuc-×3-Flag to Jurkat and CHTR74 cells compared to Kasumi cells.

A scFV-GGSG-NLuc-x3-Flag fusion protein targeting CD30 were constructed based on Ac10 scFv fragment, which also carried 3 copies of Flag tag at the carboxy-terminal. Robust expression of fusion protein was observed upon transient transfection of the CD8SP-CD30-Ac10(vL-vH)-NLuc-x3-Flag[SEQ ID NO:1142]construct in 293FT cells. The supernatants containing the CD8 SP-CD30-Ac10 (vL-vH)-NLuc-x3-Flag[SEQ ID NO:1142]fusion protein was tested for binding to Jurkat (CD30$^+$) and Kasumi (CD30$^-$) cell lines as well as CHTR74, a lymphoma cell line derived from a patient with lymphoma, using the assay described above. FIG. 9 shows strong binding of CD30-Ac10(vL-vH)-GGSG-NLuc-x3-Flag to Jurkat and CHTR74 cells as compared to Kasumi cells.

Figure 10A:
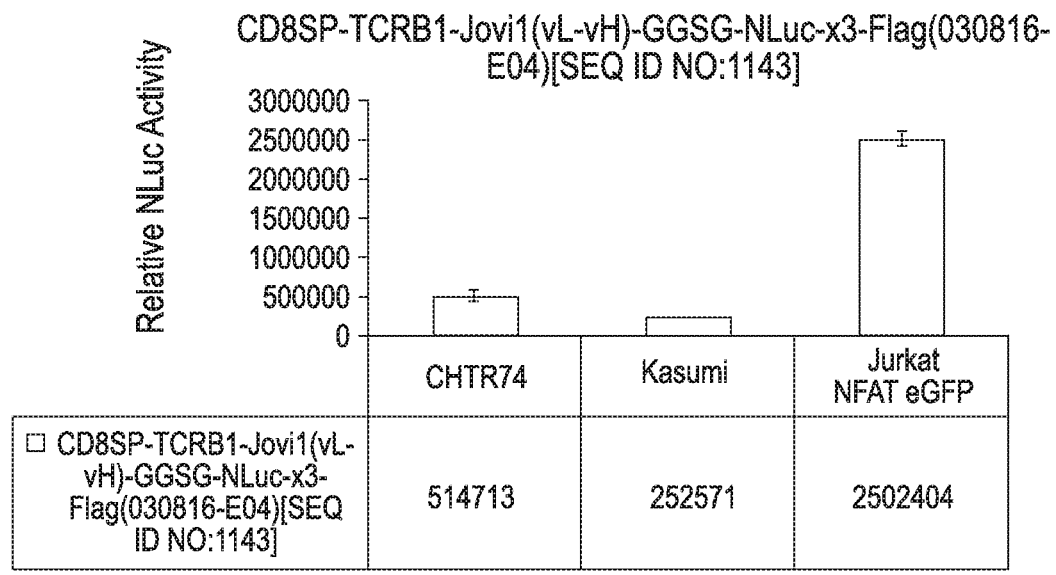
FIG. 10A-FIG. 10B depicts, in accordance with various embodiments of the invention, binding of both TCRB1-Jovi1(vL-vH)-GGSG-NLuc-×3-Flag and TCRB1-E09(vL-vH)-GGSG-NLuc-×3-Flag fusion proteins to Jurkat and as compared to Kasumi and CHTR74 cells.
Figure 10B:
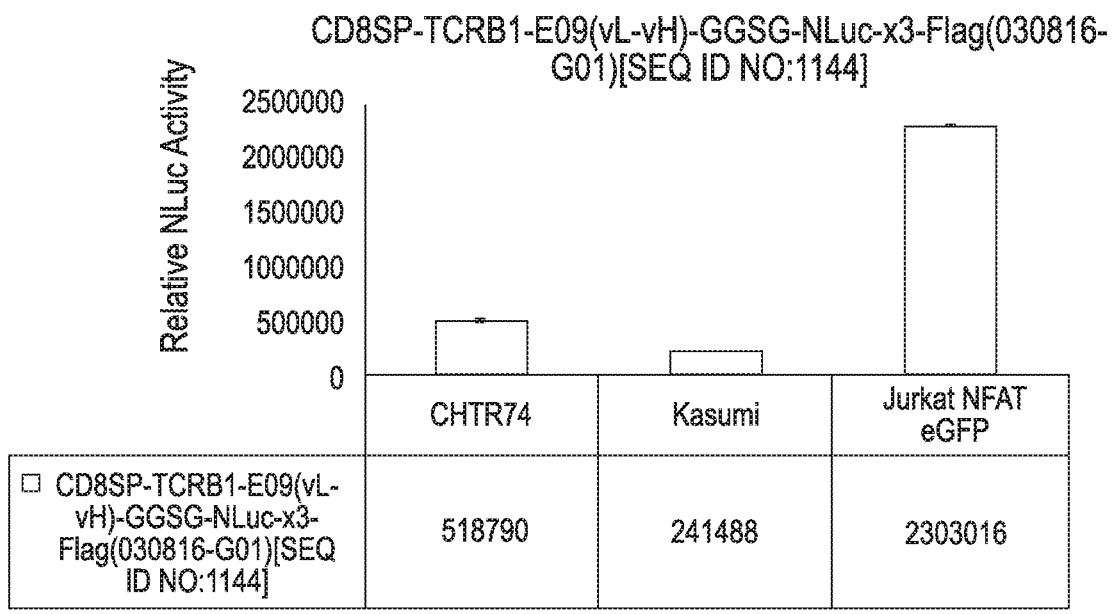

Example 10. scFv-NLuc Fusion Proteins Targeting the Human TCR β1 Isoform Constant Region Two scFV-GGSG-NLuc-x3-Flag fusion proteins targeting the constant region of the β1 isoform of human T cell receptor β were constructed based on Jov1 and E09 scFv fragments, which also carried three copies of a Flag tag at the carboxy-terminal. Robust expression of fusion proteins was observed upon transient transfection of the two fusion protein encoding constructs in 293FT cells. The supernatants containing the two fusion proteins were tested for binding to Jurkat (TCRB1+) and Kasumi (TCRB$^-$) cell lines as well as CHTR74, a lymphoma cell line derived from a patient with lymphoma using the assay described above. FIG. 10A-FIG. 10B show strong binding of both CD8SP-TCRB1-Jovi1(vL-vH)-GGSG-NLuc-x3-FLAG(030816-E04)[ SEQ ID NO:1143] and CD8SP-TCRB1-E09(vL-vH)-GGSG-NLuc-x3-Flag(030816-G01)[ SEQ ID NO:1144] fusion proteins to Jurkat cells as compared to Kasumi and CHTR74 cells.

Example 11. Generation of scFV-NLuc-4×Flag-2×-Streptag-8×His Fusion Proteins

Next expression constructs were constructed in which the FMC63-scFV and CD30-Ac10-scFV fragments were fused in frame at their carboxy-termini to an NLuc-4×Flag-2× Streptag-8×His cassette via a GGSG linker. The NLuc-4× Flag-2×-Streptag-8×His cassette was in turn fused in frame to a puromycin resistance gene through a T2A ribosome skip sequence. The 4× Flag-2×-Streptag-8×His tag can be used for detection of the fusion protein by FACS analysis and immunofluorescence microscopy as well as allows purification of the fusion protein. Similar construct in which NLuc was replaced by H-tanneri, TurboLuc16 and GLuc were also constructed. The pLenti-EF1a-CD30-Ac10(vL-vH)-GGSG-NLuc-4×Flag-2×Strep-8×His-T2A-Pac construct encoding SEQ ID NO:909 was used to generate scFV-NLuc fusion proteins targeting a number of antigens as described in Table 15 by replacing the CD30 Ac10 scFV region (i.e. vL-vH) with the corresponding regions of the above scFV fragments targeting the different antigens. In addition, camelid derived vHH fragments targeting EGFR1, Her2, Her3, c-Met, IL6Ra are fused to the NLuc-4×Flag-2×Strep-8×His-T2A-Pac cassettes to generate the corresponding secreted fusion proteins. Affibody targeting Her3 and Her2 are also fused to NLuc-4×Flag-2×Strep-8×His-T2A-Pac cassette to generate the corresponding secreted fusion proteins. In addition, Darpins targeting Her2 are fused to NLuc-4×Flag-2×Strep-8×His-T2A-Pac cassettes to generate the corresponding secreted fusion proteins. A number of intracellular proteins, such as gp100, WT1, NY-ESO, tyrosinase, Muc1, MART1, TERT, HTLV-Tax, EBV-derived EBNA-c3, HIV-1 gap and CMV pp65 etc. are expressed on cell surface in association with HLA antigens. T Cell Receptor (TCR) mimics against such peptide antigens have been generated which recognize the peptide in association with the HLA molecules. The DNA encoding the scFV fragments targeting the peptides derived from the above antigens in complex with HLA-A2 (i.e. TCR mimics) are generated and fused in frame to the NLuc-4× Flag-2×Strep-8×His-T2A-Pac cassettes to generate the corresponding secreted fusion proteins of the above TCR mimics. The sequence of some of the peptide antigens used to generate the TCR mimics is given in Table 20.

TABLE 20

HLA-A2 restricted peptides used for generation of TCR mimics-Luc fusion proteins

| Protein | Fragment Name | Amino Acid Seq |
|---|---|---|
| gp100 | G9-209 | (IMDQVPFSV) |
| gp100 | G9-280 | (YLEPGPVTV) |
| gp100 | G9-154 | (KTWGQYWQV) |
| MUC1-A7 (130-138) | A7 | (NLTISDVSV) |
| MUC1-D6 (13-21) | D6 | (LLLTVLTVV) |
| TAX (11-19) | | (LLFGYPVYV) |
| hTERT(540-548) | T540 | (ILAKFLHWL) |
| hTERT(865-873) | T865 | (RLVDDFLLV) |
| HIV1 gag (77-85) | SL9 | (SLYNTVATL) |
| CMV-pp65(495-503) | | (NLVPMVATV) |

TABLE 20-continued

HLA-A2 restricted peptides used for generation of TCR mimics-Luc fusion proteins

| Protein | Fragment Name | Amino Acid Seq |
|---|---|---|
| MART (26-35) | | (EAAGIGILTV) |
| EBNA-3A (596-604) | | (SVRDRLARL) |
| EBNA-3c | | (LLDFVRFMGV) |
| WT1 | | (RMFPNAPYL) |
| PR1 | | (VLQELNVTV) |
| AFP | AFP-158 | (FMNKFIYEI) |
| HPV16-E7 | E7(11-19) | (YMLDLQPET) |
| Tyrosinase | Tyr(369-377) | (YMDGTMSQV) |

Example 12. Generation of scFV-Fusion Proteins Targeting CD33, CD19 and CD20

Expression constructs encoding multiple scFv-NLuc fusion proteins targeting CD33, CD19 and CD20 antigens were constructed. These fusion proteins differed in the scFv fragments. They either carried 4xFLAG-x2STREP-8xHis tag or the AcV5 tag. The expression constructs were transfected in 293FT cells and supernatant containing the fusion proteins collected as described above. The supernatants were tested for binding to RAJI (CD19+, CD20+, CD33-) and HL60 (CD19-, CD20-, CD33+) cell lines. Table 21 shows stronger binding of several CD33 specific scFv-Luc fusion proteins to HL60 cells as compared to RAJI cells. Table 21 also shows stronger binding of several CD19- and CD20-specific scFv-Luc fusion proteins to RAJI cells as compared to HL60 cells. However, there was a difference in the binding of the different scFv-fusion proteins to the cell lines expressing their target antigens. In particular, several CD19 specific scFv-Luc fusion proteins, such as CD8SP-CD19-huSJ25C1-(vL-vH)-GGSG-NLuc-4xFLAG-x 2STREP-8xHis-T2A-PAC(022817-004)[ SEQ ID NO:865], CD8SP-Ritx-CD19-hB4-(vL-vH)-GGSG-NLuc-4xFLAG-x 2STREP-8xHis-T2A-PAC(022817-F06)[ SEQ ID NO:866] and CD8SP-CD19-hA19-(vL-vH)-GGSG-NLuc-4x FLAG-x2 STREP-8xHis-T2A-PAC(022817-H03)[ SEQ ID NO:868] showed relatively weak to negligible binding to RAJI cells. This difference could be due to the difference in the expression and/or antigen-affinity of the different scFv fusion proteins. The CD8SP-CD19-huSJ25C1-(vL-vH)-GGSG-NLuc-4xFLAG-x2STREP-8xHis-T2A-PAC (022817-004)[ SEQ ID NO:865] was generated by humanizing the sequence of the mouse monoclonal antibody SJ25C1 directed against CD19. The weak binding of this scFv-Luc fusion protein to RAJI cells suggest that it has lost its binding affinity during the process of humanization. Thus, the luciferase based antigen detection method of the instant invention can be used in the process of protein engineering (e.g. antibody engineering) to rapidly identify the candidate clones with different properties. For example, the assay can be used in the process of humanization of antibodies and antibody fragments (e.g., scFvs) to identify clones that have lost the binding affinity to their target antigens. The method can be also used to rapidly identify scFv fragments and other antigen binding domains for incorporation into CARs based on their relative expression levels and binding affinities.

TABLE 21

Binding of CD33, CD19 and CD20 fusion proteins

| | TARGET | LUC SUPERNATANT | Raji | | HL60 | |
|---|---|---|---|---|---|---|
| | | | Mean | STD | Mean | STD |
| 1 | CD33 | CD8SP-CD33-SGNh2H12-(vL-vH)-GGSG-NLuc-4xFLAG-x2STREP-8xHis-T2A-PAC[SEQ ID NO: 915] | 4702 | 271 | 67728 | 9770 |
| 2 | CD33 | CD8SP-CD33-33H4-(vL-vH)-GGSG-NLuc-4xFLAG-x2STREP-8xHis-T2A-PAC(022217-D03)[SEQ ID NO: 917] | 171 | 48 | 1137 | 343 |
| 3 | CD33 | CD8SP-CD33-9C3-2-(vL-vH)-GGSG-NLuc-4xFLAG-x2STREP-8xHis-T2A-PAC(022217-E04)[SEQ ID NO: 918] | 167 | 40 | 533 | 179 |
| 4 | CD33 | CD8SP-CD33-33H4-(vL-vH)-GGSG-NLuc-4xFLAG-x2STREP-8xHis-T2A-PAC(022217-D03)[SEQ ID NO: 917] | 541 | 83 | 20472 | 3736 |
| 5 | CD33 | CD8SP-CD33-9C3-2-(vL-vH)-GGSG-NLuc-4xFLAG-x2STREP-8xHis-T2A-PAC(022217-E04)[SEQ ID NO: 918] | 3489 | 135 | 32213 | 3464 |
| 6 | CD33 | CD8SP-CD33-Him3-4-(vL-vH)-GGSG-NLuc-4xFLAG-x2STREP-8xHis-T2A-PAC(022217-A02)[SEQ ID NO: 914] | 4195 | 1052 | 2919 | 91 |
| 7 | CD19 | CD8SP-CD19-huSJ25C1-(vL-vH)-GGSG-NLuc-4xFLAG-x2STREP-8xHis-T2A-PAC(022817-C04)[SEQ ID NO: 865] | 1120 | 30 | 705 | 63 |
| 8 | CD19 | CD8SP-Ritx-CD19-hB4-(vL-vH)-GGSG-NLuc-4xFLAG-x2STREP-8xHis-T2A-PAC(022817-F06)[SEQ ID NO: 866] | 562 | 170 | 465 | 164 |
| 9 | CD19 | CD8SP-CD19-hA19-(vL-vH)-GGSG-NLuc-4xFLAG-x2STREP-8xHis-T2A-PAC(022817-H03)[SEQ ID NO: 868] | 673 | 398 | 682 | 92 |
| 10 | CD19 | CD8SP-hCD19-Bu12-(vL-vH)-GGSG-NLuc-AcV5(021417-T05)[SEQ ID NO: 1145] | 358453 | 36785 | 1606 | 134 |
| 11 | CD19 | CD8SP-hCD19MM-(vL-vH)-GGSG-NLuc-AcV5(021417-U01)[SEQ ID NO: 1146] | 213706 | 32671 | 223 | 38 |

TABLE 21-continued

Binding of CD33, CD19 and CD20 fusion proteins

|  | TARGET | LUC SUPERNATANT | Raji Mean | Raji STD | HL60 Mean | HL60 STD |
|---|---|---|---|---|---|---|
| 12 | CD19 | CD8SP-huFMC63-11-(vL-vH)-GGSG-NLuc-AcV5(021417-V05)[SEQ ID NO: 1147] | 283921 | 29103 | 1865 | 42 |
| 13 | CD19 | CD8SP-huFMC63-11-N203Q-(vL-vH)-GGSG-NLuc-AcV5(021417-W05)[SEQ ID NO: 1148] | 264816 | 7404 | 1218 | 75 |
| 14 | CD19 | CD8SP-huFMC63-11-N203S-(vL-VH)-GGSG-NLuc-AcV5(021417-X05)[SEQ ID NO: 1149] | 247192 | 20801 | 1462 | 82 |
| 15 | CD19 | CD8SP-CD19-Medi-3649-(vL-vH)-GGSG-NLuc-AcV5(021417-Y05)[SEQ ID NO: 1150] | 1428 | 693 | 298 | 97 |
| 16 | CD19 | CD8SP-CD19-4G7-Mlu-GSG-NLuc-AcV5(021417-Z04)[SEQ ID NO: 1151] | 380049 | 17232 | 4320 | 548 |
| 17 | CD19 | CD8SP-RTX-CD19-MOR0028-(vL-vH)-GGSG-NLuc-AcV5(021417-A05)[SEQ ID NO: 1152] | 210868 | 10706 | 1069 | 29 |
| 18 | CD19 | CD8SP-huFMC63-11-(vL-vH)-GGSG-NLuc-4xFLAG-x2STREP-8xHis-T2A-PAC(020317-E05)[SEQ ID NO: 855] | 242476 | 1841 | 31121 | 5049 |
| 19 | CD20 | CD8SP-CD20-2H7-(vL-vH)-GGSG-NLuc-4xFLAG-x2STREP-8xHis-T2A-PAC(022817-E05)[SEQ ID NO: 900] | 11192 | 302 | 3716 | 372 |
| 20 | CD20 | CD8SP-CD20-GA101-(vL-vH)-GGSG-NLuc-4xFLAG-x2STREP-8xHis-T2A-PAC(121516-G07)[SEQ ID NO: 892] | 6015 | 479 | 3336 | 317 |
| 21 |  | Control | 173 | 68 | 151 | 64 |

Example 13. Generation of scFV-Fusion Proteins Targeting Multiple Antigens

Expression constructs encoding multiple scFv-Luc fusion proteins targeting different antigens were constructed. The fusion proteins were expressed in 293FT cells and supernatants tested for binding to BC1 (primary effusion lymphoma) and RAJI (lymphoma) cell lines. Table 22 shows differential binding of the different scFv-Luc fusion proteins to the two cell lines. For example, CD8SP-CD138-(vL-vH)-GGSG-NLuc-4xFLAG-x2STREP-8xHis-T2A-PAC(041715-D08)[SEQ ID NO:938] showed stronger binding to BC1 cells as compared to RAJI cells, while CD8SP-FMC63(vL-vH)-GGS-GLuc-x3-FLAG(113015-B02)[SEQ ID NO:1136] showed stronger binding to RAJI cells as compared to BC1 cells.

TABLE 22 differential binding of scFv-Luc fusion proteins to two cell lines

|  | TARGET | LUC SUPERNATANT | BC1 Mean | BC1 SD | RAJI Mean | RAJI SD |
|---|---|---|---|---|---|---|
| 1 |  | Control | 61 | 1 | 60 | 561.4 |
| 2 | CD33 | CD8SP-CD33(vL-vH)-GGSG-NLuc-AcV5(041715-E01)[SEQ ID NO: 1122] | 3259 | 51 | 1796 | 70.7 |
| 3 | CS1 | CD8SP-Luc63-(vL-vH)-GGGS-NLuc-AcV5(041415-V08)[SEQ ID NO: 1126] | 4310 | 1913 | 1458 | 140.0 |
| 4 | CD138 | CD8SP-CD138-(vL-vH)-GGSG-NLuc-4xFLAG-x2STREP-8xHis-T2A-PAC(041715-D08)[SEQ ID NO: 938] | 1648679 | 36109 | 22100 | 671.0 |
| 5 | CD19 | CD8SP-FMC63(vL-vH)-GGS-NLuc-x3-FLAG(021216-A06)[SEQ ID NO: 1134] | 24611 | 249 | 746186 | 2568.2 |
| 6 | CD19 | CD8SP-FMC63(vL-vH)-GGS-GLuc-x3-FLAG(113015-B02)[SEQ ID NO: 1136] | 57529 | 970 | 893290 | 14181.0 |
| 7 | CD30 | CD8SP-CD30-5F11(vL-vH)-GGSG-NLuc-x3-Flag(030916-B02)[SEQ ID NO: 1141] | 7553 | 419 | 2651 | 1003.4 |
| 8 | IL11Ra | CD8SP-IL11Ra-8E2-Ts107-(vL-vH)-GGSG-NLuc-4xFLAG-x2STREP-8xHis-T2A-PAC(060716-D06)[SEQ ID NO: 1026] | 948 | 4 | 99 | 16.3 |
| 9 | IL13Ra2 | CD8SP-IL13Ra2-Hu108-(vL-vH)-GGSG-NLuc-4xFLAG-x2STREP-8xHis-T2A-PAC(060716-F03)[SEQ ID NO: 1029] | 12049 | 270 | 5553 | 59.4 |
| 10 | CLEC5A | CD8SP-CLEC5A-8H8F5-(vL-vH)-GGSG-NLuc-4xFLAG-x2STREP-8xHis-T2A-PAC(060716-E05)[SEQ ID NO: 948] | 124 | 1 | 56 | 9.2 |

TABLE 22-continued differential binding of scFv-Luc fusion proteins to two cell lines

| | | | BC1 | | RAJI | |
|---|---|---|---|---|---|---|
| | TARGET | LUC SUPERNATANT | Mean | SD | Mean | SD |
| 11 | CLEC5A | CD8SP-CLEC5A-3E12A2-(vL-vH)-GGSG-NLuc-4xFLAG-x2STREP-8xHis-T2A-PAC(060716-G01)[SEQ ID NO: 949] | 765 | 0 | 284 | 1.4 |
| 12 | CD22 | CD8SP-CD22-H22Rhov2ACDRKA-(vL-vH)-GGSG-NLuc-4xFLAG-x2STREP-8xHis-T2A-PAC(060716-H05)[SEQ ID NO: 905] | 183 | 6 | 97 | 3.5 |
| 13 | CD19 | CD8SP-CD19-4G7-(vL-vH)-GGSG-NLuc-4xFLAG-x2STREP-8xHis-T2A-PAC(062916-008)[SEQ ID NO: 859] | 52301 | 415 | 397429 | 6269.9 |
| 14 | CD32 | CD8SP-CD32-Med9-(vL-vH)-GGSG-NLuc-4xFLAG-x2STREP-8xHis-T2A PAC(081516-W03)[SEQ ID NO: 910] | 8615 | 173 | 1618 | 14.1 |

Example 14. Generation of scFV-Fusion Proteins Targeting HIV1 Envelop Glycoprotein gp120

Expression constructs encoding multiple scFv-Luc fusion proteins targeting HIV1 envelop glycoprotein gp120 were constructed. The fusion proteins were generated in 293FT cells and supernatants containing the fusion proteins tested for binding to HL2/3 cells which express HIV1 envelop glycoprotein gp120. Table 23 shows strong binding of the different scFv-Luc fusion proteins to the HL2/3 cell line as compared to media alone (control).

TABLE 23

Bidning of scFv-Luc fusion proteins to HL2/3 cell line

| | | HL2/3 | |
|---|---|---|---|
| | LUC SUPERNATANT | Mean Luc Activity | STD |
| 1 | Control | 5700 | 138 |
| 2 | CD8SP-HIV1-3BNC117-(vL-vH)-GGSG-NLuc-4xFLAG-x2STREP-8xHis-T2A-PAC(093016-Z11)[SEQ ID NO: 1016] | 8872 | 107 |
| 3 | CD8SP-HIV1-VR-C01-(vL-vH)-GGSG-NLuc-4xFLAG-x2STREP-8xHis-T2A-PAC(093016-X10)[SEQ ID NO: 1018] | 9330 | 384 |
| 4 | CD8SP-HIV1-X5-(vL-vH)-GGSG-NLuc-4xFLAG-x2STREP-8xHis-T2A-PAC(093016-Y15)[SEQ ID NO: 1019] | 12868 | 464 |

Example 15. Generation of scFV-Fusion Proteins Targeting BCMA

Expression constructs encoding multiple scFv-Luc fusion proteins targeting BCMA protein were constructed. The fusion proteins were generated in 293FT cells and supernatants containing the fusion proteins tested for binding to U266 cells which express BCMA. Table 24 shows strong binding (Mean +/− STD) of the different scFv-Luc fusion proteins to the U266 cell line as compared to media alone (control).

TABLE 24

Binding of the different scFv-Luc fusion proteins to the U266 cell line

| | | U266 | |
|---|---|---|---|
| | LUC SUPERNATANT | Mean Luc Activity | STD |
| 1 | Control | 766 | 20 |
| 2 | CD8SP-BCMA-ET-40-(vL-vH)-GGSG-NLuc-4xFLAG-x2STREP-8xHis-T2A-PAC(092016-A02)[SEQ ID NO: 880] | 11973 | 118 |
| 3 | CD8SP-BCMA-ET-54-(vL-vH)-GGSG-NLuc-4xFLAG-x2STREP-8xHis-T2A-PAC(092016-B04)[SEQ ID NO: 881] | 10701 | 68 |
| 4 | CD8SP-GPRC5D-ET150-5-(vL-vH)-GGSG-NLuc-4xFLAG-x2STREP-8xHis-T2A-PAC(092016-C06)[SEQ ID NO: 997] | 18545 | 334 |

Example 16. Generation of scFV-Fusion Proteins Targeting PDL1

Expression constructs encoding multiple scFv-Luc fusion proteins targeting PDL1 protein were constructed. The fusion proteins were generated in 293FT cells and supernatants containing the fusion proteins tested for binding to L363 cells which express PDL1. Table 25 shows strong binding (Mean +/− STD) of the different scFv-Luc fusion proteins to the L363 cell line as compared to media alone (control).

Table 25 shows strong binding of the different scFv-Luc fusion proteins to the L363 cell line

| | | | L363 | |
|---|---|---|---|---|
| | | LUC SUPERNATANT | MEAN LUC ACTIVITY | STD |
| 1 | | Control | 5467 | 589 |
| 2 | PDL1 | CD8SP-PDL1-SP142-(vL-vH)-GGSG-NLuc-4xFLAG-x2STREP-8xHis-T2A-PAC(100516-H05)[SEQ ID NO: 1063] | 52984 | 145 |

-continued

| | LUC SUPERNATANT | L363 MEAN LUC ACTIVITY | STD |
|---|---|---|---|
| 3 PDL1 | CD8SP-PDL1-10A5-(vL-vH)-GGSG-NLuc-4xFLAG-x2STREP-8xHis-T2A-PAC(100516-F03)[SEQ ID NO: 1064] | 45924 | 498 |
| 4 PDL1 | CD8SP-PDL1-Atezoli-(vL-vH)-GGSG-NLuc-4xFLAG-x2STREP-8xHis-T2A-PAC(100516-G03)[SEQ ID NO: 1062] | 35251 | 2252 |

Example 17. Generation of scFV-Luc Fusion Proteins Targeting Lym1 and Lym2

Expression constructs encoding scFv-Luc fusion proteins targeting Lym1 and Lym2 proteins were constructed. The fusion proteins were generated in 293FT cells and supernatant containing the fusion protein tested for binding to a panel of cell lines. Table 26 and Table 27 show differential binding (Mean +/− STD) of the different scFv-Luc fusion proteins to different cell line.

TABLE 26

Differential binding of CD8SP-Lym1(vL-vH)-GGSG-NLuc-AcV5(040915-J04)[SEQ ID NO: 1120] to different cell lines CD8SP-Lym1(vL-vH)-GGSG-NLuc-AcV5(040915-J04)[SEQ ID NO: 1120]

| CELL LINE | MEAN LUC ACTIVITY | STD |
|---|---|---|
| BC-1 | 7386 | 165 |
| BC-3 | 11664 | 587 |
| BCBL-1 | 7779 | 669 |
| JSC-1 | 6766 | 498 |
| MM1S | 1579 | 13 |
| U266 | 258 | 9 |
| BV173 | 5561 | 112 |
| Raji | 579907 | 18122 |

TABLE 27

Differential binding of CD8SP-Lym2(vL-vH)-GGSG-NLuc-AcV5(040915-K05)[SEQ ID NO: 1121] to different cell lines CD8SP-Lym2(vL-vH)-GGSG-NLuc-AcV5(040915-K05)[SEQ ID NO: 1121]

| CELL LINE | MEAN LUC ACTIVITY | STD |
|---|---|---|
| BC-1 | 86094 | 747 |
| BC-3 | 1743 | 144 |
| BCBL-1 | 3076 | 427 |
| JSC-1 | 13256 | 419 |
| MM1S | 1111 | 131 |
| U266 | 621 | 3 |
| BV173 | 915 | 25 |
| Raji | 54186 | 344 |

Example 18. Generation of a scFV-Luc Fusion Protein Targeting FITC

An expression construct encoding a scFv-Luc fusion protein targeting FITC was constructed. The fusion protein was generated in the supernatant of 293FT cells and supernatant containing the fusion proteins tested for binding to RAJI cells (CD45+/TCRB1−) that had been pre-labeled with a FITC-conjugated CD45 antibody (clone 2D1, eBioscience Dx) or a FITC-conjugated TCRB1(JOV1) antibody (Santa-Cruz Biotech). For labeling, approximately 100,000 Raji cells were incubated with 100 µl of 1:100 diluted FITC-Abs for an hour at 4° C., washed 3 times with PBS and then stained with 100 µl of supernatant containing the CD8SP-FITC-E2-HL-(vH-vL)-GGSG-NLuc-4×FLAG-×2STREP-8×His-T2A-PAC(030617-H05)[ SEQ ID NO:985] fusion protein. Cells were washed 3 times and then assayed for NLuc activity as described before. Table 28 shows strong binding (Mean +/− STD) of the CD8SP-FITC-E2-HL-(vH-vL)-GGSG-NLuc-4×FLAG-×2STREP-8×His-T2A-PAC (030617-H05)[ SEQ ID NO:985] fusion protein to the RAJI cells that had been pre-labelled with a FITC-CD45 antibody while only weak binding was observed on RAJI cells that had been pre-labelled with the negative control FITC-TCRB1(JOV1) antibody or had not been prelabelled.

TABLE 28 binding (Mean +/− STD) of the CD8SP-FITC-E2-HL-(vH-vL)-GGSG-NLuc-4xFLAG-x2STREP-8xHis-T2A-PAC(030617-H05)[SEQ ID NO: 985] fusion protein.

| | FITC-Conjugated Ab | Luc Supernatant | RAJI CELLS Mean Luc | STD |
|---|---|---|---|---|
| 1 | | MEDIA | 44.5 | 5.1962 |
| 2 | | CD8SP-FITC-E2-HL-(vH-vL)-GGSG-NLuc-4xFLAG-x2STREP-8xHis-T2A-PAC(030617-H05)[SEQ ID NO: 985] | 1227 | 508.62 |
| 3 | TCRB1 (JOVI)-FITC | CD8SP-FITC-E2-HL-(vH-vL)-GGSG-NLuc-4xFLAG-x2STREP-8xHis-T2A-PAC(030617-H05)[SEQ ID NO: 985] | 1435 | 760.21 |
| 4 | CD45-FITC | CD8SP-FITC-E2-HL-(vH-vL)-GGSG-NLuc-4xFLAG-x2STREP-8xHis-T2A-PAC(030617-H05)[SEQ ID NO: 985] | 57647 | 11022 |

Example 19. Generation of scFV-Fusion Proteins Targeting Alpha Fetal Protein (AFP)

Expression constructs encoding multiple scFv-Luc fusion proteins targeting an AFP-derived peptide in complex with MHC class I (HLA-A2) were constructed. The fusion proteins were generated in 293FT cells and supernatants containing the fusion proteins tested for binding to HepG2 cells which express AFP and HLA-A2. Table 29 shows strong binding (Mean +/− STD) of the different scFv-Luc fusion proteins to the HepG2 cell line as compared to media alone (control). These results demonstrate that scFv-Luc fusion proteins can be used to detect cell surface expression of intracellular protein antigens when they are presented in association with MHC molecules.

TABLE 29

Binding (Mean +/− STD) of the different scFv-Luc fusion proteins to the HepG2 cell line

| | Luc Supernatant | HepG2 Cells Mean | STD |
|---|---|---|---|
| 1 | Media | 23 | 1 |
| 2 | CD8SP-AFP-61-(vL-vH)-GGSG-NLuc-4xFLAG-x2STREP-8xHis-T2A-PAC(022217-K04)[SEQ ID NO: 869] | 2460 | 95 |
| 3 | CD8SP-AFP-76-(vL-vH)-GGSG-NLuc-4xFLAG-x2STREP-8xHis-T2A-PAC(022217-L01)[SEQ ID NO: 870] | 1417 | 20 |

Example 20. Generation of scFV-Fusion Proteins Targeting Multiple Antigens

Expression constructs encoding multiple scFv-Luc fusion proteins targeting different antigens were constructed. The fusion proteins were expressed in 293FT cells and supernatants tested for binding to a panel of cell lines. Table 30 shows differential binding of the different scFv-Luc fusion proteins to the different cell lines.

TABLE 30

Differential binding of scFv-Luc fusion proteins to the different cell lines

| TARGET | LUC SUPERNATANT | BC-3 | BCBL-1 | JSC-1 | MM1S | U266 | BV173 |
|---|---|---|---|---|---|---|---|
| CD19 | CD8SP-FMC63(vL-vH)-GGSG-NLuc-AcV5(021015-U09)[SEQ ID NO: 1119] | 2517 | 5687 | 3209 | 4040 | 2358 | 181552 |
| CD19 | CD8SP-FMC63(vL-vH)-GGS-NLuc-x3-FLAG(021216-A06)[SEQ ID NO: 1134] | 2770 | 7817 | 5698 | 4601 | 6206 | 234481 |
| CD19 | CD8SP-FMC63(vL-vH)-GGS-GLuc-x3-FLAG(113015-B02)[SEQ ID NO: 1136] | 5656 | 12685 | 12371 | 9053 | 9897 | 212871 |
| CD19 | CD8SP-CD19-4G7-(vL-vH)-GGSG-NLuc-4xFLAG-x2STREP-8xHis-T2A-PAC(062916-C08)[SEQ ID NO: 859] | 6182 | 13985 | 13285 | 10443 | 6540 | 121316 |
| CD19 | CD8SP-CD19-hA19-(vL-vH)-GGSG-NLuc-4xFLAG-x2STREP-8xHis-T2A-PAC(022817-H03)[SEQ ID NO: 868] | 52 | 76 | 106 | 67 | 68 | 125 |
| CD22 | CD8SP-CD22-H22Rhov2ACDRKA-(vL-vH)-GGSG-NLuc-4xFLAG-x2STREP-8xHis-T2A-PAC(060716-H05)[SEQ ID NO: 905] | 305 | 4410 | 638 | 1437 | 2806 | 413 |
| CD30 | CD8SP-CD30-Ac10-(vL-vH)-GGSG-NLuc-4xFLAG-x2STREP-8xHis-T2A-PAC(031816-D02)[SEQ ID NO: 909] | 10348 | 25996 | 2093 | 2097 | 1464 | 1697 |
| CD33 | CD8SP-CD33(vL-vH)-GGSG-NLuc-AcV5(041715-E01)[SEQ ID NO: 1122] | 241 | 653 | 328 | 1995 | 509 | 13114 |
| Lym1 | CD8SP-Lym1(vL-vH)-GGSG-NLuc-AcV5(040915-J04)[SEQ ID NO: 1120] | 11664 | 7779 | 6766 | 1579 | 258 | 5561 |
| Lym2 | CD8SP-Lym2(vL-vH)-GGSG-NLuc-AcV5(040915-K05)[SEQ ID NO: 1121] | 1743 | 3076 | 13256 | 1111 | 621 | 915 |
| GRP78 | CD8SP-GRP78-GC18-(vL-vH)-GGSG-NLuc-4xFLAG-x2STREP-8xHis-T2A-PAC[SEQ ID NO: 1005] | 106 | 173 | 183 | 304 | 141 | 142 |
| GRP78 | CD8SP-GRP78-GC18(vL-vH)-NLuc-AcV5(040915-M06)[SEQ ID NO: 1130] | 1142 | 2531 | 1587 | 2444 | 1348 | 1112 |

TABLE 30-continued

Differential binding of scFv-Luc fusion proteins to the different cell lines

| TARGET | LUC SUPERNATANT | BC-3 | BCBL-1 | JSC-1 | MM1S | U266 | BV173 |
|---|---|---|---|---|---|---|---|
| CD79b | CD8SP-huMA79bv28-(vL-vH)-GGGS-NLuc-AcV5(041515-U04)[SEQ ID NO: 1128] | 806 | 1826 | 1136 | 988 | 635 | 1173 |
| CS1 | CD8SP-Luc90-(vL-vH)-NLuc-AcV5(041515-W03)[SEQ ID NO: 1127] | 22092 | 80958 | 111342 | 53941 | 17226 | 603 |
| BCMA | CD8SP-BCMA-J6MO-(vL-vH)-NLuc-AcV5(041615-X08)[SEQ ID NO: 1124] | 23676 | 11444 | 24487 | 58922 | 27132 | 855 |
| Amyloid | SP-Amyloid-158-(vL-vH)-GGSG-NLuc-4xFLAG-x2STREP-8xHis-T2A-PAC[SEQ ID NO: 875] | 3112 | 5686 | 8229 | 8168 | 3933 | 6220 |
| FLT3 | CD8SP-FLT3-NC7-(vL-vH)-NLuc-AcV5(041715-C06)[SEQ ID NO: 1125] | 1146 | 2821 | 1167 | 1023 | 714 | 13551 |
| CD45 | CD8SP-CD45-BC8-(vL-vH)-GGSG-NLuc-AcV5(042115-A09)[SEQ ID NO: 1129] | 2507 | 35103 | 67510 | 1086 | 10977 | 1041 |
| CD138 | CD8SP-CD138-(vL-vH)-GGSG-NLuc-4xFLAG-x2STREP-8xHis-T2A-PAC(041715-D08)[SEQ ID NO: 938] | 72070 | 250385 | 132808 | 496546 | 1232482 | 14690 |
| IL13Ra2 | CD8SP-IL13Ra2-Hu108-(vL-vH)-GGSG-NLuc-4xFLAG-x2STREP-8xHis-T2A-PAC(060716-F03)[SEQ ID NO: 1029] | 60 | 86 | 80 | 72 | 67 | 151 |
| IL13Ra2 | CD8SP-IL13Ra2-Hu108-(vL-vH)-GGSG-NLuc-4xFLAG-x2STREP-8xHis-T2A-PAC(060716-F03)[SEQ ID NO: 1029] | 3375 | 4623 | 4211 | 3792 | 3469 | 2509 |
| CLEC5A | CD8SP-CLEC5A-8H8F5-(vL-vH)-GGSG-NLuc-4xFLAG-x2STREP-8xHis-T2A-PAC(060716-E05)[SEQ ID NO: 948] | 31 | 42 | 45 | 45 | 34 | 53 |
| CLEC5A | CD8SP-CLEC5A-3E12A2-(vL-vH)-GGSG-NLuc-4xFLAG-x2STREP-8xHis-T2A-PAC(060716-G01)[SEQ ID NO: 949] | 311 | 7804 | 502 | 526 | 634 | 677 |

Example 21. Generation of a CD20-ECx2-ECD-Luc Fusion Protein to Detect CD20-Specific CARs CD20 is a type III membrane protein with two extracellular loops. The CD20-ECx2-ECD-GGSG-TurboLuc16-4xFlag-2xStreptag-8xHis-T2A-Pac(060816-I04)[ SEQ ID NO:1196] fusion construct was generated which contains a CD20-ECx2-ECD domain as represented by SEQ ID NO: 546. The fusion proteins were expressed in 293FT cells and supernatants tested for binding to parental NK92MI and Jurkat cells and those expressing a CD20-specific CAR CD20-GA10-(vL-vH)-MYC-BBz-T2A-PAC(111815-A03)[ SEQ ID NO:1220]. Table 31 shows strong binding of CD20-ECx2-ECD-GGSG-TurboLuc16-4xFlag-2xStreptag-8xHis-T2A-Pac(060816-I04)[ SEQ ID NO:1196] fusion protein to NK92MI and Jurkat cells expressing the CD20-specific CAR CD20-GA10-(vL-vH)-MYC-BBz-T2A-PAC (111815-A03)[ SEQ ID NO:1220]. These results demonstrate that Luc fusion proteins can be generated using the extracellular domains of type III membrane proteins and such fusion proteins can be used to detect CARs directed against the said type III membrane protein.

TABLE 31

Binding of CD20 fusion protein to CD20-specific CARs.

| | | NK92MI | | Jurkat | |
|---|---|---|---|---|---|
| CAR | Luc Supernatant | Mean | STD | Mean | STD |
| 1 None | CD20-ECx2-ECD-GGSG-TurboLuc16-4xFlag-2xStreptag-8xHis-T2A-Pac(060816-I04) [SEQ ID NO: 1196] | 510 | 146 | 484 | 320 |
| 2 CD20-GA10-(vL-vH)-MYC-BBz-T2A-PAC(111815-A03) [SEQ ID NO: 1220] | CD20-ECx2-ECD-GGSG-TurboLuc16-4xFlag-2xStreptag-8xHis-T2A-Pac(060816-I04) [SEQ ID NO: 1196] | 1417 | 415 | 7606 | 5791 |

Example 22. Generation of a BCMA-ECD-Luc Fusion Protein to Detect BCMA-Specific CARs A BCMA-ECD-NLuc fusion construct was generated. The fusion protein was expressed in 293FT cells and supernatants tested for binding to parental NK92MI cells and those expressing BCMA- or CD19-specific CAR constructs. Table 32 shows strong binding of BCMA-ECD-GGSG-NLuc-4xFlag-2xStreptag-8xHis-T2A-Pac(103116-Q07)[SEQ ID NO:1201] fusion protein to NK92MI cells expressing the BCMA-specific CAR J6MO-(vL-vH)-MYC-28z-T2A-Pac(031915-G02)[SEQ ID NO:1213] as compared to parental NK92MI cells. As a control the binding of FLAG-CD19-ECD-GGSG-NLuc-AcV5(062615-004)[SEQ ID NO:1170] fusion protein, which contains the extracellular domain of CD19, to NK92MI cells expressing the BCMA-specific CAR J6MO-(vL-vH)-MYC-28z-T2A-Pac(031915-G02)[SEQ ID NO:1213] and CD19-specific CAR FMC63-(vL-vH)-Myc-BBz-T2A-Pac(112014-A13)[SEQ ID NO:1208] was examined. The FLAG-CD19-ECD-GGSG-NLuc-AcV5(062615-004)[SEQ ID NO:1170] fusion protein failed to show significant binding to NK92MI cells expressing the BCMA-specific CAR J6MO-(vL-vH)-MYC-28z-T2A-Pac(031915-G02)[SEQ ID NO:1213] but showed strong binding to NK92MI cells expressing the CD19-specific CAR FMC63-(vL-vH)-Myc-BBz-T2A-Pac(112014-A13)[SEQ ID NO:1208], thereby demonstrating the specificity of the assay.

TABLE 32

| | | Binding of BCMA fusion protein to BCMA-specific CARs | | |
| --- | --- | --- | --- | --- |
| Cell Line | CAR-Construct | Luc Supernatant | Mean | STD |
| NK92MI | J6MO-(vL-vH)-MYC-28z-T2A-Pac(031915-G02)[SEQ ID NO: 1213] | BCMA-ECD-GGSG-NLuc-4xFlag-2xStreptag-8xHis-T2A-Pac(103116-Q07)[SEQ ID NO: 1201] | 602 | 102 |
| NK92MI | None | BCMA-ECD-GGSG-NLuc-4xFlag-2xStreptag-8xHis-T2A-Pac(103116-Q07)[SEQ ID NO:1201] | 89 | 10 |
| NK92MI | J6MO-(vL-vH)-MYC-28z-T2A-Pac(031915-G02)[SEQ ID NO: 1213] | FLAG-CD19-ECD-GGSG-NLuc-AcV5(062615-C04)[SEQ ID NO: 1170] | 57 | 3 |
| NK92MI | FMC63-(vL-vH)-Myc-BBz-T2A-Pac(112014-A13)[SEQ ID NO: 1208] | FLAG-CD19-ECD-GGSG-NLuc-AcV5(062615-C04)[SEQ ID NO: 1170] | 217346 | 49538 |

Example 23. Generation of a SLAMF7-CS1-ECD-GGSG-NLuc Fusion Protein to Detect SLAMF7/CS1-Specific CARS A SLAMF7-CS1-ECD-GGSG-NLuc fusion construct was generated. The fusion protein was expressed in 293FT cells and supernatants tested for binding to parental Jurkat cells and those expressing SLAMF7/CS1-specific CAR constructs. Table 33 shows strong binding of SLAMF7-CS1-ECD-GGSG-NLuc-4xFlag-2xStreptag-8xHis-T2A-Pac (062816-A01)[SEQ ID NO:1202] fusion protein to Jurkat cells expressing the SLAMF7/CS1-specific CARs HuLuc64-(vL-vH)-Myc-BBz-T2A-Pac(052616-U05)[SEQ ID NO:1228] and Luc90-(vL-vH)-MYC-CD28z-T2A-Pac (031915-F03)[SEQ ID NO:1229] as compared to parental Jurkat cells.

TABLE 33

| | Binding of SLAMF7-CS1 fusion protein to SLAMF7-CS1-specific CARs | | | |
| --- | --- | --- | --- | --- |
| | Jurkat Cells CAR | Luc supernatant | Mean | STD |
| 1 | None | SLAMF7-CS1-ECD-GGSG-NLuc-4xFlag-2xStreptag-8xHis-T2A-Pac(062816-A01)[SEQ ID NO: 1202] | 354 | 19 |
| 2 | HuLuc64-(vL-vH)-Myc-BBz-T2A-Pac(052616-U05)[SEQ ID NO: 1228] | SLAMF7-CS1-ECD-GGSG-NLuc-4xFlag-2xStreptag-8xHis-T2A-Pac(062816-A01)[SEQ ID NO: 1202] | 2932 | 103 |
| 3 | Luc90-(vL-vH)-MYC-CD28z-T2A-Pac(031915-F03)[SEQ ID NO: 1229] | SLAMF7-CS1-ECD-GGSG-NLuc-4xFlag-2xStreptag-8xHis-T2A-Pac(062816-A01)[SEQ ID NO: 1202] | 1143 | 24 |

Example 24. Generation of a
SLAMF7-CS1-ECD-GGSG-NLuc Fusion Protein to
Detect SLAMF7/CS1-Specific CARS 293FT cells were transiently transfected with a SLAMF7/CS1-specific CAR Luc90-(vL-vH)-MYC-CD28z-T2A-Pac (031915-F03)[ SEQ ID NO:1229] and a CD19-specific CAR FMC63-(vL-vH)-Myc-BBz-T2A-Pac(112014-A13)[ SEQ ID NO:1208]. Approximately 24 hours later, cells were stained with supernatants containing SLAMF7-CS1-ECD-GGSG-NLuc-4×Flag-2×Streptag-8×His-T2A-Pac(062816-A01)[ SEQ ID NO:1202] and FLAG-CD19-ECD-GGSG-NLuc-AcV5(062615-004)[ SEQ ID NO:1170] fusion proteins. Table 34 shows strong binding of SLAMF7-CS1-ECD-GGSG-NLuc-4×Flag-2×Streptag-8×His-T2A-Pac (062816-A01)[ SEQ ID NO:1202] to 293FT cells expressing the SLAMF7/CS1-specific CAR Luc90-(vL-vH)-MYC-CD28z-T2A-Pac(031915-F03)[ SEQ ID NO:1229] and strong binding of FLAG-CD19-ECD-GGSG-NLuc-AcV5 (062615-004)[ SEQ ID NO:1170] to cells expressing the CD19-specific CAR FMC63-(vL-vH)-Myc-BBz-T2A-Pac (112014-A13)[ SEQ ID NO:1208]. However, no significant binding of FLAG-CD19-ECD-GGSG-NLuc-AcV5 (062615-004)[ SEQ ID NO:1170] to 293FT cells transfected with the SLAMF7/CS1-specific CAR was observed, thereby demonstrating the specificity of the assay.

TABLE 34

Binding of SLAMF7-CS1 and CD19 fusion protein to SLAMF7-CS1-specific and CD19-specific CARs

| 293FT CELLS CAR | Luc Supernatant | Mean Luc Activity | STD |
|---|---|---|---|
| Luc90-(vL-vH)-MYC-CD28z-T2A-Pac(031915-F03)[SEQ ID NO: 1229] | SLAMF7-CS1-ECD-GGSG-NLuc-4xFlag-2xStreptag-8xHis-T2A-Pac(062816-A01)[SEQ ID NO: 1202] | 100008 | 2740 |
| FMC63-(vL-vH)-Myc-BBz-T2A-Pac(112014-A13)[SEQ ID NO: 1208] | SLAMF7-CS1-ECD-GGSG-NLuc-4xFlag-2xStreptag-8xHis-T2A-Pac(062816-A01)[SEQ ID NO: 1202] | 37801 | 624 |
| Luc90-(vL-vH)-MYC-CD28z-T2A-Pac(031915-F03)[SEQ ID NO: 1229] | FLAG-CD19-ECD-GGSG-NLuc-AcV5(062615-C04)[SEQ ID NO: 1170] | 3827 | 738 |
| FMC63-(vL-vH)-Myc-BBz-T2A-Pac(112014-A13)[SEQ ID NO: 1208] | FLAG-CD19-ECD-GGSG-NLuc-AcV5(062615-C04)[SEQ ID NO: 1170] | 237068 | 7993 |

Example 25. Generation of a
CDH1-ECD-GGSG-NLuc Fusion Protein to Detect
CDH1/CD324-Specific CARS The CDH1-ECD-GGSG-NLuc-4×Flag-2×Streptag-8×His-T2A-Pac(062816-G02)[ SEQ ID NO:1189] fusion protein was expressed in the supernatant of 293FT cells as described previously. Another batch of 293FT cells were transiently transfected with CDH1/CD324-specific CARs CD324-SC10-6-(vL-vH)-MYC-BBz-T2A-PAC(052516-B07)[ SEQ ID NO:1221] and CD324-hSC10-17-(vL-vH)-MYC-BBz-T2A-PAC(052516-A07)[ SEQ ID NO:1222] and a CD19-specific CAR Luc90-(vL-vH)-MYC-CD28z-T2A-Pac(031915-F03)[ SEQ ID NO:1229]. Approximately 24 hours later, cells were stained with supernatants containing CDH1-ECD-GGSG-NLuc-4×Flag-2×Streptag-8×His-T2A-Pac(062816-G02)[ SEQ ID NO:1189] and FLAG-CD19-ECD-GGSG-NLuc-AcV5(062615-004)[ SEQ ID NO:1170] fusion proteins. Table 35 shows strong binding of CDH1-ECD-GGSG-NLuc-4×Flag-2×Streptag-8×His-T2A-Pac(062816-G02)[ SEQ ID NO:1189] fusion protein to 293FT cells expressing the CDH1/CD324-specific CARs CD324-SC10-6-(vL-vH)-MYC-BBz-T2A-PAC(052516-B07)[ SEQ ID NO:1221] and CD324-hSC10-17-(vL-vH)-MYC-BBz-T2A-PAC(052516-A07)[ SEQ ID NO:1222] and strong binding of FLAG-CD19-ECD-GGSG-NLuc-AcV5(062615-004)[ SEQ ID NO:1170] to cells expressing the CD19-specific CAR FMC63-(vL-vH)-Myc-BBz-T2A-Pac(112014-A13)[ SEQ ID NO:1208]. However, no significant binding of FLAG-CD19-ECD-GGSG-NLuc-AcV5 (062615-C04)[ SEQ ID NO:1170] to 293FT cells transfected with the CDH1-specific CARs was observed, thereby demonstrating the specificity of the assay.

TABLE 35

Binding of CDH1-ECD fusion protein to CDH1/CD324-specific CARs

| 293FT CELLS CAR | Luc Supernatant | Mean | STD |
|---|---|---|---|
| CD324-SC10-6-(vL-vH)-MYC-BBz-T2A-PAC(052516-B07)[SEQ ID NO: 1221] | CDH1-ECD-GGSG-NLuc-4xFlag-2xStreptag-8xHis-T2A-Pac(062816-G02)[SEQ ID NO: 1189] | 2904158 | 44104 |
| CD324-hSC10-17-(vL-vH)-MYC-BBz-T2A-PAC(052516-A07)[SEQ ID NO: 1222] | CDH1-ECD-GGSG-NLuc-4xFlag-2xStreptag-8xHis-T2A-Pac(062816-G02)[SEQ ID NO: 1189] | 2018952 | 23267 |
| CD324-SC10-6-(vL-vH)-MYC-BBz-T2A-PAC(052516-B07)[SEQ ID NO: 1221] | FLAG-CD19-ECD-GGSG-NLuc-AcV5(062615-C04)[SEQ ID NO: 1170] | 16409 | 1159 |
| CD324-hSC10-17-(vL-vH)-MYC-BBz-T2A-PAC(052516-A07)[SEQ ID NO: 1222] | FLAG-CD19-ECD-GGSG-NLuc-AcV5(062615-C04)[SEQ ID NO: 1170] | 5186 | 232 |
| FMC63-(vL-vH)-Myc-BBz-T2A-Pac(112014-A13)[SEQ ID NO: 1208] | FLAG-CD19-ECD-GGSG-NLuc-AcV5(062615-C04)[SEQ ID NO: 1170] | 237068 | 7993 |

Example 26. Generation of a CD200R-ECD-GGSG-NLuc Fusion Protein to Detect CD200R-Specific CARS 293FT cells were transiently transfected with a CD200R-specific CAR CD200R-huDx182-(vL-vH)-Myc-BBz-T2A-PAC[SEQ ID NO:1218] and a CD19-specific CAR FMC63-(vL-vH)-Myc-BBz-T2A-Pac(112014-A13)[ SEQ ID NO:1208]. Approximately 24 hours later, cells were stained with supernatants containing CD200R-ECD-GGSG-NLuc-4xFlag-2xStreptag-8xHis-T2A-Pac(082616-007)[ SEQ ID NO:1190] and FLAG-CD19-ECD-GGSG-NLuc-AcV5 (062615-004)[ SEQ ID NO:1170] fusion proteins. Table 36 shows strong binding of CD200R-ECD-GGSG-NLuc-4×Flag-2xStreptag-8xHis-T2A-Pac(082616-007)[ SEQ ID NO:1190] to 293FT cells expressing the CD200R-specific CAR CD200R-huDx182-(vL-vH)-Myc-BBz-T2A-PAC [SEQ ID NO:1218] and strong binding of FLAG-CD19-ECD-GGSG-NLuc-AcV5(062615-004)[ SEQ ID NO:1170] to cells expressing the CD19-specific CAR FMC63-(vL-vH)-Myc-BBz-T2A-Pac(112014-A13)[ SEQ ID NO:1208]. However, no significant binding of FLAG-CD19-ECD-GGSG-NLuc-AcV5(062615-004)[ SEQ ID NO:1170] to 293FT cells transfected with the CD200R-specific CAR was observed, thereby demonstrating the specificity of the assay.

TABLE 36

CD200R-ECD fusion protein to detect CD200R-specific CARs

| 293FT CELLS CAR | Luc Supernatant | Mean | STD |
|---|---|---|---|
| CD200R-huDx182-(vL-vH)-Myc-BBz-T2A-PAC[SEQ ID NO: 1218] | CD200R-ECD-GGSG-NLuc-4xFlag-2xStreptag-8xHis-T2A-Pac(082616-C07)[SEQ ID NO: 1190] | 18736 | 3038 |
| CD200R-huDx182-(vL-vH)-Myc-BBz-T2A-PAC[SEQ ID NO: 1218] | FLAG-CD19-ECD-GGSG-NLuc-AcV5(062615-C04)[SEQ ID NO: 1170] | 1063 | 165 |
| FMC63-(vL-vH)-Myc-BBz-T2A-Pac(112014-A13)[SEQ ID NO: 1208] | FLAG-CD19-ECD-GGSG-NLuc-AcV5(0626I5-C04)[SEQ ID NO: 1170] | 237068 | 7993 |

Example 27. Generation of Fusion Protein Containing Different Luc Fragments to Detect CD19-Specific CARS Multiple constructs containing the extracellular domain of CD19 in fusion with different Luc reporter fragments were generated. The fusion protein was expressed in 293FT cells and supernatants tested for binding to parental NK92MI cells and those expressing a CD19-specific CAR construct. Table 37 shows strong binding of all fusion protein to NK92MI cells expressing the CD19-specific CAR FMC63-(vL-vH)-Myc-BBz-T2A-Pac(112014-A13)[ SEQ ID NO:1208] as compared to parental NK92MI cells. However, there was a difference in signal intensity observed with the different fusion proteins with the FLAG-CD19-ECD-GGS-LoLuc-AcV5(111616-L02)[ SEQ ID NO:1174] and CD19-ECD-GGS-HtLuc-x3Flag(111616-N05)[ SEQ ID NO:1176] fusion proteins showing relatively weak signal. This is probably due to the lower brightness of LoLuc and HtLuc as compared to the other luciferases.

TABLE 37

Binding of fusion proteins to NK92MI cells expressing the CD19-specific CAR

| | LUC SUPERNATANT | NK92-MI-Parental | | NK92MI-FMC63-(vL-vH)-Myc-BBz-T2A-Pac(112014-A13)[SEQ ID NO: 1208] | |
|---|---|---|---|---|---|
| | | MEAN | STD | MEAN | STD |
| 1 | FLAG-CD19-ECD-GGSG-NLuc-AcV5(062615-C04)[SEQ ID NO: 1170] | 80 | 23 | 217346 | 49538 |
| 2 | FLAG-CD19-ECD-GGS-PaLuc1-HA-Streptag-3xHA-8xHis-T2A-pac(111616-K07)[SEQ ID NO: 1173] | 70 | 9 | 14064 | 2569 |
| 3 | FLAG-CD19-ECD-GGS-Turboluc16-4xFlag-2xStreptag-8xHis-T2A-Pac(111616-J04)[SEQ ID NO: 1172] | 350 | 44 | 14172 | 2197 |
| 4 | FLAG-CD19-ECD-GGS-LoLuc-AcV5(111616-L02)[SEQ ID NO: 1174] | 77 | 7 | 185 | 75 |
| 5 | FLAG-CD19-ECD-GGS-MLuc7-MM-LL-HA(111616-M07)[SEQ ID NO: 1175] | 229 | 93 | 9045 | 1637 |
| 6 | CD19-ECD-GGS-HtLuc-x3Flag(111616-N05)[SEQ ID NO: 1176] | 88 | 56 | 205 | 155 |

Example 28. Generation of Fusion Protein Containing Different Luc Fragments to Detect CD33-Specific CARS Multiple constructs containing the extracellular domain of CD33 in fusion with different Luc reporter fragments were generated. The fusion protein was expressed in 293FT cells and supernatants tested for binding to parental NK92MI cells and those expressing a CD33-specific CAR construct. Table 38 shows stronger binding of all fusion protein to NK92MI cells expressing the CD33-specific CAR CD33-(vL-vH)-Myc-28z-T2A-Pac(032415-001)[ SEQ ID NO:1211] as compared to the parental NK92MI cells. However, there was a difference in signal intensity observed with the different fusion proteins with the CD33-ECD-LoLuc-AcV5(100616-L07)[ SEQ ID NO:1180] and CD33-ECD-HtLuc-x3Flag(100616-N05)[ SEQ ID NO:1182] fusion proteins showing relatively weak signal. This is probably due to the lower brightness of LoLuc and HtLuc as compared to the other luciferases.

TABLE 38

Binding of fusion proteins to NK92MI cells expressing the CD33-specific CAR

| LUC SUPERNATANT | NK92-MI-Parental | | NK92MI-CD33-(vL-vH)-Myc-28z-T2A-Pac(032415-O01)[SEQ ID NO: 1211] | |
|---|---|---|---|---|
| | MEAN | STD | MEAN | STD |
| 1 CD33-ECD-GGSG-NLuc-4xFlag-2xStreptag-8xHis-T2A-Pac(060816-A02)[SEQ ID NO: 1177] | 68 | 15 | 2453 | 315 |
| 2 CD33-ECD-GGSG-Turboluc16-4xFlag-2xStreptag-8xHis-T2A-Pac(100616-J04)[SEQ ID NO: 1178] | 5679 | 318 | 2148794 | 150613 |
| 3 CD33-ECD-PaLuc1-HA-Streptag-3xHA-8xHis-T2A-pac(100616-K07)[SEQ ID NO: 1179] | 404 | 46 | 285377 | 20648 |
| 4 CD33-ECD-LoLuc-AcV5(100616-L07)[SEQ ID NO: 1180] | 55 | 3 | 2158 | 426 |
| 5 CD33-ECD-MLuc7-MM-LL-HA(100616-M02)[SEQ ID NO: 1181] | 1318 | 140 | 955672 | 48712 |
| 6 CD33-ECD-HtLuc-x3Flag(100616-N05)[SEQ ID NO: 1182] | 87 | 21 | 1871 | 1925 |

Example 29. Generation of Fusion Protein Containing Different Luc Fragments to Detect CD138-Specific CARs Multiple constructs containing the extracellular domain of CD138 in fusion with different Luc reporter fragments were generated. The fusion protein was expressed in 293FT cells and supernatants tested for binding to parental NK92MI cells and those expressing CD138-specific CARs construct. Table 39 shows stronger binding of all fusion protein to NK92MI cells expressing the CD138-specific CARs CD138-(vL-vH)-Myc-28z-T2A-Pac(032415-N06)[ SEQ ID NO:1210] and CD138-(vL-vH)-MYC-BBz-T2A-Pac (052115-A02)[ SEQ ID NO:1212] as compared to the parental NK92MI cells. However, there was a difference in signal intensity observed with the different fusion proteins with the CD138-SDC1-ECD-GGS-LoLuc-AcV5(101216-G04)[ SEQ ID NO:1186] fusion protein showing relatively weak signal. This is probably due to the lower brightness of LoLuc as compared to the other luciferases.

TABLE 39

Binding of fusion proteins to NK92MI cells expressing the CD138-specific CAR

| LUC SUPERNATANT | NK92-MI-Parental | | CD138-(vL-vH)-Myc-28z-T2A-Pac(032415-N06)[SEQ ID NO: 1210] | | CD138-(vL-vH)-MYC-BBz-T2A-Pac(052115-A02)[SEQ ID NO: 1212] | |
|---|---|---|---|---|---|---|
| | MEAN | STD | MEAN | STD | MEAN | STD |
| 1 CD138-SDC1-ECD-GGS-Turboluc16-4xFlag-2xStreptag-8xHis-T2A-Pac(101216-E04)[SEQ ID NO: 1184] | 49199 | 5404 | 136266 | 29578 | 186935 | 9085 |
| 2 CD138-SDC1-ECD-GGS-PaLuc1-HA-Streptag-3xHA-8xHis-T2A-pac(101216-F04)[SEQ ID NO: 1185] | 6988 | 503 | 26350 | 3272 | 38653 | 4182 |
| 3 CD138-SDC1-ECD-GGS-LoLuc-Luc-AcV5(101216-G04)[SEQ ID NO: 1186] | 185 | 50 | 850 | 110 | 782 | 59 |
| 4 CD138-SDC1-ECD-GGS-MLuc7-MM-LL-HA(111616-H04)[SEQ ID NO: 1187] | 1303 | 217 | 47765 | 4000 | 72967 | 1037 |

Figure 11:
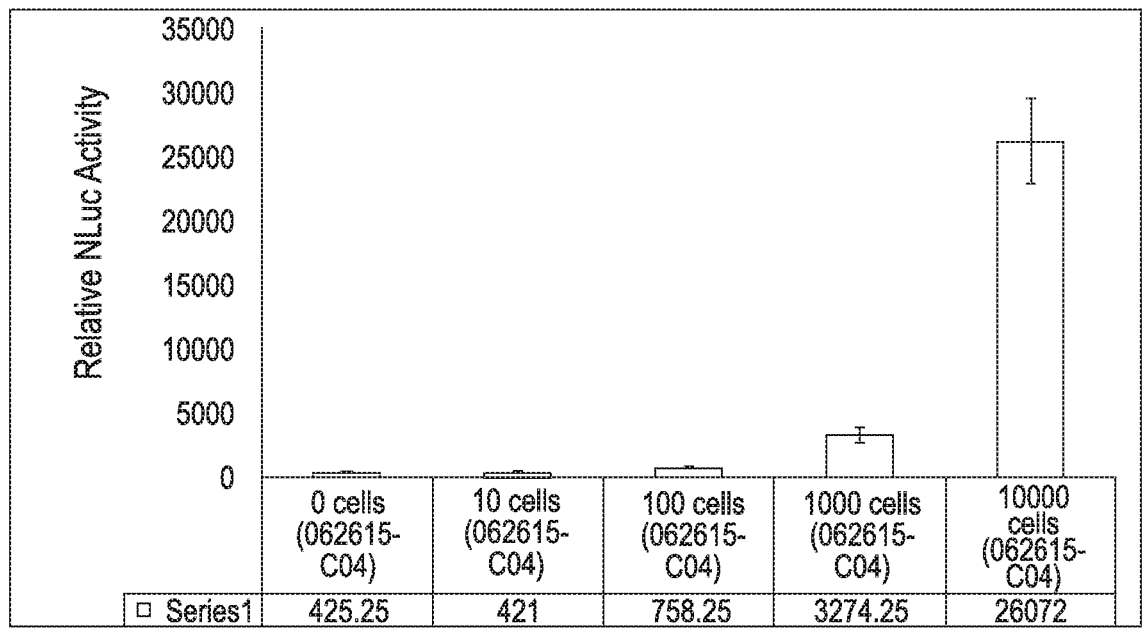
FIG. 11 depicts, in accordance with various embodiments of the invention, the sensitivity of the FLAG-CD19-ECD-GGSG-NLuc-AcV5(062615-004)[ SEQ ID NO:1170] fusion protein to detect 100 NK92MI cells expressing the CD19-specific CAR FMC63-(vL-vH)-Myc-BBz-T2A-Pac (112014-A13)[ SEQ ID NO:1208] in the background of 1 million parental NK92MI cells.

Example 30: Sensitivity of Luc Fusion Protein Assay for Detecting CAR-Expressing Cells To determine the sensitivity of the Luc fusion protein assay for detecting CAR-expressing cells, the indicated numbers of NK92MI cells stably expressing a CD19-specific CAR FMC63-(vL-vH)-Myc-BBz-T2A-Pac(112014-A13)[ SEQ ID NO:1208] in 25 µl volume were added to 1 million parental NK92MI cells (in 25 µl volume) in a 96 well U-bottom plate. Next, 100 µl of 293FT supernatant containing FLAG-CD19-ECD-GGSG-NLuc-AcV5(062615-004)[ SEQ ID NO:1170] fusion protein was added to each well and cells were mixed by pipetting up and down a couple of times and then incubated for 1 hour on ice. After incubation, cells were spun down at 1400 rpm for 5 minutes at 4° C., followed by 5 washes with ice-cold wash buffer (0.5% FBS in PBS). Finally, the pellets were resuspended in 40 µl. 30 µl of the resuspended mixture was transferred to one well of a 384 well plate. The experiment was conducted in quadruplicate. The luminescence was read by adding 30 µl of 1× CTZ assay buffer. FIG. 11 shows that 100 CAR-expressing NK92MI cells in the background of a million parental cells can be easily detected by the assay giving a sensitivity of 1 CAR cell in the background of 10,000 non-CAR cells. The sensitivity of the assay can be further improved by using purified and concentrated fusion protein.

Figure 12:
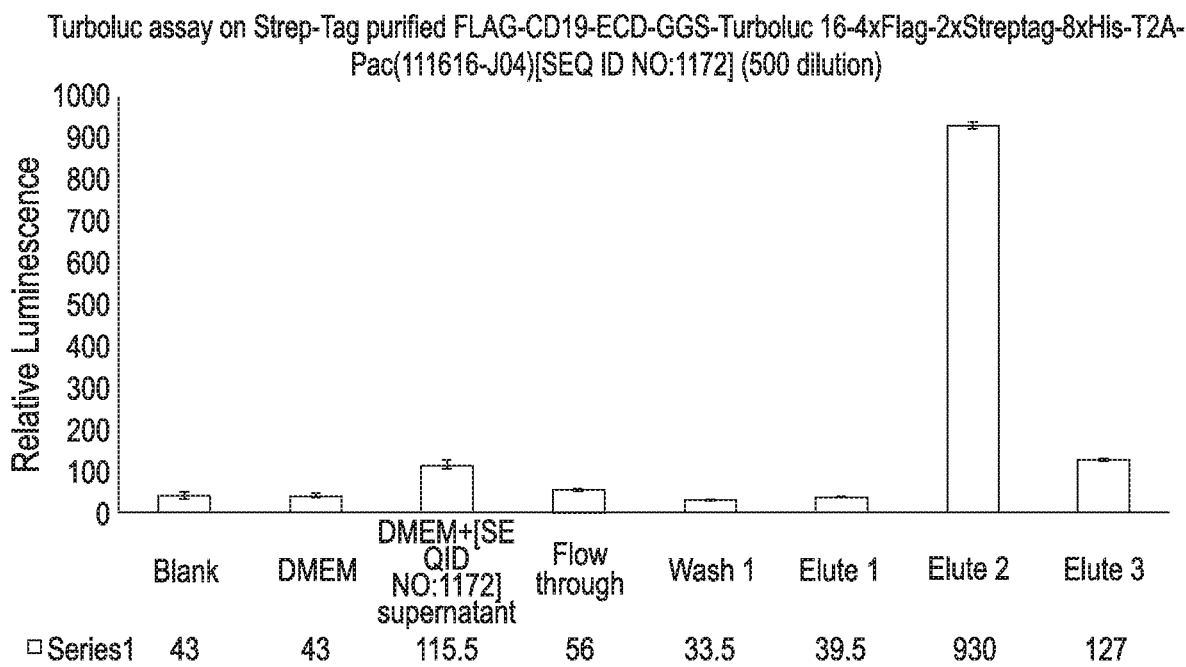
FIG. 12 depicts, in accordance with various embodiments of the invention, TurboLuc activity in various fractions of the protocol for purification of FLAG-CD19-ECD-GGS-Turboluc16-4×Flag-2×Streptag-8×His-T2A-Pac(111616-J04)[ SEQ ID NO:1172] fusion protein from the supernatant of 293FT cells using Strep-Tactin resin.

Example 31: Single-Step Purification of Luc Fusion Protein Containing Streptag Using Strep-Tactin 293FT cells were transfected with expression vector encoding FLAG-CD19-ECD-GGS-Turboluc16-4×Flag-2×Streptag-8×His-T2A-Pac(111616-J04)[ SEQ ID NO:1172]. The supernatant containing the secreted fusion protein was collected between 48-72 h post-transfection and secreted protein purified over a Strep-Tactin resin (IBA Lifesciences) and following the manufacturer's recommendations. The Turboluc activity in the starting supernatant and each step of purification was determined by adding 30 µl of 1×CTZ assay buffer to 30 µl of 1:500 diluted samples. FIG. 12 shows that FLAG-CD19-ECD-GGS-Turboluc16-4×Flag-2×Streptag-8×His-T2A-Pac(111616-J04)[ SEQ ID NO:1172] fusion protein can be purified in a single step from crude supernatant with excellent yield and recovery. The purified sample (Elute 2) was tested for binding to RAJI cells and was found to be biologically active in this assay.

Example 32: Use of Protein L-Luc Fusion Protein for Detection of CAR

Figure 13:
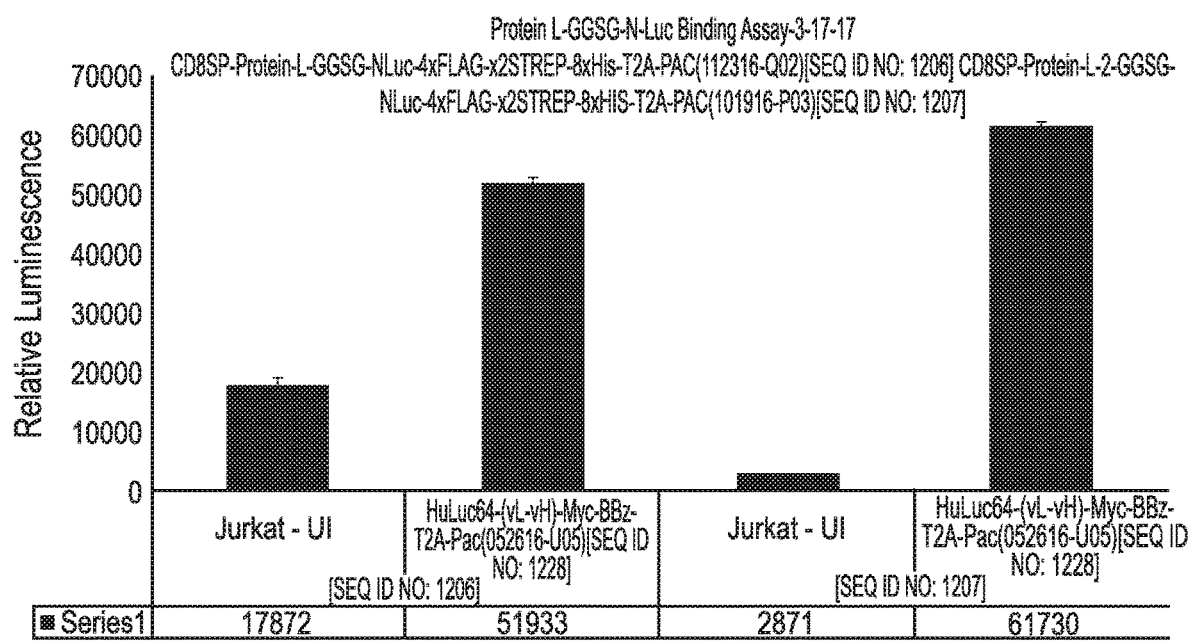
FIG. 13 depicts, in accordance with various embodiments of the invention, binding of two Protein L-NLuc fusion proteins to Jurkat cells expressing the CAR HuLuc64-(vL-vH)-Myc-BBz-T2A-Pac(052616-U05)[ SEQ ID NO:1228], indicating that Protein L based Luc fusion proteins can be used to detect the expression of CARs containing a kappa light chain.

Two NLuc fusion constructs containing an N-terminal Protein L coding region downstream of a CD8 signal peptide were constructed. The two constructs are identical except that the construct CD8SP-Protein-L-2-GGSG-NLuc-4×FLAG-×2STREP-8×His-T2A-PAC(101916-P03)[ SEQ ID NO:1207] lacks a single amino acid in the Protein L coding region, which is present in the construct CD8SP-Protein-L-GGSG-NLuc-4×FLAG-×2STREP-8×His-T2A-PAC (112316-Q02)[ SEQ ID NO:1206]. 293FT cells were transfected with the two constructs and supernatants containing the secreted fusion proteins collected between 48 to 72 hours post-transfection. The secreted proteins were tested for binding to Jurkat cells expressing the CS1-specific CAR HuLuc64-(vL-vH)-Myc-BBz-T2A-Pac(052616-U05)[ SEQ ID NO:1228] that comprises a humanized scFv fragment as its antigen recognition domain. FIG. 13 shows effective binding of the CD8SP-Protein-L-2-GGSG-NLuc-4×FLAG-×2STREP-8×His-T2A-PAC(101916-P03)[ SEQ ID NO:1207] and CD8SP-Protein-L-GGSG-NLuc-4×FLAG-×2STREP-8×His-T2A-PAC(112316-Q02)[ SEQ ID NO:1206] fusion proteins to Jurkat cells expressing the CS1-specific CAR HuLuc64-(vL-vH)-Myc-BBz-T2A-Pac (052616-U05)[ SEQ ID NO:1228] as compared to parental cells (Jurkat cells-UI). These results demonstrate that Protein L containing Luc fusion proteins can be used to detect a kappa light chain containing CAR where the kappa light chain binds to Protein L.

REFERENCES

1. Kohn D B et al. (2011). "CARs on track in the clinic." *Mol. Ther.* 19(3): 432.
2. De Oliveira, S. N., J. Wang, C. Ryan, S. L. Morrison, D. B. Kohn and R. P. Hollis (2013). "A CD19/Fc fusion protein for detection of anti-CD19 chimeric antigen receptors." *Journal of translational medicine* 11: 23.
3. Hajek, R., S. A. Okubote and H. Svachova (2013). "Myeloma stem cell concepts, heterogeneity and plasticity of multiple myeloma." *Br J Haematol* 163(5): 551-564.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

The present application and invention further includes the subject matter of the following numbered clauses.

1. A method for detecting the presence of an antigen in a subject in need thereof comprising: providing a fusion protein comprising an antigen specific single chain antibody or a nanobody (camel or LAMA vHH fragment), or an affibody or a DARPIN or a non-immunoglobulin antigen binding domain or the extracellular domain of a receptor or the extracellular domain of a ligand fused to a reporter; providing a sample from the subject; exposing the sample to the fusion protein for sufficient time and under conditions to allow the fusion protein to bind to the sample; washing the sample to remove any unbound fusion protein; and assaying the activity of the reporter; wherein a change in reporter activity relative to a reference value is indicative of the presence of an antigen in the subject.

2. A method for detecting the expression of a chimeric antigen receptor or a T cell receptor or a synthetic T cell receptor or a chimeric T cell receptor or a hybrid T cell receptor on the cells of a subject comprising: providing a fusion protein comprising a reporter fused to an extracellular domain of the antigen targeted by the chimeric antigen receptor or a T cell receptor or a synthetic T cell receptor or a chimeric T cell receptor or a hybrid T cell receptor; providing a sample from the subject; exposing the sample to the fusion protein for sufficient time and under conditions to allow the fusion protein to bind to the sample; washing the sample to remove any unbound fusion protein; and assaying the activity of the reporter; wherein a change in reporter activity relative to a reference value is indicative of the expression of the chimeric antigen receptor or an exogenous T cell receptor or a synthetic T cell receptor or a chimeric T cell receptor or a hybrid T cell receptor on the cells of the subject.

3. The method of clauses 1 or 2, wherein the reporter is a non-secretory form of a luciferase.

4. The method of clause 3, wherein the non-secretory form of luciferase is obtained from copepods, deep sea shrimp or homologs or orthologs thereof or mutants or derivatives thereof.

5. The method of clause 4, wherein the copepods are selected from the group consisting of any one or more of *Gaussia princeps, Pleuromamma abdominalis, Metridia pacifica, Metridia curticauda, Metridia asymmetrica, Metridia okhotensis, Metridia longa, Lucicutia ovaliformis, Heterorhabdus tanneri*, and *Pleuromamma scutullata*.

6. The method of clause 3, wherein the luciferase is any one or more of GLuc, NLuc, MLuc7, PaLuc1, PaLuc2, MpLuc1, MoLuc1, MoLuc2, MLuc39, HtLuc, HtLuc2, PsLuc1, *Lucicutia ovaliformis* Luc (LoLuc), LoLuc1-3, *Renilla* or TLuc (TurboLuc16) or derivatives thereof.

7. The method of clauses 1 or 2, wherein the reporter activity is assayed by exposing the target cells to a luciferase specific substrate.

8. The method of clause 7, wherein the luciferase-specific substrate is coelentrazine or a derivative thereof.

9. The method of clause 7, wherein the luciferase-specific substrate is imidazopyrazinone substrate (furimazine) or a derivative thereof.

10. The method of clause 1, wherein the luciferase activity is measured by any one or more of methods for measuring light production such as a luminometer, Western blotting, ELISA, x-ray films, microscopy, BRET, nanoBRET, or combinations thereof.

11. The method of clause 1, wherein the antigen is expressed on a cancer cell.

12. The method of clause 11, wherein the antigen is any one or more of but are not limited to 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-R α, PDL192, phosphatidylserine, prostatic carcinoma cells, RANKL, RON, ROR1, SCH 900105, SDC1, SLAMF7, thrombopoietin receptor, TAG-72, tenascin C, TGF beta 2, TGF-β, TRAIL-R1, TRAIL-R2, tumor antigen CTAA16.88, VEGF-A, VEGFR-1, VEGFR2, MPL, or vimentin.

13. The method of clauses 1 or 11, wherein the antigen is the complex of an HLA molecule with a peptide antigen.

14. The method of clause 13, wherein the HLA molecule is HLA-A2.

15. The method of clause 13, wherein the antigen is derived from any one or more of the following proteins but are not limited to NY-ESO, Mart-1, TERT, MAGE, gp100, Tyrosinase, WT1, PR1, HTLV1-Tax, EBNA3c, CMV-pp65, HIV1 gag and HTLV1-Tax.

16. The method of clause 2, wherein the CAR or a T cell receptor or a synthetic T cell receptor or a chimeric T cell receptor or a hybrid T cell receptor is expressed on an immune cell.

17. The method of clause 16, wherein the immune cell is a T cell.

18. The method of clause 17, wherein the immune cell is a CD4 T cell.

19. The method of clause 17, wherein the immune cell is a CD8 T cell.

20. The method of clause 17, wherein the immune cell is a Treg cell.

21. The method of clause 17, wherein the immune cell is a naive T cell.

22. The method of clause 17, wherein the immune cell is a memory T cell.

23. The method of clause 17, wherein the immune cell is central memory T cell.

24. The method of clause 17, wherein the immune cell is an effector memory T cell.

25. The method of clause 16, wherein the immune cell is an NK cell

26. The method of clause 2, wherein the CAR or a T cell receptor or a synthetic T cell receptor or a chimeric T cell receptor or a hybrid T cell receptor is expressed on a stem cell.

27. The method of clause 2, wherein the CAR or a T cell receptor or a synthetic T cell receptor or a chimeric T cell receptor or a hybrid T cell receptor is expressed on a hematopoietic stem cell.

28. The method of clause 2, wherein the CAR or a T cell receptor or a synthetic T cell receptor or a chimeric T cell receptor or a hybrid T cell receptor is expressed on an induced pluripotent stem cell.

29. The method of any one of clauses 2, 16 or 26-28, wherein the target antigen of CAR or a T cell receptor or a synthetic T cell receptor or a chimeric T cell receptor or a hybrid T cell receptor is any one or more of but are not limited to 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD123, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, integrin α5β1, integrin αvβ3, Lym1, Lym2, FLT3, MORAb-009, MS4A1, MUC1, mucin CanAg, N-glycolylneuraminic acid, NPC-1C, PDGF-R α, PDL192, phosphatidylserine, prostatic carcinoma cells, RANKL, RON, ROR1, SCH 900105, SDC1, SLAMF7, thrombopoietin receptor (MPL), TAG-72, tenascin C, TGF beta 2, TGF-β, TRAIL-R1, TRAIL-R2, tumor antigen CTAA16.88, VEGF-A, VEGFR-1, VEGFR2, or vimentin.

30. The method of any one of clauses 2, 16 or 26-28, wherein the target antigen of CAR or a T cell receptor or a synthetic T cell receptor or a chimeric T cell receptor or a hybrid T cell receptor is a complex of a HLA molecule with a peptide antigen.

31. The method of clause 11, wherein the target antigen of CAR or a T cell receptor or a synthetic T cell receptor or a chimeric T cell receptor or a hybrid T cell receptor is the complex of an HLA molecule with a peptide antigen.

32. The method of clauses 30 and 31, wherein the HLA molecule is HLA-A2.

33. The method of clauses 30 and 31, wherein the antigen is derived from any one or more of but are not limited to NY-ESO, Mart-1, TERT, MAGE, gp100, Tyrosinase, WT1, PR1, HTLV1-Tax, EBNA3c, CMV-pp65, HIV1 gag and HTLV1-Tax.

34. The method of clause 1, wherein the subject has cancer or an immune disorder and is being assessed for immune therapy.

35. The method of clause 34, wherein the immune therapy involves CAR T cells.

36. The method of clause 34, wherein the immune therapy involves exogenous T cell receptor expressing T cells.

37. The method of clause 34, wherein the immune therapy involves synthetic T cell receptor therapy or a chimeric T cell receptor therapy or a hybrid T cell receptor therapy.

38. The method of clause 34, wherein the immune therapy involves antibody therapy.

39. The method of clause 34, wherein the immune therapy involves antibody-drug conjugate therapy.

40. The method of clause 34, wherein the immune therapy involves bispecific antibody.

41. The method of clause 34, wherein the immune therapy involves BiTE.

42. The method of clause 34, wherein the immune therapy involves DART.

43. The method of clause 34, wherein the immune therapy involves NK cells.

44. The method of clause 34, wherein the immune therapy involves stem cells.

45. The method of clause 34, wherein the immune therapy involves pluripotent stem cells.

46. The method of clause 34, wherein the immune therapy involves induced pluripotent stem cells. The method of clause 34, wherein the immune therapy involves stem cell transplantation.

47. The method of clauses 1 or 2, wherein the fusion protein further comprises a tag.

48. The method of clause 47, wherein the tag is any one or more of chitin binding protein (CBP), glutathione-S-transferase (GST), polyhistidine (His) tag, FLAG tag, HA tag, Myc tag, V5 tag, AcV5 tag, Streptag or a combination thereof.

49. The method of clause 1, wherein the reference value is the reporter activity in any one or more of (i) control cells or samples that do not express the target antigen; (ii) control cells or samples that express reporter but are not treated with the test agent(s); (iii) controls cells or samples that are not treated with the substrate for the reporter; (iv) control cells or samples that do express the target antigen but are treated with a fusion protein directed against an antigen that is not expressed on the target cells; (v) a combination thereof.

50. The method of clause 2, wherein the reference value is the reporter activity in any one or more of (i) cells that do not express the CAR, or an exogenous T cell receptor or a synthetic T cell receptor or a chimeric T cell receptor or a hybrid T cell receptor; (ii) cells that express the CAR, or an exogenous T cell receptor or a synthetic T cell receptor or a chimeric T cell receptor or a hybrid T cell receptor but are treated with fusion protein which is not targeted by the CAR, or an exogenous T cell receptor or a synthetic T cell receptor or a chimeric T cell receptor or a hybrid T cell receptor; (iii) cells that are not treated with the substrate for the reporter.

51. The method of clauses 1 or 2, wherein the assay is performed on samples outside the patient (in vitro).

52. The method of clauses 1 or 2, wherein the assay is performed in vivo.

SEQUENCE LISTING

The patent contains a lengthy sequence listing. A copy of the sequence listing is available in electronic form from the USPTO web site (https://seqdata.uspto.gov/?pageRequest=docDetail&DocID=US11768203B2). An electronic copy of the sequence listing will also be available from the USPTO upon request and payment of the fee set forth in 37 CFR 1.19(b)(3).

The invention claimed is:

1. A method for detecting expression of a chimeric antigen receptor (CAR), comprising:
    obtaining a sample comprising cells from a subject wherein the cells are expected to have CAR expressed on their surface and in need of determination of expression of the CAR;
    contacting the sample with a fusion protein comprising a luciferase reporter operably linked to an extracellular domain of an antigen targeted by the CAR under conditions such that the fusion protein binds to cells in the sample expressing the CAR; wherein the extracellular domain targeted by CAR is linked to the luciferase reporter through a Gly-Gly-Ser (GGS) or Gly-Gly-Ser-Gly (GGSG) peptide linker and wherein the luciferase reporter is selected from the group consisting of Nano-Luc (NLuc), MLuc7, PaLuc1 and TurboLuc16 (TLuc);
    washing the sample after the contacting step to remove any unbound fusion protein; and
    assaying the activity of the luciferase reporter bound to the cells expressing the CAR; wherein presence of luciferase reporter activity or increase in luciferase reporter activity relative to a reference value of cells lacking the CAR is indicative of the expression of the CAR in the sample;
    wherein the method is capable of detecting at least 1000 CAR expressing cells in the background of 1 million non-CAR expressing cells; and
    wherein the fusion protein is encoded by a nucleic acid sequence wherein nucleotide sequence encoding the extracellular domain is fused in-frame to nucleotide sequence encoding the GGS or GGSG linker and the luciferase reporter.

2. The method of claim 1, wherein the reporter is a non-secretory form of a luciferase.

3. The method of claim 2, wherein the non-secretory form of luciferase is obtained from copepods, deep sea shrimp or homologs or orthologs thereof or mutants or derivatives thereof.

4. The method of claim 1, wherein the reporter activity is assayed by exposing the target cells to a luciferase specific substrate.

5. The method of claim 4, wherein the luciferase-specific substrate is (a) coelentrazine or a derivative thereof, or (b) imidazopyrazinone or a derivative thereof.

6. The method of claim 1, wherein the CAR is expressed on an immune cell.

7. The method of claim 6, wherein the immune cell is a T cell, a CD4 T cell, a CD8 T cell, a Treg cells, a naïve T cell, a memory T cells, a central memory T cell, an effector memory T cell or an NK cell.

8. The method of claim 1, wherein the CAR is expressed on a stem cell.

9. The method of claim 1, wherein the CAR is expressed on a hematopoietic stem cell.

10. The method of claim 1, wherein the CAR is expressed on an induced pluripotent stem cell.

11. The method of claim 1, wherein the target antigen of the CAR is CD19, CD20, CS1/SLAMF7, BCMA, CD123, CD33, MPL, Lym1, Lym2, CD200R, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD200, CD22, CD221, CD23 (IgE receptor), CD28, CD30 (TNFRSF8), CD4, CD40, CD44 v6, CD51, CD52, CD56, CD74, CD80, CEA, CNTO888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, L1-CAM, IL-13, IL-6, insulin-like growth factor I receptor, integrin α5β1, integrin αvβ3, FLT3, MORAb-009, MS4A1, MUC1, mucin CanAg, N-glycolylneuraminic acid, NPC-1C, PDGF-R α, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, or vimentin.

12. The method of claim 1, wherein the target antigen of CAR is a complex of a HLA molecule with a peptide antigen.

13. The method of claim 12, wherein the HLA molecule is HLA-A2.

14. The method of claim 1, wherein the subject has cancer or an immune disorder.

15. The method of claim 14, wherein the subject is being assessed for immune therapy.

16. The method of claim 15, wherein the immune therapy comprises CAR T cells.

17. The method of claim 1, wherein the fusion protein further comprises a tag.

18. The method of claim 17, wherein the tag is any one or more of chitin binding protein (CBP), glutathione-S-transferase (GST), polyhistidine (His) tag, FLAG tag, HA tag, Myc tag, V5 tag, AcV5 tag, Streptag or a combination thereof.

19. The method of claim 1, wherein the reference value is the reporter activity in any one or more of (i) cells that do not express the CAR; (ii) cells that express the CAR but are treated with fusion protein which is not targeted by the CAR; (iii) cells that are not treated with the substrate for the reporter; or (iv) combinations thereof.

20. The method of claim 1, wherein more than one molecules of the reporter are fused to the extracellular domain of an antigen targeted by the chimeric antigen receptor.

\* \* \* \* \*